(12) United States Patent
Yu et al.

(10) Patent No.: US 10,975,094 B2
(45) Date of Patent: Apr. 13, 2021

(54) HETEROCYCLIC COMPOUNDS AS RSV INHIBITORS

(71) Applicant: Enanta Pharmaceuticals, Inc., Watertown, MA (US)

(72) Inventors: Jianming Yu, Plainsboro, NJ (US); Solymar Negretti-Emmanuelli, Watertown, MA (US); In Jong Kim, Lexington, MA (US); Yat Sun Or, Waltham, MA (US)

(73) Assignee: Enanta Pharmaceuticals, Inc., Watertown, MA (US)

( * ) Notice: Subject to any disclaimer, the term of this patent is extended or adjusted under 35 U.S.C. 154(b) by 0 days.

(21) Appl. No.: 16/379,881

(22) Filed: Apr. 10, 2019

(65) Prior Publication Data

US 2019/0315766 A1    Oct. 17, 2019

Related U.S. Application Data

(60) Provisional application No. 62/656,271, filed on Apr. 11, 2018.

(51) Int. Cl.

| C07D 495/14 | (2006.01) |
|---|---|
| C07D 493/14 | (2006.01) |
| C07D 413/14 | (2006.01) |
| C07D 493/10 | (2006.01) |
| A61P 31/16 | (2006.01) |
| C07D 519/00 | (2006.01) |

(52) U.S. Cl.
CPC ............ *C07D 495/14* (2013.01); *A61P 31/16* (2018.01); *C07D 413/14* (2013.01); *C07D 493/10* (2013.01); *C07D 493/14* (2013.01); *C07D 519/00* (2013.01)

(58) Field of Classification Search
CPC .. C07D 413/14; C07D 519/00; C07D 493/10; A61P 31/16
USPC ........................................................ 514/210
See application file for complete search history.

(56) References Cited

U.S. PATENT DOCUMENTS

| 4,010,153 | A | 3/1977 | Kajfez et al. |
|---|---|---|---|
| 4,511,510 | A | 4/1985 | Mauri |
| 4,988,692 | A | 1/1991 | Gasc et al. |
| 5,571,809 | A | 11/1996 | Hargrave et al. |
| 5,637,697 | A | 6/1997 | Finch et al. |
| 5,646,140 | A | 7/1997 | Sugg et al. |
| 5,681,833 | A | 10/1997 | Castro et al. |
| 7,582,624 | B2 | 9/2009 | Carter et al. |
| 8,999,969 | B2 | 4/2015 | Mackman et al. |
| 9,732,098 | B2 | 8/2017 | Hunt et al. |
| 9,957,281 | B2 | 5/2018 | Shook et al. |
| 10,358,441 | B2 | 7/2019 | Kim et al. |
| 10,398,706 | B2 | 9/2019 | Shook et al. |
| 2006/0040923 | A1 | 2/2006 | Carter et al. |
| 2006/0083741 | A1 | 4/2006 | Hoffman et al. |
| 2007/0142403 | A1 | 6/2007 | Powell et al. |
| 2007/0185094 | A1 | 8/2007 | Lattmann et al. |
| 2007/0185096 | A1 | 8/2007 | Powell et al. |
| 2007/0293482 | A1 | 12/2007 | Dowdell et al. |

(Continued)

FOREIGN PATENT DOCUMENTS

| EP | 0703222 A1 | 3/1996 |
|---|---|---|
| WO | 9308175 A1 | 4/1993 |

(Continued)

OTHER PUBLICATIONS

PUBCHEM-CID: 10595203, p. 3, Fig, Oct. 25, 2006, 1-9.

(Continued)

*Primary Examiner* — Tracy Vivlemore
*Assistant Examiner* — Ebenezer O Sackey
(74) *Attorney, Agent, or Firm* — Edgar W. Harlan; Carolyn S. Elmore; Elmore Patent Law Group, P.C.

(57) ABSTRACT

The present invention discloses compounds of Formula (I), and pharmaceutically acceptable salts, esters, or prodrugs thereof:

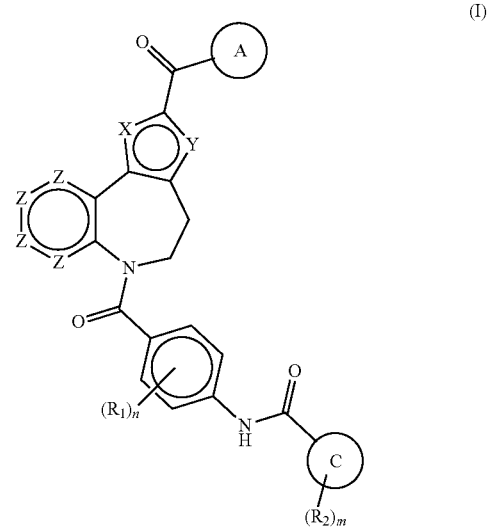

(I)

which inhibit Respiratory Syncytial Virus (RSV). The present invention further relates to pharmaceutical compositions comprising the aforementioned compounds for administration to a subject suffering from RSV infection. The invention also relates to methods of treating an RSV infection in a subject by administering a pharmaceutical composition comprising the compounds of the present invention.

17 Claims, No Drawings

(56) References Cited

U.S. PATENT DOCUMENTS

| | | |
|---|---|---|
| 2008/0139536 A1 | 6/2008 | Dowdell et al. |
| 2009/0274655 A1 | 11/2009 | Grimes et al. |
| 2010/0015063 A1 | 1/2010 | Carter et al. |
| 2012/0196846 A1 | 8/2012 | Mackman et al. |
| 2014/0038947 A1 | 2/2014 | Glick et al. |
| 2014/0100365 A1 | 4/2014 | Gavai et al. |
| 2015/0065504 A1 | 3/2015 | Wang et al. |
| 2015/0299210 A1 | 10/2015 | Bailey et al. |
| 2017/0022221 A1 | 1/2017 | Blaisdell et al. |
| 2017/0226127 A1 | 8/2017 | Estrada et al. |
| 2017/0226129 A1* | 8/2017 | Yu .................. A61K 31/554 |
| 2017/0305935 A1 | 10/2017 | Hunt et al. |
| 2017/0355717 A1 | 12/2017 | Hunt et al. |
| 2018/0193352 A1 | 7/2018 | Shook et al. |
| 2018/0237425 A1 | 8/2018 | Kim et al. |
| 2018/0258102 A1 | 9/2018 | Shook et al. |
| 2018/0354912 A1 | 12/2018 | Or et al. |
| 2019/0002478 A1 | 1/2019 | Kim et al. |
| 2019/0002479 A1 | 1/2019 | Kim et al. |
| 2019/0040084 A1 | 2/2019 | Yu et al. |
| 2019/0092791 A1 | 3/2019 | Hunt et al. |
| 2019/0152968 A1 | 5/2019 | Blaisdell et al. |
| 2019/0177283 A1 | 6/2019 | Hague |
| 2019/0192535 A1 | 6/2019 | Shook et al. |
| 2019/0315766 A1 | 10/2019 | Yu et al. |

FOREIGN PATENT DOCUMENTS

| | | | |
|---|---|---|---|
| WO | 9426718 A1 | | 11/1994 |
| WO | 2004026843 A1 | | 4/2004 |
| WO | 2004106310 A1 | | 12/2004 |
| WO | 2005089769 A1 | | 9/2005 |
| WO | 2005090319 A1 | | 9/2005 |
| WO | 2006081389 A1 | | 8/2006 |
| WO | 2011005842 A1 | | 1/2011 |
| WO | 2011151651 A1 | | 12/2011 |
| WO | 2014047369 A1 | | 3/2014 |
| WO | 2010/103305 | * | 7/2014 |
| WO | 2014125444 A1 | | 8/2014 |
| WO | 2014184350 A1 | | 11/2014 |
| WO | 2016022464 A1 | | 2/2016 |
| WO | 2016055791 A1 | | 4/2016 |
| WO | 2016055792 A1 | | 4/2016 |
| WO | 2016097761 A1 | | 6/2016 |
| WO | 2016166546 A1 | | 10/2016 |
| WO | 2017015449 A1 | | 1/2017 |
| WO | 2017123884 A1 | | 7/2017 |
| WO | 2017175000 A1 | | 10/2017 |

OTHER PUBLICATIONS

Albright, et al., (Document No. 129:54301) retrieved from STN; entered in STN on Jun. 17, 1998.
Albright, et al., (Document No. 130:153583) retrieved from STN; entered in STN on Feb. 16, 1999.
Andrzej, et al., (Document No. 144:274313) retrieved from STN; entered in STN on Mar. 3, 2006.
Aquino, Christopher J. et al., "Discovery of 1,5-Benzodiazepines with Peripheral Cholecystokinin (CCK-A) Receptor Agonist Activity. 1. Optimization of the Agonist "Trigger"", J. Med. Chem. 1996, 39, 1996, 562-569.
Carter, M. C. et al., "1,4-Benzodiazepines as Inhibitors of Respiratory Syncytial Virus", Journal of Medicinal Chemistry, vol. 49, Mar. 9, 2006, 2311-2319.
Chapman, Joanna et al., "RSV604, a Novel Inhibitor of Respiratory Syncytial Virus Replication", Antimicrobial Agents and Chemotherapy, vol. 51, No. 9, 2007, 3346-3353.
Fordyce, et al., "Discovery of novel benzothienoazepine derivatives as potent inhibitors of respiratory syncytial virus", Bioorganic & Medicinal Chemistry Letters, 27, 2017, 2201-2206.
Heeney, et al., (Document No. 153:359062) retrieved from STN; entered in STN on Sep. 2, 2010.
Henderson, E. A. et al., "1,4-Benzodiazepines as Inhibitors of Respiratory Syncytial Virus. The Identification of a Clinical Candidate", Journal of Medicinal Chemistry, vol. 50, Mar. 7, 2007, 1685-1692.
Lee, et al., (Document No. 140:69941) retrieved from STN; entered in STN on Jul. 8, 2003.
Mayo Clinic Staff, Respiratory syncytial virus (RSV) [online], retrieved from from internet on Jun. 25, 2017.; URL http://www.mayoclinic.org/diseases-condiitons/respiratory-syncytial-virus/basics/prevention.
Offel, M. et al., "Synthesis of Substituted 3-Anilino-5-phenyl-1,3-dihydro- 2H-I, 4-benzodiazepine-2-ones and their Evaluation as Cholecystokinin-Ligands", Archiv Der Pharmazie, vol. 339, No. 4, Apr. 1, 2006, 163-173.
Peesapati, et al., (Document No. 120:244848) retrieved from STN; entered in STN on May 14, 1994.
Setoi, Hiroyuki et al., "Preparation of heterocyclylbenzamide derivatives as vasopressin antagonists", Document No. 131:116236, retrieved from STN; entered in STN on Aug. 6, 1999, Aug. 6, 1999.
Wang, et al., (Document No. 160:385666) retrieved from STN; entered in STN on Feb. 27, 2014.
Xiong, et al., (Document No. 160:101182) retrieved from STN; entered in STN on Nov. 12, 2013.
Xiong, H., "Discovery of a Potent Respiratory Syncytial Virus RNA Polymerase Inhibitor", Bioorganic & Medicinal Chemistry Letters, 23, 2013, 6789-6793.
Zheng, et al., (Document No. 161 :399872) retrieved from STN; entered in STN on Jul. 23, 2014.
Armstrong, et al., "An Efficient Asymmetric Synthesis of (R)-3-Amino-2,3,4,5-tetrahydro-1H-[1]benzazepine-2-one", Tetrahedron Letters, 35(20), 1994, 3239-3242.
Karmakar, et al., "Crystallization-Induced Dynamic Resolution toward the Synthesis of (S)-7-Amino-5H,7H-dibenzo[b,d]-azepin-6-one: An Important Scaffold for γ-Secretase Inhibitors", Organic Process Research & Development, 20, 2016, 1717-1720.
Olszewska, Wieslawa et al., "Emerging drugs for respiratory syncytial virus infection", Expert Opin. Emerg. Drugs (2009), 14(2), 207-217.
Perron, Michel et al., "GS-5806 Inhibits a Broad Range of Respiratory Syncytial Virus Clinical Isolates by Blocking the Virus-Cell Fusion Process", Antimicrobial Agents and Chemotherapy, 2016, 60(3), 1264-1273.
Reider, et al., "Metalated Allylaminosilane: A New, Practical Reagent for Stereoselective a-Hydroxyallylation of Aldehydes to Erythro-1,2-diol Skeletons", J. Org. Chem, 52, 1987, 957.
Sudo, Kenji et al., "YM-53403, a unique anti-respiratory syncytial virus agent with a novel mechanism of action", Antiviral Research, 2005, vol. 65, 2005, 125-131.
STN Registry database entry: CAS RN 1348849-53-5 (Entered STN: Dec. 5, 2011) (Year: 2011).
STN Registry database entry: CAS RN 1349533-81-8 (Entered STN: Dec. 6, 2011) (Year: 2011).
STN Registry database entry: CAS RN 1350148-32-1 (Entered STN: Dec. 7, 2011) (Year: 2011).

* cited by examiner

HETEROCYCLIC COMPOUNDS AS RSV INHIBITORS

RELATED APPLICATIONS

This application claims the benefit of U.S. Provisional Application No. 62/656,271, filed on Apr. 11, 2018. The entire teachings of the above application are incorporated herein by reference.

TECHNICAL FIELD

The present invention relates generally to compounds and pharmaceutical compositions useful as Respiratory Syncytial Virus (RSV) inhibitors.

BACKGROUND OF THE INVENTION

Human respiratory syncytial virus (HRSV) is a negative-sense, single stranded, RNA paramyxovirus (KM. Empey, et al., *Rev. Anti-Infective Agents,* 2010, 50 (1 May), 1258-1267). RSV is the leading cause of acute lower respiratory tract infections (ALRI) and affects patients of all ages. The symptoms in adults are usually not severe and are typically analogous to a mild cold. However, in infants and toddlers the virus can cause lower respiratory tract infections including bronchiolitis or pneumonia with many of them requiring hospitalization. Nearly all children have been infected by age 3. There are known high-risk groups that infection with RSV is more likely to progress into the ALRI. Premature infants and/or infants suffering from lung or cardiac disease are at the highest risk to develop ALRI. Additional high-risk groups include the elderly, adults with chronic heart and/or lung disease, stem cell transplant patients and the immuno-suppressed.

Currently, there is no vaccine available to prevent HRSV infection. Palivizumab is a monoclonal antibody that is used prophylactically to prevent HRSV infection in high risk infants, e.g. premature infants, and infants with cardiac and/or lung disease. The high cost of palivizumab treatment limits its use for general purposes. Ribavirin has also been used to treat HRSV infections but its effectiveness is limited. There is a major medical need for new and effective HRSV treatments that can be used generally by all population types and ages.

There have been several RSV fusion inhibitors that have been disclosed in the following publications: WO2010/103306, WO2012/068622, WO2013/096681, WO2014/060411, WO2013/186995, WO2013/186334, WO 2013/186332, WO 2012 080451, WO 2012/080450, WO2012/080449, WO 2012/080447, WO 2012/080446, WO 2016/055792, WO 2016/097761, WO 2017/123884, WO2017/175000, and *J. Med. Chem.* 2015, 58, 1630-1643. Examples of other N-protein inhibitors for treatment of HRSV have been disclosed in the following publications: WO 2004/026843, *J. Med. Chem.* 2006, 49, 2311-2319, and *J. Med. Chem.* 2007, 50, 1685-1692. Examples of L-protein inhibitors for HRSV have been disclosed in the following publications: WO 2011/005842, WO 2005/042530, *Antiviral Res.* 2005, 65, 125-131, and *Bioorg. Med. Chem. Lett.* 2013, 23, 6789-6793, *Bioorg. Med. Chem. Lett.* 2017, 27, 2201-2206. Examples of nucleosides/polymerase inhibitors have been disclosed in the following publications: WO 2013/242525 and J. Med. Chem. 2015, 58, 1862-1878.

There is a need for the development of effective treatments for HRSV. The present invention has identified these novel compounds and their inhibitory activity against HRSV. The invention includes methods to prepare the compounds as well as methods of using these compounds to treat disease.

SUMMARY OF THE INVENTION

The present invention provides compounds represented by Formula (I), and pharmaceutically acceptable salts, esters and prodrugs thereof that can be used to treat or prevent a viral infection, such as an HSRV infection:

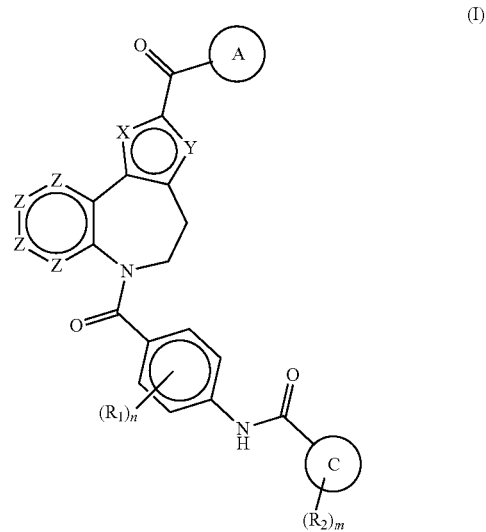

wherein:

Ⓐ is optionally substituted aryl or optionally substituted heteroaryl;

Ⓒ is aryl or heteroaryl, which, when possible, is optionally substituted with one or more substituents which are not $R_2$; X is O, S or $NR_4$, and Y is N or $CR_5$; or X is N or $CR_5$, and Y is O, S or $NR_4$;

One Z is $CR_3$, the other Zs are each independently selected from N and $CR_3$;

Each $R_1$ selected from the group consisting of: halogen, hydroxyl, protected hydroxyl, amino, protected amino, optionally substituted —$C_1$-$C_8$ alkyl, and optionally substituted —$C_1$-$C_8$ alkoxy;

Each $R_2$ is selected from the group consisting of:
1) halogen;
2) optionally substituted —$C_1$-$C_8$ alkoxy;
3) optionally substituted —$C_1$-$C_8$ alkyl;
4) optionally substituted —$C_2$-$C_8$ alkenyl;
5) optionally substituted —$C_2$-$C_8$ alkynyl;
6) optionally substituted —$C_3$-$C_{12}$ cycloalkyl;
7) optionally substituted —$C_3$-$C_{12}$ cycloalkenyl;
8) optionally substituted 3- to 12-membered heterocloalkyl;
9) optionally substituted aryl;
10) optionally substituted heteroaryl;
11) optionally substituted arylalkyl;
12) optionally substituted aryloxy;
13) —$C(O)R_{12}$;
14) —$C(O)NR_{13}R_{14}$;
15) —$C(O)NR_{11}S(O)_2R_{12}$;
16) —$S(O)_2NR_{13}R_{14}$;
17) —$NR_{13}R_{14}$;

18) —NR₁₁S(O)₂R₁₂;
19) —NR₁₁C(O)R₁₂;
20) —NR₁₁C(O)NR₁₃R₁₄; and
21) —NR₁₁C(O)NHS(O)₂R₁₂;

n is 0, 1, 2, 3 or 4;
m is 0, 1, 2, or 3;
R₃ is selected from the group consisting of: hydrogen, halogen, cyano, nitro, hydroxyl, protected hydroxyl, amino, protected amino, optionally substituted —C₁-C₈ alkyl, and optionally substituted —C₁-C₈ alkoxy;
R₄ is hydrogen or optionally substituted —C₁-C₈ alkyl;
R₅ is hydrogen, halogen, optionally substituted —C₁-C₈ alkyl, or optionally substituted —C₁-C₈ alkoxy;
R₁₂ at each occurrence is independently selected from the group consisting of:
1) Hydrogen;
2) Halogen;
3) Hydroxyl;
4) optionally substituted —C₁-C₈ alkoxy;
5) optionally substituted —C₁-C₈ alkyl;
6) optionally substituted —C₂-C₈ alkenyl;
7) optionally substituted —C₂-C₈ alkynyl;
8) optionally substituted —C₃-C₈ cycloalkyl;
9) optionally substituted —C₃-C₈ cycloalkenyl;
10) optionally substituted 3- to 8-membered heterocycloalkyl;
11) optionally substituted aryl;
12) optionally substituted arylalkyl;
13) optionally substituted heteroaryl; and
14) optionally substituted heteroarylalkyl;

R₁₁, R₁₃ and R₁₄ are each independently selected from hydrogen, optionally substituted —C₁-C₈-alkyl, optionally substituted —C₂-C₈-alkenyl, optionally substituted —C₂-C₈-alkynyl; optionally substituted —C₃-C₈-cycloalkyl, optionally substituted 3- to 8-membered heterocyclic, optionally substituted aryl, optionally substituted arylalkyl, optionally substituted heteroaryl, and optionally substituted heteroarylalkyl; alternatively, R₁₃ and R₁₄ are taken together with the nitrogen atom they attached to form a heterocyclic ring.

Each preferred group stated above can be taken in combination with one, any or all other preferred groups.

DETAILED DESCRIPTION OF THE INVENTION

In one embodiment, the present invention provides a compound represented by Formula (I) as described above, or a pharmaceutically acceptable salt, ester or prodrug thereof.

In certain embodiments, the present invention relates to compounds of Formula (I), and pharmaceutically acceptable salts, esters and prodrugs thereof, wherein Ⓐ is optionally substituted aryl; preferably Ⓐ is optionally substituted phenyl. The optional substituents are preferably independently selected from, but not limited to, halogen, —CN, —OH, —NH₂, —NO₂, —CH₃, —CF₃, —OCH₃, —OCF₃, —SO₂CH₃, —CH₂N(CH₃)₂, and —C(O)CH₃. In preferred embodiments, there are 0 to 2 substituents and, more preferably, 0 or 1 substituent.

In certain embodiments, the present invention relates to compounds of Formula (I), and pharmaceutically acceptable salts, esters and prodrugs thereof, wherein Ⓐ is optionally substituted heteroaryl; preferably optionally substituted fused bicyclic heteroaryl. When present the substituent or substituents are preferably independently selected from halogen, —CN, —OH, —NH₂, —NO₂, —CH₃, —CF₃, —OCH₃, —OCF₃, —SO₂CH₃, —CH₂N(CH₃)₂, and —C(O)CH₃. In preferred embodiments, there are 0 to 2 substituents and, more preferably, 0 or 1 substituent.

In one embodiment, the present invention relates to compounds of Formula (I), and pharmaceutically acceptable salts, esters and prodrugs thereof, wherein Ⓐ is derived from one of the following by removal of a hydrogen atom:

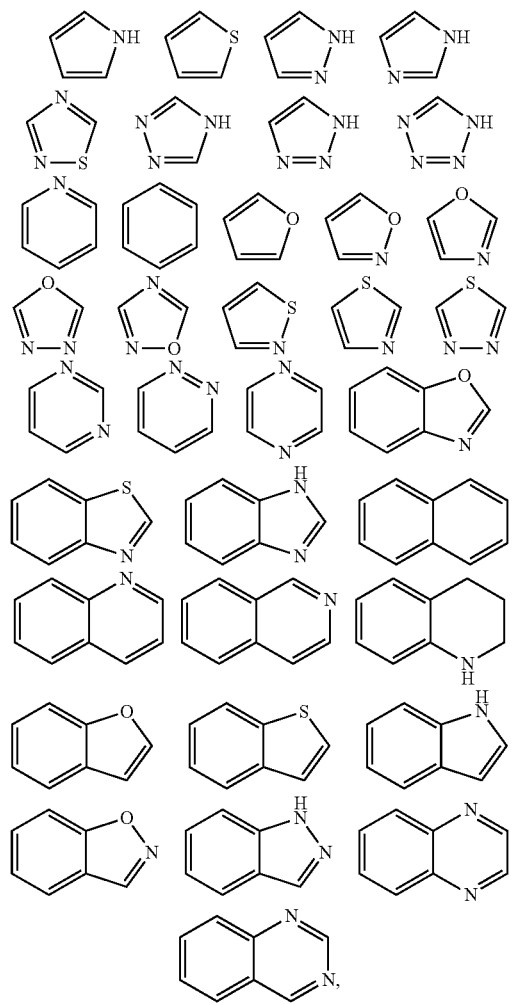

wherein each of the above is optionally substituted when possible. When Ⓐ is a 5/6 fused rings, it is preferably attached to —C(O)— via an available atom in the 5-membered ring.

In one embodiment, the present invention relates to compounds of Formula (I), and Ⓐ pharmaceutically acceptable salts, esters and prodrugs thereof, wherein Ⓒ is one of the following:

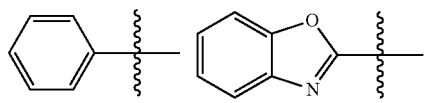

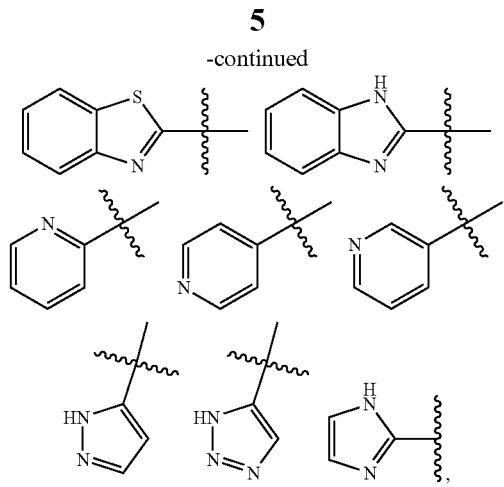

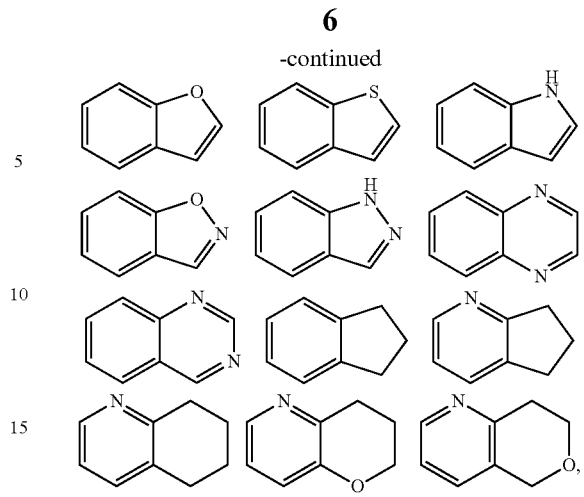

wherein each of the above is optionally substituted. Preferably, when present, the substituents are independently selected from, but not limited to, —F, —Cl, —CH$_3$, CF$_3$, —OCH$_3$, and —OCF$_3$.

In certain embodiments, the present invention relates to compounds of Formula (I), and pharmaceutically acceptable salts, esters and prodrugs thereof, wherein Ⓒ is heteroaryl, preferably Ⓒ is pyridinyl or fused bicyclic heteroaryl, each of which is optionally substituted with one or more substituents in addition to any R$_2$ groups. When present, preferably these substituents, are independently selected from, but not limited to, —CN, —OH, —NH$_2$, —NO$_2$, —SO$_2$CH$_3$, and —CH$_2$N(CH$_3$)$_2$.

In one embodiment, the present invention relates to compounds of Formula (I), and pharmaceutically acceptable salts, esters and prodrugs thereof, wherein Ⓒ is derived from one of the following by removal of a hydrogen atom:

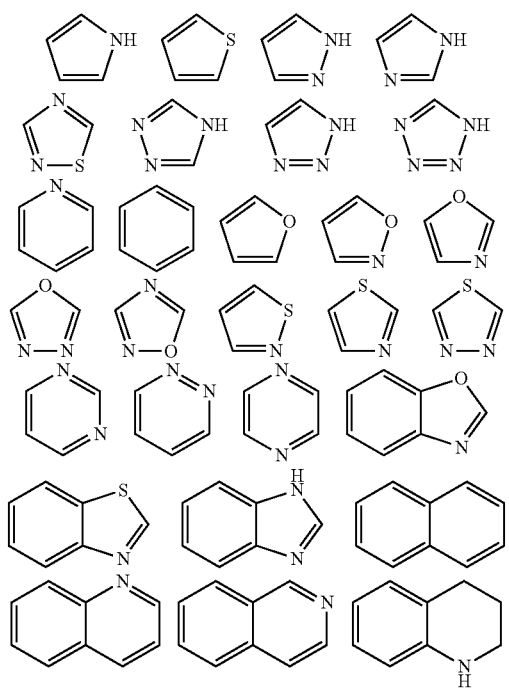

wherein each of the above is, in addition to any R$_2$ groups present, optionally further substituted with one or more substituents which are not R$_2$.

In one embodiment, the present invention relates to compounds of Formula (I), and pharmaceutically acceptable salts, esters and prodrugs thereof, wherein Ⓒ is one of the following:

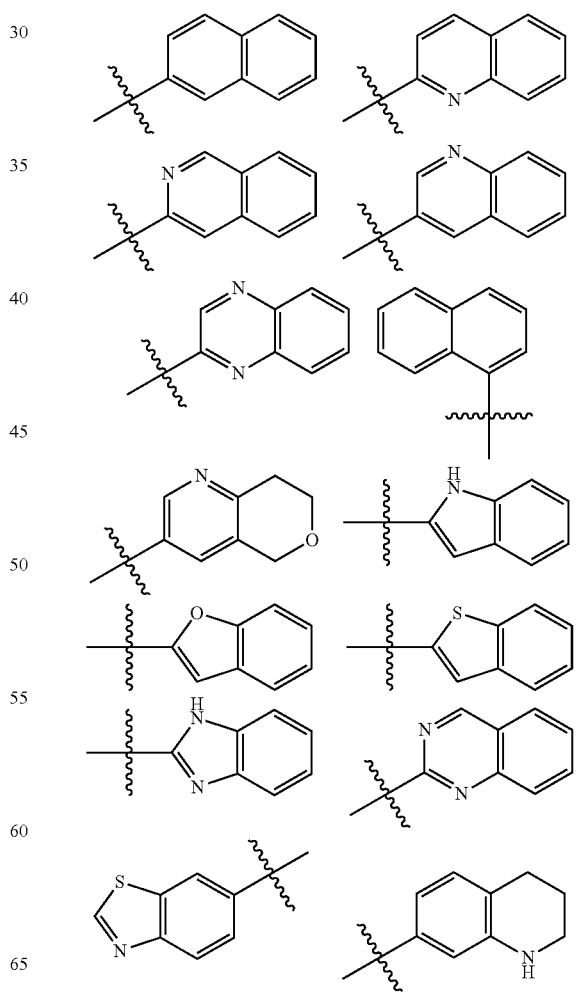

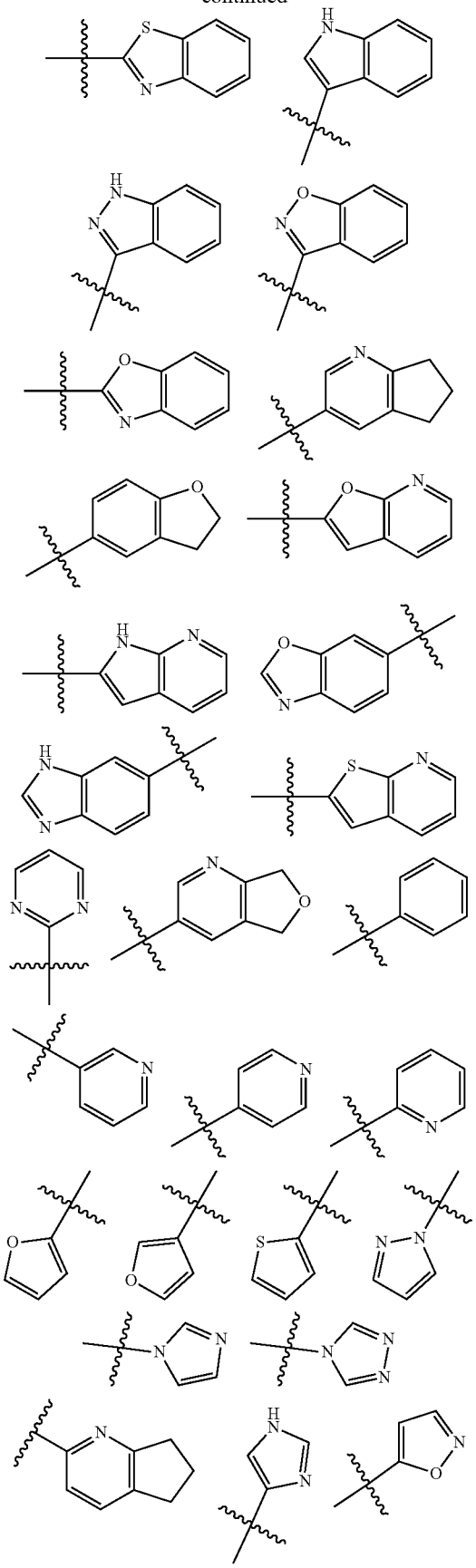
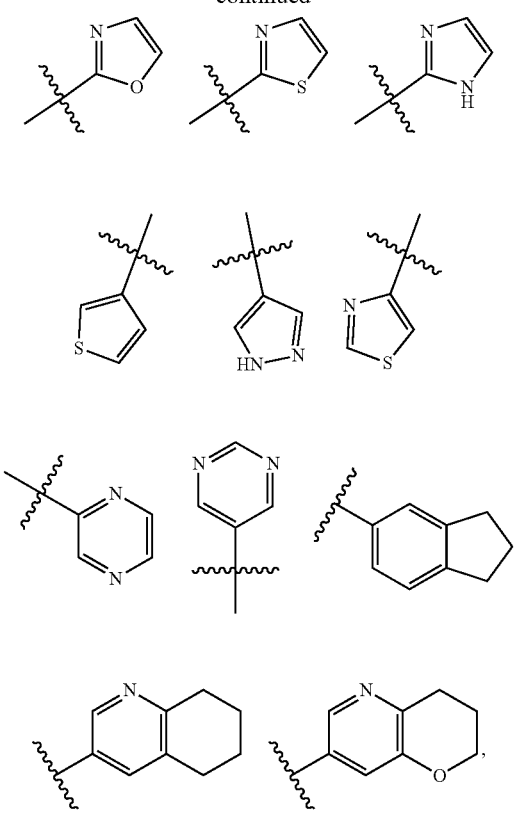
wherein each of the above is, in addition to any $R_2$ groups present, optionally further substituted with one or more substituents which are not $R_2$.
In certain embodiments,
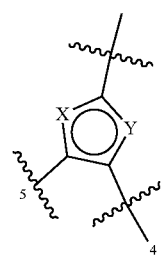
is selected from the groups below, where "4" and "5" indicate respectively the point of attachment to the 4- and 5-positions of the benzoazepine ring system:
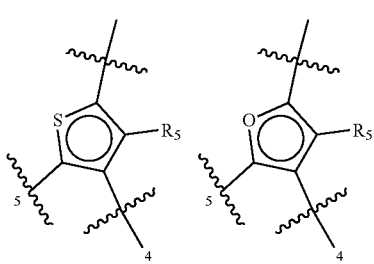

-continued

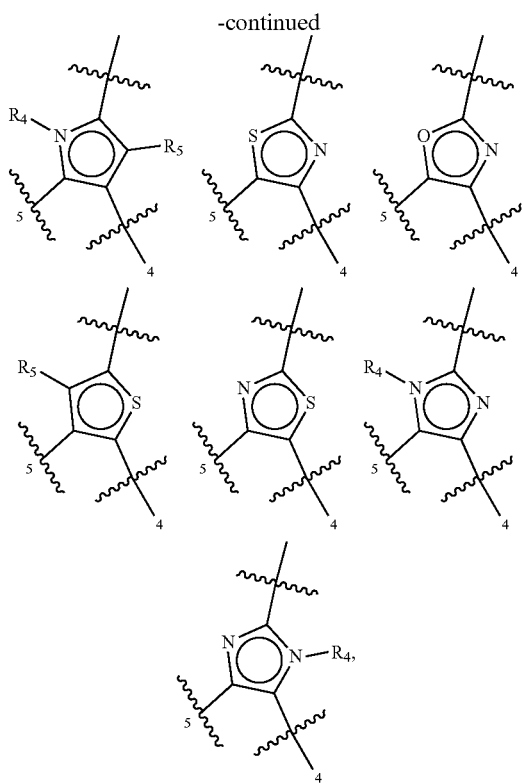

wherein $R_4$ and $R_5$ are previously defined; preferably, $R_4$ is hydrogen and $R_5$ is hydrogen or halogen.

In certain embodiments, the present invention relates to compounds of Formula (I), and pharmaceutically acceptable salts, esters and prodrugs thereof, wherein each $R_3$ is independently halogen or optionally substituted —$C_1$-$C_8$ alkyl. Preferably each $R_3$ is independently —Cl, —F, —$CH_3$, or —$CF_3$.

In certain embodiments, the present invention relates to compounds of Formula (I), and pharmaceutically acceptable salts, esters and prodrugs thereof, wherein n is 0, 1 or 2, and, when n is 1 or 2, each $R_1$ is independently halogen or optionally substituted —$C_1$-$C_8$ alkyl. Preferably n is 0, or n is 1 and $R_1$ is F, Cl, —$CH_3$, or —$CF_3$.

In certain embodiments, the present invention relates to compounds of Formula (I), and pharmaceutically acceptable salts, esters and prodrugs thereof, wherein each $R_3$ is Cl, F, —$CH_3$, or —$CF_3$; and n is 0.

In certain embodiments, the present invention relates to compounds of Formula (I), and pharmaceutically acceptable salts, esters and prodrugs thereof, wherein at least one $R_2$ is optionally substituted aryl or optionally substituted heteroaryl.

In certain embodiments, the present invention relates to compounds of Formula (I), and pharmaceutically acceptable salts, esters and prodrugs thereof, wherein at least one $R_2$ is optionally substituted 3- to 12-membered heterocycloalkyl, preferably optionally substituted 3- to 12-membered spiro bicyclic heterocycloalkyl.

In certain embodiments, the present invention relates to compounds of Formula (I), and pharmaceutically acceptable salts, esters and prodrugs thereof, wherein at least one $R_2$ is —$NR_{13}R_{14}$, wherein $R_{13}$ and $R_{14}$ are previously defined.

In certain embodiments, the present invention relates to compounds of Formula (I), and pharmaceutically acceptable salts, esters and prodrugs thereof, wherein at least one $R_2$ is —$NR_{13}R_{14}$, wherein $R_{13}$ and $R_{14}$ are taken together with the nitrogen atom they are attached to form an optionally substituted 3- to 10- or 3- to 12-membered heterocyclic, preferably the said heterocyclic is spiro heterocyclic.

In one embodiment, the present invention relates to compounds of Formula (I), and pharmaceutically acceptable salts, esters and prodrugs thereof, wherein m is not 0, and at least one $R_2$ is derived from one of the groups below by removal of one hydrogen atom, wherein each of these groups is optionally substituted:

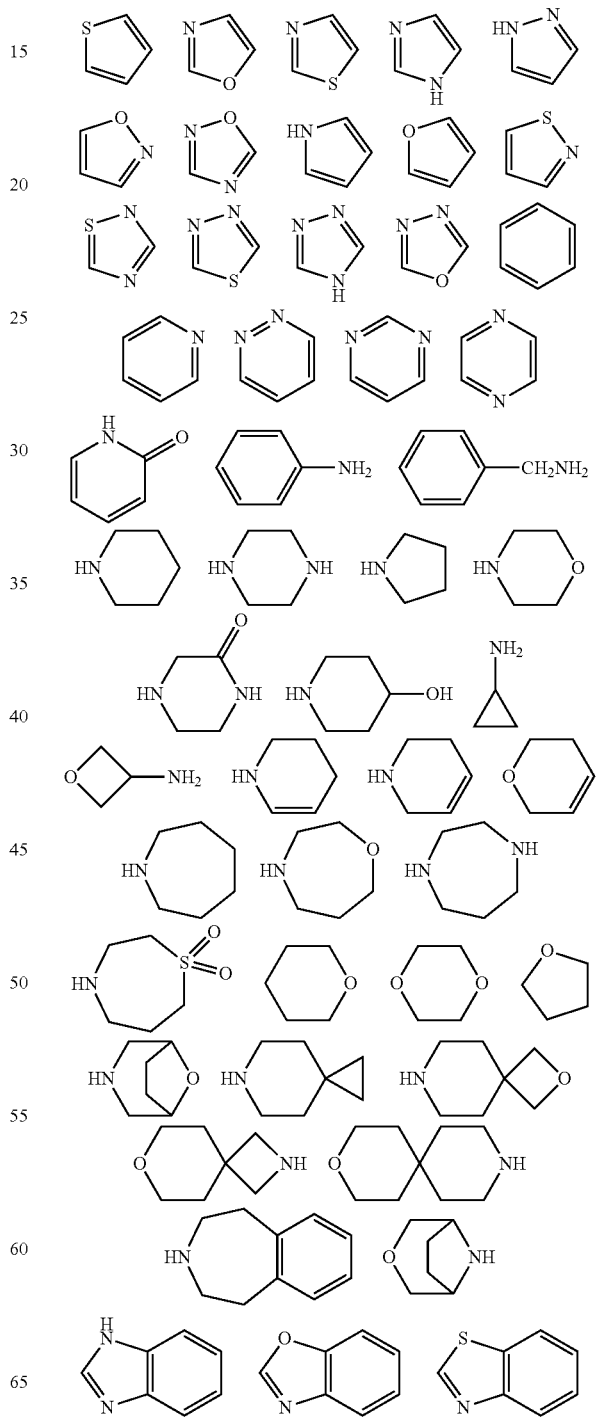

-continued
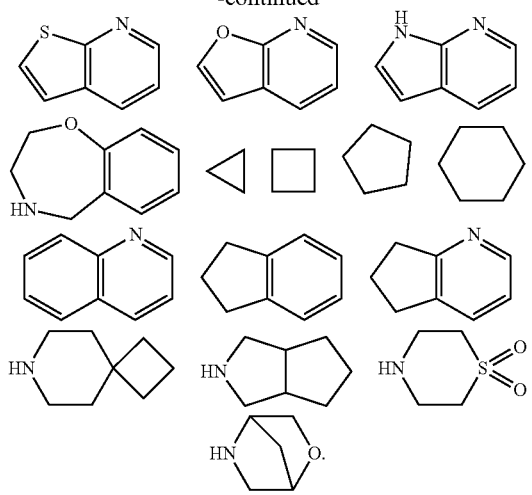
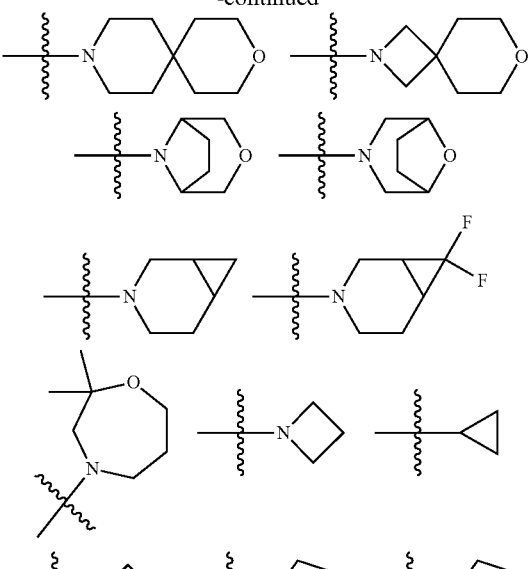
In one embodiment, the present invention relates to compounds of Formula (I), and pharmaceutically acceptable salts, esters and prodrugs thereof, wherein m is not 0, and at least one $R_2$ is selected from the groups shown below, each of which is optionally substituted:
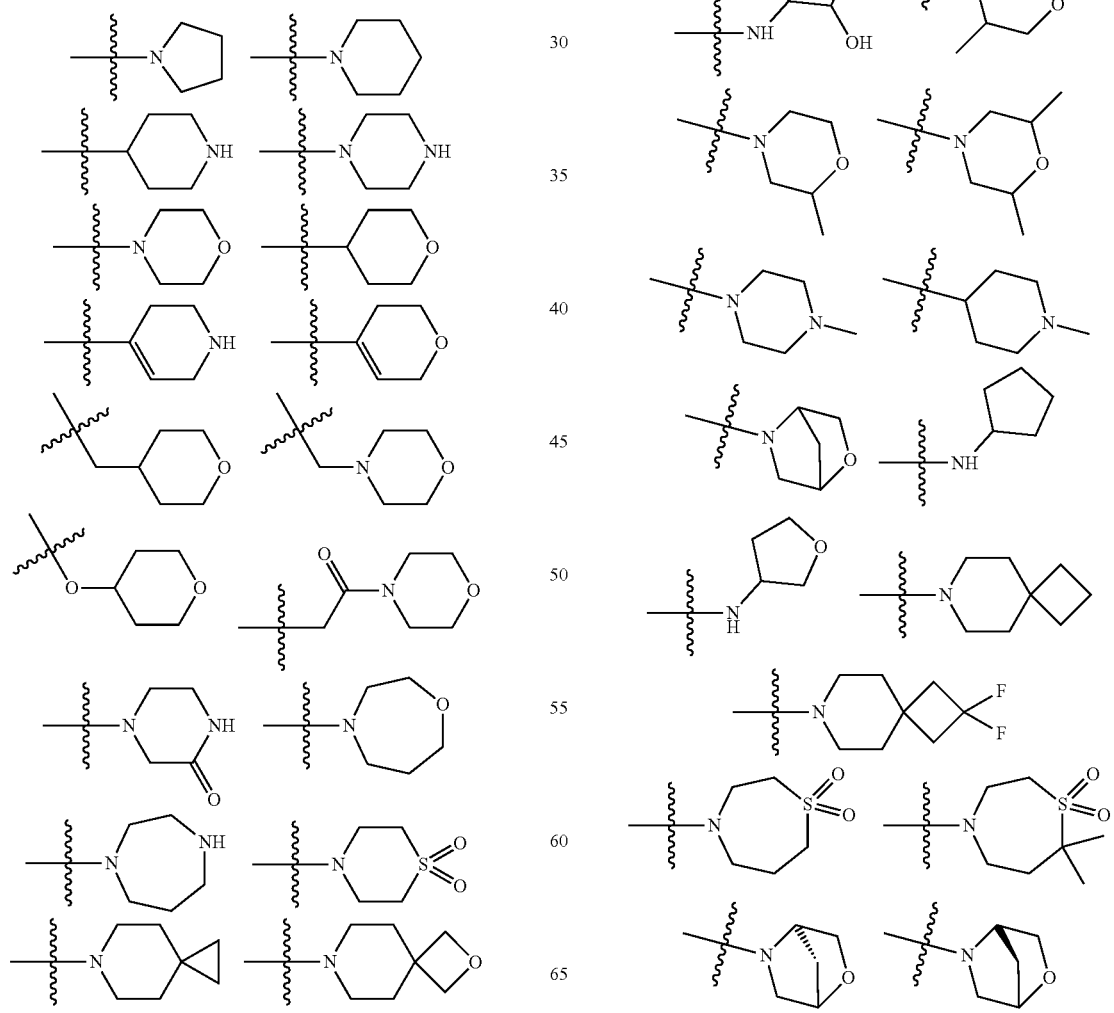

-continued

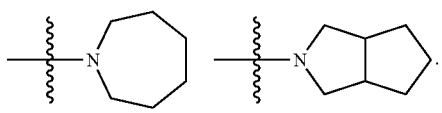

In one embodiment, the present invention relates to compounds of Formula (I), and pharmaceutically acceptable salts, esters and prodrugs thereof, wherein m is not 0, and at least one $R_2$ is selected from the groups shown below, each of which is optionally substituted:

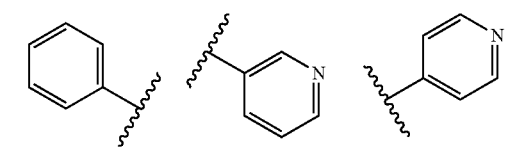

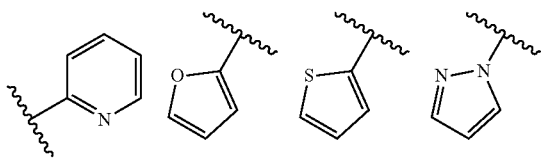

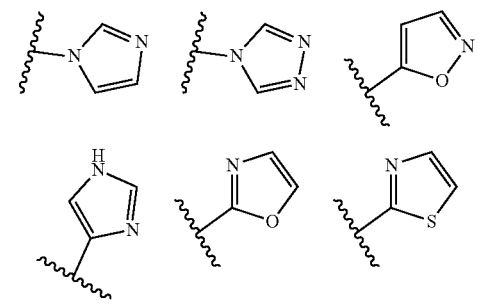

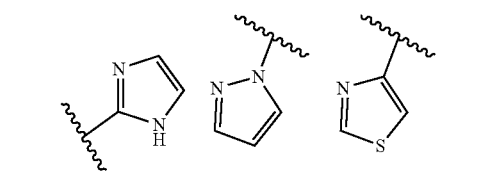

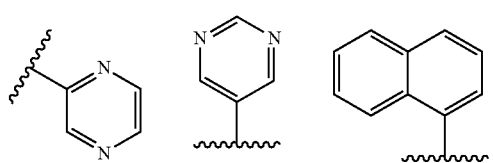

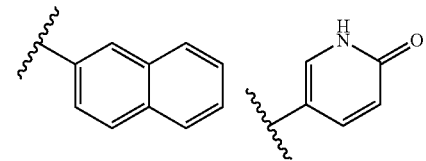

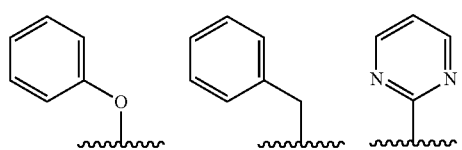

-continued

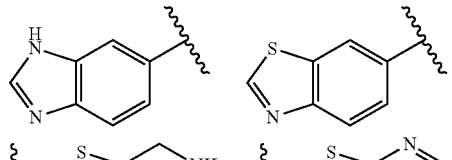

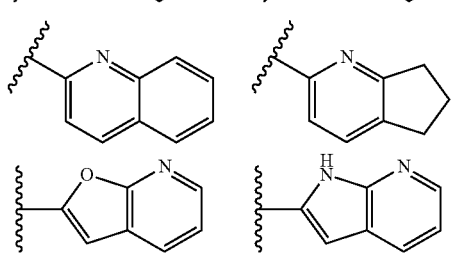

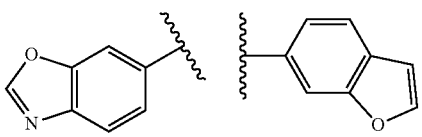

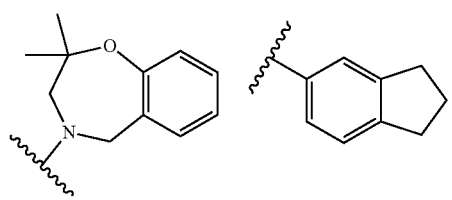

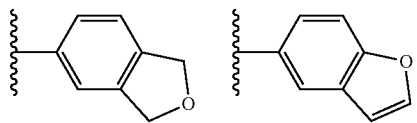

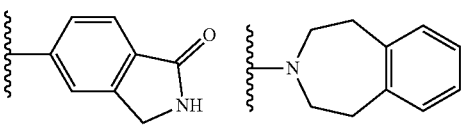

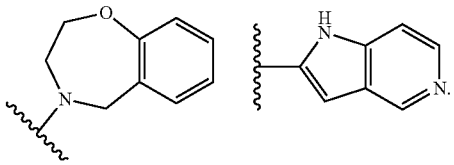

In certain embodiments of the compounds of the invention, m is 0 to 3, 0 to 2, 1 or 0 More preferably, m is 1 or 2.

In another embodiment, the invention provides a compound represented by one of Formulas (IIa)~(IIe), or a pharmaceutically acceptable salt, ester or prodrug thereof:

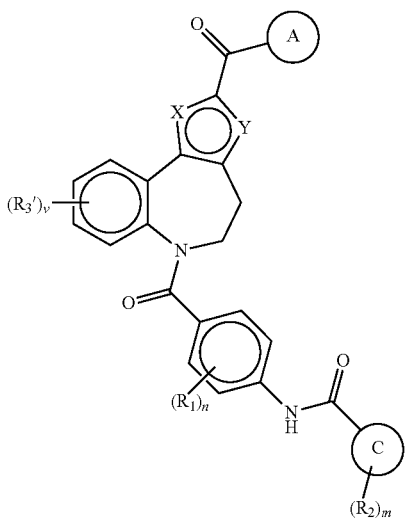
(IIa)

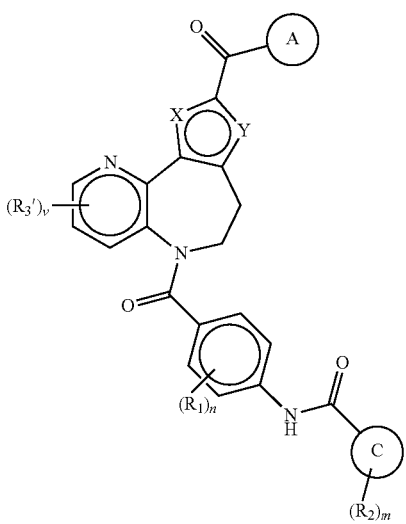
(IIb)

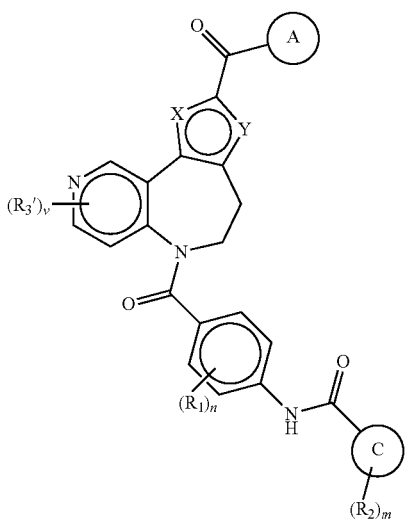
(IIc)

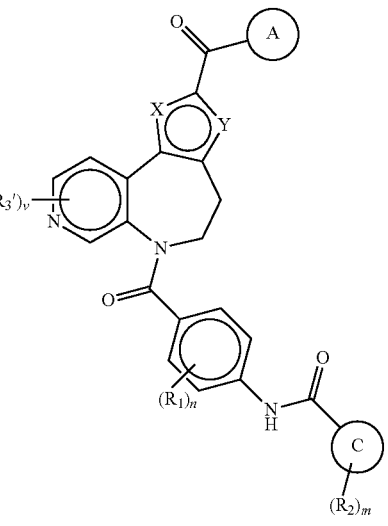
(IId)

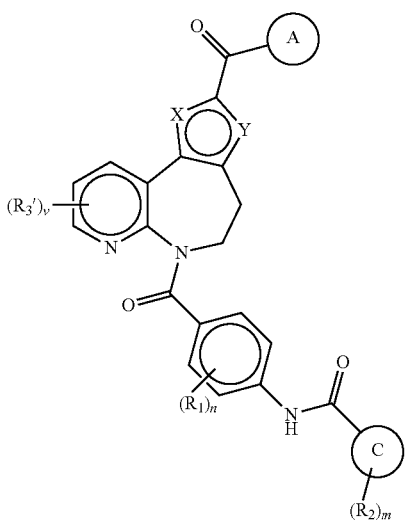
(IIe)

wherein $R_3'$ is selected from the group consisting of: halogen, cyano, nitro, hydroxyl, protected hydroxyl, amino, protected amino, optionally substituted —$C_1$-$C_8$ alkyl, and optionally substituted —$C_1$-$C_8$ alkoxy; v is 0, 1, 2 or 3; Ⓐ, Ⓒ, X, Y, $R_1$, $R_2$, m, and n are as previously defined.

In another embodiment, invention provides a compound represented by Formulas (IIa)~(IIe), or a pharmaceutically acceptable salt, ester or prodrug thereof, wherein each $R_3'$ is halogen and v is 1, 2 or 3; preferably, each $R_3'$ is —F, and v is 1 or 2.

In another embodiment, the invention provides a compound represented by one of Formulas (IIIa)~(IIId), or a pharmaceutically acceptable salt, ester or prodrug thereof:

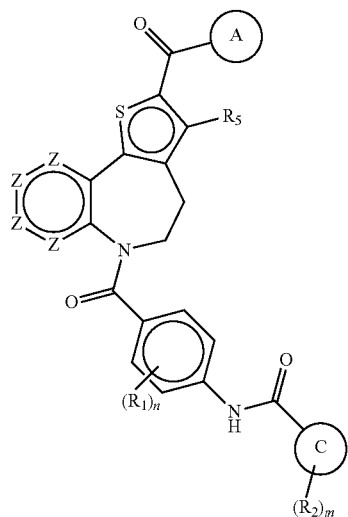
(IIIa)
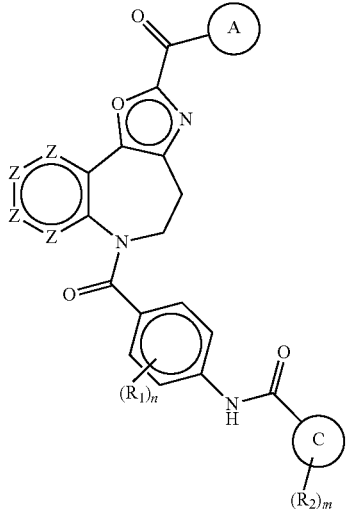
(IIId)
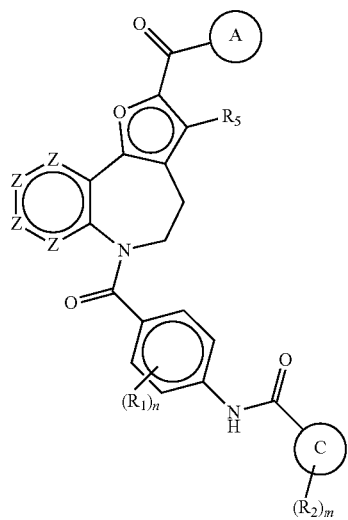
(IIIb)
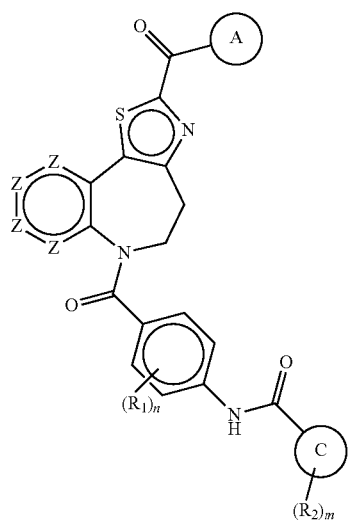
(IIIc)
wherein Ⓐ, Ⓒ, $R_1$, $R_2$, $R_5$, n, m, and Z are as previously defined. Preferably $R_5$ is hydrogen or —F.
In another embodiment, the invention provides a compound represented by one of Formulas (IVa)~(IVh), or a pharmaceutically acceptable salt, ester or prodrug thereof,
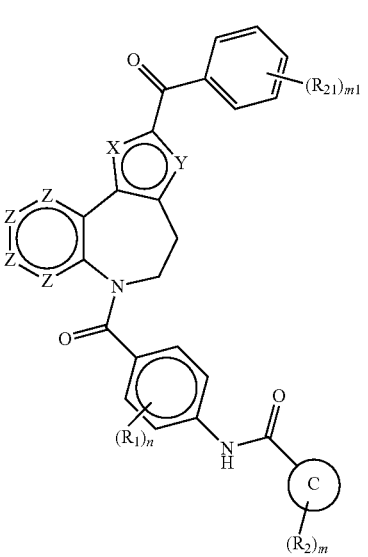
(IVa)

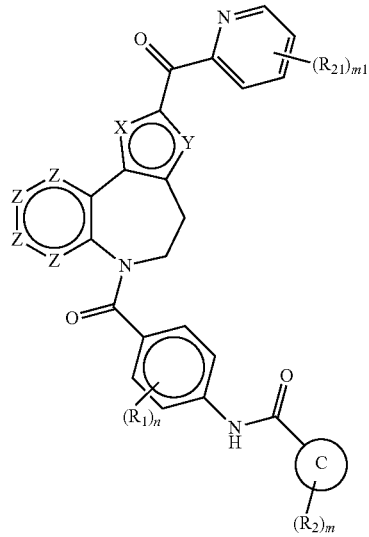
(IVb)
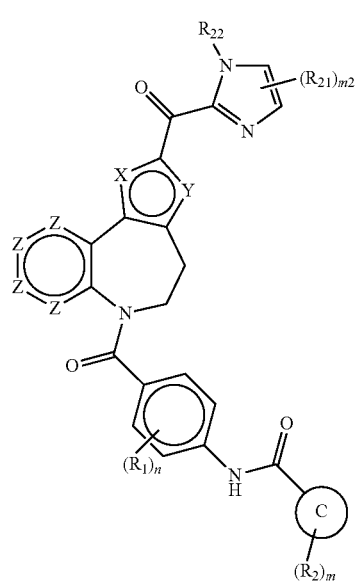
(IVc)
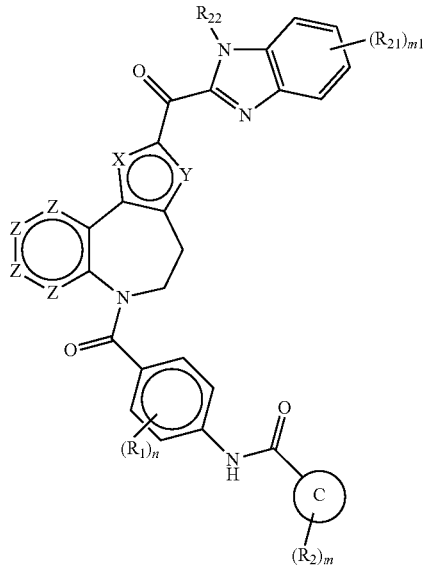
(IVd)
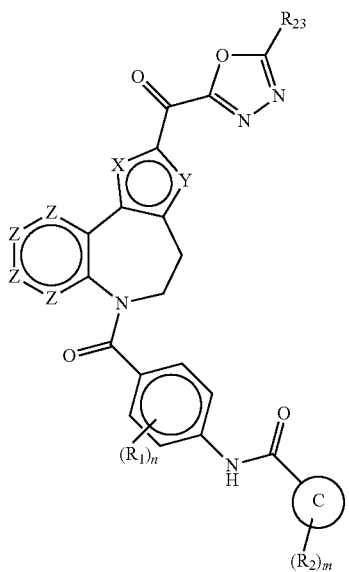
(IVe)

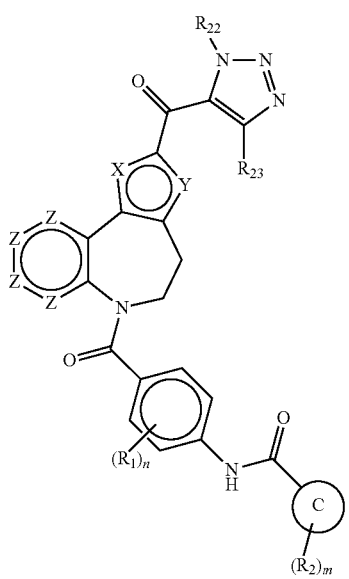

(IVf)

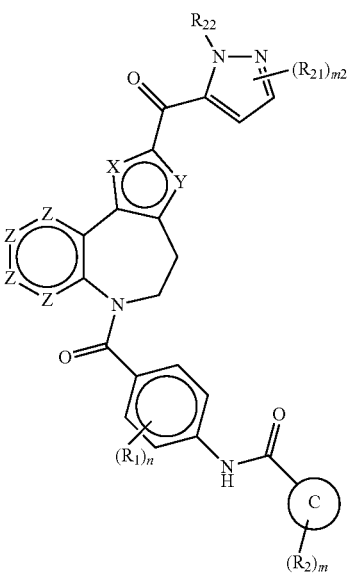

(IVg)

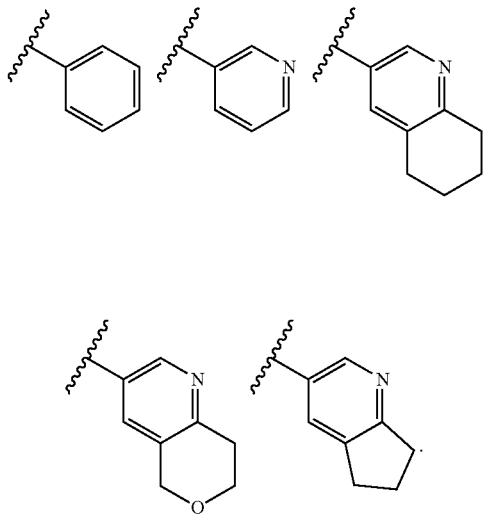

(IVh)

wherein Ⓒ, X, Y, Z, $R_1$, $R_2$, m, and n are as previously defined; m1 is 0, 1, 2, 3 or 4; m2 is 0, 1 or 2. Each $R_{21}$ is independently selected from halogen, —$NH_2$, optionally substituted —$C_1$-$C_3$ alkyl, and optionally substituted —$C_1$-$C_3$ alkoxy, preferably each $R_{21}$ is independently selected from —F, —Cl, —$NH_2$, and optionally substituted-$CH_3$. Each $R_{22}$ is independently selected from hydrogen and —$CH_3$. Each $R_{23}$ is independently selected from hydrogen, halogen, —$NH_2$, optionally substituted —$C_1$-$C_3$ alkyl, and optionally substituted —$C_1$-$C_3$ alkoxy.

In another embodiment of the invention is a compound represented by one of Formulae (IVa)~(IVh), or a pharmaceutically acceptable salt, ester or prodrug thereof, wherein Ⓒ is selected from the groups shown below:

In another embodiment, the invention provides a compound represented by one of Formulas (Va-1)~(Va-5), (Vb-1)~(Vb-5), or a pharmaceutically acceptable salt, ester or prodrug thereof:

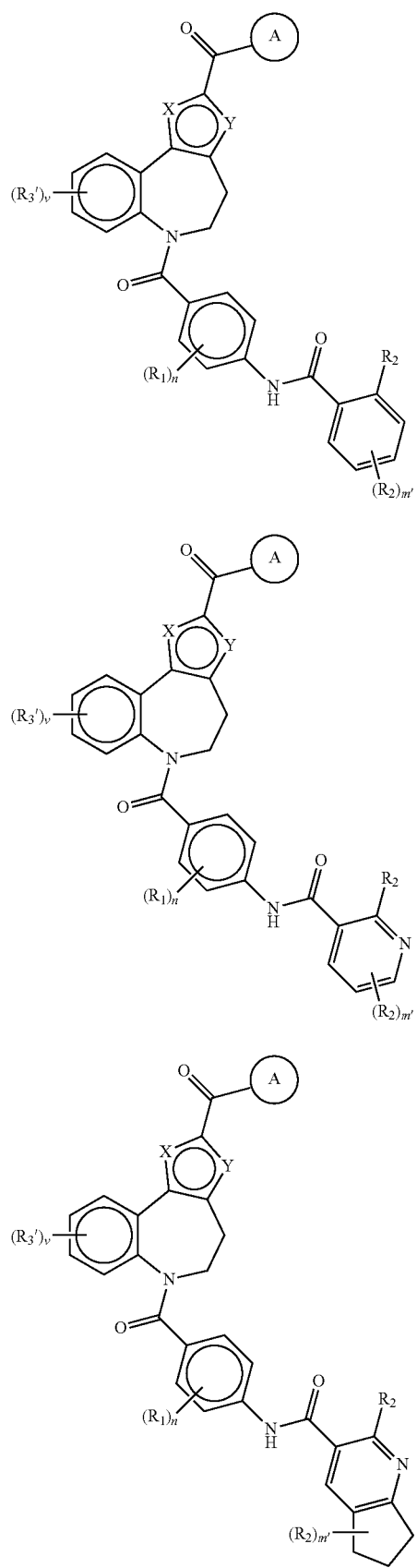

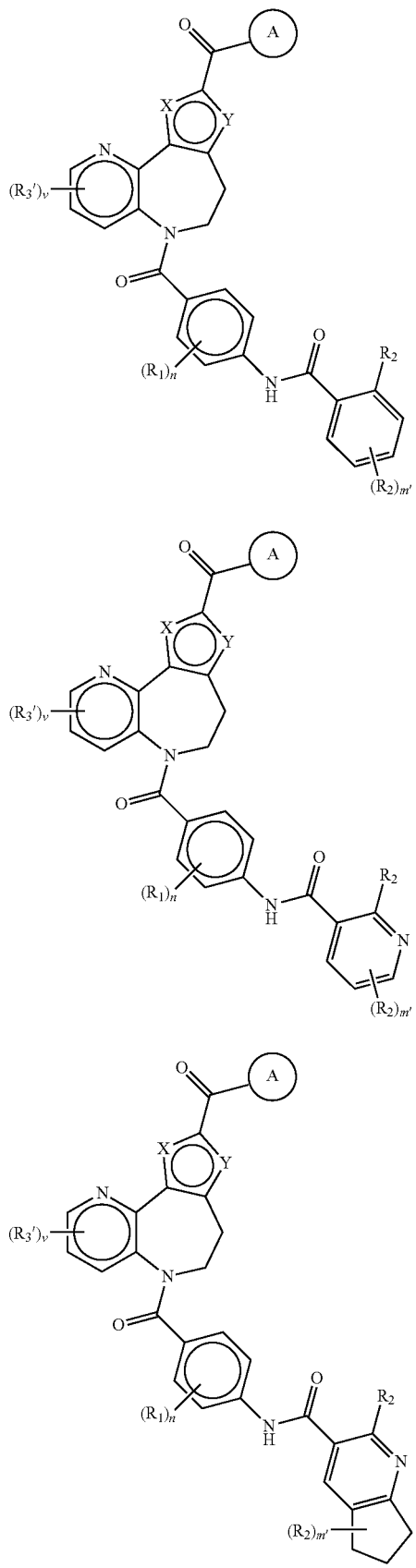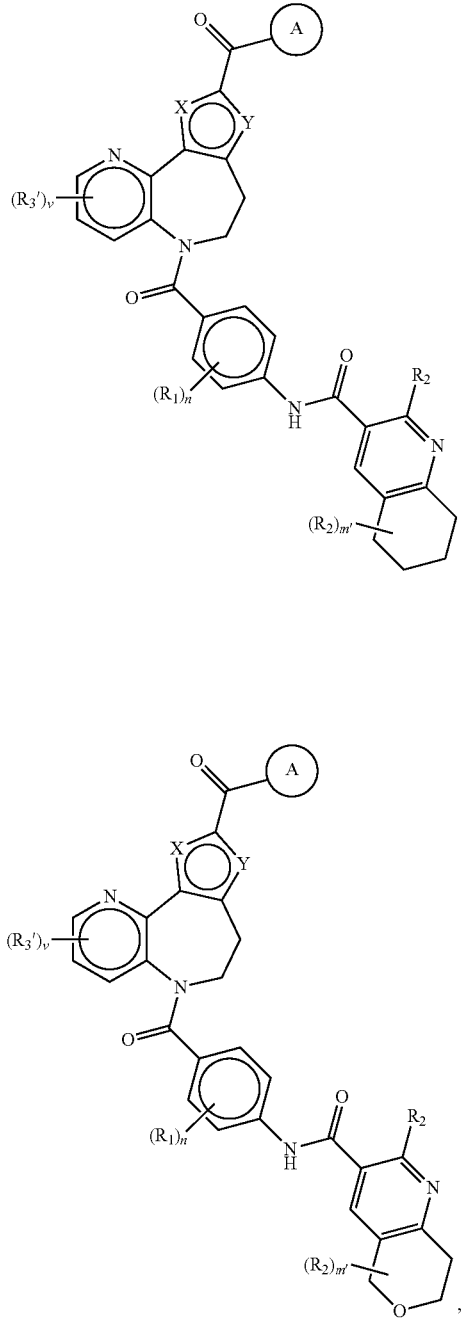
wherein Ⓐ, X, Y, $R_1$, $R_2$, $R_3'$, v, and n are as previously defined; m' is 0, 1, or 2.
In another embodiment, the invention provides a compound represented by one of Formulas (VI-1)~(VI-2), or a pharmaceutically acceptable salt, ester or prodrug thereof:

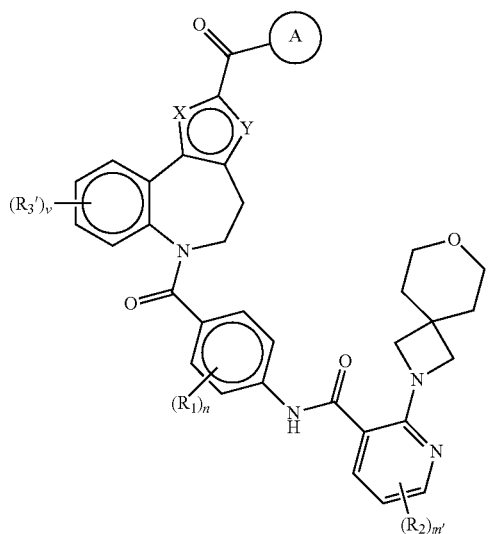

(VI-1)

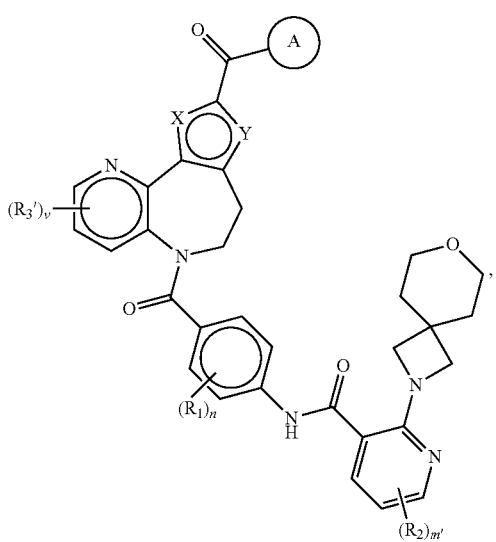

(VI-2)

wherein Ⓐ, X, Y, R₁, R₂, R₃', v, m', and n are as previously defined; preferably, m' is 1, and R₂ is —F, —Cl, —CH₃, —CF₃, —OCH₃, or —OCF₃.

In another embodiment of the invention is a compound represented by one of Formulas (Va-1)~(Va-5), (Vb-1)~(Vb-5), and (VI-1)~(VI-2), or a pharmaceutically acceptable salt, ester or prodrug thereof, wherein Ⓐ is selected from the groups shown below, each of which can be optionally substituted:

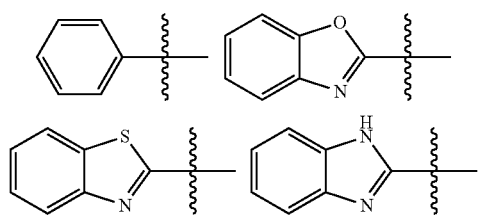

-continued

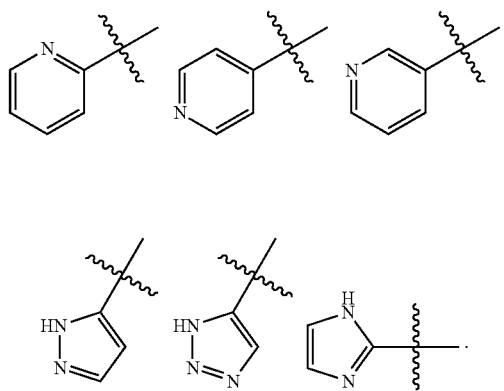

In another embodiment of the invention is a compound represented by one of Formulas (Va-1)~(Va-5), (Vb-1)~(Vb-5), (VI-1)~(VI-2), or a pharmaceutically acceptable salt, ester or prodrug thereof, wherein

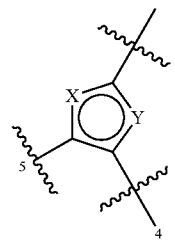

is selected from the groups shown below:

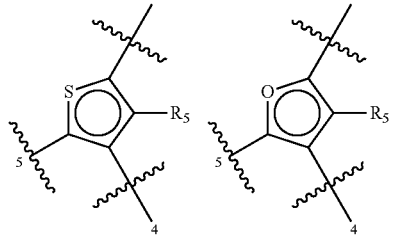

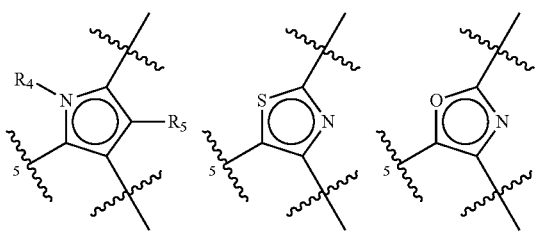

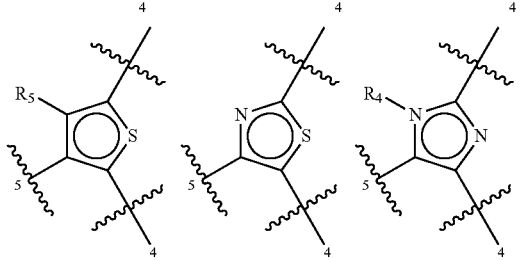

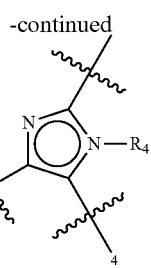
wherein R₄ and R₅ are previously defined.
In another embodiment of the invention is a compound represented by one of Formulas (Va-1)~(Va-5), and (Vb-1)~(Vb-5), or a pharmaceutically acceptable salt, ester or prodrug thereof, wherein $R_2$ is halogen, $-NH_2$, optionally substituted $-C_1$-$C_3$ alkyl, optionally substituted $-C_1$-$C_3$ alkoxy or selected from the groups shown below:
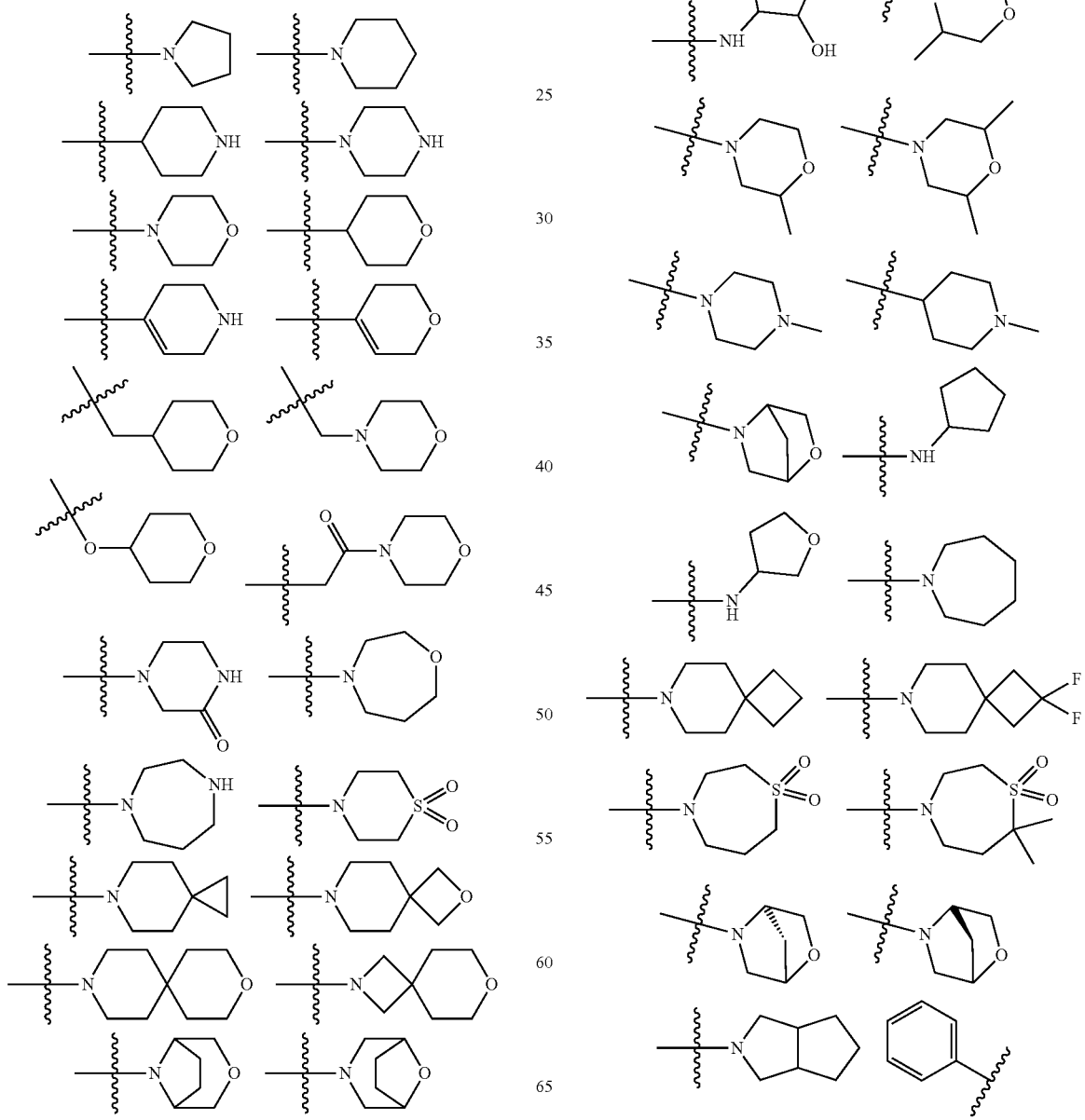

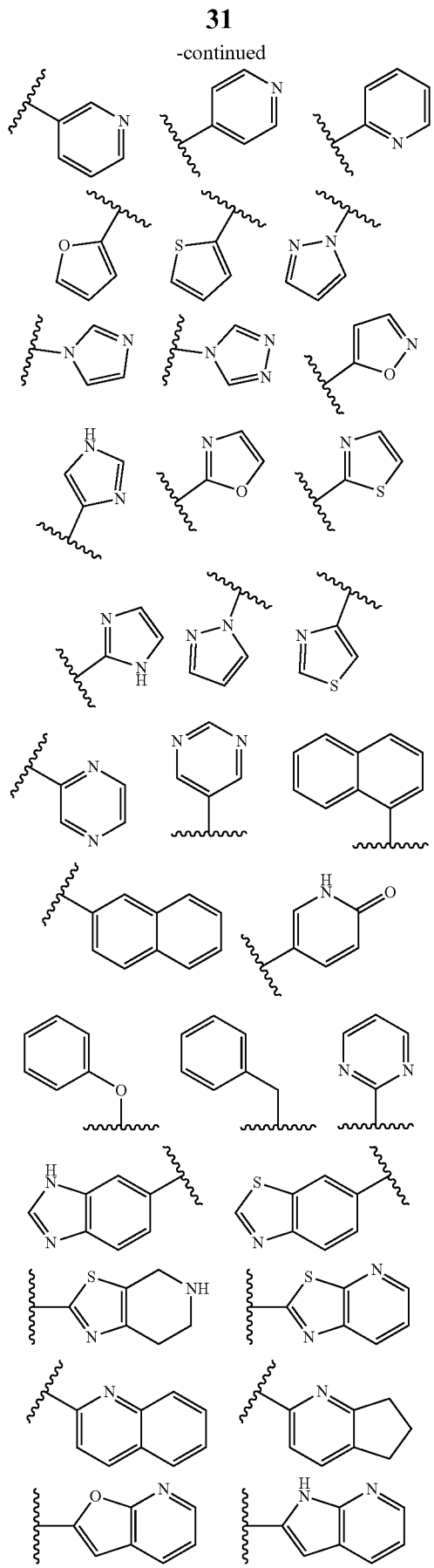
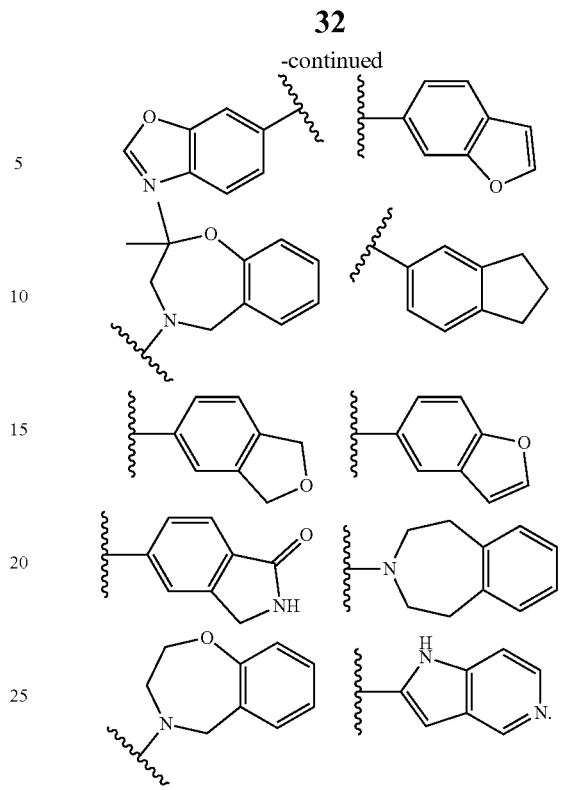

It will be appreciated that the description of the present invention herein should be constructed in congruity with the laws and principles of chemical bonding. In some instances it may be necessary to remove a hydrogen atom in order to accommodate a substituent at any given location.

It is intended that the definition of any substituent or variable (e.g., $R_1$, $R_2$, etc.) at a particular location in a molecule be independent of its definitions elsewhere in that molecule.

It will be yet appreciated that the compounds of the present invention may contain one or more asymmetric carbon atoms and may exist in racemic, diastereoisomeric, and optically active forms. It will still be appreciated that certain compounds of the present invention may exist in different tautomeric forms. All tautomers are contemplated to be within the scope of the present invention.

In certain embodiments, the present invention provides a method for the prevention or treatment of RSV activities and for treating RSV infection in a subject in need thereof. The method comprises administering to the subject a therapeutically effective amount of a compound of formula (I).

The present invention also provides the use of a compound of formula (I) for the preparation of a medicament for the prevention or treatment of RSV.

Thus, in one embodiment, a compound of formula (I), or pharmaceutically acceptable salt thereof, is combined with a steroid anti-inflammatory compound, for example budesonide or fluticasone. In a preferred embodiment, the steroid is administered in low doses to minimize immuno-suppressant effects. In another embodiment a compound of formula (I), or a pharmaceutically acceptable salt thereof, is combined with a non-steroid anti-inflammatory compound, for example leukotriene antagonists such as Singulair (Merck) or Accolate (Astra Zeneca), phosphodiesterase 4 inhibitors such as roflumilast (Altana), TNF alpha inhibitors such as Enbrel (Amgen), Remicade (Centocor), Humira (Abbott) or CDP870 (Celltech) or NSAIDS. In a further embodiment, a compound of formula (I) is combined with interleukin 8 or interleukin 9 inhibitors. The present invention thus also relates to a product containing a compound of formula (I), or a pharmaceutically acceptable salt thereof, and an anti-inflammatory compound for simultaneous, separate or sequential use in the treatment of RSV.

The present invention also relates to a combination of a compound of formula (I), or a pharmaceutically acceptable salt thereof, with an anti-influenza compound and the use of such a combination in the treatment of concomitant RSV and influenza infections. The present invention thus also relates to a product containing a compound of formula (I), or a pharmaceutically acceptable salt thereof, and an anti-influenza compound for simultaneous, separate or sequential use in the treatment of concomitant RSV and influenza infections. The compounds of the invention may be administered in a variety of dosage forms. Thus, they can be administered orally, for example as tablets, troches, lozenges, aqueous or oily suspensions, dispersible powders or granules. The compounds of the invention may also be administered parenterally, whether subcutaneously, intravenously, intramuscularly, intrasternally, transdermally or by infusion techniques. The compounds may also be administered as suppositories.

In an embodiment, the compounds of the invention are administered by intranasal or intrabronchial administration. The present invention also provides an inhaler or nebuliser containing a medicament which comprises (a) a benzodiazepine derivative of the formula (I), as defined above, or a pharmaceutically acceptable salt thereof, and (b) a pharmaceutically acceptable carrier or diluent.

The present invention also provides a pharmaceutical composition containing such a benzodiazepine derivative, or a pharmaceutically acceptable salt thereof, and a pharmaceutically acceptable carrier or diluent.

The compounds of the invention are typically formulated for administration with a pharmaceutically acceptable carrier or diluent. For example, solid oral forms may contain, together with the active compound, diluents, e.g. lactose, dextrose, saccharose, cellulose, corn starch or potato starch; lubricants, e.g. silica, talc, stearic acid, magnesium or calcium stearate, and/or polyethylene glycols; binding agents; e.g. starches, arabic gums, gelatin, methylcellulose, carboxymethylcellulose or polyvinyl pyrrolidone; disaggregating agents, e.g. starch, alginic acid, alginates or sodium starch glycolate; effervescing mixtures; dyestuffs; sweeteners; wetting agents, such as lecithin, polysorbates, laurylsulphates; and, in general, non toxic and pharmacologically inactive substances used in pharmaceutical formulations. Such pharmaceutical preparations may be manufactured in known manner, for example, by means of mixing, granulating, tableting, sugar coating, or film coating processes.

Liquid dispersions for oral administration may be syrups, emulsions and suspensions. The syrups may contain as carriers, for example, saccharose or saccharose with glycerine and/or mannitol and/or sorbitol.

Suspensions and emulsions may contain as carrier, for example a natural gum, agar, sodium alginate, pectin, methylcellulose, carboxymethylcellulose, or polyvinyl alcohol. The suspension or solutions for intramuscular injections may contain, together with the active compound, a pharmaceutically acceptable carrier, e.g., sterile water, olive oil, ethyl oleate, glycols, e.g. propylene glycol, and if desired, a suitable amount of lidocaine hydrochloride.

Solutions for injection or infusion may contain as carrier, for example, sterile water or preferably they may be in the form of sterile, aqueous, isotonic saline solutions.

The present invention also relates to the novel compounds, as defined above; or a pharmaceutically acceptable salt thereof, for use in a method of treating the human or animal body.

The present invention also relates to a pharmaceutical composition comprising a novel compound as defined above and a pharmaceutically acceptable diluent or carrier. Preferably, the pharmaceutical composition comprises a pharmaceutically acceptable salt of a novel compound as defined above. A pharmaceutically acceptable salt is as defined above. The novel compounds of the invention are typically administered in the manner defined above and the compounds are typically formulated for administration in the manner defined above.

Preferably, the pharmaceutical compositions comprise optically active isomers of the novel compounds of the invention. Thus, for example, preferred novel compounds of the invention containing only one chiral centre include an R enantiomer in substantially pure form, an S enantiomer in substantially pure form and enantiomeric mixtures which contain an excess of the R enantiomer or an excess of the S enantiomer. It is particularly preferred that pharmaceutical contains a compound of the invention which is a substantially pure optical isomer. For the avoidance of doubt, the novel compounds of the invention can, if desired, be used in the form of solvates.

Yet a further aspect of the present invention is a process of making any of the compounds delineated herein employing any of the synthetic means delineated herein.

Definitions

Listed below are definitions of various terms used to describe this invention. These definitions apply to the terms as they are used throughout this specification and claims, unless otherwise limited in specific instances, either individually or as part of a larger group.

The term "aryl," as used herein, refers to a mono-, bi-, or polycyclic carbocyclic ring system comprising at least one aromatic ring, including, but not limited to, phenyl, naphthyl, tetrahydronaphthyl, indanyl, and indenyl. A polycyclic aryl is a polycyclic ring system that comprises at least one aromatic ring. Polycyclic aryls can comprise fused rings, covalently attached rings or a combination thereof.

The term "heteroaryl," as used herein, refers to a mono-, bi-, or polycyclic aromatic radical having one or more ring atom selected from S, O and N; and the remaining ring atoms are carbon, wherein any N or S contained within the ring may be optionally oxidized. Heteroaryl includes, but is not limited to, pyridinyl, pyrazinyl, pyrimidinyl, pyrrolyl, pyrazolyl, imidazolyl, thiazolyl, oxazolyl, isoxazolyl, thiadiazolyl, oxadiazolyl, thiophenyl, furanyl, quinolinyl, isoquinolinyl, benzimidazolyl, benzoxazolyl, quinoxalinyl. A polycyclic heteroaryl can comprise fused rings, covalently attached rings or a combination thereof.

In accordance with the invention, aromatic groups can be substituted or unsubstituted.

The term "bicyclic aryl" or "bicyclic heteroaryl" refers to a ring system consisting of two rings wherein at least one ring is aromatic; and the two rings can be fused or covalently attached.

The term "alkyl" as used herein, refers to saturated, straight- or branched-chain hydrocarbon radicals. "$C_1$-$C_3$ alkyl," "$C_1$-$C_6$ alkyl," "$C_1$-$C_{10}$ alkyl", "$C_2$-$C_4$ alkyl", or "$C_3$-$C_6$ alkyl," refer to alkyl groups containing from one to three, one to six, one to ten carbon atoms, 2 to 4 and 3 to 6 carbon atoms respectively. Examples of $C_1$-$C_8$ alkyl radicals include, but are not limited to, methyl, ethyl, propyl, isopropyl, n-butyl, tert-butyl, neopentyl, n-hexyl, heptyl and octyl radicals.

The term "alkenyl" as used herein, refers to straight- or branched-chain hydrocarbon radicals having at least one carbon-carbon double bond by the removal of a single hydrogen atom. "$C_2$-$C_{10}$ alkenyl," "$C_2$-$C_8$ alkenyl," "$C_2$-$C_4$ alkenyl," or "$C_3$-$C_6$ alkenyl," refer to alkenyl groups containing from two to ten, two to eight, two to four or three to six carbon atoms respectively. Alkenyl groups include, but are not limited to, for example, ethenyl, propenyl, butenyl, 1-methyl-2-buten-1-yl, heptenyl, octenyl, and the like.

The term "alkynyl" as used herein, refers to straight- or branched-chain hydrocarbon radicals having at least one carbon-carbon triple bond by the removal of a single hydrogen atom. "$C_2$-$C_{10}$ alkynyl," "$C_2$-$C_8$ alkynyl," "$C_2$-$C_4$ alkynyl," or "$C_3$-$C_6$ alkynyl," refer to alkynyl groups containing from two to ten, two to eight, two to four or three to six carbon atoms respectively. Representative alkynyl groups include, but are not limited to, for example, ethynyl, 1-propynyl, 1-butynyl, heptynyl, octynyl, and the like.

The term "cycloalkyl", as used herein, refers to a monocyclic or polycyclic saturated carbocyclic ring or a bi- or tri-cyclic group fused, bridged or spiro system, and the carbon atoms may be optionally oxo-substituted or optionally substituted with exocyclic olefinic, iminic or oximic double bond. Preferred cycloalkyl groups include $C_3$-$C_{12}$ cycloalkyl, $C_3$-$C_6$ cycloalkyl, $C_3$-$C_8$ cycloalkyl and $C_4$-$C_7$ cycloalkyl. Examples of $C_3$-$C_{12}$ cycloalkyl include, but not limited to, cyclopropyl, cyclobutyl, cyclopentyl, cyclohexyl, cyclopentyl, cyclooctyl, 4-methylene-cyclohexyl, bicyclo[2.2.1]heptyl, bicyclo[3.1.0]hexyl, spiro[2.5]octyl, 3-methylenebicyclo[3.2.1]octyl, spiro[4.4]nonanyl, and the like.

The term "cycloalkenyl", as used herein, refers to monocyclic or polycyclic carbocyclic ring or a bi- or tri-cyclic group fused, bridged or spiro system having at least one carbon-carbon double bond and the carbon atoms may be optionally oxo-substituted or optionally substituted with exocyclic olefinic, iminic or oximic double bond. Preferred cycloalkenyl groups include $C_3$-$C_{12}$ cycloalkenyl, $C_3$-$C_8$ cycloalkenyl or $C_5$-$C_7$ cycloalkenyl groups. Examples of $C_3$-$C_{12}$ cycloalkenyl include, but not limited to, cyclopropenyl, cyclobutenyl, cyclopentenyl, cyclohexenyl, cycloheptenyl, cyclooctenyl, bicyclo[2.2.1]hept-2-enyl, bicyclo[3.1.0]hex-2-enyl, spiro[2.5]oct-4-enyl, spiro[4.4]non-1-enyl, bicyclo[4.2.1]non-3-en-9-yl, and the like.

As used herein, the term "arylalkyl" means a functional group wherein an alkylene chain is attached to an aryl group, e.g., —$CH_2CH_2$-phenyl. The term "substituted arylalkyl" means an arylalkyl functional group in which the aryl group is substituted. Similarly, the term "heteroarylalkyl" means a functional group wherein an alkylene chain is attached to a heteroaryl group. The term "substituted heteroarylalkyl" means a heteroarylalkyl functional group in which the heteroaryl group is substituted.

As used herein, the term "alkoxy" employed alone or in combination with other terms means, unless otherwise stated, an alkyl group having the designated number of carbon atoms connected to the rest of the molecule via an oxygen atom, such as, for example, methoxy, ethoxy, 1-propoxy, 2-propoxy (isopropoxy) and the higher homologs and isomers. Preferred alkoxy are ($C_1$-$C_3$) alkoxy.

It is understood that any alkyl, alkenyl, alkynyl, cycloalkyl, heterocyclic and cycloalkenyl moiety described herein can also be an aliphatic group or an alicyclic group.

An "aliphatic" group is a non-aromatic moiety comprised of any combination of carbon atoms, hydrogen atoms, halogen atoms, oxygen, nitrogen or other atoms, and optionally contains one or more units of unsaturation, e.g., double and/or triple bonds. Examples of aliphatic groups are functional groups, such as alkyl, alkenyl, alkynyl, O, OH, NH, $NH_2$, C(O), S(O)$_2$, C(O)O, C(O)NH, OC(O)O, OC(O)NH, OC(O)NH$_2$, S(O)$_2$NH, S(O)$_2$NH$_2$, NHC(O)NH$_2$, NHC(O)C(O)NH, NHS(O)$_2$NH, NHS(O)$_2$NH$_2$, C(O)NHS(O)$_2$, C(O)NHS(O)$_2$NH or C(O)NHS(O)$_2$NH$_2$, and the like, groups comprising one or more functional groups, non-aromatic hydrocarbons (optionally substituted), and groups wherein one or more carbons of a non-aromatic hydrocarbon (optionally substituted) is replaced by a functional group. Carbon atoms of an aliphatic group can be optionally oxo-substituted. An aliphatic group may be straight chained, branched, cyclic, or a combination thereof and preferably contains between about 1 and about 24 carbon atoms, more typically between about 1 and about 12 carbon atoms. In addition to aliphatic hydrocarbon groups, as used herein, aliphatic groups expressly include, for example, alkoxyalkyls, polyalkoxyalkyls, such as polyalkylene glycols, polyamines, and polyimines, for example. Aliphatic groups may be optionally substituted.

The terms "heterocyclic" or "heterocycloalkyl" can be used interchangeably and referred to a non-aromatic ring or a bi- or tri-cyclic group fused, bridged or spiro system, where (i) each ring system contains at least one heteroatom independently selected from oxygen, sulfur and nitrogen, (ii) each ring system can be saturated or unsaturated (iii) the nitrogen and sulfur heteroatoms may optionally be oxidized, (iv) the nitrogen heteroatom may optionally be quaternized, (v) any of the above rings may be fused to an aromatic ring, and (vi) the remaining ring atoms are carbon atoms which may be optionally oxo-substituted or optionally substituted with exocyclic olefinic, iminic or oximic double bond. Representative heterocycloalkyl groups include, but are not limited to, 1,3-dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, 2-azabicyclo[2.2.1]-heptyl, 8-azabicyclo[3.2.1]octyl, 5-azaspiro[2.5]octyl, 1-oxa-7-azaspiro[4.4]nonanyl, 7-oxooxepan-4-yl, and tetrahydrofuryl. Such heterocyclic groups may be further substituted. Heteroaryl or heterocyclic groups can be C-attached or N-attached (where possible).

It is understood that any alkyl, alkenyl, alkynyl, alicyclic, cycloalkyl, cycloalkenyl, aryl, heteroaryl, heterocyclic, aliphatic moiety or the like, described herein can also be a divalent or multivalent group when used as a linkage to connect two or more groups or substituents, which can be at the same or different atom(s). One of skill in the art can readily determine the valence of any such group from the context in which it occurs.

The term "substituted" as used herein, refers to independent replacement of one, two, three or more of the hydrogen atoms thereon with substituents including, but not limited to, deuterium, tritium, —F, —Cl, —Br, —I, —OH, $C_1$-$C_{12}$-alkyl; $C_2$-$C_{12}$-alkenyl, $C_2$-$C_{12}$-alkynyl, protected hydroxy, —$NO_2$, —CN, —$NH_2$, —$N_3$, protected amino, alkoxy, thioalkoxy, oxo, thioxo, -halo-$C_1$-$C_{12}$-alkyl, -halo-$C_2$-$C_{12}$-alkenyl, -halo-$C_2$-$C_{12}$-alkynyl, -halo-$C_3$-$C_{12}$-cycloalkyl, —NH—$C_1$-$C_{12}$-alkyl, —NH—$C_2$-$C_{12}$-alkenyl, —NH—$C_2$-$C_{12}$-alkynyl, —NH—$C_3$-$C_{12}$-cycloalkyl, —NH-aryl, —NH-heteroaryl, —NH-heterocycloalkyl, -dialkylamino, -diarylamino, -diheteroarylamino, —O—$C_1$-$C_{12}$-alkyl, —O—$C_2$-$C_{12}$-alkenyl, —O—$C_2$-$C_{12}$-alkynyl, —O—$C_3$-$C_{12}$-cycloalkyl, —O-aryl, —O-heteroaryl, —O— heterocycloalkyl, —C(O)—$C_1$-$C_{12}$-alkyl, —C(O)—$C_2$-$C_{12}$-alkenyl, —C(O)—C$_2$-C$_{12}$-alkynyl, —C(O)—C$_3$-C$_{12}$-cycloalkyl, —C(O)-aryl, —C(O)-heteroaryl, —C(O)-heterocycloalkyl, —CONH$_2$, —CONH—C$_1$-C$_{12}$-alkyl, —CONH—C$_2$-C$_{12}$-alkenyl, —CONH—C$_2$-C$_{12}$-alkynyl, —CONH—C$_3$-C$_{12}$-cycloalkyl, —CONH-aryl, —CONH-heteroaryl, —CONH-heterocycloalkyl, —OCO$_2$—C$_1$-C$_{12}$-alkyl, —OCO$_2$—C$_2$-C$_{12}$-alkenyl, —OCO$_2$—C$_2$-C$_{12}$-alkynyl, —OCO$_2$—C$_3$-C$_{12}$-cycloalkyl, —OCO$_2$-aryl, —OCO$_2$-heteroaryl, —OCO$_2$-heterocycloalkyl, —OCONH$_2$, —OCONH—C$_1$-C$_{12}$-alkyl, —OCONH—C$_2$-C$_{12}$-alkenyl, —OCONH—C$_2$-C$_{12}$-alkynyl, —OCONH—C$_3$-C$_{12}$-cycloalkyl, —OCONH-aryl, —OCONH-heteroaryl, —OCONH-heterocycloalkyl, —NHC(O)—C$_1$-C$_{12}$-alkyl, —NHC(O)—C$_2$-C$_{12}$-alkenyl, —NHC(O)—C$_2$-C$_{12}$-alkynyl, —NHC(O)—C$_3$-C$_{12}$-cycloalkyl, —NHC(O)-aryl, —NHC(O)-heteroaryl, —NHC(O)-heterocycloalkyl, —NHCO$_2$—C$_1$-C$_{12}$-alkyl, —NHCO$_2$—C$_2$-C$_{12}$-alkenyl, —NHCO$_2$—C$_2$-C$_{12}$-alkynyl, —NHCO$_2$—C$_3$-C$_{12}$-cycloalkyl, —NHCO$_2$-aryl, —NHCO$_2$-heteroaryl, —NHCO$_2$-heterocycloalkyl, —NHC(O)NH$_2$, —NHC(O)NH—C$_1$-C$_{12}$-alkyl, —NHC(O)NH—C$_2$-C$_{12}$-alkenyl, —NHC(O)NH—C$_2$-C$_{12}$-alkynyl, —NHC(O)NH—C$_3$-C$_{12}$-cycloalkyl, —NHC(O)NH-aryl, —NHC(O)NH-heteroaryl, —NHC(O)NH-heterocycloalkyl, NHC(S)NH$_2$, —NHC(S)NH—C$_1$-C$_{12}$-alkyl, —NHC(S)NH—C$_2$-C$_{12}$-alkenyl, —NHC(S)NH—C$_2$-C$_{12}$-alkynyl, —NHC(S)NH—C$_3$-C$_{12}$-cycloalkyl, —NHC(S)NH-aryl, —NHC(S)NH— heteroaryl, —NHC(S)NH-heterocycloalkyl, —NHC(NH)NH$_2$, —NHC(NH)NH—C$_1$-C$_{12}$-alkyl, —NHC(NH)NH—C$_2$-C$_{12}$-alkenyl, —NHC(NH)NH—C$_2$-C$_{12}$-alkynyl, —NHC(NH)NH—C$_3$-C$_{12}$-cycloalkyl, —NHC(NH)NH-aryl, —NHC(NH)NH-heteroaryl, —NHC(NH)NH-heterocycloalkyl, —NHC(NH)—C$_1$-C$_{12}$-alkyl, —NHC(NH)—C$_2$-C$_{12}$-alkenyl, —NHC(NH)—C$_2$-C$_{12}$-alkynyl, —NHC(NH)—C$_3$-C$_{12}$-cycloalkyl, —NHC(NH)-aryl, —NHC(NH)-heteroaryl, —NHC(NH)-heterocycloalkyl, —C(NH)NH—C$_1$-C$_{12}$-alkyl, —C(NH)NH—C$_2$-C$_{12}$-alkenyl, —C(NH)NH—C$_2$-C$_{12}$-alkynyl, —C(NH)NH—C$_3$-C$_{12}$-cycloalkyl, —C(NH)NH-aryl, —C(NH)NH-heteroaryl, —C(NH)NH-heterocycloalkyl, —S(O)—C$_1$-C$_{12}$-alkyl, —S(O)—C$_2$-C$_{12}$-alkenyl, —S(O)—C$_2$-C$_{12}$-alkynyl, —S(O)—C$_3$-C$_{12}$-cycloalkyl, —S(O)-aryl, —S(O)-heteroaryl, —S(O)-heterocycloalkyl-SO$_2$NH$_2$, —SO$_2$NH—C$_1$-C$_{12}$-alkyl, —SO$_2$NH—C$_2$-C$_{12}$-alkenyl, —SO$_2$NH—C$_2$-C$_{12}$-alkynyl, —SO$_2$NH—C$_3$-C$_{12}$-cycloalkyl, —SO$_2$NH-aryl, —SO$_2$NH—heteroaryl, —SO$_2$NH-heterocycloalkyl, —NHSO$_2$—C$_1$-C$_{12}$-alkyl, —NHSO$_2$—C$_2$-C$_{12}$-alkenyl, —NHSO$_2$—C$_2$-C$_{12}$-alkynyl, —NHSO$_2$—C$_3$-C$_{12}$-cycloalkyl, —NHSO$_2$-aryl, —NHSO$_2$-heteroaryl, —NHSO$_2$-heterocycloalkyl, —CH$_2$NH$_2$, —CH$_2$SO$_2$CH$_3$, -aryl, -arylalkyl, -heteroaryl, -heteroarylalkyl, -heterocycloalkyl, —C$_3$-C$_{12}$-cycloalkyl, polyalkoxyalkyl, polyalkoxy, -methoxymethoxy, -methoxyethoxy, —SH, —S—C$_1$-C$_{12}$-alkyl, —S—C$_2$-C$_{12}$-alkenyl, —S—C$_2$-C$_{12}$-alkynyl, —S—C$_3$-C$_{12}$-cycloalkyl, —S-aryl, —S-heteroaryl, —S-heterocycloalkyl, methylthiomethyl, or -L'-R', wherein L' is C$_1$-C$_6$alkylene, C$_2$-C$_6$alkenylene or C$_2$-C$_6$alkynylene, and R' is aryl, heteroaryl, heterocyclic, C$_3$-C$_{12}$cycloalkyl or C$_3$-C$_{12}$cycloalkenyl. In certain embodiments, the substituents are independently selected from halo, preferably Cl and F; C$_1$-C$_4$-alkyl, preferably methyl and ethyl; halo-C$_1$-C$_4$-alkyl, such as fluoromethyl, difluoromethyl, and trifluoromethyl; C$_2$-C$_4$-alkenyl; halo-C$_2$-C$_4$-alkenyl; C$_3$-C$_6$-cycloalkyl, such as cyclopropyl; C$_1$-C$_4$-alkoxy, such as methoxy and ethoxy; halo-C$_1$-C$_4$-alkoxy, such as fluoromethoxy, difluoromethoxy, and trifluoromethoxy; —CN; —OH; NH$_2$; C$_1$-C$_4$-alkylamino; di(C$_1$-C$_4$-alkyl)amino; and NO$_2$. It is understood that the aryls, heteroaryls, alkyls, and the like can be further substituted. In some cases, each substituent in a substituted moiety, for example, each alkyl, alkenyl, alkynyl, cycloalkyl, hetercyclic, aryl or heteroaryl, is additionally optionally substituted with one or more groups, each group being independently selected from C$_1$-C$_6$-alkyl, CF$_3$, —F, —Cl, —Br, —I, —OH, —NO$_2$, —CN, or —NH$_2$. Preferably, a substituted alkyl group, such as a substituted methyl group, is substituted with one or more halogen atoms, more preferably one or more fluorine or chlorine atoms.

The term "halo" or halogen" alone or as part of another substituent, as used herein, refers to a fluorine, chlorine, bromine, or iodine atom.

The term "optionally substituted", as used herein, means that the referenced group may be substituted or unsubstituted. In one embodiment, the referenced group is optionally substituted with zero substituents, i.e., the referenced group is unsubstituted. In another embodiment, the referenced group is optionally substituted with one or more additional group(s) individually and independently selected from groups described herein.

The term "hydrogen" includes hydrogen and deuterium. In addition, the recitation of an atom includes other isotopes of that atom so long as the resulting compound is pharmaceutically acceptable.

In certain embodiments, the compounds of each formula herein are defined to include isotopically labelled compounds. An "isotopically labelled compound" is a compound in which at least one atomic position is enriched in a specific isotope of the designated element to a level which is significantly greater than the natural abundance of that isotope. For example, one or more hydrogen atom positions in a compound can be enriched with deuterium to a level which is significantly greater than the natural abundance of deuterium, for example, enrichment to a level of at least 1%, preferably at least 20% or at least 50%. Such a deuterated compound may, for example, be metabolized more slowly than its non-deuterated analog, and therefore exhibit a longer half-life when administered to a subject. Such compounds can synthesize using methods known in the art, for example by employing deuterated starting materials. Unless stated to the contrary, isotopically labelled compounds are pharmaceutically acceptable.

The term "hydroxy activating group," as used herein, refers to a labile chemical moiety which is known in the art to activate a hydroxyl group so that it will depart during synthetic procedures such as in a substitution or an elimination reaction. Examples of hydroxyl activating group include, but not limited to, mesylate, tosylate, triflate, p-nitrobenzoate, phosphonate and the like.

The term "activated hydroxyl," as used herein, refers to a hydroxy group activated with a hydroxyl activating group, as defined above, including mesylate, tosylate, triflate, p-nitrobenzoate, phosphonate groups, for example.

The term "hydroxy protecting group," as used herein, refers to a labile chemical moiety which is known in the art to protect a hydroxyl group against undesired reactions during synthetic procedures. After said synthetic procedure (s) the hydroxy protecting group as described herein may be selectively removed. Hydroxy protecting groups as known in the art are described generally in T. H. Greene and P. G. M. Wuts, *Protective Groups in Organic Synthesis,* 3rd edition, John Wiley & Sons, New York (1999). Examples of hydroxyl protecting groups include benzyloxycarbonyl, 4-methoxybenzyloxycarbonyl, tert-butoxy-carbonyl, isopropoxycarbonyl, diphenylmethoxycarbonyl, 2,2,2-trichloroethoxycarbonyl, allyloxycarbonyl, acetyl, formyl, chloro-acetyl, trifluoroacetyl, methoxyacetyl, phenoxyacetyl, benzoyl, methyl, t-butyl, 2,2,2-trichloroethyl, 2-trimethylsilyl ethyl, allyl, benzyl, triphenyl-methyl (trityl), methoxymethyl, methylthiomethyl, benzyloxymethyl, 2-(trimethylsilyl)-ethoxymethyl, methanesulfonyl, trimethylsilyl, triisopropylsilyl, and the like.

The term "protected hydroxy," as used herein, refers to a hydroxy group protected with a hydroxy protecting group, as defined above, including benzoyl, acetyl, trimethylsilyl, triethylsilyl, methoxymethyl groups, for example.

The term "hydroxy prodrug group," as used herein, refers to a promoiety group which is known in the art to change the physicochemical, and hence the biological properties of a parent drug in a transient manner by covering or masking the hydroxy group. After said synthetic procedure(s), the hydroxy prodrug group as described herein must be capable of reverting back to hydroxy group in vivo. Hydroxy prodrug groups as known in the art are described generally in Kenneth B. Sloan, *Prodrugs, Topical and Ocular Drug Delivery*, (Drugs and the Pharmaceutical Sciences; Volume 53), Marcel Dekker, Inc., New York (1992) and in "Prodrugs of Alcohols and Phenols" by S. S. Dhareshwar and V. J. Stella, in *Prodrugs Challenges and Rewards Part-2*, (Biotechnology: Pharmaceutical Aspects), edited by V. J. Stella, et al, Springer and AAPSPress, 2007, pp 31-99.

The term "amino protecting group," as used herein, refers to a labile chemical moiety which is known in the art to protect an amino group against undesired reactions during synthetic procedures. After said synthetic procedure(s) the amino protecting group as described herein may be selectively removed. Amino protecting groups as known in the art are described generally in T. H. Greene and P. G. M. Wuts, *Protective Groups in Organic Synthesis,* 3rd edition, John Wiley & Sons, New York (1999). Examples of amino protecting groups include, but are not limited to, methoxycarbonyl, t-butoxycarbonyl, 9-fluorenyl-methoxycarbonyl, benzyloxycarbonyl, and the like.

The term "protected amino," as used herein, refers to an amino group protected with an amino protecting group as defined above.

The term "leaving group" means a functional group or atom which can be displaced by another functional group or atom in a substitution reaction, such as a nucleophilic substitution reaction. By way of example, representative leaving groups include chloro, bromo and iodo groups; sulfonic ester groups, such as mesylate, tosylate, brosylate, nosylate and the like; and acyloxy groups, such as acetoxy, trifluoroacetoxy and the like.

The term "aprotic solvent," as used herein, refers to a solvent that is relatively inert to proton activity, i.e., not acting as a proton-donor. Examples include, but are not limited to, hydrocarbons, such as hexane and toluene, for example, halogenated hydrocarbons, such as, for example, methylene chloride, ethylene chloride, chloroform, and the like, heterocyclic compounds, such as, for example, tetrahydrofuran and N-methylpyrrolidinone, and ethers such as diethyl ether, bis-methoxymethyl ether. Such compounds are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: *Organic Solvents Physical Properties and Methods of Purification,* 4th ed., edited by John A. Riddick et al., Vol. II, in the *Techniques of Chemistry Series*, John Wiley & Sons, N Y, 1986.

The term "protic solvent," as used herein, refers to a solvent that tends to provide protons, such as an alcohol, for example, methanol, ethanol, propanol, isopropanol, butanol, t-butanol, and the like. Such solvents are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of protogenic solvents may be found in organic chemistry textbooks or in specialized monographs, for example: *Organic Solvents Physical Properties and Methods of Purification,* 4th ed., edited by John A. Riddick et al., Vol. II, in the *Techniques of Chemistry Series*, John Wiley & Sons, N Y, 1986.

Combinations of substituents and variables envisioned by this invention are only those that result in the formation of stable compounds. The term "stable," as used herein, refers to compounds which possess stability sufficient to allow manufacture and which maintains the integrity of the compound for a sufficient period of time to be useful for the purposes detailed herein (e.g., therapeutic or prophylactic administration to a subject).

The synthesized compounds can be separated from a reaction mixture and further purified by a method such as column chromatography, high pressure liquid chromatography, or recrystallization. As can be appreciated by the skilled artisan, further methods of synthesizing the compounds of the Formula herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations,* $2^{nd}$ Ed. Wiley-VCH (1999); T. W. Greene and P. G. M. Wuts, *Protective Groups in Organic Synthesis,* 3rd Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

The term "subject," as used herein, refers to an animal. Preferably, the animal is a mammal. More preferably, the mammal is a human. A subject also refers to, for example, dogs, cats, horses, cows, pigs, guinea pigs, fish, birds and the like.

The compounds of this invention may be modified by appending appropriate functionalities to enhance selective biological properties. Such modifications are known in the art and may include those which increase biological penetration into a given biological system (e.g., blood, lymphatic system, central nervous system), increase oral availability, increase solubility to allow administration by injection, alter metabolism and alter rate of excretion.

The compounds described herein contain one or more asymmetric centers and thus give rise to enantiomers, diastereomers, and other stereoisomeric forms that may be defined, in terms of absolute stereochemistry, as (R)- or (S)-, or as (D)- or (L)- for amino acids. The present invention is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions* (John Wiley & Sons, 1981). When the compounds described herein contain olefinic double bonds, other unsaturation, or other centers of geometric asymmetry, and unless specified otherwise, it is intended that the compounds include both E and Z geometric isomers or cis- and trans-isomers. Likewise, all tautomeric forms are also intended to be included. Tautomers may be in cyclic or acyclic. The configuration of any carbon-carbon double bond appearing herein is selected for convenience only and is not intended to designate a particular configuration unless the text so states; thus a carbon-carbon double bond or carbon-heteroatom double bond depicted arbitrarily herein as trans may be cis, trans, or a mixture of the two in any proportion.

Certain compounds of the present invention may also exist in different stable conformational forms which may be separable. Torsional asymmetry due to restricted rotation about an asymmetric single bond, for example because of steric hindrance or ring strain, may permit separation of different conformers. The present invention includes each conformational isomer of these compounds and mixtures thereof.

As used herein, the term "pharmaceutically acceptable salt," refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 1-19 (1977). The salts can be prepared in situ during the final isolation and purification of the compounds of the invention, or separately by reacting the free base function with a suitable organic acid. Examples of pharmaceutically acceptable salts include, but are not limited to, nontoxic acid addition salts are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentane-propionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

Pharmaceutically acceptable salts can also be prepared by deprotonation of the parent compound with a suitable base, thereby forming the anionic conjugate base of the parent compound. In such salts the counter ion is a cation. Suitable cations include ammonium and metal cations, such as alkali metal cations, including $Li^+$, $Na^+$, $K^+$ and $Cs^+$, and alkaline earth metal cations, such as $Mg^{2+}$ and $Ca^{2+}$.

As used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, esters of $C_1$-$C_6$-alkanoic acids, such as acetate, propionate, butyrate and pivalate esters.

In certain embodiments, the invention provides pharmaceutically acceptable prodrugs of the compounds disclosed herein. The term "pharmaceutically acceptable prodrugs" as used herein refers to those prodrugs of the compounds formed by the process of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present invention. "Prodrug", as used herein means a compound, which is convertible in vivo by metabolic means (e.g. by hydrolysis) to afford any compound delineated by the formulae of the instant invention. Various forms of prodrugs are known in the art, for example, as discussed in Bundgaard, (ed.), *Design of Prodrugs*, Elsevier (1985); Widder, et al. (ed.), *Methods in Enzymology*, Vol. 4, Academic Press (1985); Krogsgaard-Larsen, et al., (ed.). "Design and Application of Prodrugs, *Textbook of Drug Design and Development*, Chapter 5, 113-191 (1991); Bundgaard, et al., *Journal of Drug Deliver Reviews*, 8:1-38(1992); Bundgaard, J. of *Pharmaceutical Sciences*, 77:285 et seq. (1988); Higuchi and Stella (eds.) Prodrugs as Novel Drug Delivery Systems, *American Chemical Society* (1975); and Bernard Testa & Joachim Mayer, "Hydrolysis In Drug And Prodrug Metabolism: Chemistry, Biochemistry And Enzymology," John Wiley and Sons, Ltd. (2002).

Additional types of prodrugs are also encompassed. For instance, free carboxyl groups can be derivatized as amides or alkyl esters. Free hydroxy groups may be derivatized using groups including but not limited to hemisuccinates, ethyl succinate, phosphate esters, dimethylaminoacetates, and phosphoryloxymethyloxycarbonyls, as outlined in Advanced Drug Delivery Reviews, 1996, 19, 115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in J. Med. Chem. 1996, 39, 10. Free amines can also be derivatized as amides, sulfonamides or phosphonamides. All of these prodrug moieties may incorporate groups including but not limited to ether, amine and carboxylic acid functionalities. In certain embodiments, a compound of the invention can incorporate two or more groups that are metabolically removed in vivo to yield the active parent compound. For example, a compound of formula I wherein $R_1$ is an amino acid residue can also be esterified, for example at a hydroxyl group of the sugar residue, to form a compound with two groups that can be removed in vivo to yield the active compound.

The term "treating", as used herein, means relieving, lessening, reducing, eliminating, modulating, or ameliorating, i.e. causing regression of the disease state or condition. Treating can also include inhibiting, i.e. arresting the development, of a existing disease state or condition, and relieving or ameliorating, i.e. causing regression of an existing disease state or condition, for example when the disease state or condition may already be present.

The term "preventing", as used herein means, to completely or almost completely stop a disease state or condition, from occurring in a patient or subject, especially when the patient or subject is predisposed to such or at risk of contracting a disease state or condition.

Additionally, the compounds of the present invention, for example, the salts of the compounds, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc. "Solvates" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

As used herein, the term "analog" refers to a chemical compound that is structurally similar to another but differs slightly in composition (as in the replacement of one atom by an atom of a different element or in the presence of a particular functional group, or the replacement of one functional group by another functional group). Thus, an analog is a compound that is similar to or comparable in function and appearance to the reference compound.

The term "aprotic solvent," as used herein, refers to a solvent that is relatively inert to proton activity, i.e., not acting as a proton-donor. Examples include, but are not limited to, hydrocarbons, such as hexane and toluene, for example, halogenated hydrocarbons, such as, for example, methylene chloride, ethylene chloride, chloroform, and the like, heterocyclic compounds, such as, for example, tetrahydrofuran and N-methylpyrrolidinone, and ethers such as diethyl ether, bis-methoxymethyl ether. Such solvents are well known to those skilled in the art, and individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: *Organic Solvents Physical Properties and Methods of Purification*, 4th ed., edited by John A. Riddick et al., Vol. II, in the *Techniques of Chemistry Series*, John Wiley & Sons, N Y, 1986.

The terms "protogenic organic solvent" or "protic solvent" as used herein, refer to a solvent that tends to provide protons, such as an alcohol, for example, methanol, ethanol, propanol, isopropanol, butanol, t-butanol, and the like. Such solvents are well known to those skilled in the art, and individual solvents or mixtures thereof may be preferred for specific compounds and reaction conditions, depending upon such factors as the solubility of reagents, reactivity of reagents and preferred temperature ranges, for example. Further discussions of protogenic solvents may be found in organic chemistry textbooks or in specialized monographs, for example: *Organic Solvents Physical Properties and Methods of Purification*, 4th ed., edited by John A. Riddick et al., Vol. II, in the *Techniques of Chemistry Series*, John Wiley & Sons, N Y, 1986.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

The synthesized compounds can be separated from a reaction mixture and further purified by a method such as column chromatography, high pressure liquid chromatography, or recrystallization. Additionally, the various synthetic steps may be performed in an alternate sequence or order to give the desired compounds. In addition, the solvents, temperatures, reaction durations, etc. delineated herein are for purposes of illustration only and variation of the reaction conditions can produce the desired bridged macrocyclic products of the present invention. Synthetic chemistry transformations and protecting group methodologies (protection and deprotection) useful in synthesizing the compounds described herein include, for example, those described in R. Larock, *Comprehensive Organic Transformations*, VCH Publishers (1989); T. W. Greene and P. G. M. Wuts, *Protective Groups in Organic Synthesis,* 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia ofReagents for Organic Synthesis*, John Wiley and Sons (1995).

The compounds of this invention may be modified by appending various functionalities via synthetic means delineated herein to enhance selective biological properties. Such modifications include those which increase biological penetration into a given biological system (e.g., blood, lymphatic system, central nervous system), increase oral availability, increase solubility to allow administration by injection, alter metabolism and alter rate of excretion.

Pharmaceutical Compositions

The pharmaceutical compositions of the present invention comprise a therapeutically effective amount of a compound of the present invention formulated together with one or more pharmaceutically acceptable carriers. As used herein, the term "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The pharmaceutical compositions of this invention can be administered to humans and other animals orally, rectally, parenterally, intracisternally, intravaginally, intraperitoneally, topically (as by powders, ointments, or drops), buccally, or as an oral or nasal spray.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1, 3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Unless otherwise defined, all technical and scientific terms used herein are accorded the meaning commonly known to one with ordinary skill in the art. All publications, patents, published patent applications, and other references mentioned herein are hereby incorporated by reference in their entirety.

Abbreviations

Abbreviations which have been used in the descriptions of the schemes and the examples that follow are:
ACN for acetonitrile;
BME for 2-mercaptoethanol;
BOP for benzotriazol-1-yloxy-tris(dimethylamino)phosphonium hexafluorophosphate;
BTC for bis(trichloromethyl)carbonate; triphosgene;
BzCl for benzoyl chloride;
CDI for carbonyldiimidazole;
COD for cyclooctadiene;
Cp*RuCl(PPh$_3$)$_2$ for chloropentamethylcyclopentadienylbis(triphenylphosphine)ruthenium(II);
DABCO for 1,4-diazabicyclo[2.2.2]octane;
DAST for diethylaminosulfur trifluoride;
DBU for 1, 8-Diazabicycloundec-7-ene;
DCC for N, N'-dicyclohexylcarbodiimide;
DCM for dichloromethane;
DIAD for diisopropyl azodicarboxylate;
Dess-Martin for 1,1,1-Tris(acetyloxy)-1,1-dihydro-1,2-benziodoxol-3(1H)-one;
DIBAL-H for diisobutylaluminum hydride;
DIPEA for diisopropyl ethylamine;
DMAP for N,N-dimethylaminopyridine;
DME for ethylene glycol dimethyl ether;
DMEM for Dulbecco's Modified Eagles Media;
DMF for N,N-dimethyl formamide;
DMSO for dimethylsulfoxide;
DSC for N, N'-disuccinimidyl carbonate;
EDCI or EDC for 1-(3-diethylaminopropyl)-3-ethylcarbodiimide hydrochloride;
EtOAc for ethyl acetate;
EtOH for ethyl alcohol;
HATU for O (7-Azabenzotriazole-1-yl)-N,N,N',N'-tetramethyluronium hexafluorophosphate;
HCl for hydrochloric acid;
In for indium;
KHMDS is potassium bis(trimethylsilyl) amide;
Ms for mesyl;
NMM for N-4-methylmorpholine;
PE for petroleum ether;
RT-PCR for reverse transcription-polymerase chain reaction;
SEMCl for 2-(Trimethylsilyl)ethoxymethyl chloride;
TBME for tert-butyl methyl ether;
TCDI for 1,1'-thiocarbonyldiimidazole;
TEA for triethylamine;
Tf$_2$O for trifluoromethanesulfonic anhydride;
TFA for trifluoroacetic acid;
THF for tetrahydrofuran;
TLC for thin layer chromatography;
TMEDA for N,N,N',N'-tetramethylethylenediamine;
TPAP tetrapropylammonium perruthenate;
TPP or PPh$_3$ for triphenylphosphine;
TrCl for trityl chloride;
Ts for p-CH$_3$C$_6$H$_4$SO$_2$—
tBOC or Boc for tert-butyloxy carbonyl;
Xantphos for 4,5-Bis-diphenylphosphanyl-9,9-dimethyl-9H-xanthene; and
Zhan 1 B for,

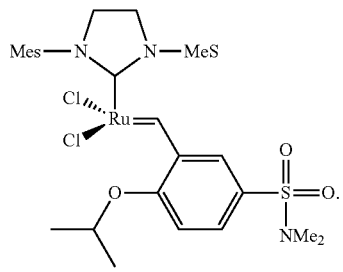

Synthetic Methods

The compounds and processes of the present invention will be better understood in connection with the following synthetic schemes that illustrate the methods by which the compounds of the invention may be prepared, which are intended as an illustration only and not to limit the scope of the invention. Various changes and modifications to the disclosed embodiments will be apparent to those skilled in the art and such changes and modifications including, without limitation, those relating to the chemical structures, substituents, derivatives, and/or methods of the invention may be made without departing from the spirit of the invention and the scope of the appended claims.

Scheme 1
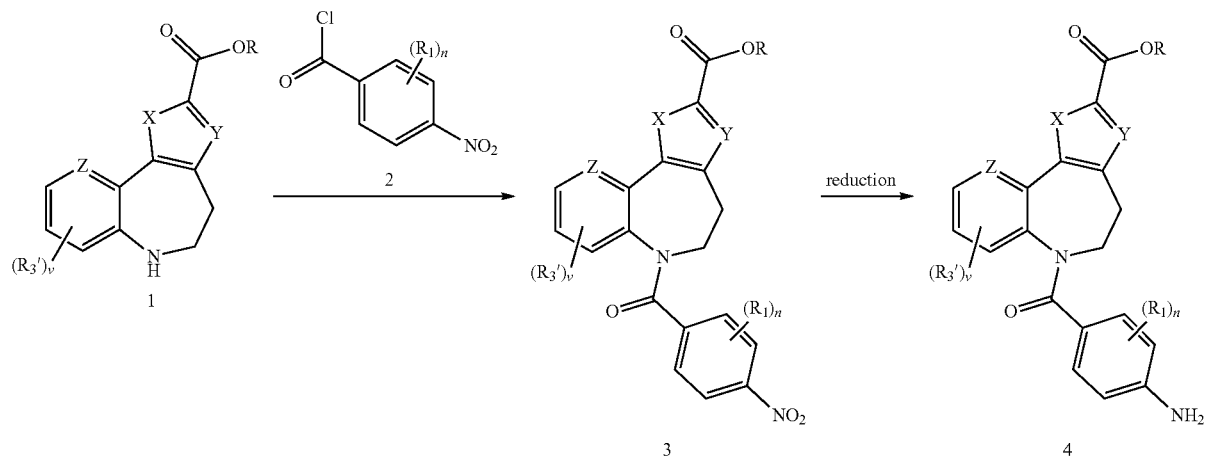
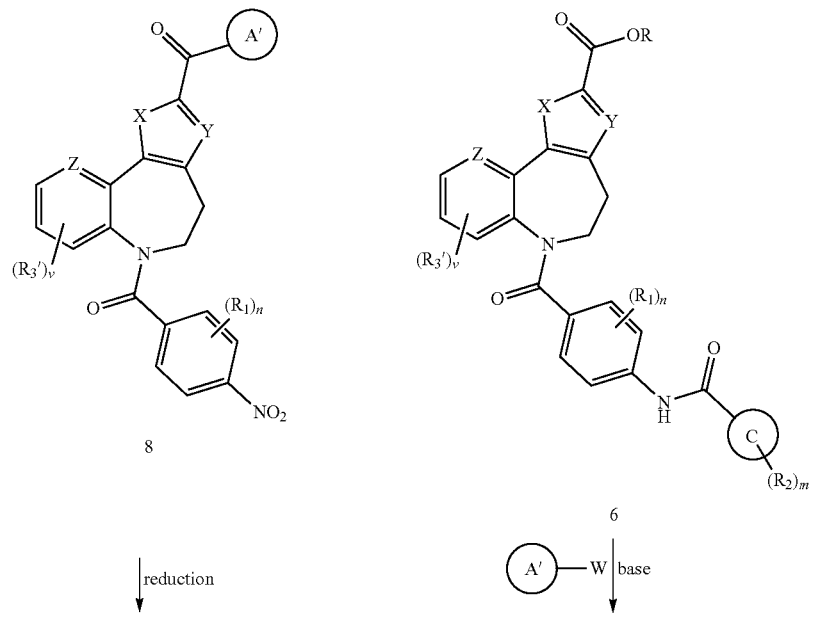

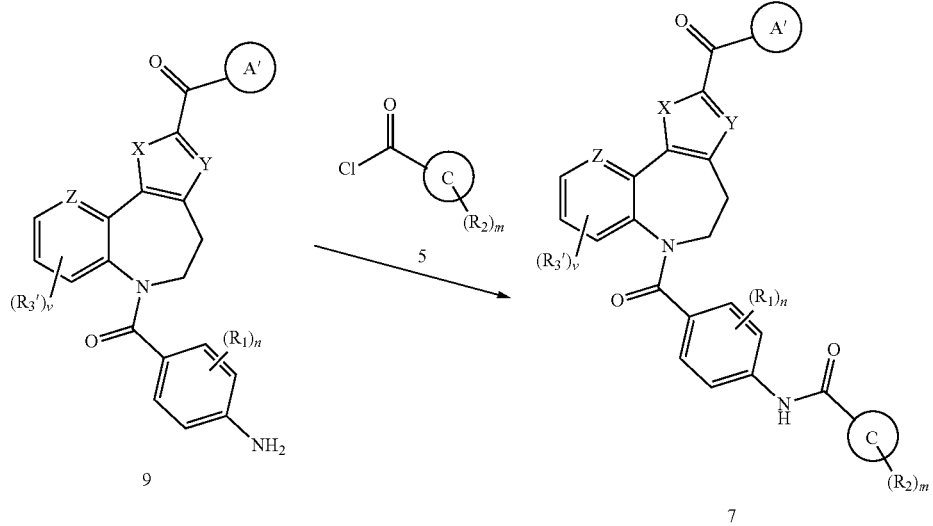

Scheme 1 illustrates a method for preparing compounds of formula 7 beginning with compound 1, which can be prepared according to the general procedure described in US Published Application No. 2019/0002479, wherein $R_1$, $R_2$, $R_3'$, n, m, X, Y, Z, v, and C are as previously defined, ring A' is optionally substituted imidazole, W is hydrogen or halogen, and R is $C_1$-$C_4$ alkyl. Compound 1 is coupled with substituted or unsubstituted 4-nitrobenzoyl chloride 2 and subsequently reduced with a reducing agent such as but not limited to, iron, to give compound 4. Acyl chloride 5 is reacted with 4 to yield amide 6. Subjecting 6 to imidazole or a substituted imidazole in the presence of a strong base such as, but not limited to, n-BuLi, t-BuLi, or LDA, furnished 7. This procedure is well described in the literature, Hu, E. et al. *J. Med. Chem.* 2014, 57, 6632-6641. Alternatively, compound 1 is coupled with substituted or unsubstituted 4-nitrobenzoyl chloride to afford 3, which is reacted with imidazole or a substituted imidazole in the presence of a strong base such as, but not limited to, n-BuLi, t-BuLi, or LDA, to provide 8. Subsequently 8 is reduced with a reducing agent such as but not limited to, iron, to give compound 9, which is reacted with acyl chloride 5 to afford the compound of formula 7.

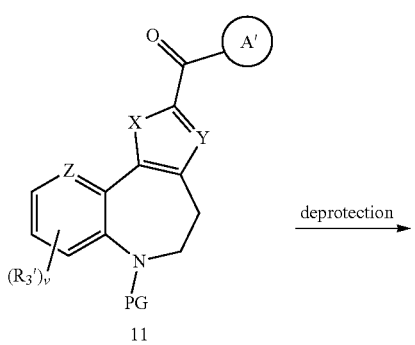

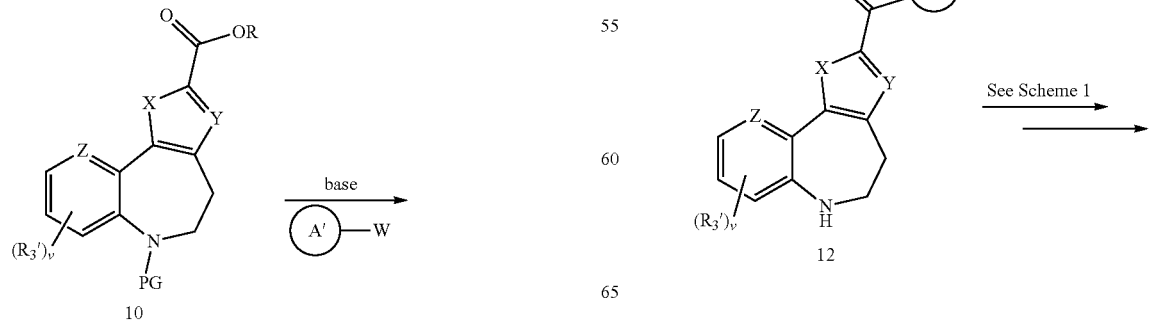

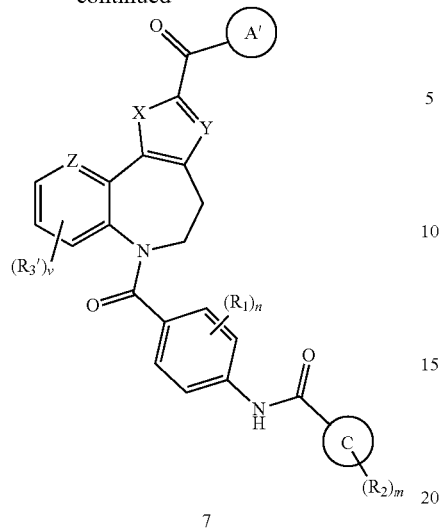

Scheme 2 illustrates an alternate method for preparing a compound of formula 7. R, $R_1$, $R_2$, $R_3'$, n, m, X, Y, Z, v, W, ring A' and ring C are previously defined and PG is an amino protecting group. N-protected 10, which can be prepared according to the general method described in US Published Application No. 2009/0002479, is reacted with a heteroaryl compound such as, but not limited to, optionally substituted imidazole, in the presence of a strong base such as, but not limited to, n-BuLi, t-BuLi or LDA, and then deprotected using reagents such as, but not limited to Pd(OAc)$_2$/PPh$_3$/1,3-dimethylpyrimidine-2,4,6-(1H,3H,5H)-trione, to produce compound 11. Compound 11 is transformed to compound 12, which is converted to the compound of formula 7 followed the procedures illustrated in Scheme 1 in three steps.

Scheme 3

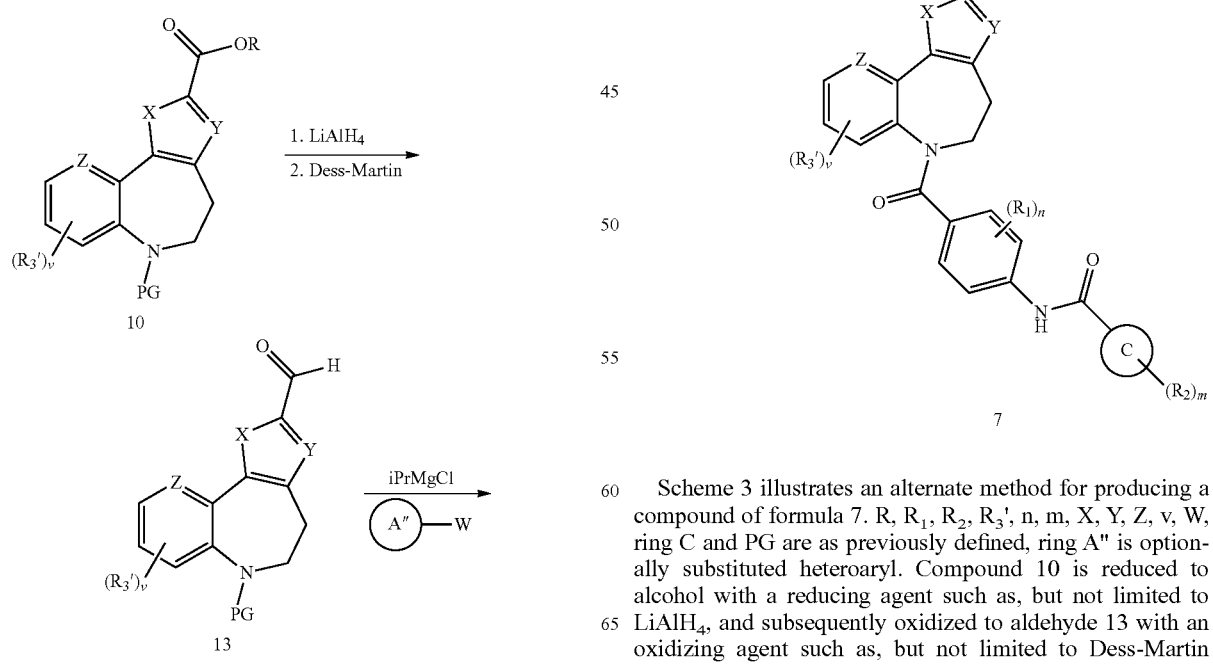

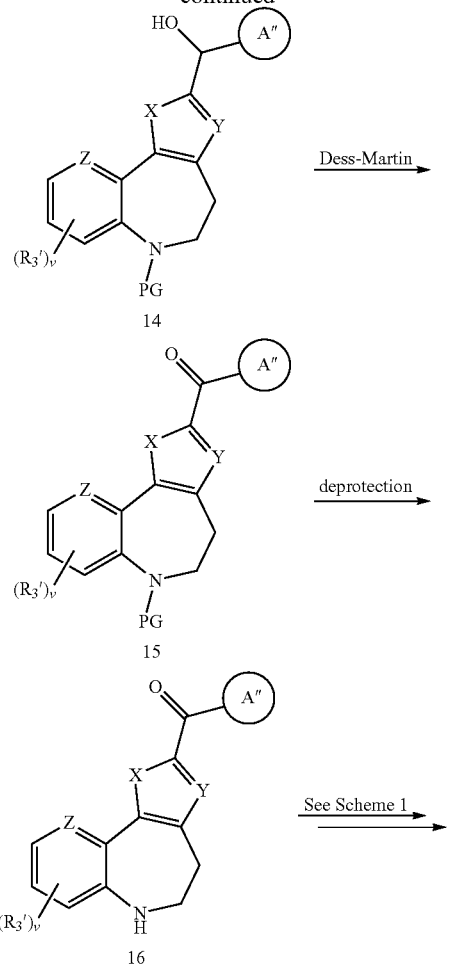

Scheme 3 illustrates an alternate method for producing a compound of formula 7. R, $R_1$, $R_2$, $R_3'$, n, m, X, Y, Z, v, W, ring C and PG are as previously defined, ring A″ is optionally substituted heteroaryl. Compound 10 is reduced to alcohol with a reducing agent such as, but not limited to LiAlH$_4$, and subsequently oxidized to aldehyde 13 with an oxidizing agent such as, but not limited to Dess-Martin reagent. Compound 13 is reacted with a heteroaryl compound such as, but not limited to, optionally substituted imidazole, oxazole, or oxadiazole in the presence of a base such as, but not limited to iPrMgCl, to afford alcohol 14, which is then oxidized to afford ketone 15 with an oxidizing agent such as, but not limited to, Dess-Martin reagent. After deprotection of 15 with such as, but not limit to, Pd(OAc)$_2$/PPh$_3$/1,3-dimethylpyrimidine-2,4,6-(1H,3H,5H)-trione, the resulting compound 16 is converted to the compound of formula 7 following the procedures illustrated in Scheme 1 in three steps.

Scheme 4

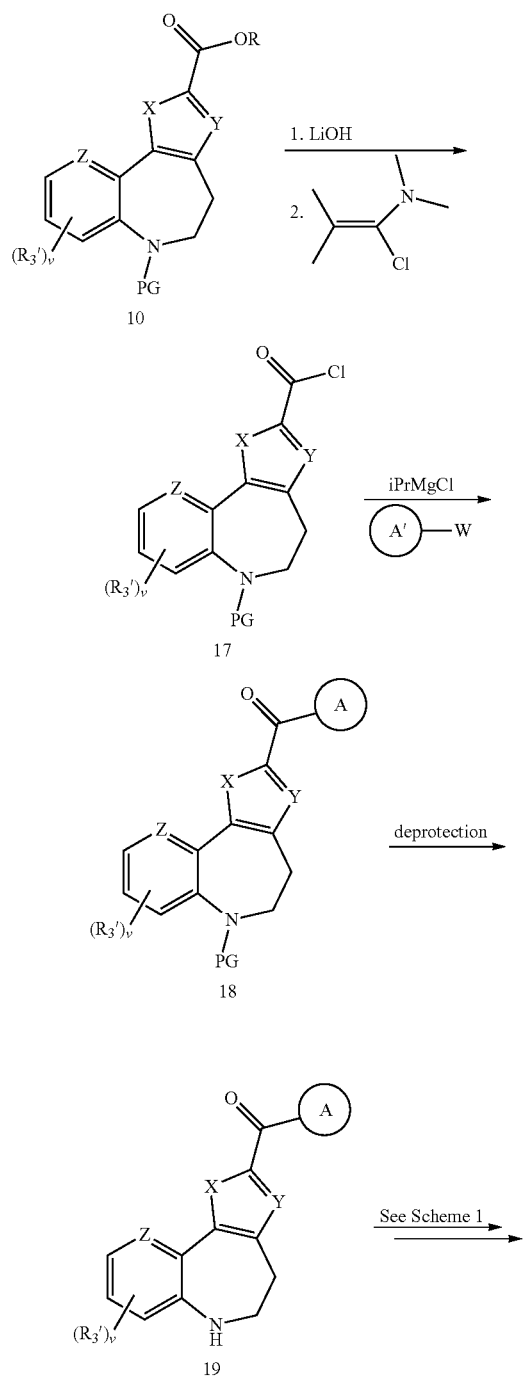

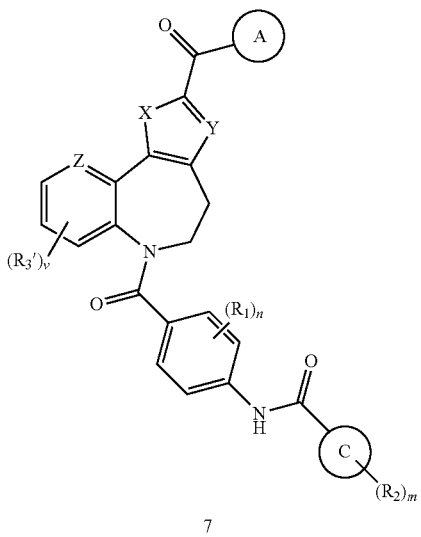

7

Scheme 4 illustrates an alternative process for preparing a compound of formula 7. methods, wherein R$_1$, R$_2$, R$_3$', n, m, X, Y, Z, v, W, ring A and C are previously defined, PG is amino protecting group. To prepare compounds of formula 7. Hydrolysis of ester 10 with a base such as, but not limited to LiOH, and subsequently transformation with a reagent such as, but not limit to 1-chloro-N,N,2-trimethyl-propenylamine afforded acetyl chloride 17. Compound 17 was converted to 18 by the procedure which is described in US Patent Application Publication 2006/0281788. N-protected 18 is then converted to the compound of formula 7 following the procedures illustrated in Scheme 3 in four steps.

Scheme 5

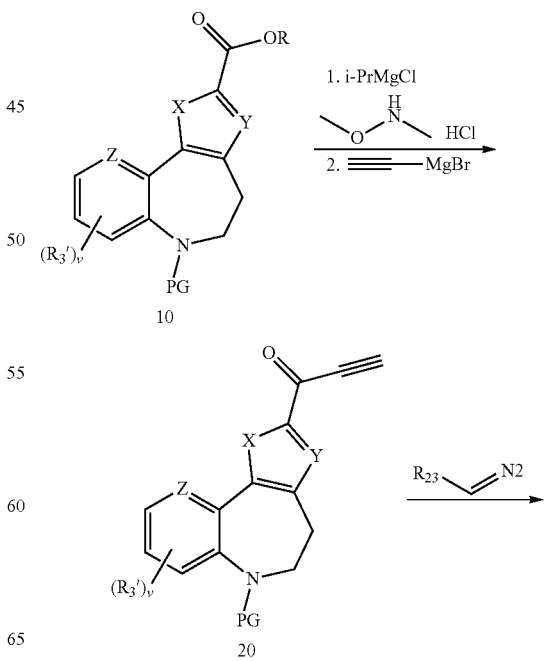

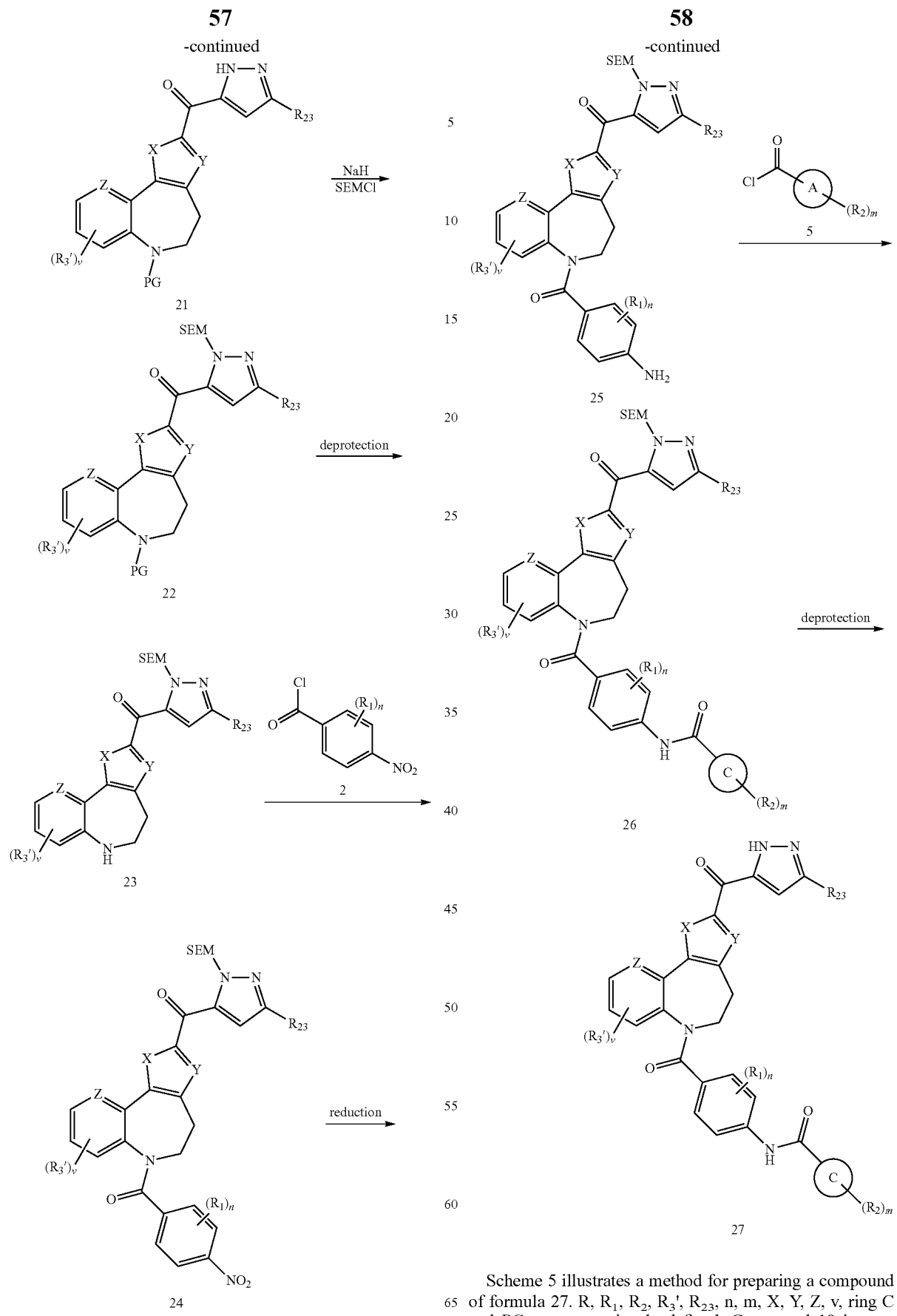
Scheme 5 illustrates a method for preparing a compound of formula 27. R, $R_1$, $R_2$, $R_3'$, $R_{23}$, n, m, X, Y, Z, v, ring C and PG are as previously defined. Compound 10 is converted to compound 20 by formation of Weinreb amide first by using an amine such as, but not limited to N,O-dimethyl-hydroxylamine and then reacted with ethynylmagnesium bromide. Compound 20 is reacted with substituted 2-diazothane to afford pyrazole 21. After N-protection of 21 with a reagent such as, but not limit to SEMCl, compound 22 is achieved. Following the procedures illustrated in Scheme 4, 26 is prepared from compound 22 in four steps. The compound of formula 27 is prepared by N-deprotection of 26 with a reagent such as, but not limited to HCl or TBAF.

Scheme 6

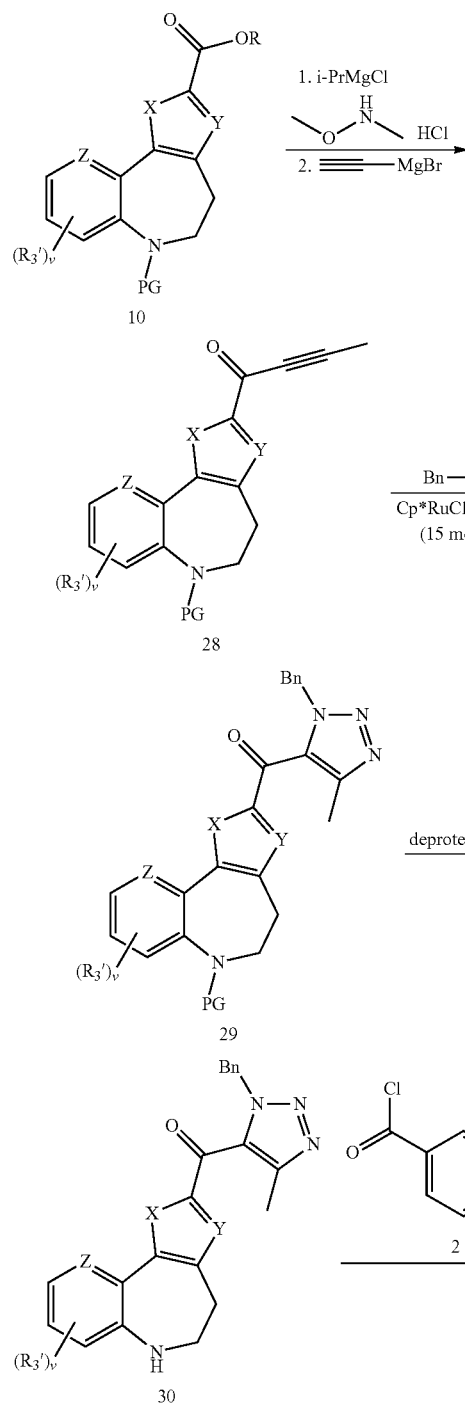

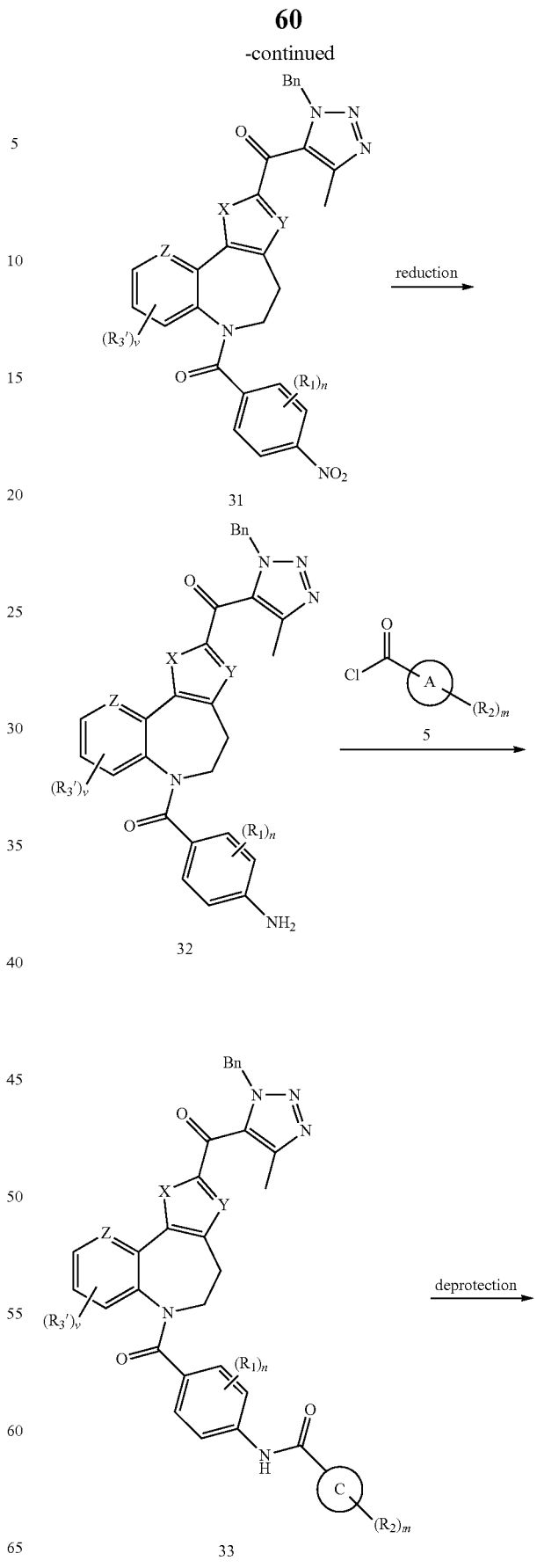

61
-continued

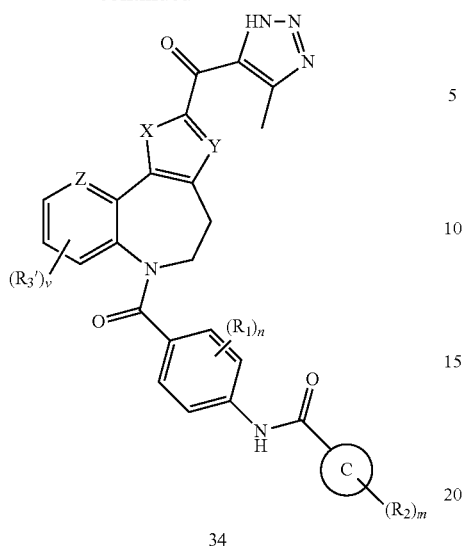
34

62
-continued

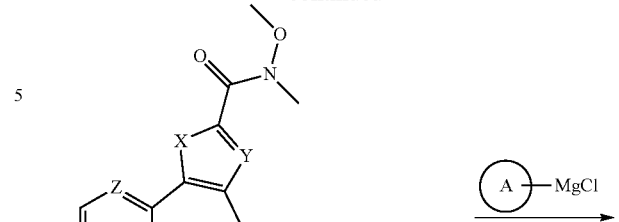
35

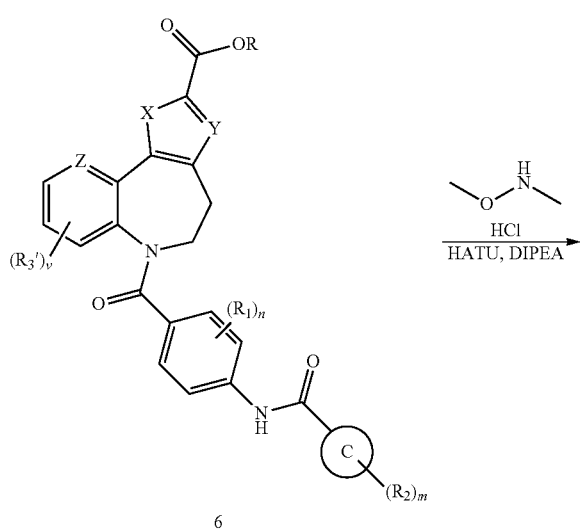
7

Scheme 6 illustrates a process for preparing a compound of formula 34. R, $R_1$, $R_2$, $R_3'$, n, m, X, Y, Z, v, ring C and PG are as previously defined. Compound 10 is converted to 28 by formation of Weinreb amide first by using an amine such as, but not limited to N,O-dimethyl-hydroxylamine, and then reacted with 1-propynylmagnesium bromide. Compound 28 reacts with a substituted azide such as, but not limited to, benzyl azide, to form 29. Followed the procedures illustrated in Scheme 5, 33 is prepared from 29 in four steps. The compound of formula 34 is prepared by N-deprotection of 33 with reagents such as, but not limited to, Pd/$H_2$ or PdCl2/$H_2$.

Scheme 7

Scheme 7 illustrates an alternate process for preparing a compound of formula 7. R, $R_1$, $R_2$, $R_3'$, n, m, X, Y, Z, v and ring C are as previously defined. Compound 6, which can be prepared according to the general method described in U.S. Provisional Application No. 62/527,384, is converted to 35 by formation of Weinreb amide first by using an amine such as, but not limited to, N,O-dimethyl-hydroxylamine and then reacting with 1-propynylmagnesium chloride. In the final step, 35 reacts with an optionally substituted aryl or heteroarylmagnesium bromide to form the compound of formula 7.

EXAMPLES

The compounds and processes of the present invention will be better understood in connection with the following examples, which are intended as an illustration only and not limiting of the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

Scheme 8
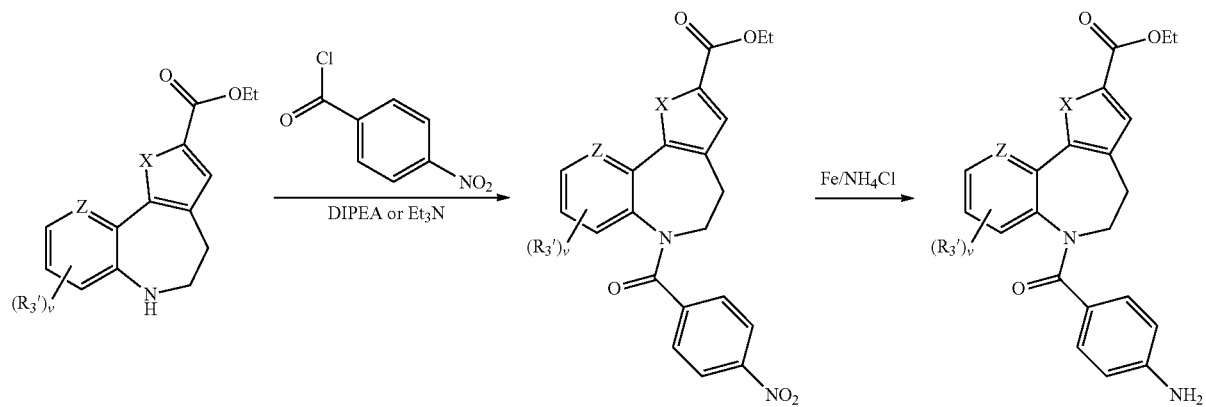
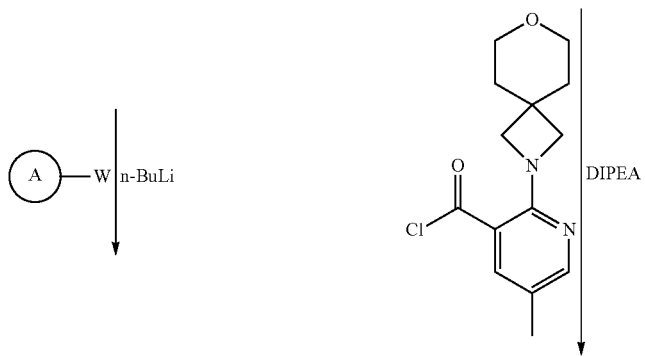
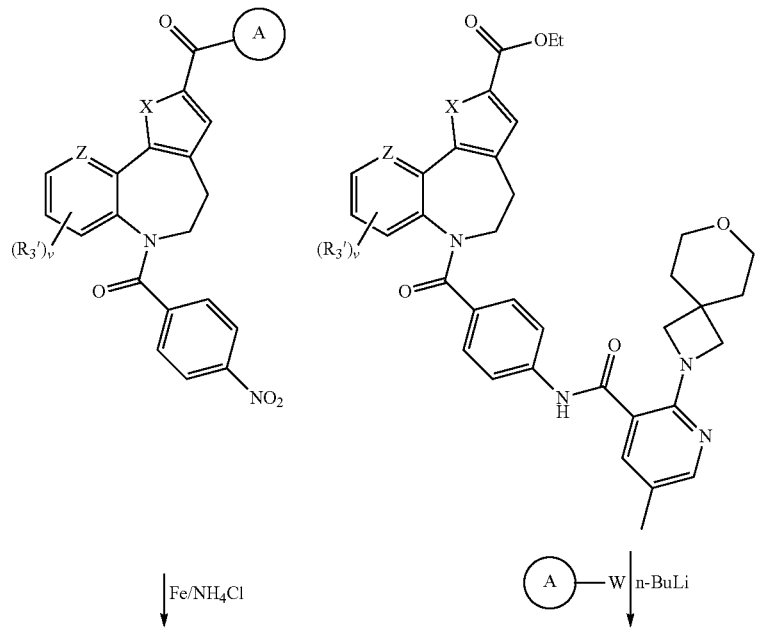

-continued

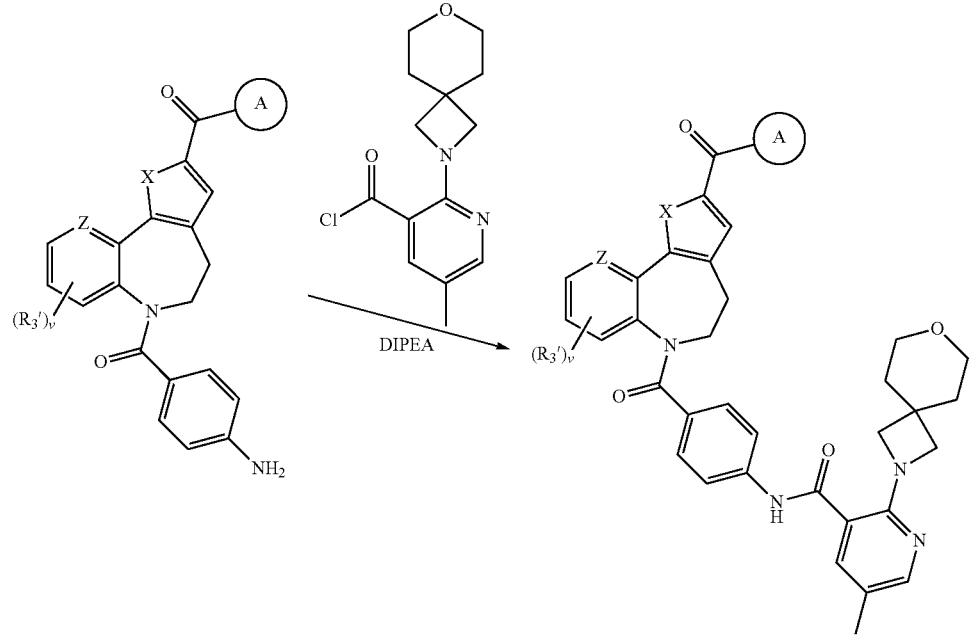

Example 1

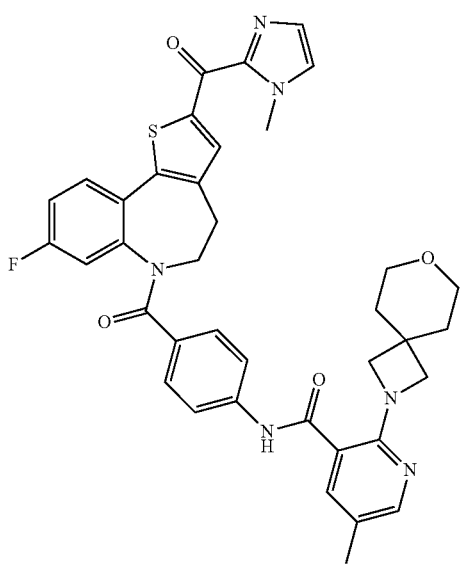 [SMILES: Cc1cnc(N2CC3(CCOCC3)C2)c(C(=O)Nc2ccc(C(=O)N3CCc4cc(C(=O)c5nccn5C)sc4-c4ccc(F)cc43)cc2)c1]

Example 1 Step a

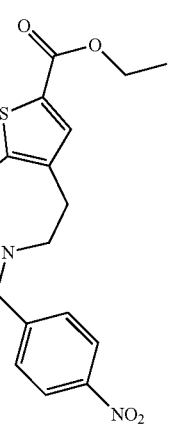

Ethyl 8-fluoro-5,6-dihydro-4H-benzo[b]thieno[2,3-d]azepine-2-carboxylate (800 mg, 2.75 mmol) and 4-nitrobenzoyl chloride (611 mg, 3.30 mmol) were dissolved in DCM (25 mL), then DIEA (1 mL) was slowly added. The reaction mixture was stirred at rt for 16 hrs. After diluting with DCM (100 mL), the organic layer was washed with brine, dried and evaporated. The residue was purified by combiflash eluting with 0-30% EtOAc/hexanes to obtain the desire product (1.17 g) as a pale yellow solid. ESI-MS m/z: 441.1 [M+H]+.

Example 1 Step b

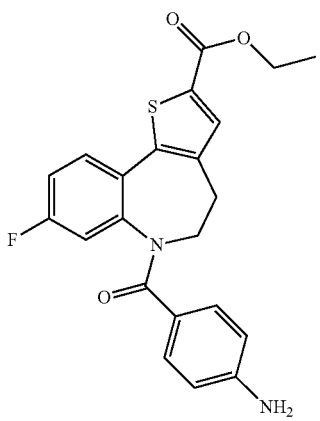 [SMILES: CCOC(=O)c1cc2c(s1)-c1ccc(F)cc1N(C(=O)c1ccc(N)cc1)CC2]

To a solution of compound from step a (1.15 g, 2.61 mmol) in MeOH (60 mL), LiOH (0.625 g, 26.1 mmol) in water (20 mL) was slowly added. The resulting mixture was heated at 55° C. and stirred for 3 hrs. After cooled down, the mixture was adjusted to pH~5 with 1N HCl. The white precipitated solid was filtered and dried in oven at 55° C. overnight to obtain the desired product (1.0 g) as a pale yellow solid. ESI-MS m/z: 411.10 [M+H]$^+$.

Example 1 Step c

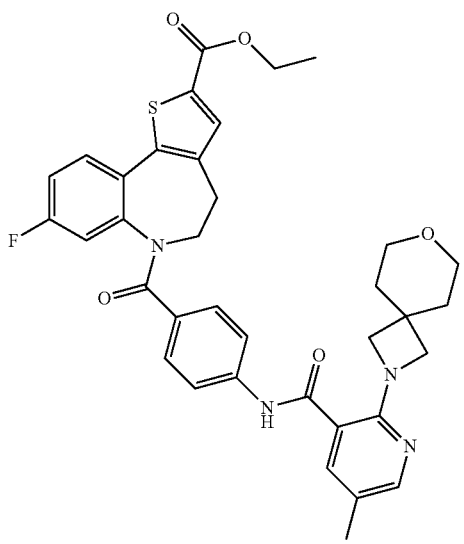 [SMILES: CCOC(=O)c1cc2c(s1)-c1ccc(F)cc1N(C(=O)c1ccc(NC(=O)c3cc(C)cnc3N3CC4(CCOCC4)C3)cc1)CC2]

To a round-bottom flask (100 mL) were added 5-methyl-2-(7-oxa-2-azaspiro[3.5]nonan-2-yl)nicotinic acid (1.1 g, 4.29 mmol), DCM (30 mL) and (1-chloro-2-methylprop-1-en-1-yl)dimethylamine (1.6 g, 11.69 mmol) at room temperature. The resulting mixture was stirred for 1 h at room temperature under N$_2$ atmosphere. The resulting mixture was concentrated under vacuum. After dried for 2 hrs, the residue was dissolved in DCM (25 mL) and then the compound from step b (1.6 g, 3.90 mmol) and pyridine (4 mL) were added. The resulting mixture was stirred for 3 h at room temperature and then concentrated under vacuum. The residue was purified by silica gel column chromatography, eluted with CH$_2$Cl$_2$/MeOH to afford crude product. The crude product was purified by reverse phase flash to afford the desired compound (1.46 g, 57.2%) as off-white solid. ESI-MS m/z: 655.30 [M+H]$^+$.

Example 1 Step d

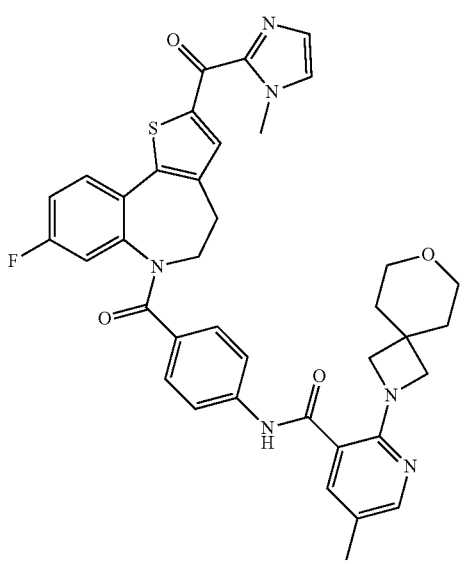 [SMILES: Cc1cnc(N2CC3(CCOCC3)C2)c(C(=O)Nc2ccc(C(=O)N3CCc4cc(C(=O)c5nccn5C)sc4-c4ccc(F)cc43)cc2)c1]

To a stirred solution of TMEDA (213.0 mg, 1.83 mmol) and n-BuLi (0.6 mL, 1.50 mmol) in THF was added 1-methyl-1H-imidazole (188.1 mg, 2.29 mmol) in THF (1 mL) dropwise at −78° C. under nitrogen atmosphere. The resulting mixture was stirred for 1 h at −78° C. under nitrogen atmosphere. To the above mixture was added the compound from step c in THF (1 mL) dropwise at −78° C. The resulting mixture was stirred for additional 1 h at −78° C. The reaction was quenched with water at room temperature, and warmed up to room temperature. The reaction mixture was diluted with EtOAc and separated. The aqueous layer was extracted with EtOAc. The combined organic layer was washed with brine, dried over sodium sulfate, filtered and concentrated to dryness. The residue was purified by Prep-TLC (PE/EtOAc=1:1) and Prep-HPLC to afford the titled compound (22 mg, 20.9%) as a light yellow solid. ESI-MS m/z: 691.25 [M+H]+. $^1$H NMR (DMSO-d$_6$) δ 1.62 (t, J=5.3 Hz, 4H), 2.18 (s, 3H), 3.16 (s, 3H), 3.46 (t, J=5.2 Hz, 4H), 3.61 (s, 4H), 4.04 (s, 3H), 4.90 (s, 1H), 6.90 (d, J=9.6 Hz, 1H), 7.04 (d, J=8.3 Hz, 2H), 7.17-7.26 (m, 1H), 7.28 (d, J=0.9 Hz, 1H), 7.48-7.63 (m, 3H), 7.65 (s, 1H), 7.93 (dd, J=8.8, 6.1 Hz, 1H), 8.05-8.13 (m, 1H), 8.33 (s, 1H), 10.42 (s, 1H).

Example 2

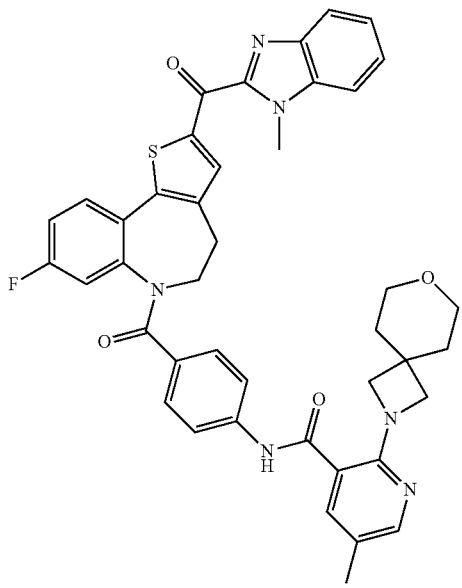 [SMILES: Cc1cnc(N2CC3(CCOCC3)C2)c(C(=O)Nc2ccc(C(=O)N3CCc4cc(C(=O)c5nc6ccccc6n5C)sc4-c4ccc(F)cc43)cc2)c1]

Example 2 was prepared using a procedure similar to that used to prepare Example 1 where 1-methyl-1H-benzo[d]imidazole was used in place of 1-methyl-1H-imidazole in step d. ESI-MS m/z: 741.20 [M+H]$^+$. $^1$H NMR (DMSO-d$_6$) δ 1.54-1.71 (m, 4H), 2.17 (s, 3H), 3.22 (s, 2H), 3.42-3.53 (m, 4H), 3.61 (s, 4H), 4.17 (s, 3H), 4.92 (s, 1H), 6.93 (d, J=9.1 Hz, 1H), 7.06 (d, J=8.5 Hz, 2H), 7.24 (t, J=8.4 Hz, 1H), 7.42 (t, J=7.6 Hz, 1H), 7.48-7.66 (m, 4H), 7.81 (d, J=8.2 Hz, 1H), 7.91-8.02 (m, 2H), 8.04 (d, J=2.2 Hz, 1H), 8.43 (s, 1H), 10.43 (s, 1H).

Example 3

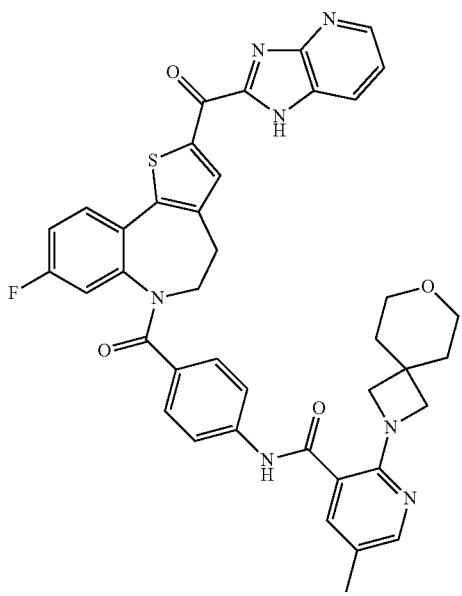 [SMILES: Cc1cnc(N2CC3(CCOCC3)C2)c(C(=O)Nc2ccc(C(=O)N3CCc4cc(C(=O)c5nc6ncccc6[nH]5)sc4-c4ccc(F)cc43)cc2)c1]

Example 3 Step a

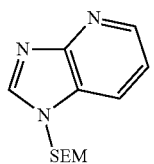 [SMILES: C[Si](C)(C)CCOCn1cnc2ncccc21]

To a round-bottom flask (50 mL) were added 1H-imidazo[4,5-b]pyridine (1.0 g, 8.39 mmol) and NaH (671.5 mg, 16.79 mmol, 60%) in DMF (10 mL) at 0° C. The resulting mixture was stirred for half an hour at 0° C. under N$_2$. To the above mixture was added SEMCl (2.8 g, 16.79 mmol) dropwise at 0° C. The resulting mixture was slowly warmed to room temperature and stirred for additional 2 h. The reaction was quenched with water at 0° C. The aqueous layer was extracted with EtOAc (30 mL×3). The combined organic layer was washed with water (three times) and brine. The residue was purified by reverse phase flash to afford the titled compound (2.1 g, 100%) as a light brown oil. ESI-MS m/z: 250.25 [M+H]$^+$.

Example 3 Step b

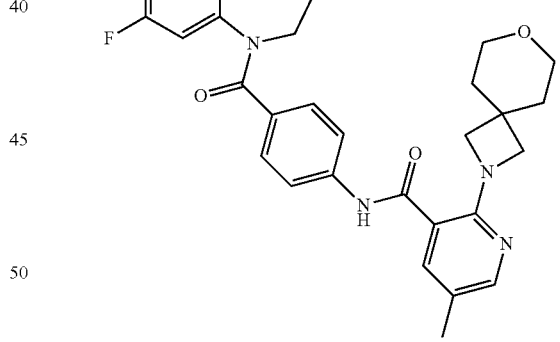

To a three-necked round-bottom flask (100 mL) were added TMEDA (0.53 g, 4.58 mmol) and n-BuLi (1.6 mL, 25.75 mmol) in THF (1 mL) at −78° C. To the above mixture was added the compound from example 3 step a (1.14 g, 4.58 mmol) in THF dropwise at −78° C. The resulting mixture was stirred for 30 min at −78° C. Then a solution of example 1 step c (150 mg, 0.23 mmol) in THF was added at −78° C. The resulting mixture was stirred for additional 0.5 h at −78° C. The reaction was quenched by the addition of water (3 mL) at room temperature. The residue product was purified by reverse phase flash to afford the desired compound (90 mg, 45.8%) as a light yellow solid. ESI-MS m/z: 858.25 [M+H]$^+$.

Example 3 Step c

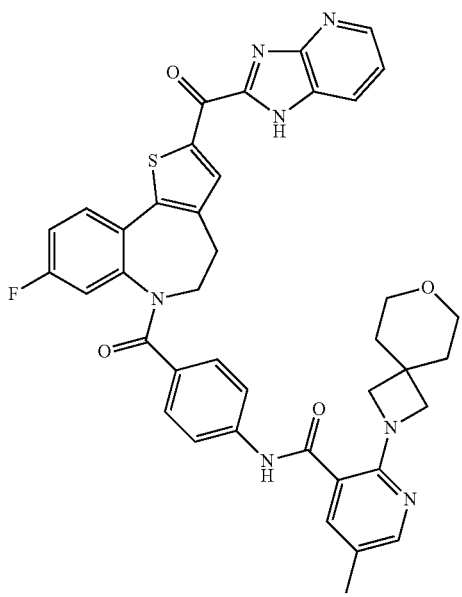 [SMILES: Cc1cnc(N2CC3(CCOCC3)C2)c(C(=O)Nc2ccc(C(=O)N3CCc4cc(C(=O)c5nc6ncccc6[nH]5)sc4-c4ccc(F)cc43)cc2)c1]

To a round-bottom flask (50 mL) were added the compound from step b (90 mg, 0.10 mmol, 1 equiv) and HCl (4M in dixoane, 2 mL) at room temperature. The resulting mixture was stirred for 2 h at room temperature under nitrogen atmosphere. The resulting mixture was concentrated under vacuum. The crude product was purified by Prep-HPLC to afford the titled compound (18.7 mg, 24.5%) as a light yellow solid. ESI-MS m/z: 557.25 [M+H]$^+$. $^1$H NMR (DMSO-d$_6$) δ 1.62 (s, 4H), 2.17 (s, 3H), 3.23 (s, 3H), 3.45 (s, 4H), 3.60 (s, 4H), 4.93 (s, 1H), 6.94 (s, 1H), 7.07 (s, 2H), 7.24 (t, J=8.1 Hz, 1H), 7.39-7.74 (m, 5H), 7.94-8.19 (m, 3H), 8.61 (d, J=22.6 Hz, 2H), 10.42 (s, 1H), 13.92 (s, 1H).

Example 4

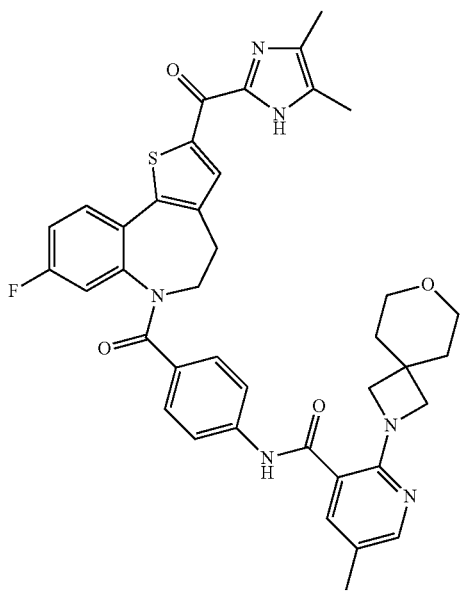 [SMILES: Cc1cnc(N2CC3(CCOCC3)C2)c(C(=O)Nc2ccc(C(=O)N3CCc4cc(C(=O)c5nc(C)c(C)[nH]5)sc4-c4ccc(F)cc43)cc2)c1]

Example 4 Step a

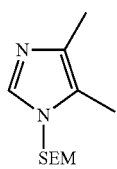

A solution of 4,5-dimethyl-1H-imidazole hydrochloride (2.0 g, 15.08 mmol) in DMF (20 mL) was added NaH (60 wt %, 908 mg, 22.63 mmol) in portions at 0° C. under N$_2$. The resulting mixture was stirred for 0.5 h at 0° C. under N$_2$. To the above mixture was added SEM-Cl (3.77 g, 22.63 mmol) dropwise at 0° C. The resulting mixture was stirred for additional 1 h. The reaction was quenched with water (50 mL) at 0° C., then extracted with EtOAc (100 mL×2), washed with brine (50 mL×2), dried and concentrated. The crude residue was purified by reverse phase C18 column chromatography (MeCN/H$_2$O) to give the desired compound (5.12 g, 81.1%) as a yellow oil. ESI-MS m/z 227.10 [M+H]$^+$.

Example 4 Step b

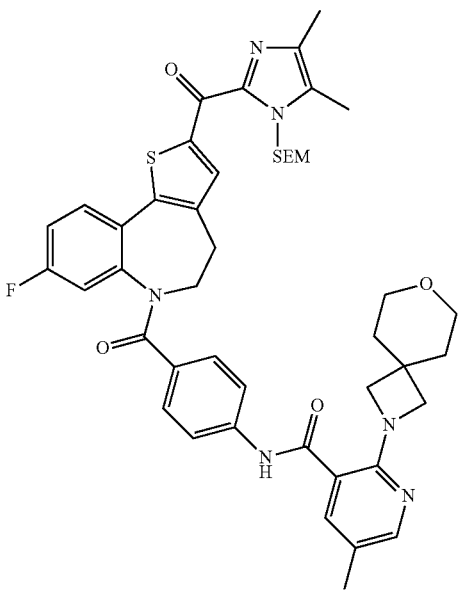 [SMILES: Cc1cnc(N2CC3(CCOCC3)C2)c(C(=O)Nc2ccc(C(=O)N3CCc4cc(C(=O)c5nc(C)c(C)n5COCC[Si](C)(C)C)sc4-c4ccc(F)cc43)cc2)c1]

To a solution of compound from step a in THF (5 mL) was added n-BuLi (0.74 mL, 1.84 mmol) at −78° C. under N$_2$. The resulting mixture was stirred for 0.5 h at the same temperature under N$_2$. The compound from example 1 step c (70 mg, 0.107 mmol) in THF (2 mL) was added dropwise at −78° C. The resulting mixture was stirred for additional 1 h. The reaction was quenched with water (10 mL) at 0° C. and extracted with EtOAc (10 mL×3). The combined organic layers were dried and concentrated. The residue was purified by Prep-HPLC (EA) to afford the desired compound (100 mg) as an oil. ESI-MS m/z: 835.40 [M+H]$^+$.

Example 4 Step c

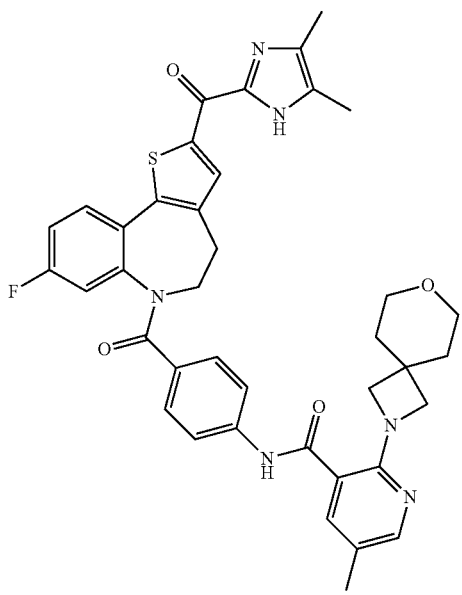 [SMILES: Cc1cnc(N2CC3(CCOCC3)C2)c(C(=O)Nc2ccc(C(=O)N3CCc4cc(C(=O)c5nc(C)c(C)[nH]5)sc4-c4ccc(F)cc43)cc2)c1]

A solution of compound from step b (100 mg, 0.12 mmol) and 4M HCl in dioxane (3 mL) was stirred at room temperature overnight. The resulting mixture was concentrated and purified by Prep-HPLC (MeCN/H$_2$O/10 mmol NH$_4$HCO$_3$) to give the titled compound (8.7 mg, 10%) as a yellow solid. ESI-MS m/z: 705.25 [M+H]$^+$. $^1$H NMR (DMSO-d$_6$) δ 0.87 (s, 1H), 1.64 (d, J=5.3 Hz, 4H), 2.14-2.27 (m, 9H), 3.25 (m, 3H), 3.47 (d, J=5.3 Hz, 4H), 3.61 (s, 4H), 4.90 (s, 1H), 6.89 (s, 1H), 7.06 (s, 2H), 7.21 (t, J=8.4 Hz, 2H), 7.50-7.63 (m, 2H), 7.92 (m, 1H), 8.05 (s, 1H), 8.42 (s, 1H), 10.42 (s, 1H), 13.17 (s, 1H).

Example 5

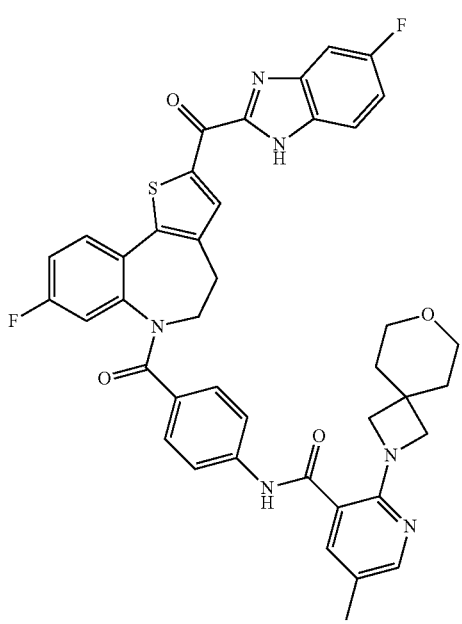 [SMILES: Cc1cnc(N2CC3(CCOCC3)C2)c(C(=O)Nc2ccc(C(=O)N3CCc4cc(C(=O)c5nc6cc(F)ccc6[nH]5)sc4-c4ccc(F)cc43)cc2)c1]

Example 5 was prepared using a procedure similar to that used to prepare example 4 where 5-fluoro-1-((2-(trimethylsilyl)ethoxy)methyl)-1H-benzo[d]imidazole was used in place of 4,5-dimethyl-1-((2-(trimethylsilyl)ethoxy)methyl)-1H-imidazole. ESI-MS m/z: 745.20 [M+H]$^+$. $^1$H NMR (DMSO-d$_6$) δ 1.62 (s, 4H), 2.18 (s, 3H), 3.23 (m, 3H), 3.45 (d, J=5.7 Hz, 4H), 3.61 (s, 4H), 4.93 (s, 1H), 6.93 (d, J=9.6 Hz, 1H), 7.06 (d, J=8.3 Hz, 2H), 7.27 (t, J=8.4 Hz, 2H), 7.46-7.63 (m, 4H), 7.98 (m, 1H), 8.04 (d, J=2.4 Hz, 1H), 8.64 (s, 1H), 10.41 (s, 1H).

Example 6

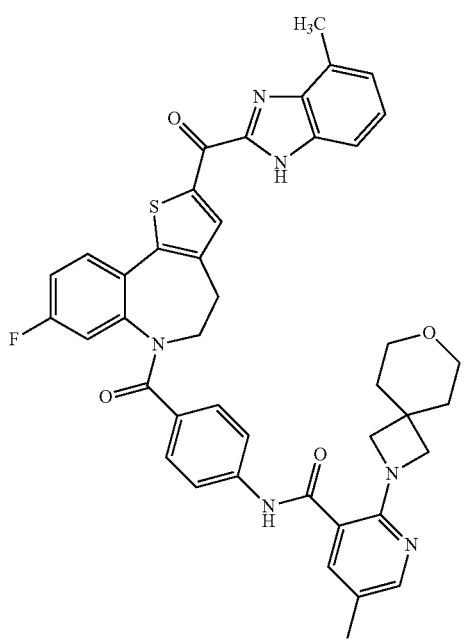 [SMILES: Cc1cnc(N2CC3(CCOCC3)C2)c(C(=O)Nc2ccc(C(=O)N3CCc4cc(C(=O)c5nc6c(C)cccc6[nH]5)sc4-c4ccc(F)cc43)cc2)c1]

Example 6 was prepared using a procedure similar to that used to prepare example 4 where 4-methyl-1-((2-(trimethylsilyl)ethoxy)methyl)-1H-benzo[d]imidazole was used in place of 4,5-dimethyl-1-((2-(trimethylsilyl)ethoxy)methyl)-1H-imidazole. ESI-MS m/z: 741.25 [M+H]$^+$. $^1$H NMR (DMSO-d$_6$) δ 1.62 (s, 4H), 2.18 (s, 3H), 2.66 (d, J=44.4 Hz, 3H), 3.23 (s, 3H), 3.46 (s, 4H), 3.61 (s, 4H), 4.99 (s, 1H), 6.95 (m, 1H), 7.07 (s, 2H), 7.15-7.46 (m, 5H), 7.51 (s, 1H), 7.57 (d, J=8.5 Hz, 2H), 7.99 (s, 1H), 8.05 (s, 1H), 8.66 (s, 1H), 10.43 (s, 1H).

Example 7

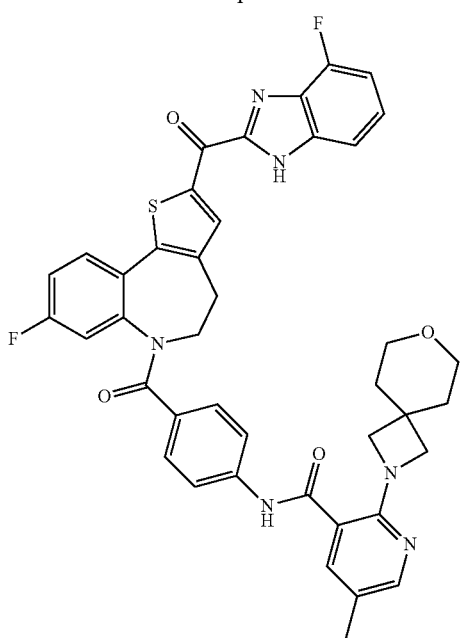

Example 7 was prepared using a procedure similar to that used to prepare example 4 where 4-fluoro-1-((2-(trimethylsilyl)ethoxy)methyl)-1H-benzo[d]imidazole was used in place of 4,5-dimethyl-1-((2-(trimethylsilyl)ethoxy)methyl)-1H-imidazole. ESI-MS m/z: 745.25 [M+H]$^+$. $^1$H NMR (DMSO-d$_6$) δ 1.62 (s, 4H), 2.17 (s, 3H), 3.24 (s, 2H), 3.45 (m, 5H), 3.60 (s, 4H), 4.93 (s, 1H), 6.94 (s, 1H), 7.07 (s, 2H), 7.14-7.33 (m, 2H), 7.33-7.75 (m, 5H), 7.95-8.09 (m, 2H), 8.65 (s, 1H), 10.43 (s, 1H).

Example 8

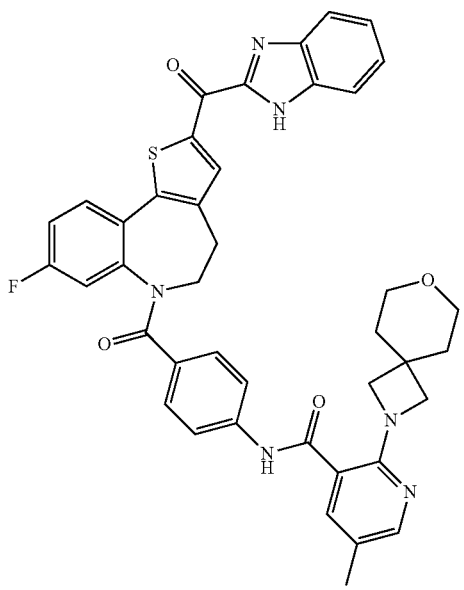 [SMILES: Cc1cnc(N2CC3(CCOCC3)C2)c(C(=O)Nc2ccc(C(=O)N3CCc4cc(C(=O)c5nc6ccccc6[nH]5)sc4-c4ccc(F)cc43)cc2)c1]

Example 8 was prepared using a procedure similar to that used to prepare example 4 where 1-((2-(trimethylsilyl)ethoxy)methyl)-1H-benzo[d]imidazole was used in place of 4,5-dimethyl-1-((2-(trimethylsilyl)ethoxy)methyl)-1H-imidazole. ESI-MS m/z: 727.15 [M+H]$^+$. $^1$H NMR (DMSO-d$_6$) δ 1.65 (d, J=5.5 Hz, 4H), 2.19 (s, 3H), 3.12-3.40 (m, 7H), 3.73 (s, 4H), 4.93 (s, 1H), 6.94 (s, 1H), 7.09 (s, 2H), 7.19-7.30 (m, 1H), 7.39-7.47 (m, 2H), 7.57 (d, J=8.3 Hz, 2H), 7.77 (s, 3H), 7.96-8.06 (m, 2H), 8.66 (s, 1H), 10.58 (s, 1H).

Example 9

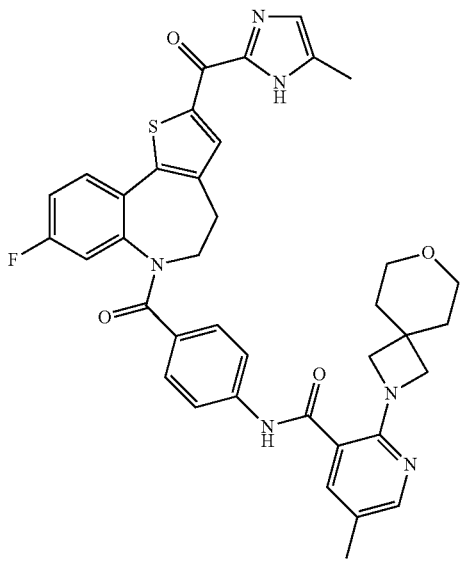 [SMILES: Cc1cnc(N2CC3(CCOCC3)C2)c(C(=O)Nc2ccc(C(=O)N3CCc4cc(C(=O)c5ncc(C)[nH]5)sc4-c4ccc(F)cc43)cc2)c1]

Example 9 was prepared using a procedure similar to that used to prepare example 4 where 5-methyl-1-((2-(trimethylsilyl)ethoxy)methyl)-1H-imidazole was used in place of 4,5-dimethyl-1-((2-(trimethylsilyl)ethoxy)methyl)-1H-imidazole. ESI-MS m/z: 691.10 [M+H]$^+$. $^1$H NMR (DMSO-d$_6$) δ 1.63 (t, J=5.2 Hz, 4H), 2.17 (s, 3H), 2.27 (s, 3H), 3.45 (m, 7H), 3.68 (s, 4H), 4.93 (s, 1H), 6.87 (d, J=9.6 Hz, 1H), 6.97-7.24 (m, 4H), 7.53 (d, J=8.5 Hz, 2H), 7.65 (s, 1H), 7.91 (m, 1H), 8.00 (d, J=2.2 Hz, 1H), 8.43 (s, 1H), 10.50 (s, 1H).

Example 10

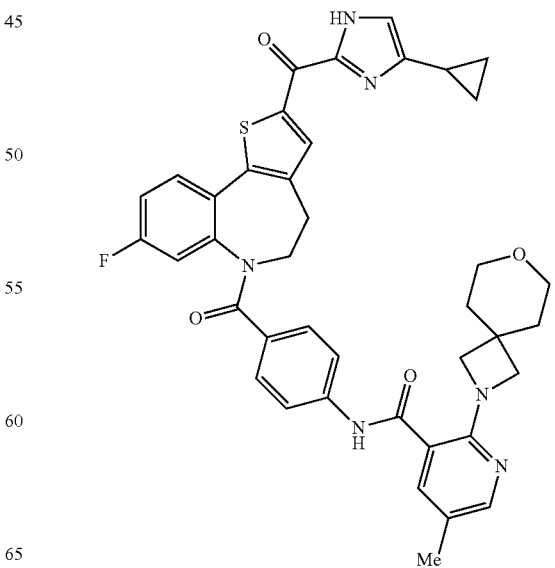

Example 10 was prepared using a procedure similar to that used to prepare example 4 where 4-cyclopropyl-1-[(2-(trimethylsilyl)ethoxy)methyl]-1H-imidazole was used in place of 4,5-dimethyl-1-((2-(trimethylsilyl)ethoxy)methyl)-1H-imidazole. ESI-MS m/z: 717.1 [M+H]⁺. ¹H NMR (CDCl₃) δ 8.41 (s, 1H), 7.88-7.80 (m, 2H), 7.75 (s, 1H), 7.48 (d, J=8.4 Hz, 2H), 7.15 (d, J=8.4 Hz, 2H), 7.03 (s, 1H), 7.01-6.92 (m, 1H), 6.49 (d, J=8.9 Hz, 1H), 5.09 (s, 1H), 3.95 (s, 4H), 3.55 (s, 4H), 3.29 (s, 1H), 3.17 (s, 1H), 2.23 (s, 3H), 1.95 (ddd, J=13.4, 8.5, 5.0 Hz, 1H), 1.75 (t, J=5.2 Hz, 4H), 1.08-0.98 (m, 2H), 0.83 (dt, J=6.7, 4.6 Hz, 2H).

Example 11

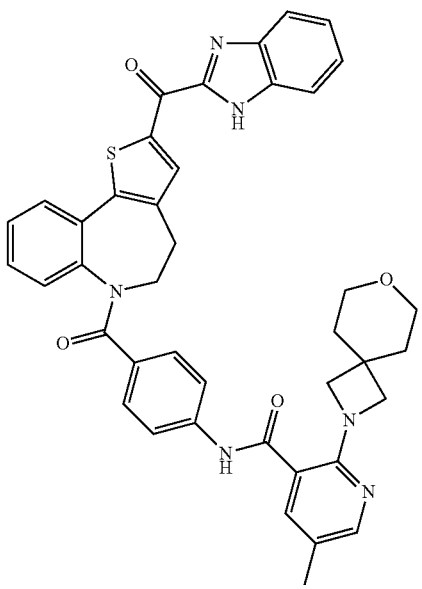

Example 11 was prepared using a procedure similar to that used to prepare example 8. ESI-MS m/z: 709.28 [M+H]⁺. ¹H NMR (DMSO-d₆) δ 13.56 (s, 1H), 10.30 (s, 1H), 8.61 (s, 1H), 7.96 (dd, J=2.3, 0.8 Hz, 1H), 7.88 (m, 2H), 7.56 (bs, 1H), 7.49-7.40 (m, 3H), 7.28 (m, 3H), 7.12 (t, J=7.7 Hz, 1H), 6.96 (d, J=8.3 Hz, 2H), 6.86 (d, J=7.9 Hz, 1H), 4.87 (m, 1H), 3.53 (s, 4H), 3.38 (t, J=4.9 Hz, 4H), 3.16 (m, 3H), 2.09 (s, 3H), 1.54 (t, J=5.2 Hz, 4H).

Example 12

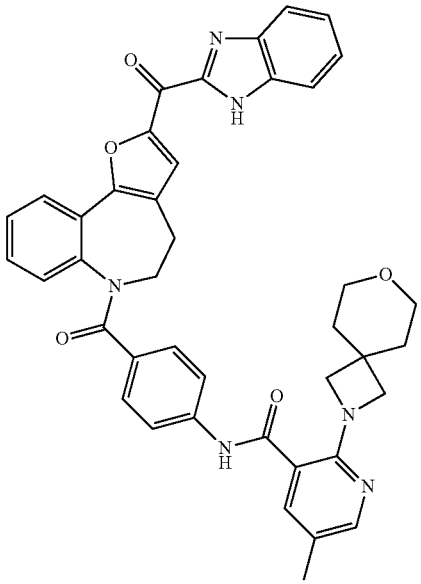 [SMILES: Cc1cnc(N2CC3(CCOCC3)C2)c(C(=O)Nc2ccc(C(=O)N3CCc4cc(C(=O)c5nc6ccccc6[nH]5)oc4-c4ccccc43)cc2)c1]

Example 12 Step a

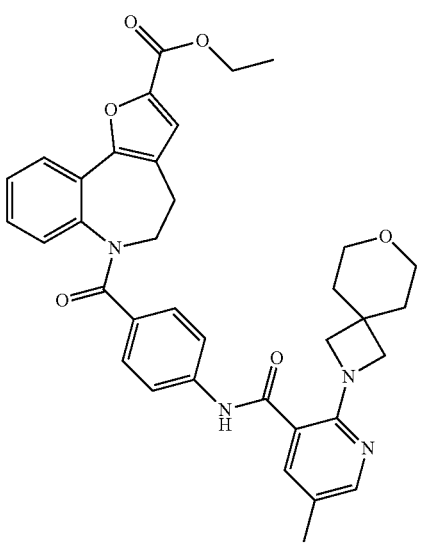 [SMILES: CCOC(=O)c1cc2c(o1)-c1ccccc1N(C(=O)c1ccc(NC(=O)c3cc(C)cnc3N3CC4(CCOCC4)C3)cc1)CC2]

A solution of the compound 5-methyl-2-(7-oxa-2-azaspiro[3.5]nonan-2-yl)nicotinic acid (826 mg, 3.19 mmol) and (1-chloro-2-methylprop-1-en-1-yl)dimethylamine (710 mg, 5.31 mmol) in DCM (10 mL) was stirred at room temperature for 1 h at N₂. The resulting mixture was evaporated, and then diluted with DCM (30 mL). To the above solution was added the ethyl 6-(4-aminobenzoyl)-5,6-dihydro-4H-benzo[b]furo[2,3-d]azepine-2-carboxylate (1.0 g, 2.66 mmol) and pyridine (3 mL) in DCM (10 mL). The resulting mixture was stirred at room temperature for 1 h. After concentrated, the residue was purified by reverse flash C18 column chromatography (MeCN/H₂O) to afford the desire product (1.3 g, 78.8%) as a yellow solid. ESI-MS m/z: 621.30 [M+H]⁺.

Example 12 Step b

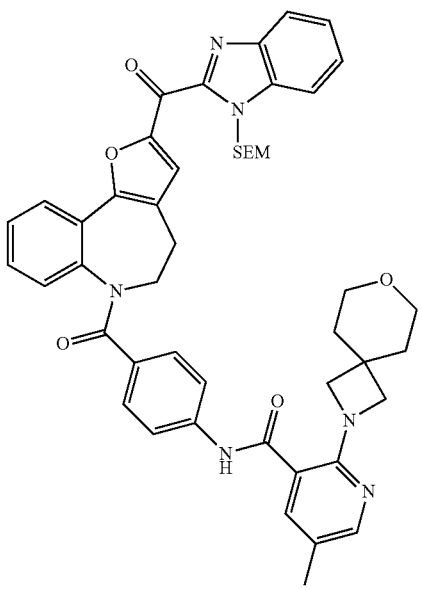 [SMILES: Cc1cnc(N2CC3(CCOCC3)C2)c(C(=O)Nc2ccc(C(=O)N3CCc4cc(C(=O)c5nc6ccccc6n5COCC[Si](C)(C)C)oc4-c4ccccc43)cc2)c1]

n-BuLi (1.45 mL, 3.62 mmol) was dropwisely added to a solution of 1-((2-(trimethylsilyl)ethoxy)methyl)-1H-benzo[d]imidazole (900 mg, 3.62 mmol) in THF (5 mL) at −78° C. under N₂. After the resulting mixture was stirred for 1 h at this temperature, the compound from step a (150 mg, 0.24 mmol) in THF (2 mL) was slowly added and stirred for 1 h. The reaction was quenched with water (10 mL) at 0° C. and extracted with EtOAc (50 mL×3). The combined organic layers were dried, filtered and concentrated. The residue was purified by Prep-TLC (EA:PE=2:1) to afford the desire product (80 mg, 40.2%) as a yellow solid. ESI-MS m/z: 823.50 [M+H]⁺.

Example 12 Step c

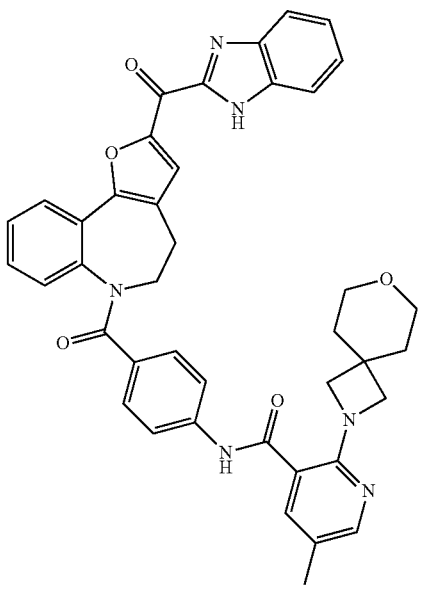 [SMILES: Cc1cnc(N2CC3(CCOCC3)C2)c(C(=O)Nc2ccc(C(=O)N3CCc4cc(C(=O)c5nc6ccccc6[nH]5)oc4-c4ccccc43)cc2)c1]

A solution of the compound from step b (80 mg, 0.097 mmol) and 4M HCl in dioxane (3 mL) was stirred at room temperature overnight. The resulting mixture was concentrated and purified by Prep-HPLC (MeCN/H₂O/10 mmol NH₄HCO₃) to give the titled compound (22.5 mg, 33%) as a yellow solid. ESI-MS m/z: 693.30 [M+H]⁺. ¹H NMR (DMSO-d₆) δ 1.63 (d, J=5.9 Hz, 4H), 2.18 (s, 3H), 3.05 (s, 1H), 3.16 (s, 2H), 3.47 (d, J=5.5 Hz, 4H), 3.61 (s, 4H), 5.07 (s, 1H), 6.91 (d, J=8.2 Hz, 1H), 7.05 (d, J=8.4 Hz, 2H), 7.18 (t, J=7.7 Hz, 1H), 7.34-7.48 (m, 3H), 7.48-7.59 (m, 3H), 7.63 (s, 1H), 7.91 (s, 1H), 8.03-8.16 (m, 2H), 8.54 (s, 1H), 10.39 (s, 1H), 13.58 (s, 1H).

Example 13

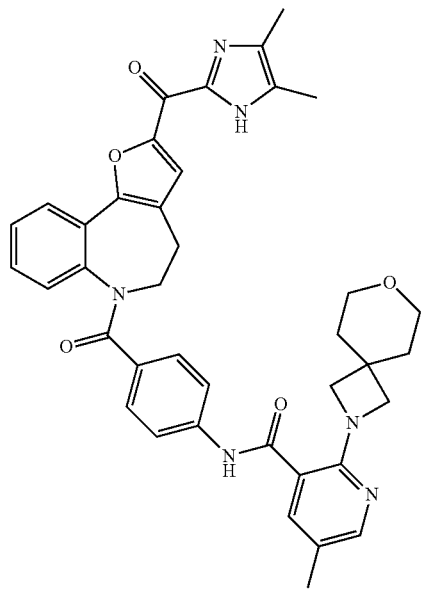 [SMILES: Cc1cnc(N2CC3(CCOCC3)C2)c(C(=O)Nc2ccc(C(=O)N3CCc4cc(C(=O)c5nc(C)c(C)[nH]5)oc4-c4ccccc43)cc2)c1]

Example 13 Step a

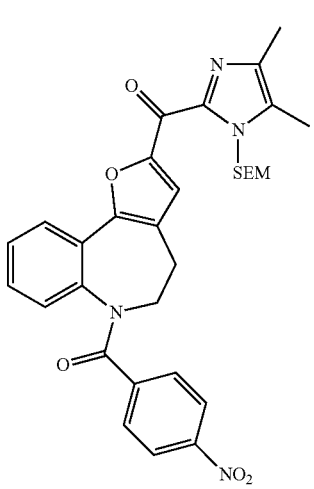 [SMILES: Cc1nc(C(=O)c2cc3c(o2)-c2ccccc2N(C(=O)c2ccc([N+](=O)[O-])cc2)CC3)n(COCC[Si](C)(C)C)c1C]

To a solution of 4,5-dimethyl-1-[[2-(trimethylsilyl)ethoxy]methyl]-1H-imidazole (668.5 mg, 2.95 mmol) in THF (4 mL) was added dropwise n-butyllithium solution (2.5 M in hexane, 0.98 mL) at −78° C. under N₂ atmosphere. The reaction mixture was stirred at −78° C. for 30 min. Then a solution of ethyl 6-(4-nitrobenzoyl)-5,6-dihydro-4H-benzo[b]furo[2,3-d]azepine-2-carboxylate (400 mg, 0.98 mmol) in THF (4 mL) was added dropwise and the mixture was stirred for another 30 min. The reaction was quenched with NH₄Cl (10 mL), and then the mixture was extracted with EtOAc (15 mL×2). The combined organic layers were concentrated under vacuum, and the residue was purified by Prep-TLC to afford the desired compound (0.46 g, 81%) as a light yellow solid. ESI-MS m/z: 587.30 [M+H]⁺.

Example 13 Step b

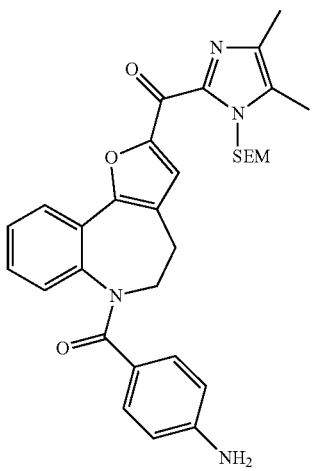

To a 100 mL round-bottom flask were added the compound from step a (0.46 g, 0.78 mmol), EtOH (20 mL), Fe (0.4 g, 7.84 mmol) and NH₄Cl (0.4 g, 7.84 mmol) in H₂O (10 mL) solution at room temperature. The resulting mixture was stirred at 80° C. for 3 h. After cooled down, most of solvents were evaporated. The reaction mixture was basified with aqueous NaHCO₃ sol'n (to pH ~8) and then extracted with DCM (100 mL×2). The organic layers were combined, dried, filtered and concentrated. The residue was purified by silica gel column chromatography eluting with CH₂Cl₂/MeOH (10:1) to afford the crude product which was further purified by reverse flash chromatography to afford the desired compound (0.23 g, 52.69%) as a yellow solid. ESI-MS m/z: 557.25 [M+H]⁺.

Example 13 Step c

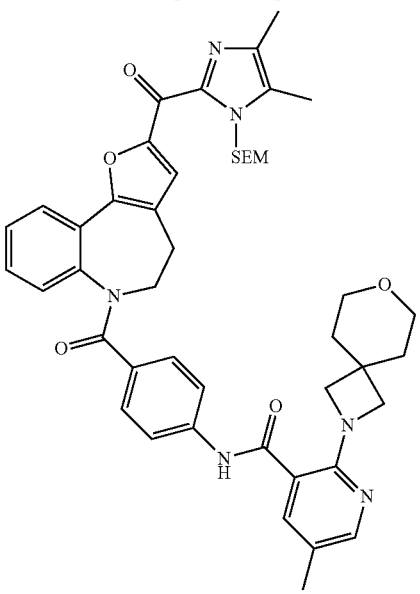 [SMILES: Cc1cnc(N2CC3(CCOCC3)C2)c(C(=O)Nc2ccc(C(=O)N3CCc4cc(C(=O)c5nc(C)c(C)n5COCC[Si](C)(C)C)oc4-c4ccccc43)cc2)c1]

To a 100 mL round-bottom flask were added 5-methyl-2-(7-oxa-2-azaspiro[3.5]nonan-2-yl)nicotinic acid (162.5 mg, 0.62 mmol) and (1-chloro-2-methylprop-1-en-1-yl)dimethylamine (248.4 mg, 1.86 mmol) in DCM (10 mL) at room temperature. The resulting mixture was stirred for 0.5 h at room temperature under N₂. The resulting mixture was concentrated under reduced pressure. To the above mixture was added pyridine (2 mL) and the compound from step b (230 mg, 0.41 mmol) dropwise at room temperature. The resulting mixture was stirred for additional 1 h at room temperature. The residue was purified by reverse flash chromatography to afford the desired compound (330 mg, crude) as a light yellow solid. ESI-MS m/z: 801.20 [M+H]⁺.

Example 13 Step d

To a 100 mL round-bottom flask were added the compound from step c (230 mg, 0.29 mmol) and 4 mL HCl (4M in 1,4-dioxane) at room temperature. The solution was stirred for 4 h at 60° C. under nitrogen atmosphere. The resulting mixture was concentrated under reduced pressure. The crude product was purified by Prep-HPLC to afford the desired compound (86.1 mg, 44.7%) as a yellow solid. ESI-MS m/z: 671.25 [M+H]⁺. ¹H NMR (DMSO-d₆) δ 1.62 (s, 4H), 2.18 (d, J=5.6 Hz, 6H), 2.23 (s, 3H), 2.95-3.14 (m, 3H), 3.45 (d, J=5.7 Hz, 4H), 3.61 (s, 4H), 5.03 (s, 1H), 6.87 (s, 1H), 7.02 (d, J=8.3 Hz, 2H), 7.13 (t, J=7.4 Hz, 1H), 7.37 (t, J=7.8 Hz, 1H), 7.46-7.57 (m, 3H), 8.04 (d, J=5.8 Hz, 2H), 8.22 (s, 1H), 10.38 (s, 1H), 13.14 (s, 1H).

Example 14

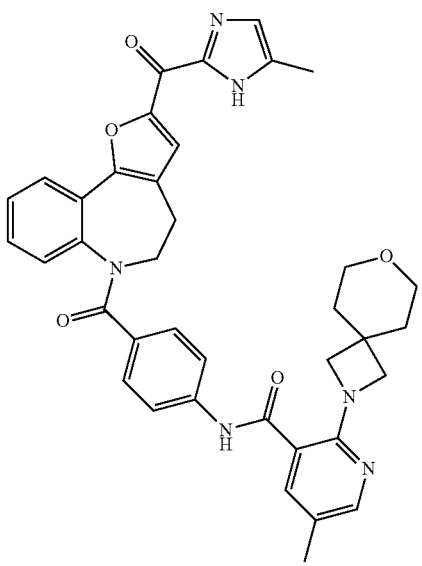 [SMILES: Cc1cnc(N2CC3(CCOCC3)C2)c(C(=O)Nc2ccc(C(=O)N3CCc4cc(C(=O)c5ncc(C)[nH]5)oc4-c4ccccc43)cc2)c1]

Example 14 was prepared using a procedure similar to that used to prepare example 13 where 5-methyl-1-((2-(trimethylsilyl)ethoxy)methyl)-1H-imidazole was used in place of 4,5-dimethyl-1-((2-(trimethylsilyl)ethoxy)methyl)-1H-imidazole. ESI-MS m/z: 657.30 [M+H]⁺. ¹H NMR (DMSO-d₆) δ 1.62 (d, J=5.7 Hz, 4H), 2.17 (s, 3H), 2.28 (d, J=9.8 Hz, 3H), 2.97-3.16 (m, 3H), 3.45 (d, J=6.0 Hz, 4H), 3.61 (s, 4H), 5.03 (s, 1H), 6.88 (s, 1H), 7.02 (d, J=9.2 Hz, 3H), 7.15 (d, J=7.8 Hz, 1H), 7.37 (t, J=7.8 Hz, 1H), 7.47-7.58 (m, 3H), 8.05 (d, J=7.9 Hz, 2H), 8.27 (d, J=10.4 Hz, 1H), 10.38 (s, 1H), 13.32 (d, J=19.9 Hz, 1H).

Example 15

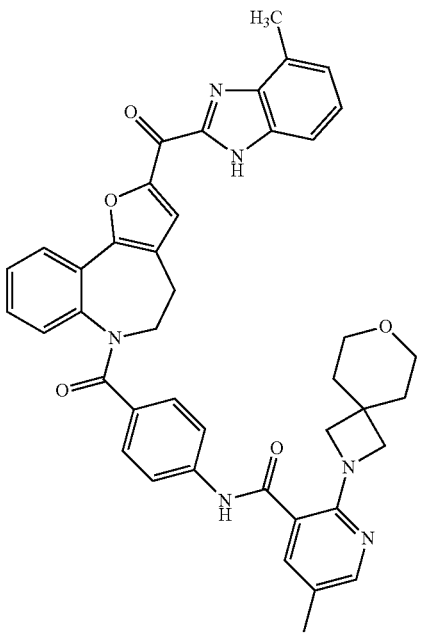 [SMILES: Cc1cnc(N2CC3(CCOCC3)C2)c(C(=O)Nc2ccc(C(=O)N3CCc4cc(C(=O)c5nc6c(C)cccc6[nH]5)oc4-c4ccccc43)cc2)c1]

Example 15 was prepared using a procedure similar to that used to prepare example 13 where 4-methyl-1-((2-(trimethylsilyl)ethoxy)methyl)-1H-benzo[d]imidazole was used in place of 4,5-dimethyl-1-((2-(trimethylsilyl)ethoxy)methyl)-1H-imidazole. ESI-MS m/z: 707.25 [M+H]⁺. ¹H NMR (DMSO-d₆) δ 1.62 (t, J=5.3 Hz, 4H), 2.17 (s, 3H), 2.61 (s, 1H), 2.69 (s, 2H), 3.10 (d, J=37.6 Hz, 3H), 3.46 (d, J=5.8 Hz, 4H), 3.61 (s, 4H), 5.09 (s, 1H), 6.91 (s, 1H), 7.05 (d, J=8.2 Hz, 2H), 7.12-7.35 (m, 3H), 7.40 (t, J=7.9 Hz, 2H), 7.46-7.58 (m, 3H), 7.71 (d, J=8.5 Hz, 1H), 8.04 (s, 1H), 8.11 (d, J=7.9 Hz, 1H), 8.53 (s, 1H), 10.39 (s, 1H).

Example 16

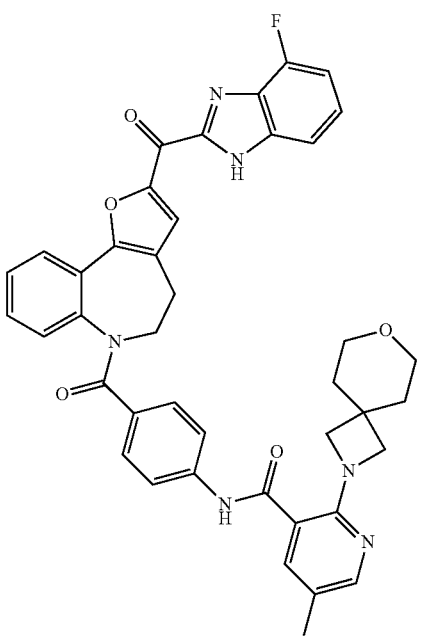 [SMILES: Cc1cnc(N2CC3(CCOCC3)C2)c(C(=O)Nc2ccc(C(=O)N3CCc4cc(C(=O)c5nc6c(F)cccc6[nH]5)oc4-c4ccccc43)cc2)c1]

Example 16 was prepared using a procedure similar to that used to prepare example 13 where 4-fluoro-1-[(2-(trimethylsilyl)ethoxy)methyl]-1H-benzo[d]imidazole was used in place of 4,5-dimethyl-1-((2-(trimethylsilyl)ethoxy)methyl)-1H-imidazole. ESI-MS m/z: 711.35 [M+H]+. 1H NMR (DMSO-d6) δ 1.62 (t, J=5.0 Hz, 4H), 2.17 (s, 3H), 3.05 (s, 1H), 3.16 (s, 2H), 3.46 (d, J=5.7 Hz, 4H), 5.07 (s, 1H), 6.90 (d, J=7.9 Hz, 1H), 7.05 (d, J=8.3 Hz, 2H), 7.19 (d, J=8.5 Hz, 2H), 7.40 (t, J=7.8 Hz, 2H), 7.45-7.59 (m, 4H), 8.04 (s, 1H), 8.10 (d, J=7.9 Hz, 1H), 8.50 (s, 1H), 10.39 (s, 1H).

Example 17

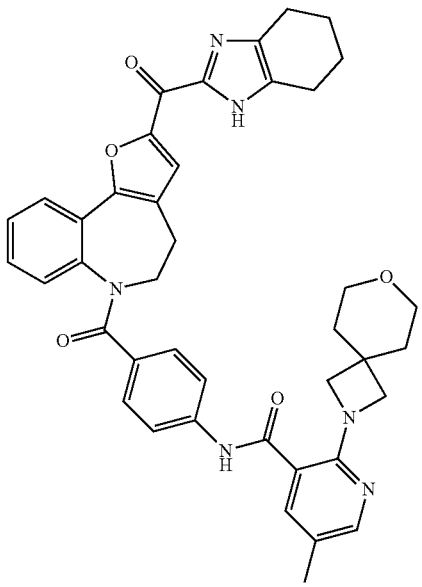 [SMILES: Cc1cnc(N2CC3(CCOCC3)C2)c(C(=O)Nc2ccc(C(=O)N3CCc4cc(C(=O)c5nc6c([nH]5)CCCC6)oc4-c4ccccc43)cc2)c1]

Example 17 was prepared using a procedure similar to that used to prepare example 13 where 4-fluoro-1-[(2-(trimethylsilyl)ethoxy)methyl]-1H-benzo[d]imidazole was used in place of 1-((2-(trimethylsilyl)ethoxy)methyl)-4,5,6,7-tetrahydro-1H-benzo[d]imidazole. ESI-MS m/z: 697.30 [M+H]+. 1H NMR (DMSO-d6) δ 1.62 (s, 4H), 1.79 (s, 4H), 2.17 (s, 3H), 2.61 (d, J=11.5 Hz, 4H), 3.05 (d, J=18.8 Hz, 3H), 3.45 (s, 4H), 3.60 (s, 4H), 5.02 (s, 1H), 6.87 (s, 1H), 7.01 (d, J=8.3 Hz, 2H), 7.13 (t, J=7.7 Hz, 1H), 7.36 (t, J=7.7 Hz, 1H), 7.45-7.58 (m, 3H), 8.04 (d, J=6.2 Hz, 2H), 8.21 (s, 1H), 10.37 (s, 1H), 13.13 (s, 1H).

Example 18

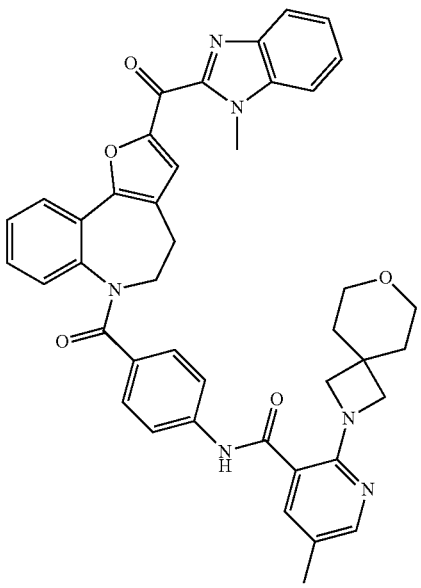

Example 18 was prepared using a procedure similar to that used to prepare example 13 where 1-methyl-1H-benzo[d]imidazole was used in place of 4,5-dimethyl-1-((2-(trimethylsilyl)ethoxy)methyl)-1H-imidazole. ESI-MS m/z: 707.25 [M+H]+. 1H NMR (DMSO-d6) δ 1.63 (t, J=5.2 Hz, 4H), 2.17 (s, 3H), 3.08 (d, J=29.3 Hz, 3H), 3.40-3.52 (m, 4H), 3.61 (s, 4H), 4.18 (s, 3H), 5.06 (d, J=11.6 Hz, 1H), 6.90 (d, J=8.0 Hz, 1H), 7.04 (d, J=8.3 Hz, 2H), 7.17 (t, J=7.6 Hz, 1H), 7.41 (td, J=7.8, 4.1 Hz, 2H), 7.47-7.51 (m, 2H), 7.53 (d, J=8.3 Hz, 2H), 7.79 (d, J=8.2 Hz, 1H), 7.91 (d, J=8.2 Hz, 1H), 8.04 (d, J=2.1 Hz, 1H), 8.06-8.12 (m, 1H), 8.26 (s, 1H), 10.38 (s, 1H).

Example 19

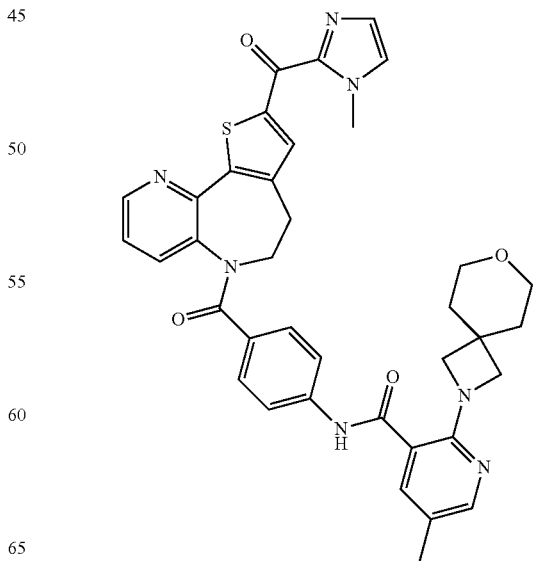

Example 19 was prepared using a procedure similar to that used to prepare example 13 where 1-methyl-1H-imidazole was used in place of 4,5-dimethyl-1-[(2-(trimethylsilyl)-ethoxy)methyl]-1H-imidazole. ESI-MS m/z: 674.20 [M+H]+. 1H NMR (DMSO-d6) δ 1.64 (t, J=5.2 Hz, 4H), 2.18 (s, 3H), 3.33 (s, 3H), 3.48 (d, J=5.4 Hz, 4H), 3.62 (s, 4H), 4.04 (s, 3H), 5.02 (s, 1H), 7.07 (d, J=8.5 Hz, 2H), 7.12-7.20 (m, 1H), 7.29 (s, 2H), 7.51 (d, J=2.2 Hz, 1H), 7.57 (d, J=8.3 Hz, 2H), 7.65 (s, 1H), 8.05 (d, J=2.1 Hz, 1H), 8.33 (s, 1H), 8.46 (d, J=4.5 Hz, 1H), 10.42 (s, 1H).

Example 20

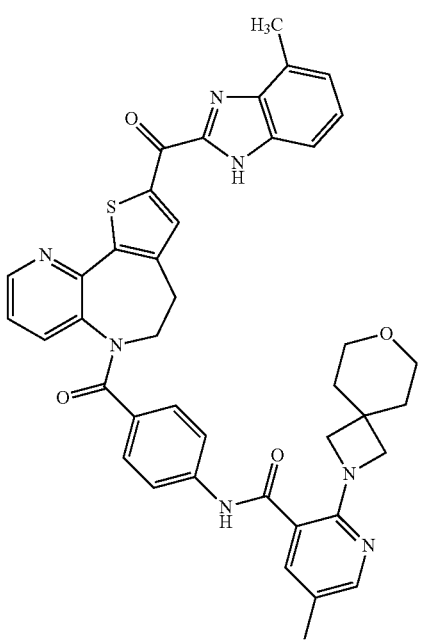 [SMILES: Cc1cnc(N2CC3(CCOCC3)C2)c(C(=O)Nc2ccc(C(=O)N3CCc4cc(C(=O)c5nc6c(C)cccc6[nH]5)sc4-c4ncccc43)cc2)c1]

Example 20 was prepared using a procedure similar to that used to prepare example 13 where 4-methyl-1-[(2-(trimethylsilyl)ethoxy)methyl]-1H-benzo[d]imidazole was used in place of 4,5-dimethyl-1-[(2-(trimethylsilyl)-ethoxy)methyl]-1H-imidazole. ESI-MS m/z: 724.20 [M+H]+. 1H NMR (DMSO-d6) δ 1.63 (d, J=5.6 Hz, 4H), 2.18 (s, 3H), 2.66 (d, J=36.7 Hz, 3H), 3.37 (s, 3H), 3.48 (d, J=5.3 Hz, 4H), 3.62 (s, 4H), 5.10 (s, 1H), 7.10 (d, J=8.4 Hz, 2H), 7.20 (d, J=5.0 Hz, 2H), 7.34 (s, 2H), 7.51 (s, 2H), 7.59 (d, J=8.4 Hz, 2H), 8.05 (d, J=2.0 Hz, 1H), 8.47-8.53 (m, 1H), 8.67 (s, 1H), 10.42 (s, 1H), 13.63 (s, 1H).

Example 21

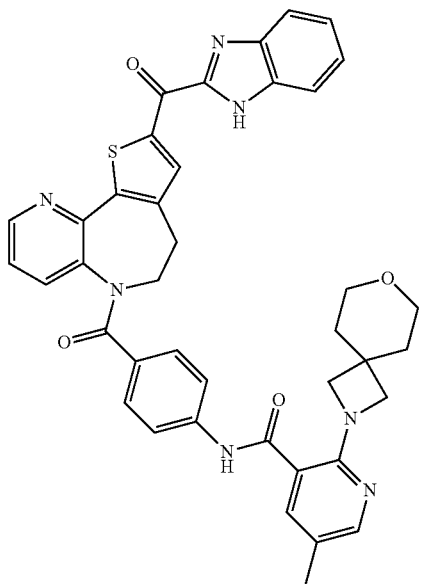 [SMILES: Cc1cnc(N2CC3(CCOCC3)C2)c(C(=O)Nc2ccc(C(=O)N3CCc4cc(C(=O)c5nc6ccccc6[nH]5)sc4-c4ncccc43)cc2)c1]

Example 21 was prepared using a procedure similar to that used to prepare example 13 where 1-[(2-(trimethylsilyl)ethoxy)methyl]-1H-benzo[d]imidazole was used in place of 4,5-dimethyl-1-[(2-(trimethylsilyl)-ethoxy)methyl]-1H-imidazole. ESI-MS m/z: 710.15 [M+H]+. 1H NMR (DMSO-d6) δ 1.63 (s, 4H), 2.18 (s, 3H), 3.37 (s, 3H), 3.47 (s, 4H), 3.62 (s, 4H), 5.05 (s, 1H), 7.09 (s, 2H), 7.19 (s, 1H), 7.28-7.41 (m, 2H), 7.44 (d, J=7.7 Hz, 1H), 7.51 (s, 1H), 7.61 (dd, J=22.5, 8.1 Hz, 3H), 7.96 (d, J=8.6 Hz, 1H), 8.05 (s, 1H), 8.49 (s, 1H), 8.63 (s, 1H), 10.43 (s, 1H), 13.62 (s, 1H).

Example 22

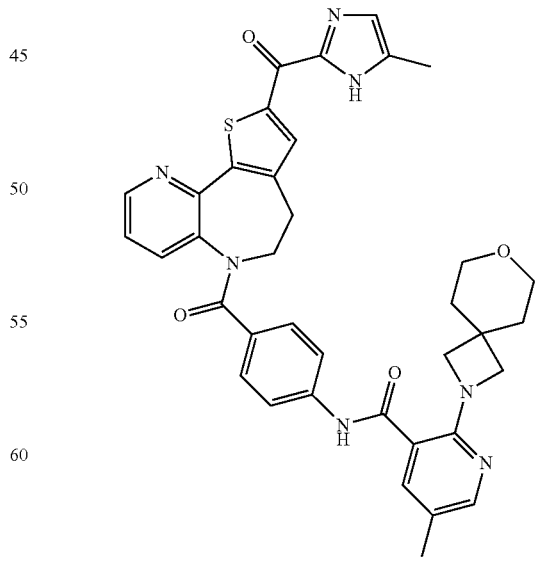

Example 22 was prepared using a procedure similar to that used to prepare example 13 where 5-methyl-1-((2-

(trimethylsilyl)ethoxy)methyl)-1H-imidazole was used in place of 4,5-dimethyl-1-[(2-(trimethylsilyl)-ethoxy)methyl]-1H-imidazole. ESI-MS m/z: 657.30 [M+H]$^+$. $^1$H NMR (DMSO-d$_6$) δ 1.62 (d, J=5.7 Hz, 4H), 2.17 (s, 3H), 2.28 (d, J=9.8 Hz, 3H), 2.97-3.16 (m, 3H), 3.45 (d, J=6.0 Hz, 4H), 3.61 (s, 4H), 5.03 (s, 1H), 6.88 (s, 1H), 7.02 (d, J=9.2 Hz, 3H), 7.15 (d, J=7.8 Hz, 1H), 7.37 (t, J=7.8 Hz, 1H), 7.47-7.58 (m, 3H), 8.05 (d, J=7.9 Hz, 2H), 8.27 (d, J=10.4 Hz, 1H), 10.38 (s, 1H), 13.32 (d, J=19.9 Hz, 1H).

Example 23

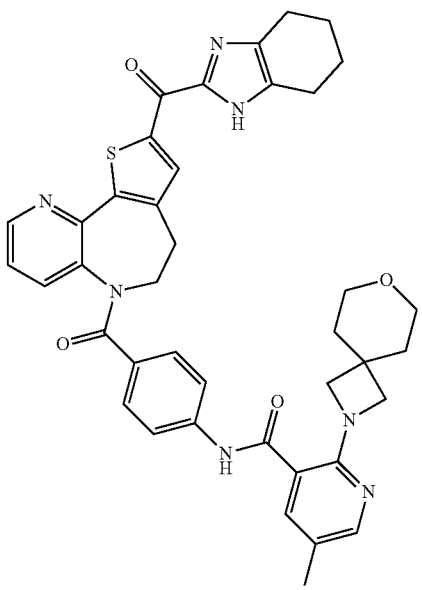

Example 23 was prepared using a procedure similar to that used to prepare example 13 where 1-((2-(trimethylsilyl)ethoxy)methyl)-4,5,6,7-tetrahydro-1H-benzo[d]-imidazole was used in place of 4,5-dimethyl-1-[(2-(trimethylsilyl)-ethoxy)methyl]-1H-imidazole. ESI-MS m/z: 714.25 [M+H]$^+$. $^1$H NMR (DMSO-d$_6$) δ 1.63 (d, J=6.3 Hz, 4H), 1.80 (s, 4H), 2.18 (s, 3H), 2.64 (s, 4H), 3.30 (s, 3H), 3.47 (s, 4H), 3.61 (s, 4H), 5.13 (s, 1H), 7.03-7.16 (m, 3H), 7.30 (s, 1H), 7.50 (s, 1H), 7.57 (d, J=8.2 Hz, 2H), 8.05 (s, 1H), 8.37 (s, 1H), 8.45 (d, J=4.8 Hz, 1H), 10.42 (s, 1H), 13.15 (s, 1H).

Example 24

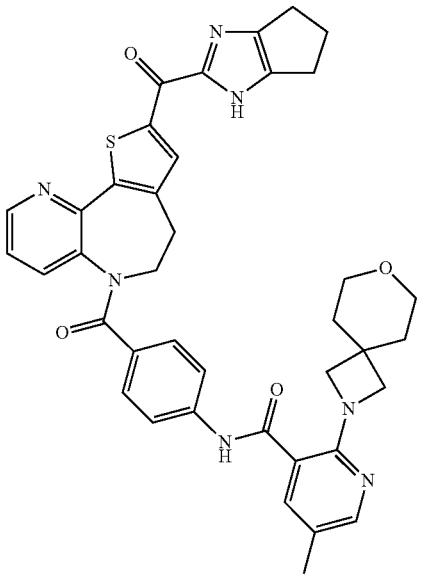 [SMILES: Cc1cnc(N2CC3(CCOCC3)C2)c(C(=O)Nc2ccc(C(=O)N3CCc4cc(C(=O)c5nc6c([nH]5)CCC6)sc4-c4ncccc43)cc2)c1]

Example 24 was prepared using a procedure similar to that used to prepare example 13 where 1-[(2-(trimethylsilyl)ethoxy)methyl]-1H,4H,5H,6H-cyclopenta[d]imidazole was used in place of 4,5-dimethyl-1-[(2-(trimethylsilyl)-ethoxy)methyl]-1H-imidazole. ESI-MS m/z: 700.25[M+H]$^+$. $^1$H NMR (DMSO-d$_6$) δ 13.25 (s, 1H), 10.42 (s, 1H), 8.48-8.36 (m, 2H), 8.05 (s, 1H), 7.61-7.49 (m, 3H), 7.30 (s, 1H), 7.17-7.03 (m, 3H), 5.02 (s, 1H), 3.61 (s, 4H), 3.47 (t, J=5.3 Hz, 4H), 3.30 (s, 3H), 2.77-2.55 (m, 6H), 2.18 (s, 3H), 1.63 (t, J=5.0 Hz, 4H).

Example 25

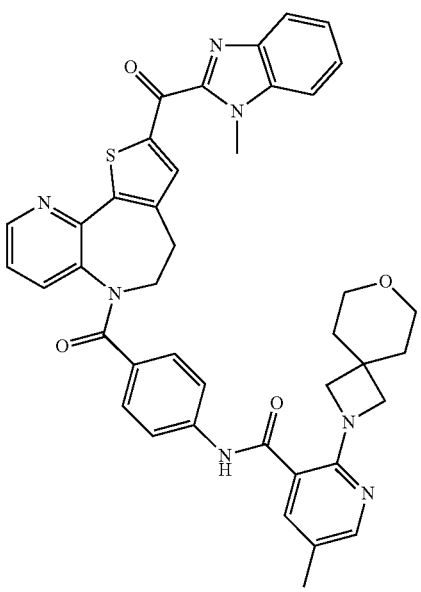 [SMILES: Cc1cnc(N2CC3(CCOCC3)C2)c(C(=O)Nc2ccc(C(=O)N3CCc4cc(C(=O)c5nc6ccccc6n5C)sc4-c4ncccc43)cc2)c1]

Example 25 was prepared using a procedure similar to that used to prepare example 13 where 1-methyl-1H-1,3- benzodiazole was used in place of 4,5-dimethyl-1-[(2-(trimethylsilyl)-ethoxy)methyl]-1H-imidazole. ESI-MS m/z: 724.25 [M+H]⁺. ¹H NMR (DMSO-d₆) δ 1.63 (t, J=5.2 Hz, 4H), 2.18 (s, 3H), 3.19 (s, 3H), 3.41-3.51 (m, 4H), 3.61 (s, 4H), 4.18 (s, 3H), 5.03 (s, 1H), 7.08 (d, J=8.3 Hz, 2H), 7.15-7.20 (m, 1H), 7.33 (d, J=7.9 Hz, 1H), 7.43 (t, J=7.6 Hz, 1H), 7.48-7.55 (m, 2H), 7.58 (d, J=8.3 Hz, 2H), 7.81 (d, J=8.3 Hz, 1H), 7.95 (d, J=8.2 Hz, 1H), 8.04 (d, J=2.1 Hz, 1H), 8.40 (s, 1H), 8.49 (d, J=4.6 Hz, 1H), 10.42 (s, 1H).

Example 26

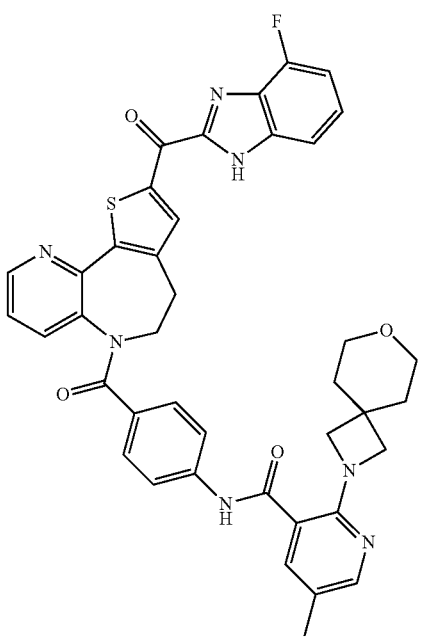

Example 27

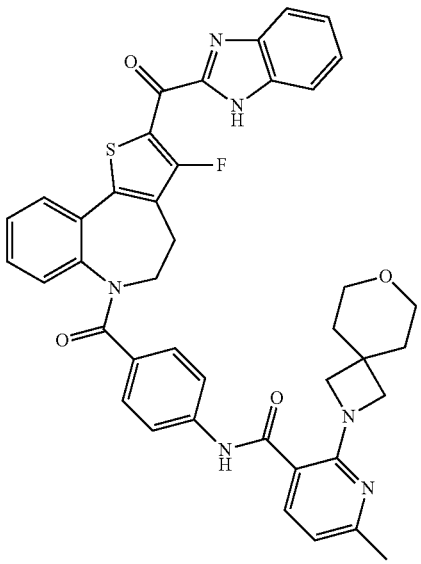 [SMILES: Cc1ccc(C(=O)Nc2ccc(C(=O)N3CCc4c(sc(C(=O)c5nc6ccccc6[nH]5)c4F)-c4ccccc43)cc2)c(N2CC3(CCOCC3)C2)n1]

Example 27 was prepared using a procedure similar to that used to prepare example 13 where 1-[(2-(trimethylsilyl)ethoxy)methyl]-1H-benzo[d]imidazole was used in place of 4,5-dimethyl-1-[(2-(trimethylsilyl)-ethoxy)methyl]-1H-imidazole. ESI-MS m/z: 727.20 [M+H]⁺. ¹H NMR (DMSO-d₆) δ 1.62 (t, J=4.9 Hz, 4H), 2.33 (s, 3H), 3.00-3.23 (m, 3H), 3.47 (d, J=5.4 Hz, 4H), 3.63 (s, 4H), 4.03 (s, 3H), 5.00 (s, 1H), 6.57 (d, J=7.7 Hz, 1H), 6.91 (s, 1H), 7.02 (d, J=8.4 Hz, 2H), 7.20 (t, J=7.6 Hz, 1H), 7.27 (s, 1H), 7.35 (t, J=7.7 Hz, 1H), 7.52 (t, J=7.1 Hz, 3H), 7.65 (s, 1H), 7.95 (d, J=7.8 Hz, 1H), 10.30 (s, 1H).

Example 28

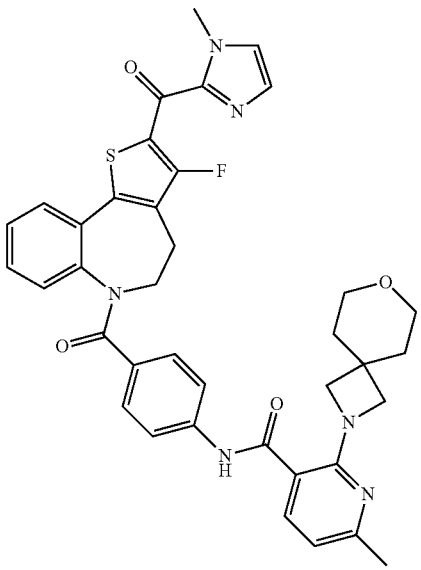 [SMILES: Cc1ccc(C(=O)Nc2ccc(C(=O)N3CCc4c(sc(C(=O)c5nccn5C)c4F)-c4ccccc43)cc2)c(N2CC3(CCOCC3)C2)n1]

Example 26 was prepared using a procedure similar to that used to prepare example 13 where 4-fluoro-1-[(2-(trimethylsilyl)ethoxy)methyl]-1H-benzo[d]imidazole was used in place of 4,5-dimethyl-1-[(2-(trimethylsilyl)-ethoxy)methyl]-1H-imidazole. ESI-MS m/z: 728.20 [M+H]⁺. ¹H NMR (DMSO-d₆) δ 1.63 (t, J=5.2 Hz, 4H), 2.17 (s, 3H), 3.46 (t, J=5.1 Hz, 4H), 3.61 (s, 4H), 5.03 (s, 1H), 7.08 (d, J=8.2 Hz, 2H), 7.19 (m, 2H), 7.33 (d, J=7.8 Hz, 1H), 7.40 (td, J=8.0, 4.7 Hz, 1H), 7.50 (d, J=2.3 Hz, 2H), 7.58 (d, J=8.3 Hz, 2H), 8.04 (d, J=2.1 Hz, 1H), 8.49 (m, 1H), 8.60 (s, 1H), 10.42 (s, 1H).

Example 28 was prepared using a procedure similar to that used to prepare Example 13 where 1-methyl-1H-imidazole was used in place of 4,5-dimethyl-1-[(2-(trimethyl-silyl)-ethoxy)-methyl]-1H-imidazole. ESI-MS m/z: 691.25 [M+H]+. 1H NMR (DMSO-d6) δ 1.62 (t, J=5.2 Hz, 4H), 2.33 (s, 3H), 3.02-3.29 (m, 3H), 3.46 (d, J=6.1 Hz, 4H), 3.63 (s, 4H), 5.03 (s, 1H), 6.56 (d, J=7.6 Hz, 1H), 6.94 (s, 1H), 7.05 (d, J=8.2 Hz, 2H), 7.24 (t, J=7.6 Hz, 1H), 7.35-7.48 (m, 3H), 7.53 (d, J=7.8 Hz, 3H), 7.63 (s, 1H), 7.94 (s, 1H), 8.04 (d, J=7.9 Hz, 1H), 10.31 (s, 1H), 13.66 (s, 1H).
Example 29
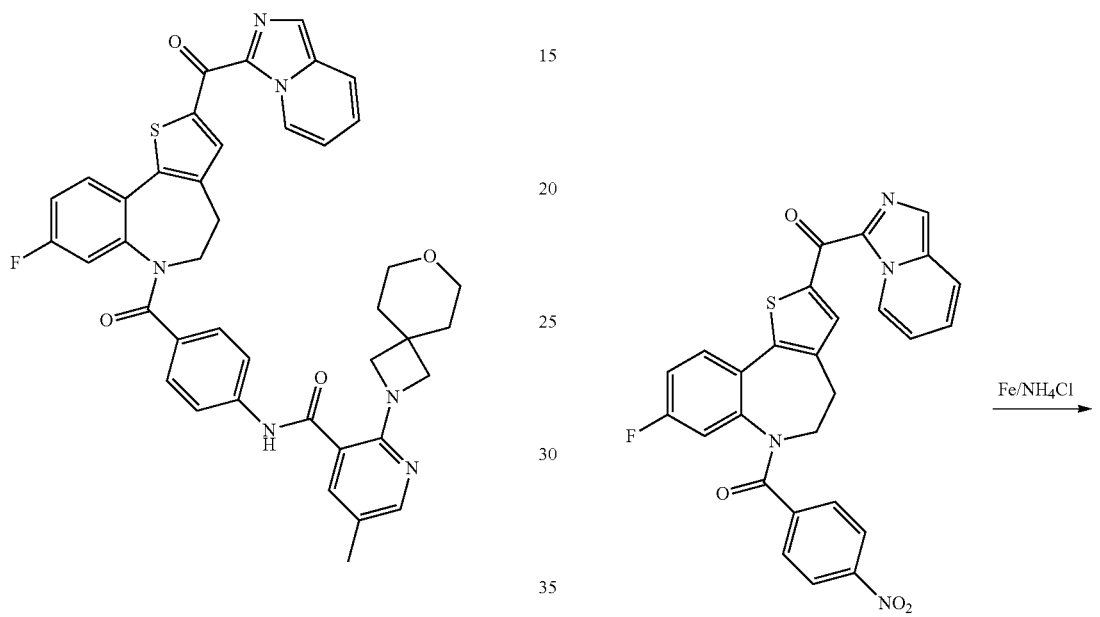
Scheme 9
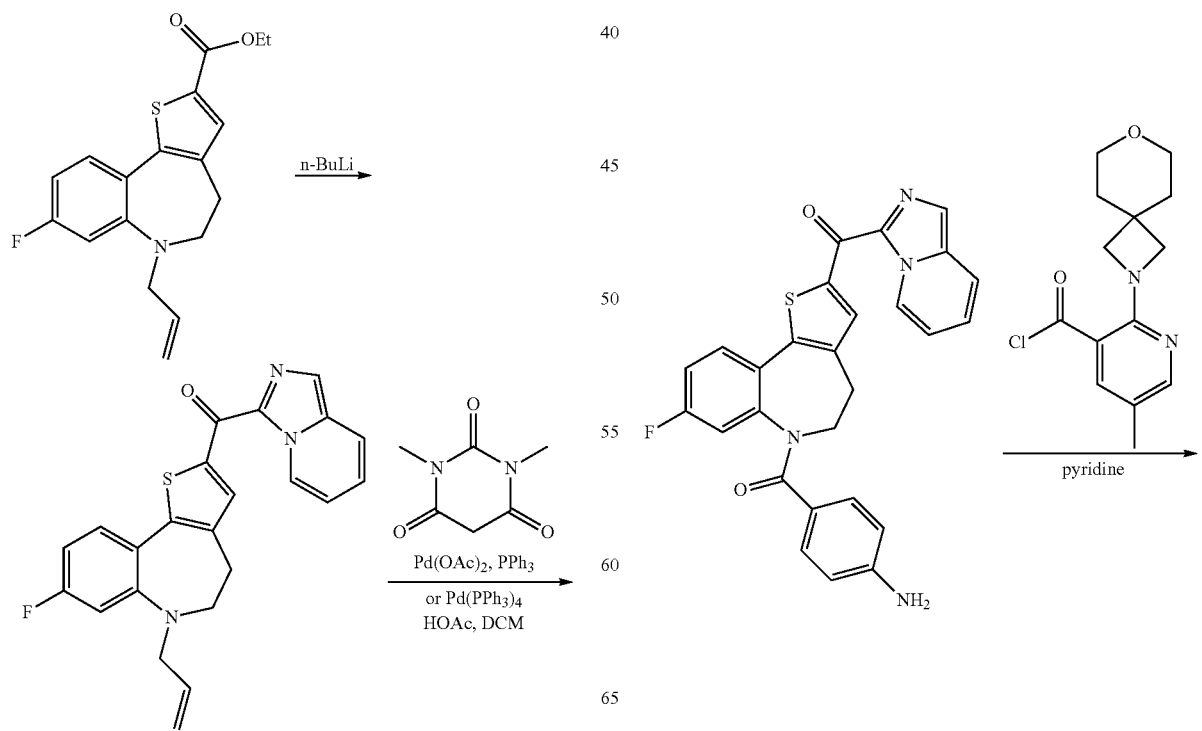

-continued

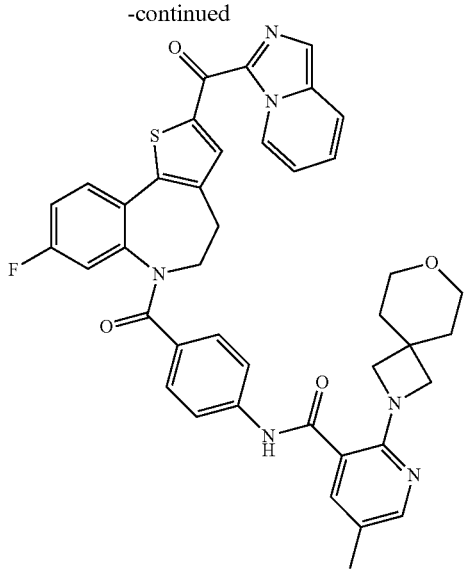

Example 29 Step a

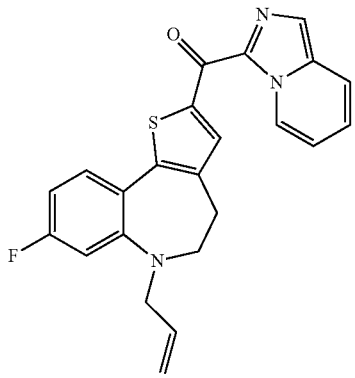 [SMILES: C=CCN1CCc2cc(C(=O)c3ncc4ccccn34)sc2-c2ccc(F)cc21]

n-BuLi (1.147 mL, 2.87 mmol) was added dropwise to a solution of imidazo[1.5-a]pyridine (0.455 g, 3.77 mmol) in THF (5 mL) at −78° C. under N$_2$. Then ethyl 6-allyl-8-fluoro-5,6-dihydro-4H-benzo[b]thieno[2,3-d]azepine-2-carboxylate (0.25 g, 0.754 mmol) in THF (2 mL) was added dropwise and stirred at −78° C. for 2 h. The resulting mixture was quenched with saturated NaHCO$_3$ (aq.) (10 mL) at 0° C. and extracted with EtOAc (50 mL×3). The combined organic layers were dried and concentrated. The residue was purified by silica gel (75% EtOAc in hexanes) to afford the desired product (78 mg, 26%) as an orange solid. ESI-MS m/z: 403.8 [M+H]$^+$. $^1$H NMR (CDCl$_3$) δ 9.82 (dd, J=7.1, 1.1 Hz, 1H), 8.38 (s, 1H), 7.90 (dd, J=8.8, 6.6 Hz, 1H), 7.77-7.68 (m, 2H), 7.24-7.15 (m, 1H), 7.01 (t, J=6.7 Hz, 1H), 6.71 (d, J=11.7 Hz, 1H), 6.64 (t, J=8.2 Hz, 1H), 5.95 (ddd, J=22.7, 10.4, 5.3 Hz, 1H), 5.28 (ddt, J=13.3, 3.4, 1.7 Hz, 2H), 3.92 (dt, J=5.6, 1.6 Hz, 2H), 3.40 (t, J=5.3 Hz, 2H), 3.17-3.09 (m, 2H).

Example 29 Step b

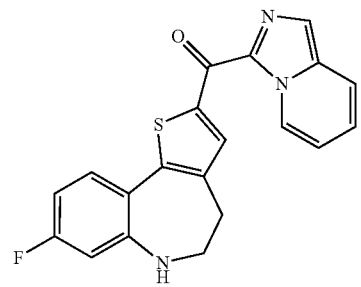 [SMILES: O=C(c1cc2c(s1)-c1ccc(F)cc1NCC2)c1ncc2ccccn12]

Triphenylphosphine (25.7 mg, 0.097 mmol), Pd(OAc)$_2$ (4.4 mg, 0.019 mmol), 1,3-dimethylpyrimidine-2,4,6(1H,3H,5H)-trione (92 mg, 0.583 mmol) and the compound from step a (78.4 mg, 0.194 mmol) were added to a dry vial and it was purged with nitrogen. Then CH$_2$Cl$_2$ (972 µL) was added, the reaction mixture was heated to 35° C. and stirred overnight. After cooling to room temperature, NaHCO$_3$ (aq.) was added to the reaction mixture to adjust the pH to 9-10 and extracted with CH$_2$Cl$_2$ (10 mL×3). The combined organic extracts were washed with brine, dried over anhydrous Na$_2$SO$_4$ and concentrated in vacuo. The residue was purified by silica flash column chromatography (60% EtOAc in hexanes as eluent) afforded the desired product (67 mg, 95% yield) as a yellow solid. ESI-MS m/z: 363.7 [M+H]$^+$. $^1$H NMR (CDCl$_3$) δ 9.81 (d, J=7.2 Hz, 1H), 8.32 (s, 1H), 7.82 (dd, J=8.8, 6.2 Hz, 1H), 7.72 (d, J=14.4 Hz, 2H), 7.26 (s, 4H), 7.23-7.15 (m, 1H), 7.01 (t, J=6.8 Hz, 1H), 6.59 (t, J=7.9 Hz, 1H), 6.49 (d, J=10.3 Hz, 1H), 3.58-3.46 (m, 2H), 3.40-3.27 (m, 1H), 3.20-3.13 (m, 2H).

Example 29 Step c

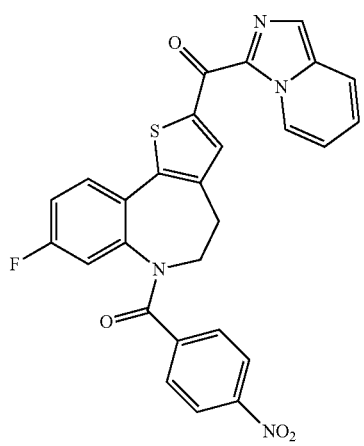 [SMILES: O=C(c1cc2c(s1)-c1ccc(F)cc1N(C(=O)c1ccc([N+](=O)[O-])cc1)CC2)c1ncc2ccccn12]

To solution of 4-nitrobenzoyl chloride (41.9 mg, 0.221 mmol) in CH$_2$Cl$_2$ (1.3 mL) under N$_2$ at rt was added the compound from step b (67 mg, 0.184 mmol) followed by DIPEA (161 µL, 0.922 mmol) and stirred for 3 h at rt. The reaction was quenched with saturated NaHCO$_3$ (aq.) and then extracted with DCM (20 mL×3). The combined organic layeres were washed with brine, dried over sodium sulfate, filtered, and concentrated. The residue was purified by silica flash column chromatography (60% EtOAc in hexanes as eluent) afforded the desired product (15 mg, 16%) as a yellow solid. ESI-MS m/z: 512.8 [M+H]⁺. ¹H NMR (CDCl₃) δ 9.83 (dd, J=7.2, 1.1 Hz, 1H), 8.41 (s, 1H), 7.92 (dd, J=8.8, 5.8 Hz, 1H), 7.81-7.68 (m, 2H), 7.34-7.21 (m, 3H), 7.12-7.03 (m, 1H), 7.05-6.96 (m, 1H), 6.45 (d, J=8.3 Hz, 1H), 5.14-5.05 (m, 1H), 3.73-3.53 (m, 2H), 3.43-3.25 (m, 2H), 3.20 (d, J=17.3 Hz, 1H), 3.10 (qd, J=7.4, 4.2 Hz, 1H).

Example 29 Step d

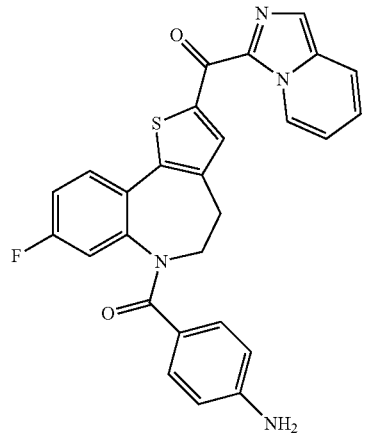

To a 2 ml vial were added the compound from step c (12 mg, 0.023 mmol), iron (6.5 mg, 0.117 mmol) and ammonium chloride (12.52 mg, 0.234 mmol) in EtOH (173 μL) and water (87 μL). The reaction was heated to 80° C. and stirred for 2 h. After cooling to rt, the reaction mixture was filtered through Celite eluting with EtOAc and then concentrated. Aqueous NaHCO₃ was added to adjust pH—8. After extracted with DCM/MeOH (100 mL×3, 10:1), the combined organic layers were washed with brine, dried over Na2SO₄ and concentrated to obtain the desired crude product (11 mg) which (11 mg, crude) was used without further purification for the next step. ESI-MS m/z 483.1 [M+H]⁺.

Example 29 Step e

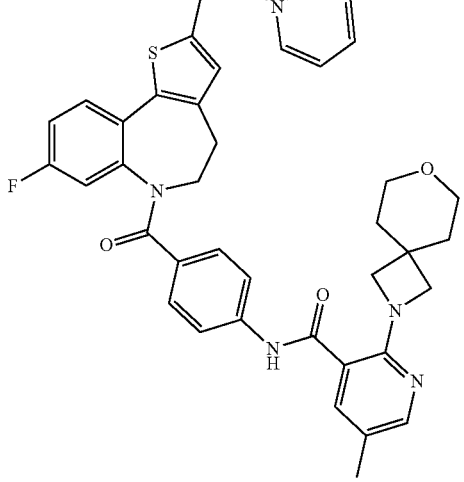

To solution of 5-methyl-2-(7-oxa-2-azaspiro[3.5]nonan-2-yl)nicotinic acid (12.29 mg, 0.047 mmol) in CH₂Cl₂ (156 μL) under N₂ at rt was added 1-chloro-N,N,2-trimethylprop-1-en-1-amine (12.91 μL, 0.094 mmol) and stirred for 1 h at rt. Then the solvent was removed under reduced pressure. The residue was redissolved in CH₂Cl₂ (156 μL) and the compound from step d (11.3 mg, 0.023 mmol) in pyridine (18.94 μL, 0.234 mmol) was added and the reaction mixture was stirred at 35° C. for overnight. After cooling to rt, the crude mixture was filtered through a plug of silica using CH₂Cl₂ as the eluent. The solvent was removed under reduced pressure and purified by reverse phase C18 HPLC (MeCN/H₂O) to obtain the titled compound (3 mg, 18%) as a yellow solid. ESI-MS m/z 727.0 [M+H]⁺. ¹H NMR (CDCl₃) δ 9.83 (d, J=7.2 Hz, 1H), 8.65 (s, 1H), 8.40 (s, 1H), 8.13 (d, J=2.2 Hz, 1H), 7.92 (dd, J=8.9, 5.9 Hz, 1H), 7.85-7.72 (m, 3H), 7.47 (d, J=8.3 Hz, 2H), 7.21 (t, J=7.5 Hz, 2H), 7.07 (t, J=6.9 Hz, 1H), 7.02-6.92 (m, 1H), 6.50 (d, J=8.8 Hz, 1H), 5.14 (s, 1H), 3.75 (s, 4H), 3.57 (t, J=5.2 Hz, 5H), 3.29 (s, 1H), 3.21 (s, 1H), 2.26 (s, 3H), 1.75 (t, J=5.2 Hz, 4H).

Scheme 10

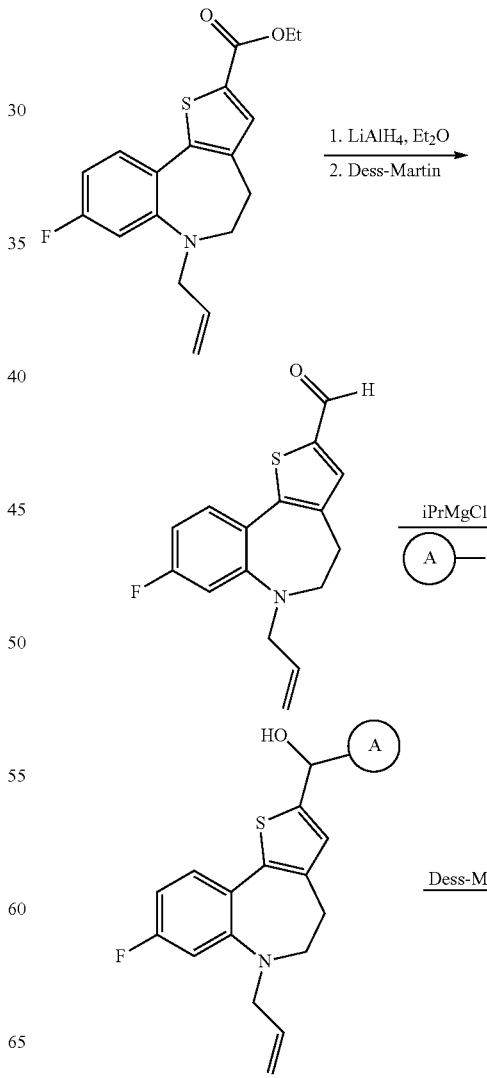

99
-continued
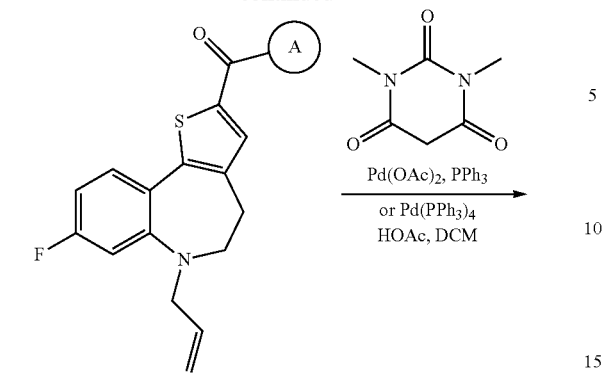
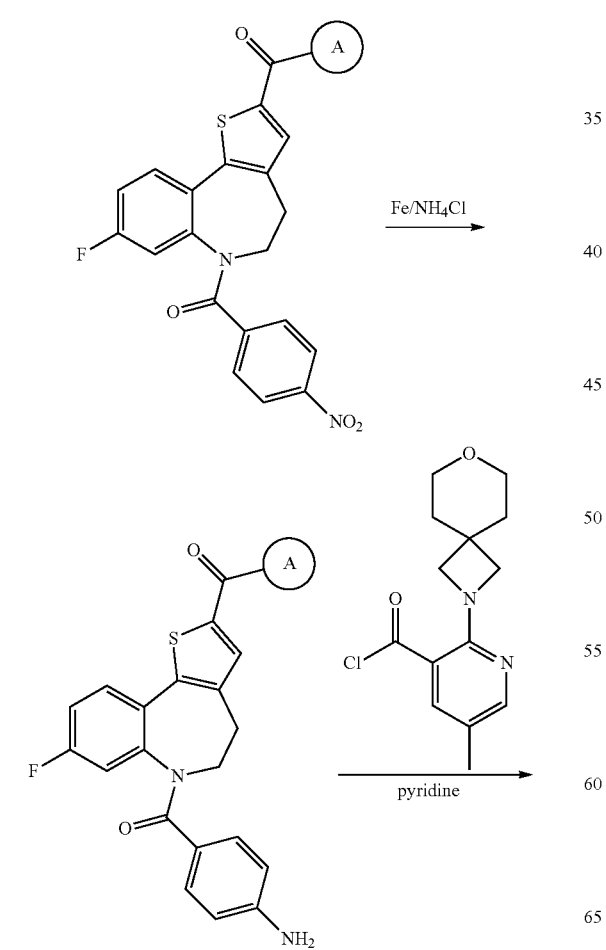
100
-continued
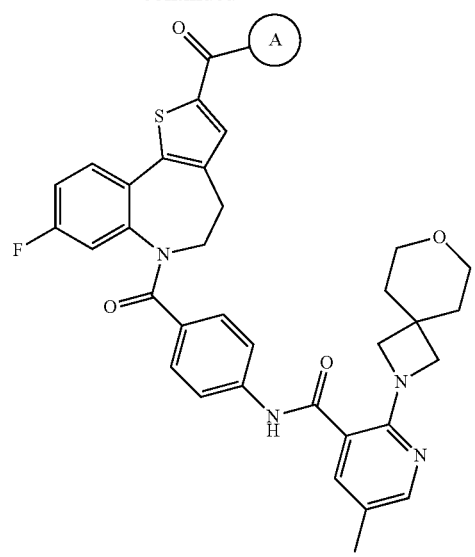
Example 30
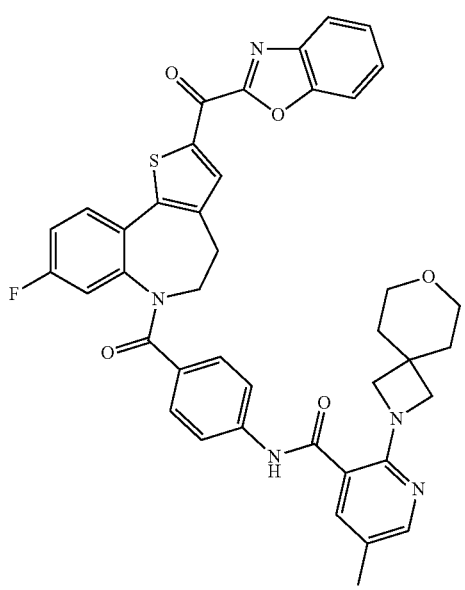 [SMILES: Cc1cnc(N2CC3(CCOCC3)C2)c(C(=O)Nc2ccc(C(=O)N3CCc4cc(C(=O)c5nc6ccccc6o5)sc4-c4ccc(F)cc43)cc2)c1]

Example 30 Step a

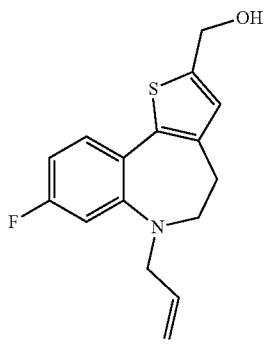 [SMILES: C=CCN1CCc2cc(CO)sc2-c2ccc(F)cc21]

To a solution of ethyl 6-allyl-8-fluoro-5,6-dihydro-4H-benzo[b]thieno[2,3-d]azepine-2-carboxylate (2.07 g, 6.25 mmol) in anhydrous THF (11 mL) at 0° C. was added 1M LiAlH$_4$ solution in THF (6.3 mL) dropwise. The resulting solution is stirred overnight and water is added to quench the reaction. The reaction mixture was stirred at room temperature for 10 min and then 1N HCl (2 mL) added and layers are then separated. The aqueous layer was extracted with EtOAc (100 mL×2). The combined organic layers were washed with water, brine, dried over Na$_2$SO$_4$, and filtered. The filtrate was concentrated and the titled crude compound was obtained (1.8 g, 100%) as a yellow oil. ESI-MS m/z 289.6 [M+H]$^+$. $^1$H NMR (CDCl$_3$) δ 7.62 (dd, J=8.8, 6.5 Hz, 1H), 6.82 (s, 1H), 6.68 (d, J=11.6 Hz, 1H), 6.60 (td, J=8.6, 2.3 Hz, 1H), 5.94 (ddt, J=16.1, 10.6, 5.5 Hz, 1H), 5.33-5.23 (m, 2H), 4.76 (s, 2H), 3.89 (dt, J=5.7, 1.7 Hz, 2H), 3.31 (t, J=5.3 Hz, 2H), 2.98 (t, J=5.4 Hz, 2H), 1.73 (s, 1H).

Example 30 Step b

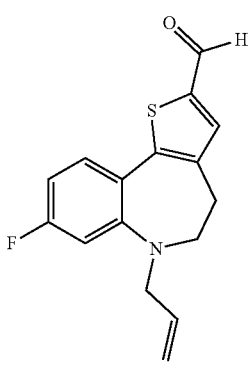 [SMILES: C=CCN1CCc2cc(C=O)sc2-c2ccc(F)cc21]

To a solution of (6-allyl-8-fluoro-5,6-dihydro-4H-benzo[b]thieno[2,3-d]azepin-2-yl)-methanol (1.15 g, 3.97 mmol) in CH$_2$Cl$_2$ (16 mL) at 0° C. was added Dess-Martin periodinane (2.53 g, 5.96 mmol) and the reaction mixture allowed to stir at 0° C. for 2 h. The reaction was quenched by addition of an aqueous solution (12 mL, 1:1) of saturated sodium carbonate and sodium thiosulfate and stirred at rt for 15 min. Then the crude mixture extracted with EtOAc (100 mL×3). The combined organic layers were washed saturated sodium carbonate and sodium thiosulfate (20 mL×3, 1:1), dried over sodium sulfate, filtered, rotovap and loaded into silica gel to obtain the desired product (572 mg, 50.1% yield) as a yellow solid. ESI-MS m/z 287.6 [M+H]$^+$. $^1$H NMR (CDCl$_3$) δ 9.81 (s, 1H), 7.75 (dd, J=8.7, 6.5 Hz, 1H), 7.54 (s, 1H), 6.69-6.57 (m, 2H), 5.92 (ddt, J=17.4, 10.5, 5.3 Hz, 1H), 5.33-5.23 (m, 2H), 3.91 (dt, J=5.4, 1.7 Hz, 2H), 3.39-3.32 (m, 2H), 3.10-3.03 (m, 2H).

Example 30 Step c

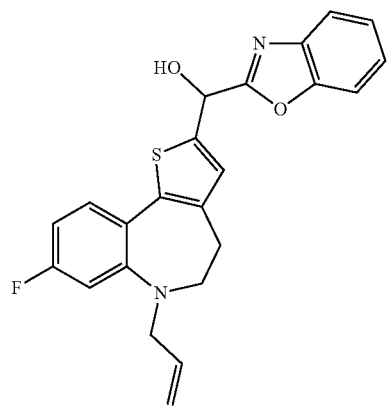 [SMILES: C=CCN1CCc2cc(C(O)c3nc4ccccc4o3)sc2-c2ccc(F)cc21]

To a solution of benzo[d]oxazole (300 mg, 2.468 mmol) in THF (3.3 mL) was added isopropylmagnesium chloride (2.0 M in THF, 1.2 mL, 2.349 mmol) at -20 OC. After stirring for 1 h at -20° C., the compound from step b (150 mg, 0.522 mmol) in THF (1.9 mL) was added and the mixture was stirred for 18 h at which point it was warmed to rt before addition of saturated aq NH$_4$Cl to quench. The mixture was extracted with EtOAc (50 mL×3), the combined organic extracts were washed with brine, dried over sodium sulfate, filtered and concentrated. The residue was purified by silica flash column chromatography (40% EtOAc in hexanes as eluent) afforded the desired product (157 mg, 74%) as a yellow solid. ESI-MS m/z: 406.8 [M+H]$^+$. $^1$H NMR (CDCl$_3$) δ 7.79-7.68 (m, 1H), 7.60 (dd, J=8.7, 6.5 Hz, 1H), 7.59-7.50 (m, 1H), 7.36 (dq, J=9.4, 4.0 Hz, 2H), 6.95 (s, 1H), 6.67-6.51 (m, 2H), 6.18 (s, 1H), 5.98-5.84 (m, 1H), 5.32-5.21 (m, 2H), 3.87 (dt, J=5.6, 1.6 Hz, 2H), 3.27 (dd, J=6.1, 4.7 Hz, 2H), 3.00-2.88 (m, 2H).

Example 30 Step d

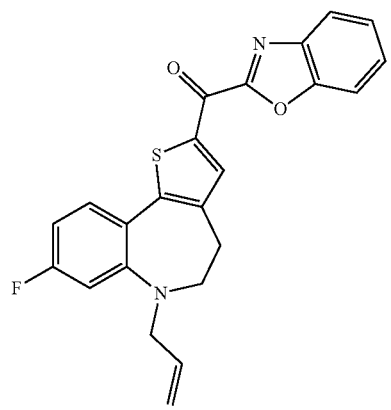 [SMILES: C=CCN1CCc2cc(C(=O)c3nc4ccccc4o3)sc2-c2ccc(F)cc21]

To a solution of the compound from step c (46 mg, 0.113 mmol) in CH$_2$Cl$_2$ (0.57 mL) at 0° C. was added Dess-Martin periodinane (73.5 mg, 0.170 mmol) and the reaction mixture was allowed to stir at 0° C. for 2 h. The reaction was quenched by addition of a solution of saturated sodium carbonate and sodium sulfate (2 mL, 1:1) and stirred at rt for 15 min. Then the crude mixture extracted with EtOAc (20 mL×3). The combined organic layers were washed solution of saturated sodium carbonate and sodium sulfate (10 mL×3, 1:1) dried over sodium sulfate, filtered, and evaporated to give the desired crude compound which was used directly for the next step. ESI-MS m/z: 404.8 [M+H]$^+$. $^1$H NMR (CDCl$_3$) δ 8.52 (s, 1H), 7.96 (dd, J=7.7, 1.2 Hz, 1H), 7.86 (dd, J=8.8, 6.5 Hz, 1H), 7.77-7.68 (m, 1H), 7.59-7.44 (m, 2H), 6.73-6.60 (m, 2H), 6.01-5.86 (m, 1H), 5.34-5.24 (m, 2H), 3.93 (dt, J=5.5, 1.7 Hz, 2H), 3.45-3.33 (m, 2H), 3.19-3.11 (m, 2H).

Example 30 Step e

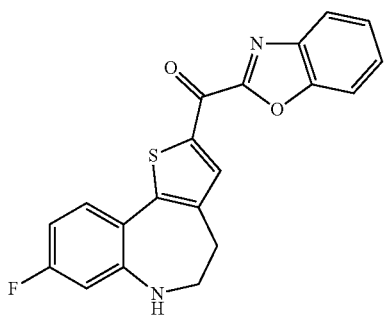 [SMILES: O=C(c1nc2ccccc2o1)c1cc2c(s1)-c1ccc(F)cc1NCC2]

The compound was prepared by the method similar to example 29 step b. ESI-MS m/z: 364.6 [M+H]$^+$. $^1$H NMR (CDCl$_3$) δ 8.45 (s, 1H), 7.95 (d, J=7.9 Hz, 1H), 7.86-7.77 (m, 1H), 7.73-7.43 (m, 3H) 6.54 (ddd, J=8.9, 7.5, 2.6 Hz, 1H), 6.37 (dd, J=10.5, 2.6 Hz, 1H), 4.65 (s, 1H), 3.52 (q, J=4.3 Hz, 2H), 3.21-3.15 (m, 2H).

Example 30 Step f

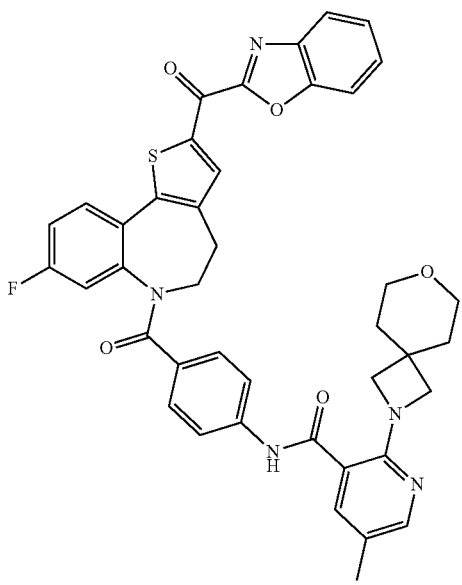 [SMILES: Cc1cnc(N2CC3(CCOCC3)C2)c(C(=O)Nc2ccc(C(=O)N3CCc4cc(C(=O)c5nc6ccccc6o5)sc4-c4ccc(F)cc43)cc2)c1]

To a solution of 4-(5-methyl-2-(7-oxa-2-azaspiro[3.5]nonan-2-yl)nicotinamido)benzoic acid (83 mg, 0.206 mmol) in CH$_2$Cl$_2$ (0.46 mL) under N$_2$ at rt was added 1-chloro-N,N,2-trimethylprop-1-en-1-amine (57 μL, 0.412 mmol) and stirred for 1 h at rt. Then the solvent was removed under reduced pressure and the crude acid chloride dried in vacuo. The residue was redissolved in pyridine (0.46 mL) and the compound from step e (25 mg, 0.069 mmol) was added and the reaction mixture was stirred overnight at 80° C. After cooling to rt, the solvent was removed under reduced pressure and filtered through silica gel. After removed the solvent, the residue was purified by reverse phase C18 HPLC (MeCN/H$_2$O) to give the desired compound (6.5 mg, 13%) as a pale orange solid. ESI-MS m/z: 728.0 [M+H]$^+$. $^1$H NMR (CDCl$_3$) δ 8.67 (s, 1H), 8.60 (s, 1H), 8.14 (s, 1H), 8.00 (d, J=7.9 Hz, 1H), 7.90 (dd, J=8.9, 5.8 Hz, 1H), 7.82 (s, 1H), 7.74 (d, J=8.2 Hz, 1H), 7.63-7.46 (m, 5H), 7.20 (d, J=8.4 Hz, 2H), 7.06-6.96 (m, 1H), 6.54 (d, J=8.8 Hz, 1H), 5.16 (s, 1H), 3.76 (s, 4H), 3.58 (s, 4H), 3.58 (d, J=10.6 Hz, 1H), 3.26 (s, 2H), 2.27 (s, 3H), 2.02 (s, 3H), 1.75 (t, J=5.2 Hz, 4H).

Example 31

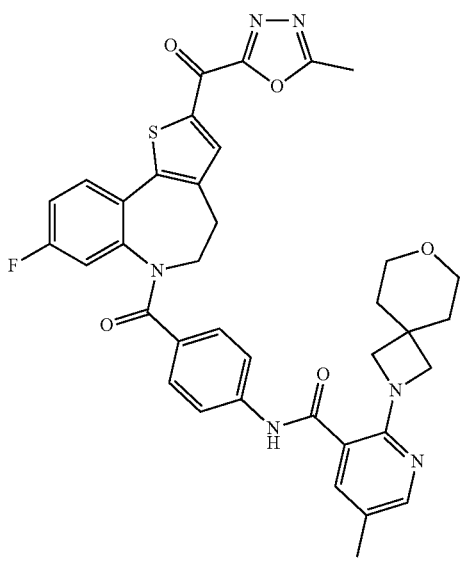 [SMILES: Cc1cnc(N2CC3(CCOCC3)C2)c(C(=O)Nc2ccc(C(=O)N3CCc4cc(C(=O)c5nnc(C)o5)sc4-c4ccc(F)cc43)cc2)c1]

Example 31 was prepared using a procedure similar to that used to prepare example 30 where 2-methyl-1,3,4-oxadiazole was used in place of benzo[d]oxazole. ESI-MS m/z: 693.1 [M+H]$^+$. $^1$H NMR (, CDCl$_3$) δ 8.67 (s, 1H), 8.57 (s, 1H), 8.17-8.11 (m, 1H), 7.90-7.79 (m, 2H), 7.49 (d, J=8.5 Hz, 2H), 7.18 (d, J=8.5 Hz, 2H), 6.57-6.49 (m, 1H), 5.15 (s, 1H), 3.76 (s, 4H), 3.58 (t, J=5.2 Hz, 4H), 3.30 (s, 1H), 3.21 (s, 1H), 2.71 (s, 3H), 2.27 (s, 3H), 1.75 (t, J=5.3 Hz, 4H).

Scheme 11

Example 32

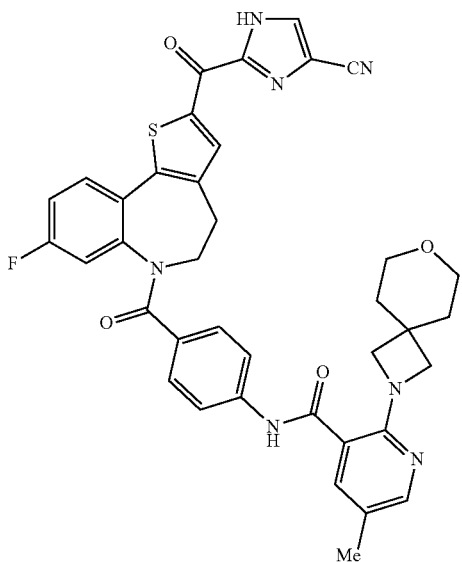 [SMILES: Cc1cnc(N2CC3(CCOCC3)C2)c(C(=O)Nc2ccc(C(=O)N3CCc4cc(C(=O)c5nc(C#N)c[nH]5)sc4-c4ccc(F)cc43)cc2)c1]

Example 32 Step a

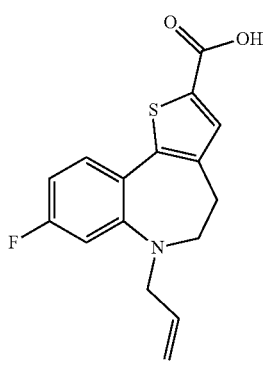 [SMILES: C=CCN1CCc2cc(C(=O)O)sc2-c2ccc(F)cc21]

To a solution of ethyl 6-allyl-8-fluoro-5,6-dihydro-4H-benzo[b]thieno[2,3-d]azepine-2-carboxylate (1.20 g, 3.62 mmol) in THF (12 mL), MeOH (12 mL) and water (12 mL) was added LiOH (0.87 g, 36.2 mmol) and stirred overnight at rt. Then it was diluted with water and the pH was adjusted to 2-3 by addition of aqueous HCl. After extracted with EtOAc (50 mL×3), the combined organic extracts were washed with brine, dried over sodium sulfate, filtered, and concentrated to give the desired compound (1.1 g, 100%) as a yellowish solid. ESI-MS m/z: 304.7 [M+H]⁺. ¹H NMR (CDCl₃) δ 7.72 (dd, J=8.8, 6.5 Hz, 1H), 7.66 (s, 1H), 6.69-6.56 (m, 2H), 5.92 (ddt, J=17.8, 10.4, 5.3 Hz, 1H), 5.28 (dq, J=14.1, 1.8 Hz, 2H), 3.91 (dt, J=5.5, 1.6 Hz, 2H), 3.34 (dd, J=6.1, 4.6 Hz, 2H), 3.08-3.00 (m, 2H).

Example 32 Step b

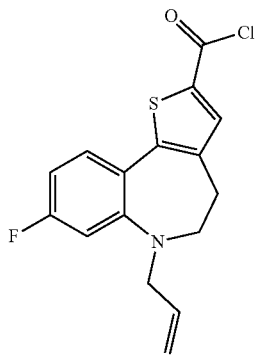 [SMILES: C=CCN1CCc2cc(C(=O)Cl)sc2-c2ccc(F)cc21]

To a solution of the compound from step a (260 mg, 0.857 mmol) in DCM (2.1 mL) was added 1-chloro-N,N,2-trimethylprop-1-en-1-amine (236 µL, 1.71 mmol). The resulting mixture was stirred at rt for 1 h. The solvent was removed under reduced pressure and the crude acid chloride dried under high vacuum was used directly without further purification.

Example 32 Step c

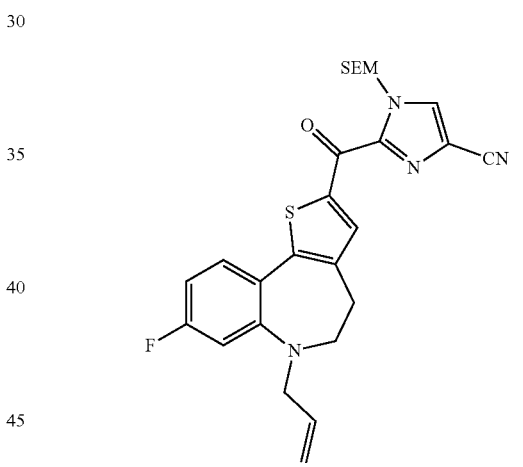

To a solution of 2-bromo-1-((2-(trimethylsilyl)ethoxy)methyl)-1H-imidazole-4-carbonitrile (150 mg, 0.496 mmol) in THF (2 mL) at −20° C. was added isopropylmagnesium chloride (2.0M in THF, 434 µL, 0.868 mmol) and stirred for 20 min before it was cooled to −78° C. Then the compound from step b (271 mg, 0.844 mmol) in THF (1.3 mL) was added to the reaction mixture dropwise and stirred for 16 h at which point it was warmed to room temperature. The reaction mixture was quenched with saturated NH₄Cl solution, extracted with EtOAc (30 mL×3). The combined organic layers were dried over Na₂SO₄, filtered, and concentrated. The crude residue purified by silica gel (20% EtOAc in hexanes as the eluent) to obtain the desired product (146 mg, 58%) as an orange oil. ESI-MS m/z: 509.2 [M+H]⁺. ¹H NMR (CDCl₃) δ 8.36 (s, 1H), 7.89-7.78 (m, 2H), 6.69-6.57 (m, 2H), 5.92 (ddt, J=16.8, 10.2, 5.2 Hz, 1H), 5.85 (s, 2H), 5.33-5.23 (m, 2H), 3.92 (dt, J=5.4, 1.7 Hz, 2H), 3.69-3.60 (m, 2H), 3.37 (dd, J=6.1, 4.5 Hz, 2H), 3.14-3.06 (m, 2H), 1.02-0.93 (m, 2H), −0.00 (s, 6H).

Example 32 Step d

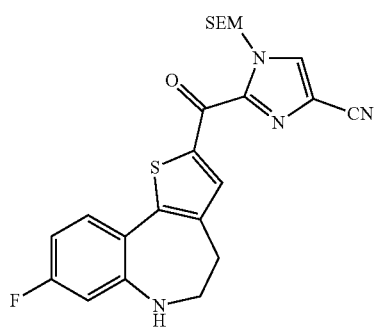 [SMILES: C[Si](C)(C)CCOCn1cc(C#N)nc1C(=O)c1cc2c(s1)-c1ccc(F)cc1NCC2]

The compound was prepared by the method similar to example 29 step b. ESI-MS m/z: 469.2 [M+H]+. 1H NMR (CDCl3) δ 8.29 (s, 1H), 7.85 (s, 1H), 7.76 (dd, J=8.9, 6.2 Hz, 1H), 6.53 (ddd, J=8.9, 7.6, 2.6 Hz, 1H), 6.36 (dd, J=10.5, 2.5 Hz, 1H), 5.85 (s, 2H), 4.57 (s, 1H), 3.69-3.60 (m, 2H), 3.61-3.46 (m, 2H), 3.19-3.11 (m, 2H), 1.02-0.91 (m, 2H), −0.00 (s, 9H).

Example 32 Step e

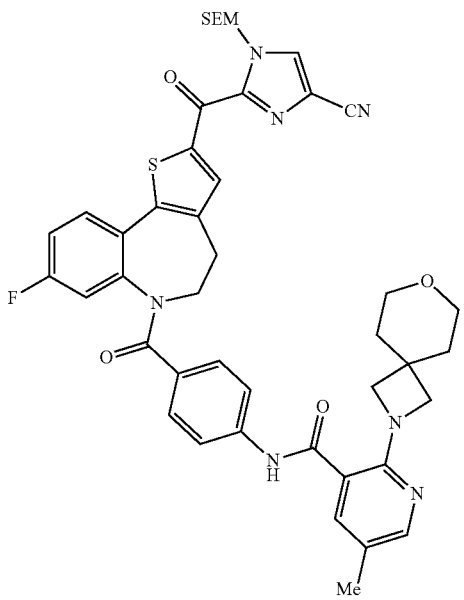 [SMILES: Cc1cnc(N2CC3(CCOCC3)C2)c(C(=O)Nc2ccc(C(=O)N3CCc4cc(C(=O)c5nc(C#N)cn5COCC[Si](C)(C)C)sc4-c4ccc(F)cc43)cc2)c1]

Compound from step d (45 mg, 0.096 mmol), 4-(5-methyl-2-(7-oxa-2-azaspiro[3.5]nonan-2-yl)nicotinamido)benzoic acid (96 mg, 0.240 mmol), 1-chloro-N,N,2-trimethylprop-1-en-1-amine (66.2 μL, 0.480 mmol) and 2-(8-fluoro-5,6-dihydro-4H-benzo[b]thieno[2,3-d]azepine-2-carbonyl)-1-((2-(trimethylsilyl)ethoxy)methyl)-1H-imidazole-4-carbonitrile were used in a procedure similar to that of example 1 step c. The titled compound was isolated (20.4 mg, 26%) as an off-white solid. ESI-MS m/z: 833.2 [M+H]+. 1H NMR (CDCl3) δ 8.66 (s, 1H), 8.38 (s, 1H), 8.14 (s, 1H), 7.92-7.79 (m, 3H), 7.48 (d, J=8.2 Hz, 2H), 7.18 (d, J=8.3 Hz, 2H), 7.00 (t, J=7.8 Hz, 1H), 6.52 (d, J=8.5 Hz, 1H), 5.87 (s, 2H), 5.13 (s, 1H), 3.76 (s, 5H), 3.72-3.63 (m, 2H), 3.58 (s, 6H), 3.31 (s, 5H), 3.19 (s, 1H), 2.27 (s, 4H), 1.75 (t, J=5.3 Hz, 5H), 0.96 (dt, J=21.3, 7.9 Hz, 2H), 0.01 (d, J=0.9 Hz, 9H).

Example 32 Step f

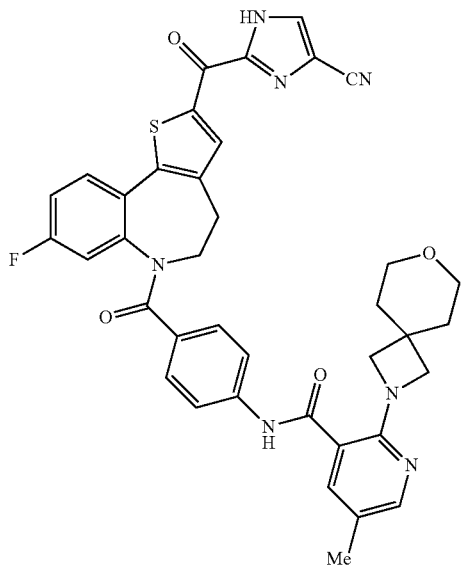 [SMILES: Cc1cnc(N2CC3(CCOCC3)C2)c(C(=O)Nc2ccc(C(=O)N3CCc4cc(C(=O)c5nc(C#N)c[nH]5)sc4-c4ccc(F)cc43)cc2)c1]

The compound was prepared by the method similar to example 3 step c. ESI-MS m/z: 703.0 [M+H]+. 1H NMR (CDCl3) δ 8.53 (s, 1H), 7.89-7.80 (m, 2H), 7.78-7.69 (m, 2H), 7.49 (d, J=8.4 Hz, 2H), 7.14 (d, J=8.6 Hz, 2H), 7.06-6.83 (m, 1H), 6.50 (d, J=8.7 Hz, 1H), 5.09 (s, 1H), 3.87 (s, 4H), 3.54 (t, J=5.2 Hz, 4H), 3.39 (p, J=1.6 Hz, 1H), 3.29 (s, 1H), 3.19 (s, 1H), 2.22 (s, 3H), 1.73 (t, J=5.2 Hz, 4H).

Example 33

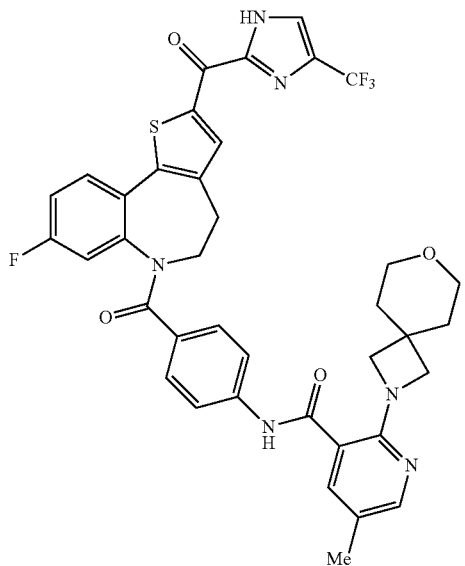

Example 33 was prepared using a procedure similar to that used to prepare example 32 where 2-bromo-4-(trifluoromethyl)-1-((2-(trimethylsilyl)ethoxy)methyl)-1H-imidazole was used in place of 2-bromo-1-((2-(trimethylsilyl)ethoxy)methyl)-1H-imidazole-4-carbonitrile. ESI-MS m/z: 745.0 [M+H]+. 1H NMR (CDCl3) δ 8.83 (s, 1H), 8.61 (s, 1H), 8.02 (s, 1H), 7.85 (dd, J=8.8, 5.8 Hz, 1H), 7.78 (s, 1H), 7.63 (s, 1H), 7.48 (d, J=8.4 Hz, 2H), 7.16 (d, J=8.4 Hz, 2H), 6.53 (d, J=9.0 Hz, 1H), 5.20-5.06 (m, 1H), 3.91 (s, 3H), 3.55 (d, J=5.5 Hz, 4H), 3.40-3.11 (m, 2H), 2.24 (s, 3H), 2.19-2.10 (m, 1H), 1.75 (t, J=5.2 Hz, 4H).
Example 34
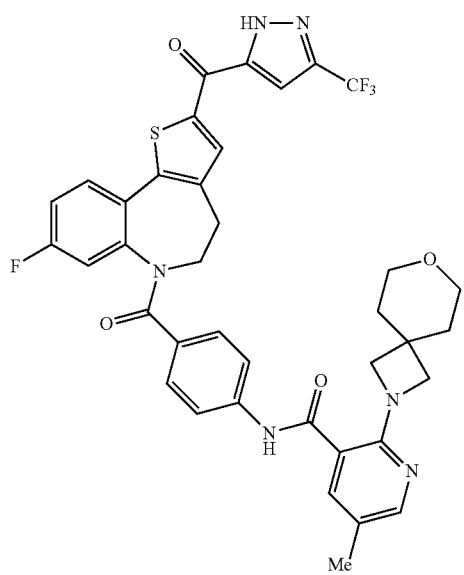 [SMILES: Cc1cnc(N2CC3(CCOCC3)C2)c(C(=O)Nc2ccc(C(=O)N3CCc4cc(C(=O)c5cc(C(F)(F)F)n[nH]5)sc4-c4ccc(F)cc43)cc2)c1]
Scheme 12
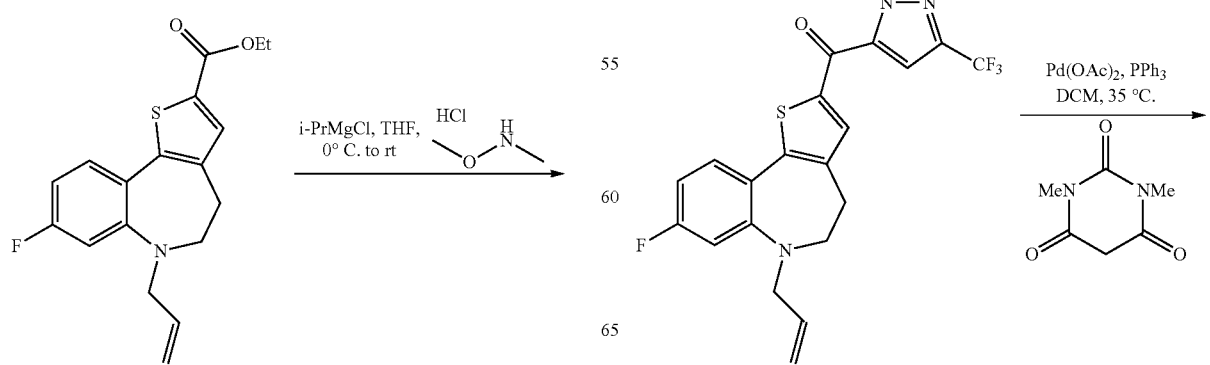
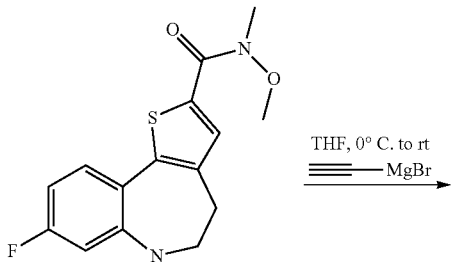

113

-continued

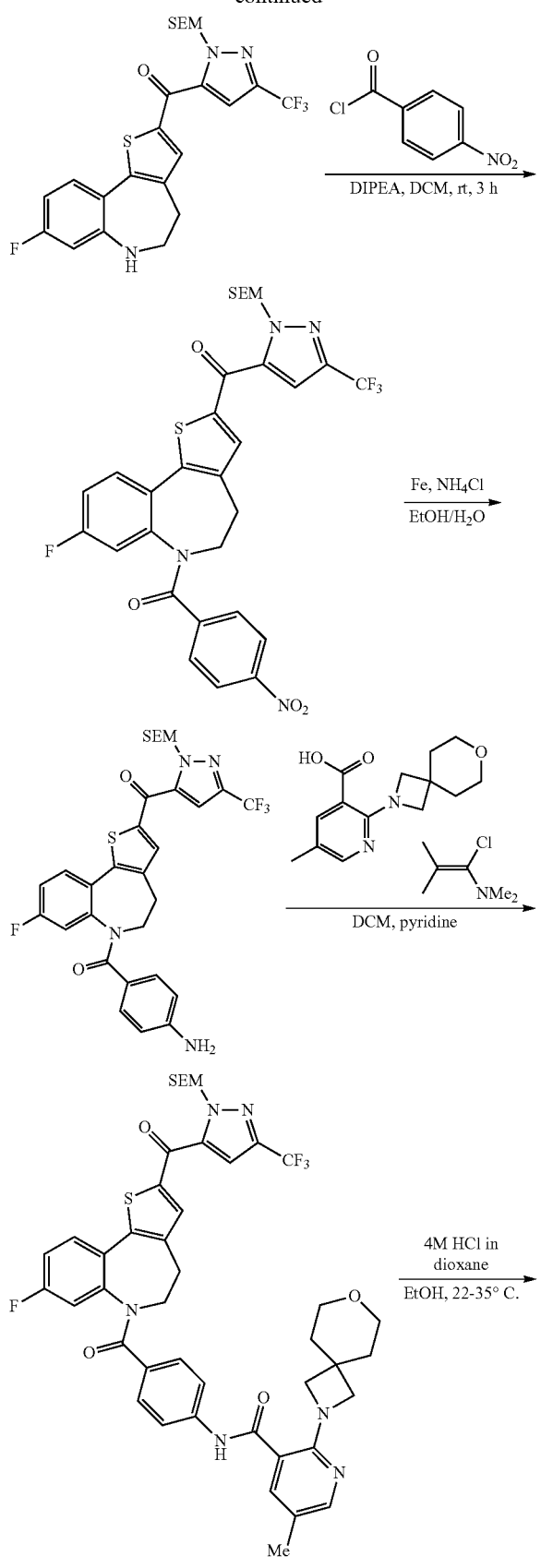

114

-continued

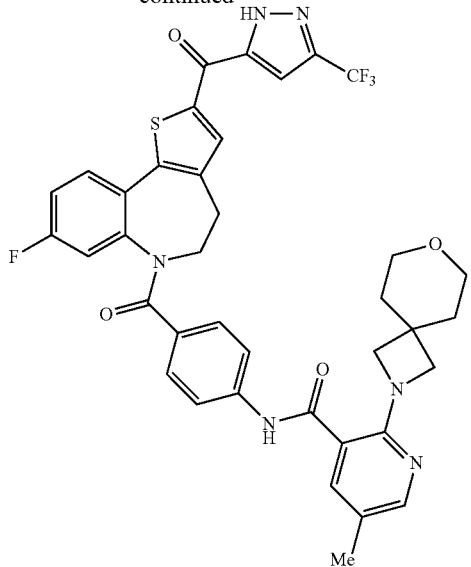

Example 34 Step a

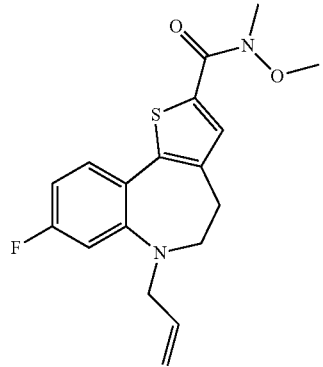 [SMILES: C=CCN1CCc2cc(C(=O)N(C)OC)sc2-c2ccc(F)cc21]

Ethyl 6-allyl-8-fluoro-5,6-dihydro-4H-benzo[b]thieno[2,3-d]azepine-2-carboxylate (0.75 g, 2.26 mmol) and N,O-dimethylhydroxylamine hydrochloride (0.45 g, 4.53 mmol) were dissolved in THF (9 mL). The solution was cooled to 0° C. and treated with isopropylmagnesium chloride (2.0 M in THF, 5.1 mL, 10.18 mmol) was added slowly over 20 min. The reaction mixture was stirred at 0° C. for 1 h before being quenched by addition of saturated aq. NH$_4$Cl. The aqueous layer was washed with EtOAc and the combined organic layer was washed with brine, dried over MgSO$_4$ and concentrated to afford the desired product (614 mg, 78%) as a white solid with a yellow tint. ESI-MS m/z: 346.9 [M+H]$^+$. $^1$H NMR (CDCl$_3$) δ 7.74 (s, 2H), 7.74 (d, J=15.3 Hz, 1H), 6.69-6.55 (m, 2H), 6.00-5.85 (m, 1H), 5.34-5.23 (m, 2H), 3.90 (dt, J=5.4, 1.7 Hz, 2H), 3.80 (s, 3H), 3.40-3.29 (m, 6H), 3.07-3.00 (m, 2H).

Example 34 Step b

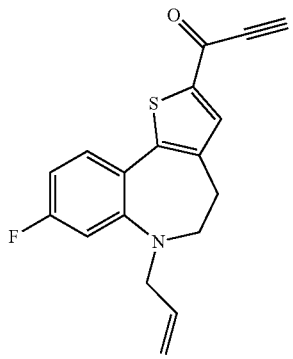 [SMILES: C#CC(=O)c1cc2c(s1)-c1ccc(F)cc1N(CC=C)CC2]

Ethynylmagnesium bromide (0.5M in THF, 2.97 mL, 1.44 mmol) was added to a solution of the compound from step a (250 mg, 0.722 mmol) in THF (4.8 mL) at 0° C. After stirring at room temperature for 18 hrs, the reaction mixture was quenched by addition of saturated aq. NH$_4$Cl. The reaction mixture was extracted with EtOAc (50 mL×3), the combined organic extracts were washed with brine, dried over sodium sulfate, filter, and concentrated. The residue was purified by silica gel column chromatography (eluent 40% EtOAc in hexanes) to obtain the desired product (100 mg, 44.5% yield) as an orange solid. ESI-MS m/z: 311.7 [M+H]$^+$. $^1$H NMR (CDCl$_3$) δ 7.78-7.70 (m, 2H), 6.68-6.56 (m, 2H), 5.91 (ddt, J=16.3, 10.7, 5.3 Hz, 1H), 5.33-5.23 (m, 2H), 3.91 (dt, J=5.3, 1.7 Hz, 2H), 3.35 (dd, J=6.1, 4.6 Hz, 2H), 3.32 (s, 1H), 3.10-3.02 (m, 2H).

Example 34 Step c

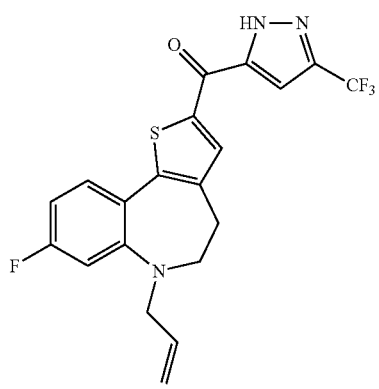 [SMILES: C=CCN1CCc2cc(C(=O)c3cc(C(F)(F)F)n[nH]3)sc2-c2ccc(F)cc21]

To a dry 2 dram vial was added the compound from step b (75 mg, 0.24 mmol) and purged with nitrogen. Then it was dissolved in toluene (602 µL) and a solution of 2-diazo-1,1,1-trifluoroethane (1445 µL, 0.723 mmol) in toluene was added. The reaction mixture was stirred at room temperature for overnight, and the solvent was removed under reduced pressure. The crude residue was purified by silica gel column chromatography to afford the desired product as a yellow solid. ESI-MS m/z: 421.8 [M+H]$^+$. $^1$H NMR (CDCl$_3$) δ 11.18 (s, 1H), 7.84-7.75 (m, 2H), 7.25 (s, 1H), 6.71-6.59 (m, 2H), 5.93 (ddt, J=16.2, 10.7, 5.3 Hz, 1H), 5.35-5.25 (m, 2H), 3.93 (dt, J=5.3, 1.7 Hz, 2H), 3.43-3.35 (m, 2H), 3.15-3.07 (m, 2H).

Example 34 Step d

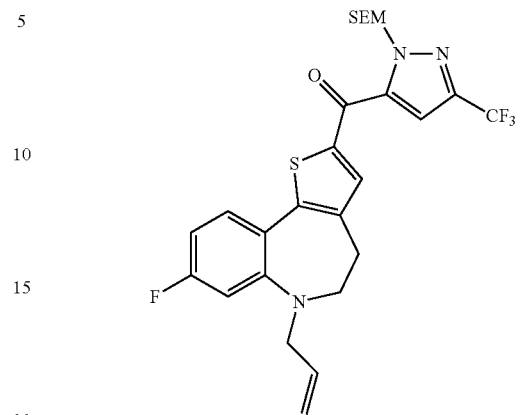

To a solution of the compound from step c (110 mg, 0.261 mmol) in DMF (2 mL) at 0° C. was added sodium hydride (13.05 mg, 0.326 mmol) and stirred at 0° C. for 30 min. Then SEM-Cl (81 µL, 0.457 mmol) was added dropwise and the reaction mixture was allowed to warm to room temperature and stirred for overnight. It was diluted in EtOAc and washed with water and brine. The organic layer was dried over sodium sulfate, filtered, and concentrated in vacuuo. The crude residue was purified by silica gel column chromatography to obtain the desired product (135 mg, 94%) as a yellow oil. ESI-MS m/z: 552.2 [M+H]$^+$. $^1$H NMR (CDCl$_3$) δ 7.79 (ddd, J=15.5, 8.7, 6.5 Hz, 1H), 7.35 (s, 1H), 7.22 (s, 1H), 6.63 (dddd, J=18.7, 10.1, 6.1, 2.3 Hz, 2H), 5.92 (ddt, J=17.8, 10.5, 5.4 Hz, 1H), 5.85 (s, 1H), 5.68 (s, 2H), 5.34-5.25 (m, 2H), 3.92 (d, J=5.1 Hz, 2H), 3.69 (dd, J=8.9, 7.6 Hz, 2H), 3.63-3.56 (m, 1H), 3.37 (t, J=5.3 Hz, 2H), 3.08 (q, J=4.8 Hz, 2H), 0.99-0.92 (m, 2H), 0.89-0.82 (m, 1H), −0.02 (d, J=1.1 Hz, 9H).

Example 34 Step e

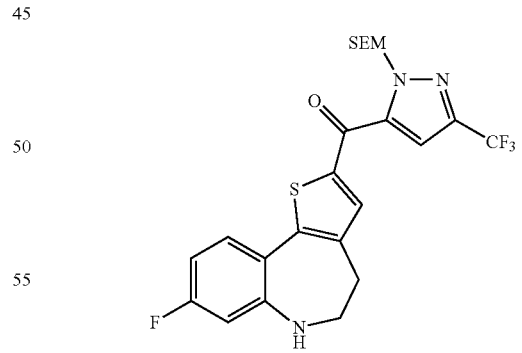

The compound was prepared by a method similar to example 29 step b. ESI-MS m/z: 512.1 [M+H]$^+$. $^1$H NMR (CDCl$_3$) δ 8.13 (s, 1H), 7.72 (ddd, J=14.6, 8.9, 6.2 Hz, 2H), 7.35 (s, 1H), 6.59-6.48 (m, 1H), 6.37 (ddd, J=10.5, 4.0, 2.5 Hz, 1H), 5.85 (s, 1H), 5.68 (s, 2H), 4.53 (s, 1H), 3.78-3.65 (m, 2H), 3.64-3.55 (m, 1H), 3.50 (t, J=5.0 Hz, 3H), 3.12 (q, J=4.7 Hz, 3H), 1.00-0.89 (m, 2H), 0.90-0.81 (m, 1H), −0.02 (s, 9H).

Example 34 Step f

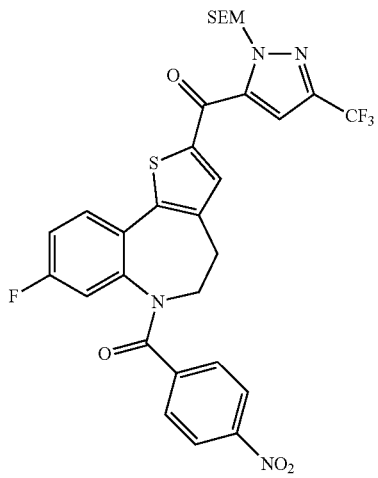

The compound was prepared by a method similar to example 29 step c. ESI-MS m/z: 661.2 [M+H]; $^1$H NMR (CDCl$_3$) δ 8.32 (s, 1H), 8.06 (t, J=7.9 Hz, 3H), 7.83 (dt, J=8.8, 5.7 Hz, 2H), 7.39 (s, 1H), 7.29 (d, J=8.4 Hz, 3H), 7.09-6.98 (m, 1H), 6.47 (d, J=8.3 Hz, 2H), 5.89 (d, J=9.2 Hz, 1H), 5.71 (s, 2H), 5.08 (s, 1H), 3.76-3.67 (m, 2H), 3.58 (d, J=18.9 Hz, 2H), 3.39 (d, J=12.7 Hz, 1H), 3.17 (d, J=16.7 Hz, 2H), 1.02-0.93 (m, 2H), −0.01 (s, 9H).

Example 34 Step g

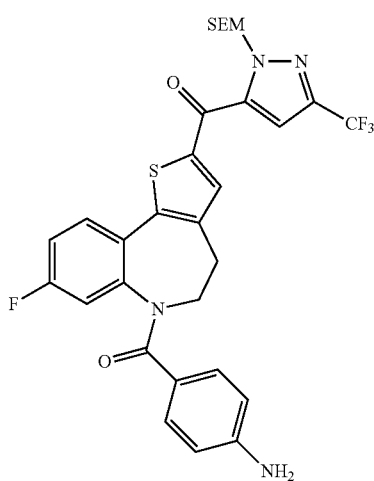 [SMILES: C[Si](C)(C)CCOCn1nc(C(F)(F)F)cc1C(=O)c1cc2c(s1)-c1ccc(F)cc1N(C(=O)c1ccc([N+](=O)[O-])cc1)CC2]

The compound was prepared by a method similar to example 29 step d. ESI-MS m/z: 631.2 [M+H]$^+$. $^1$H NMR (CDCl$_3$) δ 8.29 (s, 1H), 7.81 (td, J=9.0, 5.9 Hz, 2H), 7.38 (s, 1H), 7.02-6.90 (m, 5H), 6.58-6.49 (m, 1H), 6.46-6.37 (m, 3H), 5.87 (s, 1H), 5.70 (s, 2H), 5.13 (s, 1H), 3.83 (d, J=8.3 Hz, 3H), 3.75-3.66 (m, 2H), 3.65-3.56 (m, 1H), 3.25 (s, 6H), 1.01-0.92 (m, 2H), 0.91-0.82 (m, 1H), −0.01 (s, 9H).

Example 34 Step h

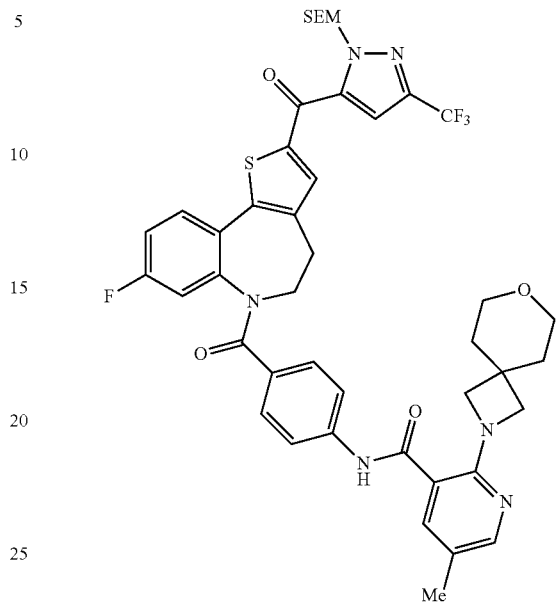

The compound was prepared by the method similar to example 29 step e. ESI-MS m/z: 875.2 [M+H]; $^1$H NMR (CDCl$_3$) δ 8.74 (s, 1H), 7.88-7.75 (m, 2H), 7.68 (d, J=9.9 Hz, 2H), 7.52 (d, J=8.4 Hz, 2H), 7.19 (d, J=7.2 Hz, 3H), 7.09-6.99 (m, 1H), 6.53 (d, J=8.7 Hz, 1H), 5.88 (d, J=7.2 Hz, 2H), 5.13 (s, 1H), 4.04 (s, 4H), 3.61 (dd, J=17.6, 9.1 Hz, 7H), 3.34 (s, 1H), 3.19 (s, 1H), 2.26 (s, 3H), 0.92-0.83 (m, 2H), −0.07 (s, 9H).

Example 34 Step i

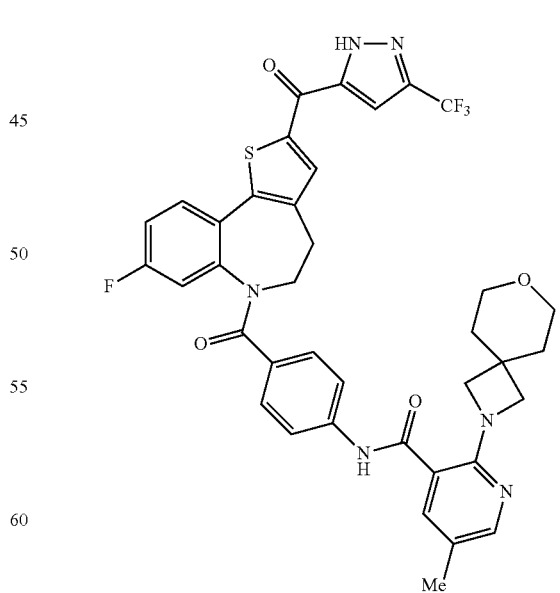

The compound was prepared by the method similar to example 13 step d. ESI-MS m/z: 745.2 [M+H]$^+$. $^1$H NMR (CDCl$_3$) δ 9.07 (s, 1H), 8.02 (s, 1H), 7.93 (s, 1H), 7.85-7.73

(m, 2H), 7.49 (d, J=8.4 Hz, 2H), 7.15 (d, J=8.3 Hz, 2H), 6.99 (t, J=8.4 Hz, 1H), 6.51 (d, J=9.0 Hz, 1H), 5.12 (s, 1H), 3.88 (s, 3H), 3.54 (s, 4H), 3.45 (s, 3H), 3.28 (s, 1H), 3.17 (s, 1H), 2.21 (s, 3H), 2.18-2.07 (m, 4H), 1.73 (t, J=5.2 Hz, 4H), 1.22 (s, 3H).
Example 35
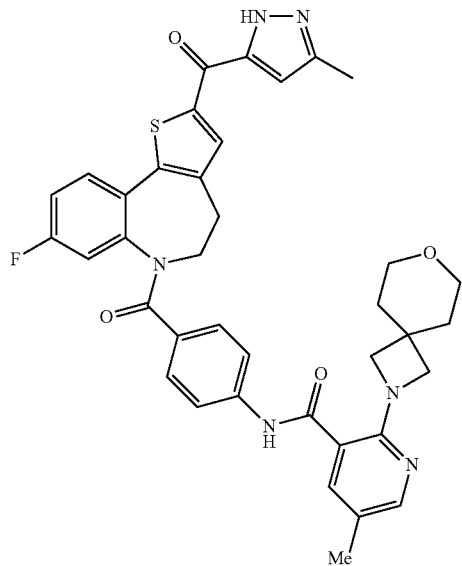 [SMILES: Cc1cnc(N2CC3(CCOCC3)C2)c(C(=O)Nc2ccc(C(=O)N3CCc4cc(C(=O)c5cc(C)n[nH]5)sc4-c4ccc(F)cc43)cc2)c1]
Example 35 was prepared using a procedure similar to that used to prepare example 34 where diazoethane was used in place of 2-diazo-1,1,1-trifluoroethane in example 34 step c. ESI-MS m/z: 691.0 [M+H]$^+$. $^1$H NMR (CDCl$_3$) δ 10.18 (s, 1H), 9.71 (s, 1H), 8.14 (s, 1H), 7.85-7.76 (m, 2H), 7.73 (s, 1H), 7.57 (d, J=8.3 Hz, 2H), 7.12 (d, J=8.4 Hz, 2H), 7.00 (td, J=8.5, 2.7 Hz, 1H), 6.72 (d, J=0.9 Hz, 1H), 6.52 (d, J=8.8 Hz, 1H), 5.06 (s, 1H), 4.03 (s, 4H), 3.69 (pd, J=6.6, 3.7 Hz, 2H), 3.54 (s, 4H), 3.41 (s, 1H), 3.32 (s, 1H), 3.12 (qd, J=7.0, 3.9 Hz, 2H), 2.42 (s, 3H), 2.14 (s, 3H), 1.75 (t, J=5.1 Hz, 4H).
Scheme 13
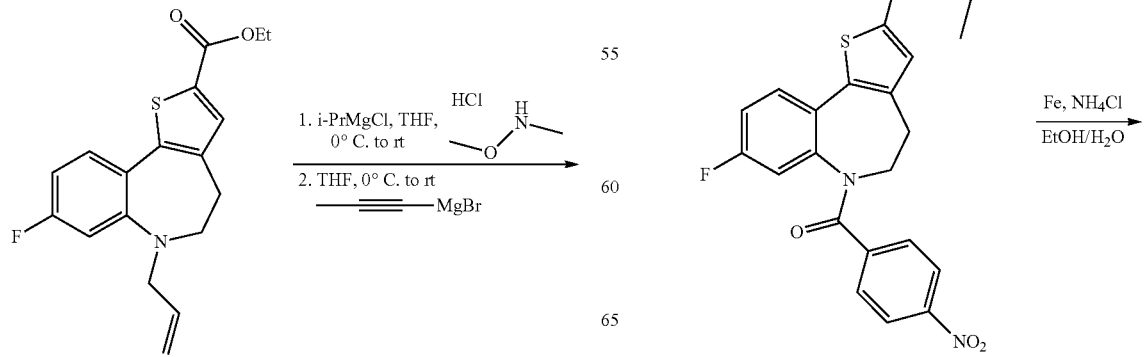
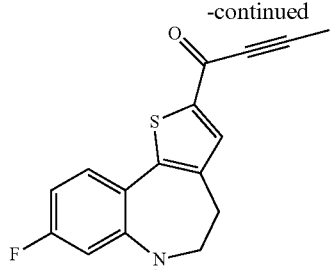
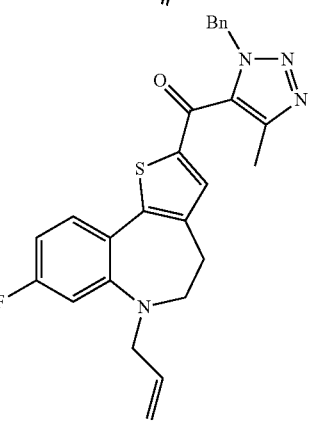
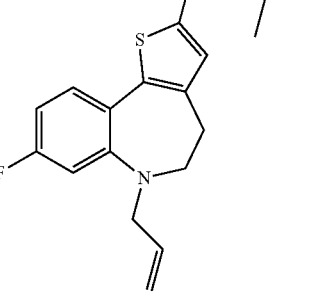
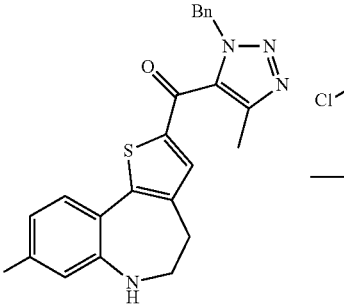
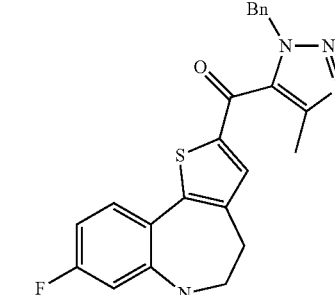
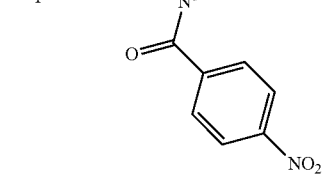

122

Example 36

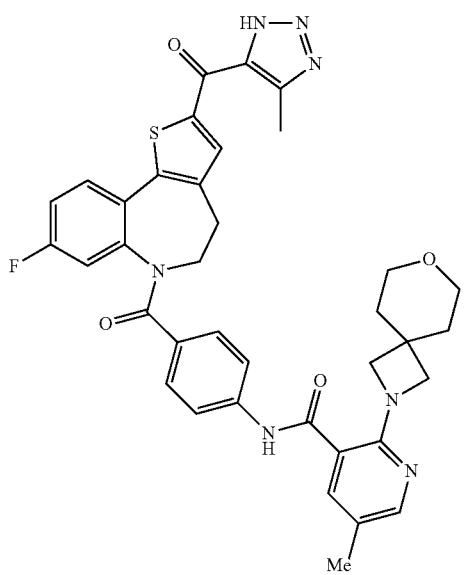

Example 36 Step a

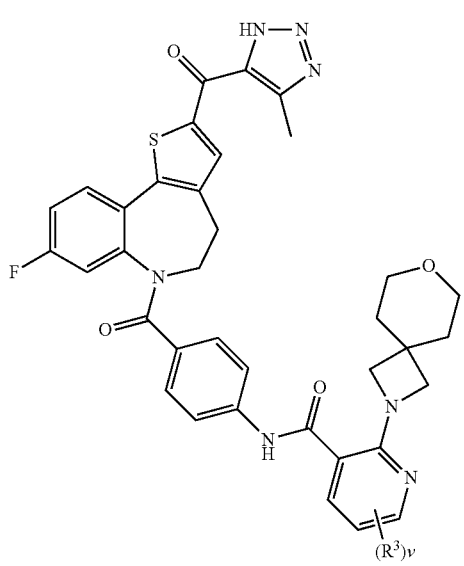

1-Propynylmagnesium bromide (0.5M in THF, 4.62 mL, 2.31 mmol) was added to a solution of 6-allyl-8-fluoro-N-methoxy-N-methyl-5,6-dihydro-4H-benzo[b]thieno[2,3-d]azepine-2-carboxamide (400 mg, 1.16 mmol) in THF (8 mL) at 0° C. After stirring for 18 h at which point it had warmed to room temperature the reaction was quenched by addition of saturated aq NH₄Cl. The mixture was extracted with EtOAc (50 mL×3), and the combined organic extracts were washed with brine, dried over sodium sulfate, filtered, and concentrated. The residue was purified by silica gel column chromatography (eluent 40% EtOAc in hexanes) to afford the desired product (288 mg, 77%) as a brownish oil. ESI-MS m/z: 325.7 [M+H]⁺. ¹H NMR (CDCl₃) δ 7.74 (dd, J=8.8, 6.5 Hz, 1H), 7.67 (s, 1H), 6.68-6.55 (m, 2H), 5.92 (ddt, J=17.4, 10.4, 5.3 Hz, 1H), 5.31-5.29 (m, 1H), 5.26 (dq, J=5.9, 1.5 Hz, 1H), 3.91 (dt, J=5.4, 1.6 Hz, 2H), 3.38-3.31 (m, 2H), 3.05 (dd, J=6.1, 4.6 Hz, 2H), 2.14 (s, 3H).

121

-continued

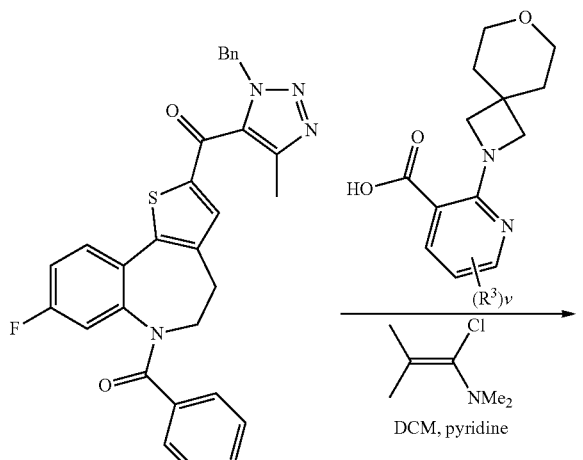

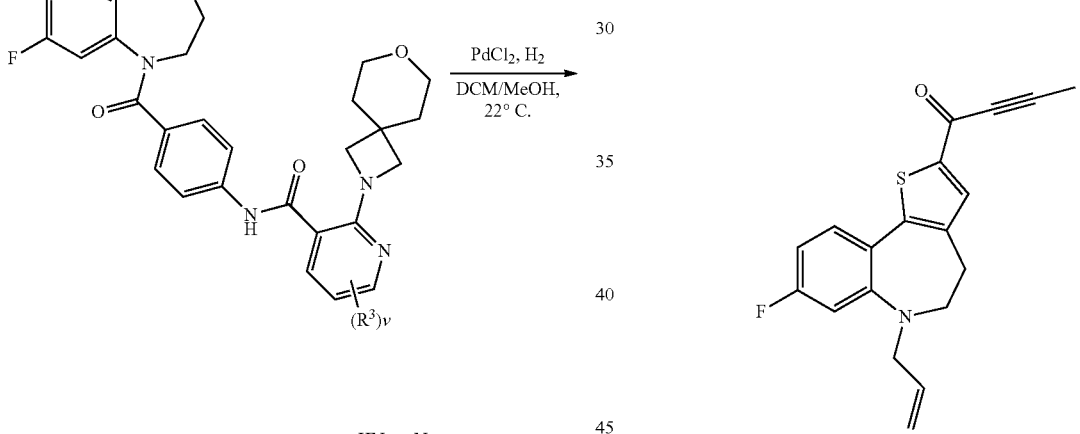

Example 36 Step b

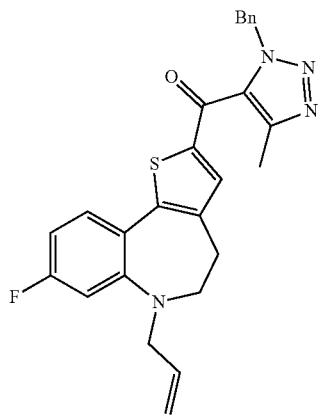 [SMILES: C=CCN1CCc2cc(C(=O)c3c(C)nnn3Cc3ccccc3)sc2-c2ccc(F)cc21]

To a dried vial were added the compound from step a (0.285 g, 0.876 mmol) and (azidomethyl)benzene (0.15 mL, 1.1 mmol). The vial was purged with nitrogen and then a solution of Cp*RuCl(PPh$_3$)$_2$ (0.11 g, 0.13 mmol) in 1.4-dioxane (8 mL) was added. After being heated at 80° C. for 12 h, the reaction mixture was cooled down and the solvent was removed under reduced pressure. The residue was purified by silica gel column chromatography to afford the desired product (157 mg, 0.342 mmol, 39.1%) as a yellow solid. ESI-MS m/z: 458.8 [M+H]$^+$. $^1$H NMR (CDCl$_3$) δ 8.49 (s, 1H), 7.84 (dd, J=8.8, 6.6 Hz, 1H), 7.42-7.29 (m, 3H), 7.25-7.17 (m, 2H), 6.68-6.56 (m, 2H), 5.93 (ddt, J=17.6, 10.4, 5.3 Hz, 1H), 5.57 (s, 2H), 5.33-5.24 (m, 2H), 3.91 (d, J=5.2 Hz, 2H), 3.36 (dd, J=6.1, 4.5 Hz, 2H), 3.14-3.06 (m, 2H), 2.56 (s, 3H).

Example 36 Step c

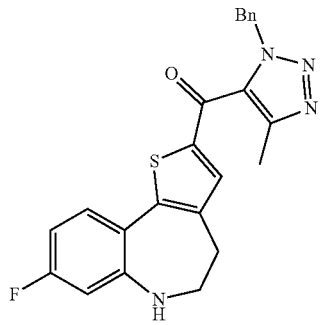 [SMILES: Cc1nnn(Cc2ccccc2)c1C(=O)c1cc2c(s1)-c1ccc(F)cc1NCC2]

The compound was prepared by the method similar to example 29 step b. ESI-MS m/z: 418.8 [M+H]$^+$. 1H NMR (CDCl$_3$) δ 8.42 (s, 1H), 7.77 (dd, J=8.9, 6.2 Hz, 1H), 7.42-7.31 (m, 3H), 7.21 (dd, J=7.6, 1.9 Hz, 2H), 6.52 (ddd, J=8.8, 7.6, 2.6 Hz, 1H), 6.35 (dd, J=10.4, 2.6 Hz, 1H), 5.57 (s, 2H), 4.51 (s, 1H), 3.49 (q, J=4.6 Hz, 2H), 3.34 (dd, J=25.8, 7.8 Hz, 1H), 3.18-3.11 (m, 2H), 2.56 (s, 3H).

Example 36 Step d

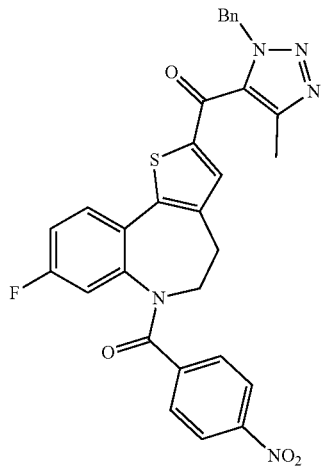 [SMILES: Cc1nnn(Cc2ccccc2)c1C(=O)c1cc2c(s1)-c1ccc(F)cc1N(C(=O)c1ccc([N+](=O)[O-])cc1)CC2]

The compound was prepared by the method similar to example 29 step c. ESI-MS m/z: 568.4 [M+H]$^+$. $^1$H NMR (CDCl$_3$) δ 8.54 (s, 1H), 8.05 (d, J=8.4 Hz, 2H), 7.86 (dd, J=8.8, 5.8 Hz, 1H), 7.43-7.30 (m, 3H), 7.33-7.19 (m, 4H), 7.05-6.96 (m, 1H), 6.45 (d, J=8.4 Hz, 1H), 5.59 (s, 2H), 5.08 (s, 1H), 3.60-3.50 (m, 1H), 3.40 (s, 1H), 3.19 (d, J=17.1 Hz, 1H), 2.59 (s, 3H).

Example 36 Step e

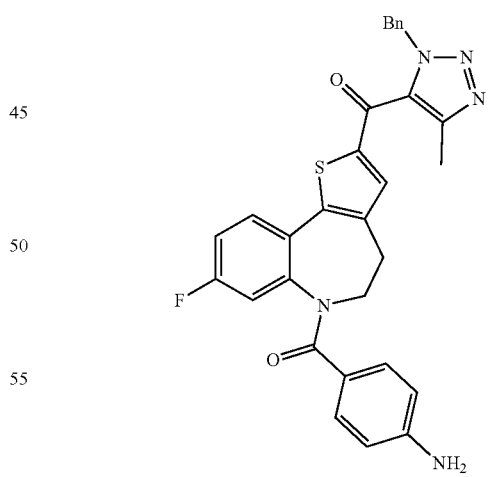

The compound was prepared by the method similar to example 29 step d. ESI-MS m/z: 538.0 [M+H]$^+$. $^1$H NMR (CDCl$_3$) δ 8.52 (d, J=15.2 Hz, 1H), 8.05 (d, J=8.4 Hz, 1H), 7.86 (dt, J=8.7, 6.1 Hz, 1H), 7.41-7.28 (m, 3H), 7.25-7.18 (m, 2H), 7.05-6.89 (m, 2H), 6.55-6.37 (m, 2H), 5.58 (d, J=3.3 Hz, 2H), 5.08 (s, 1H), 3.80 (s, 1H), 3.72-2.88 (m, 1H), 2.58 (d, J=5.9 Hz, 3H).

Example 36 Step f

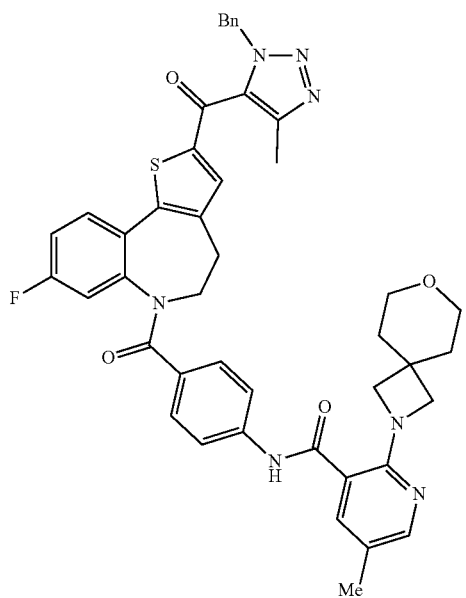 [SMILES: Cc1cnc(N2CC3(CCOCC3)C2)c(C(=O)Nc2ccc(C(=O)N3CCc4cc(C(=O)c5c(C)nnn5Cc5ccccc5)sc4-c4ccc(F)cc43)cc2)c1]

The compound was prepared by the method similar to example 29 step e. ESI-MS m/z: 782.0 [M+H]+. 1H NMR (CDCl3) δ 8.51 (s, 1H), 7.87 (dd, J=8.8, 5.8 Hz, 1H), 7.77 (s, 1H), 7.72 (s, 1H), 7.49 (d, J=8.1 Hz, 2H), 7.43-7.32 (m, 3H), 7.26-7.13 (m, 4H), 7.00 (d, J=15.8 Hz, 1H), 6.51 (d, J=8.9 Hz, 1H), 5.59 (s, 2H), 5.11 (s, 1H), 4.03 (s, 3H), 3.56 (s, 4H), 3.33 (s, 1H), 3.18 (s, 1H), 2.58 (s, 3H), 2.25 (d, J=10.6 Hz, 3H), 1.77 (d, J=10.6 Hz, 1H).

Example 36 Step g

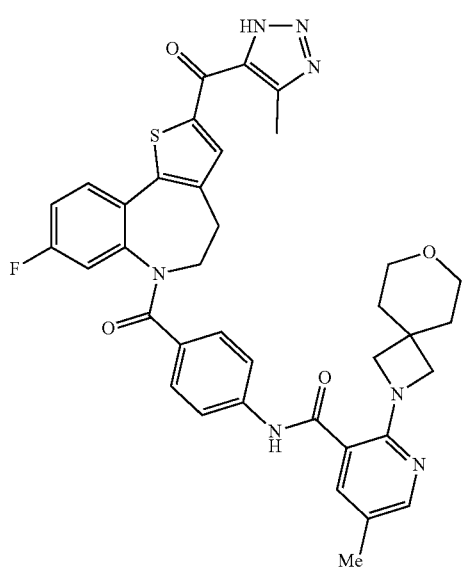 [SMILES: Cc1cnc(N2CC3(CCOCC3)C2)c(C(=O)Nc2ccc(C(=O)N3CCc4cc(C(=O)c5[nH]nnc5C)sc4-c4ccc(F)cc43)cc2)c1]

To a solution of N-(4-(2-(1-benzyl-4-methyl-1H-1,2,3-triazole-5-carbonyl)-8-fluoro-5,6-dihydro-4H-benzo[b]thieno[2,3-d]azepine-6-carbonyl)phenyl)-5-methyl-2-(7-oxa-2-azaspiro[3.5]nonan-2-yl)nicotinamide (19 mg, 0.024 mmol) in MeOH (324 µL) and DCM (162 µL) was added palladium(II) chloride (1.741 mg, 9.72 µmol) and the flask was degassed and purged with hydrogen three times. The reaction mixture was stirred overnight. The reaction mixture filtered through Celite and purified by reverse phase HPLC to the desired compound (1.4 mg, 8.33%) as a white solid. ESI-MS m/z: 692.0 [M+H]+. 1H NMR (CDCl3) δ 9.31 (s, 1H), 8.22 (s, 1H), 7.76 (dd, J=8.8, 5.8 Hz, 1H), 7.68 (s, 2H), 7.52 (d, J=8.4 Hz, 2H), 7.11 (d, J=8.3 Hz, 2H), 7.03-6.93 (m, 1H), 6.49 (d, J=8.4 Hz, 1H), 5.06 (s, 1H), 4.03 (s, 4H), 3.55 (s, 4H), 3.35-2.95 (m, 4H), 2.62 (s, 3H), 2.19 (s, 3H), 1.76 (d, J=5.4 Hz, 4H).

Example 37

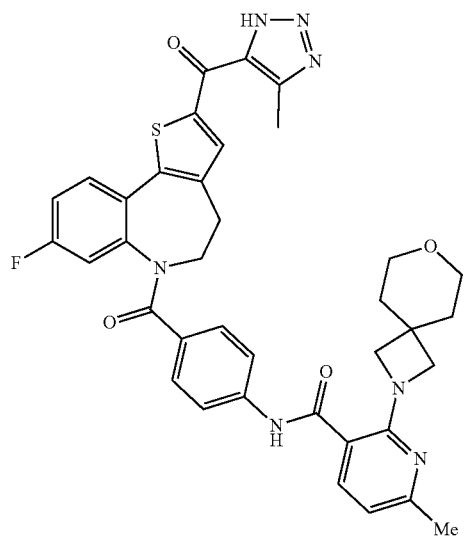 [SMILES: Cc1ccc(C(=O)Nc2ccc(C(=O)N3CCc4cc(C(=O)c5[nH]nnc5C)sc4-c4ccc(F)cc43)cc2)c(N2CC3(CCOCC3)C2)n1]

The compound was prepared by the method similar to example 36. ESI-MS m/z: 692.0 [M+H]+. 1H NMR (CDCl3) δ 8.26 (s, 1H), 7.74 (dd, J=18.8, 7.4 Hz, 2H), 7.53 (d, J=8.1 Hz, 2H), 7.14 (d, J=8.2 Hz, 2H), 7.03-6.85 (m, 1H), 6.49 (d, J=7.8 Hz, 2H), 5.08 (s, 1H), 4.05 (s, 3H), 3.53 (s, 3H), 3.27 (s, 2H), 3.12 (s, 1H), 2.68-2.58 (m, 1H), 2.62 (s, 2H), 2.52 (s, 2H), 1.74 (s, 4H).

Scheme 14

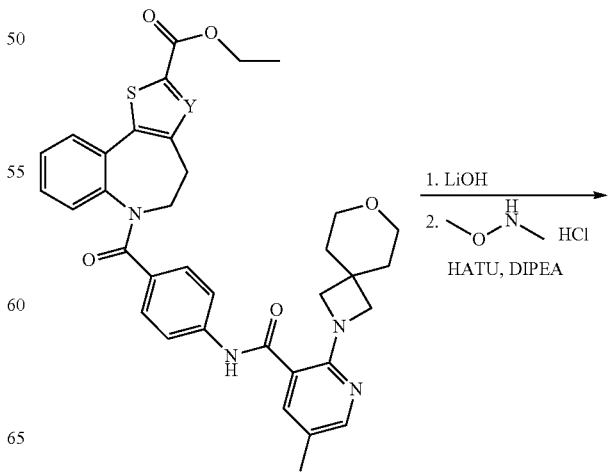

127
-continued
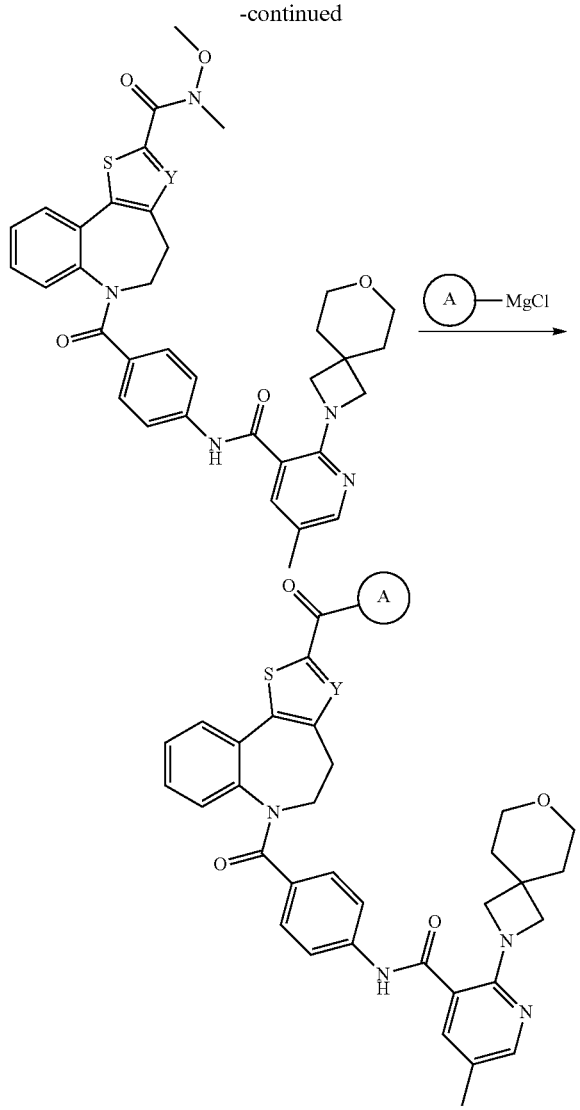
Example 38
128
Example 38 Step a
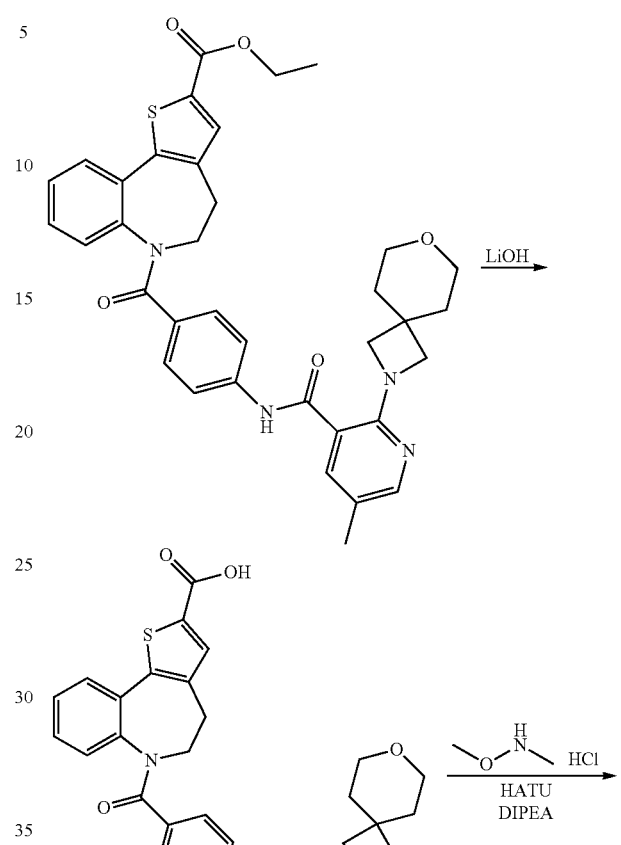
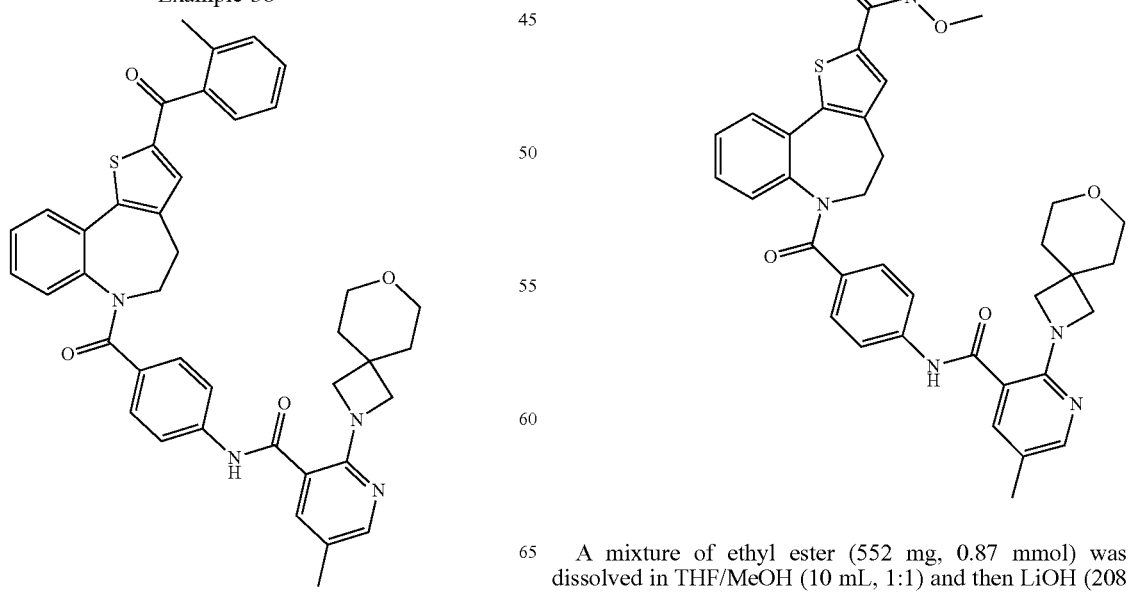
A mixture of ethyl ester (552 mg, 0.87 mmol) was dissolved in THF/MeOH (10 mL, 1:1) and then LiOH (208 mg, 8.7 mmol) in water (2 mL) and the resulting mixture was heated at 50° C. for 2 hrs. After cooling down, most of solvents were removed and acidified by addition of 1M–HC to pH~4. The precipitated white solid was filtered and washed with water and dried to obtain the carboxylic acid (500 mg, 95%). To a mixture of the obtained acid (500 mg, 0.82 mmol) and N,O-dimethyl-hydroxylyamine hydrochloride (160.2 mg, 1.64 mmol) in DMF were added DIPEA (424.6 mg, 3.29 mmol) and HATU (468.5 mg, 1.23 mmol) was stirred at room temperature for 2 hrs. The reaction mixture was diluted with EtOAc and water and separated. The aqueous layer was extracted with EtOAc. The combined organic layer was washed with water (three times) and brine, dried over anhydrous sodium sulfate, filtered and concentrated to dryness. The residue was purified by column chromatography to afford the desired compound (500 mg, 93.39%) as a brown solid. ESI-MS m/z: 652.25 [M+H]$^+$.

Example 38 Step b

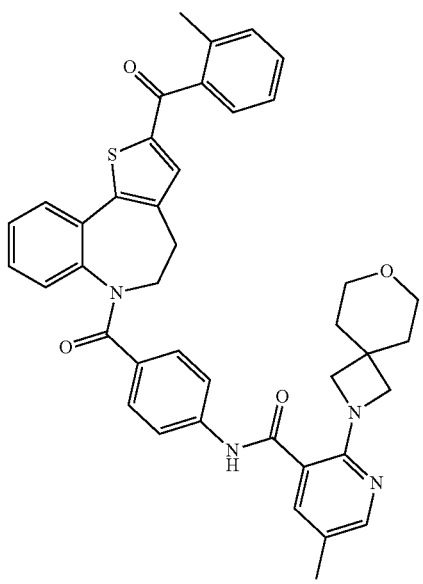 [SMILES: Cc1cnc(N2CC3(CCOCC3)C2)c(C(=O)Nc2ccc(C(=O)N3CCc4cc(C(=O)c5ccccc5C)sc4-c4ccccc43)cc2)c1]

A solution of the compound from Example 38 step a (50 mg, 0.08 mmol) in THF (3 mL) at 0° C. under N$_2$ was added bromo(2-methylphenyl)magnesium (0.15 mL, 1M in THF). The resulting mixture was stirred for 2 hrs at room temperature under N$_2$. The reaction was quenched with water at 0° C. The resulting mixture was extracted with EtOAc (20 mL×3). The combined organic layers were dried and concentrated under reduced pressure. The residue was purified by Prep-TLC and Prep-HPLC to afford the titled compound (22.2 mg, 42.38%) as a white solid. ESI-MS m/z: 683.25 [M+H]$^+$. $^1$H NMR (DMSO-d$_6$) δ 1.63 (t, J=5.2 Hz, 4H), 2.18 (s, 3H), 2.34 (s, 3H), 3.08 (d, J=15.1 Hz, 1H), 3.25 (s, 2H), 3.46 (t, J=4.9 Hz, 4H), 3.61 (s, 4H), 4.87 (s, 1H), 6.90 (s, 1H), 7.02 (d, J=8.0 Hz, 2H), 7.17 (s, 1H), 7.29-7.44 (m, 4H), 7.50 (q, J=7.0, 6.3 Hz, 4H), 7.58 (d, J=7.6 Hz, 1H), 7.89 (d, J=7.8 Hz, 1H), 8.04 (s, 1H), 10.39 (s, 1H).

Example 39

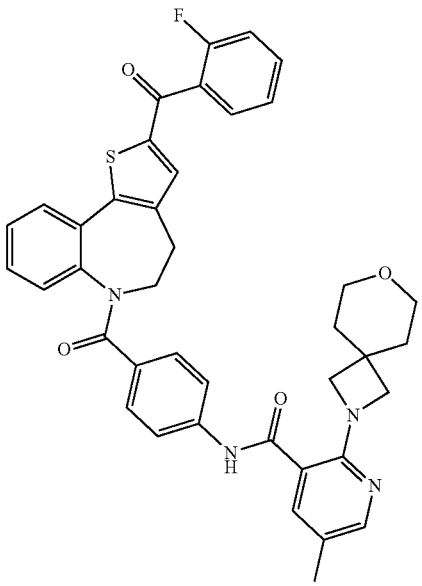 [SMILES: Cc1cnc(N2CC3(CCOCC3)C2)c(C(=O)Nc2ccc(C(=O)N3CCc4cc(C(=O)c5ccccc5F)sc4-c4ccccc43)cc2)c1]

The compound was prepared by the method similar to example 38. ESI-MS m/z: 687.20 [M+H]$^+$. $^1$H NMR (DMSO-d$_6$) δ 1.63 (t, J=5.1 Hz, 4H), 2.18 (s, 3H), 2.99-3.29 (m, 3H), 3.47 (d, J=6.5 Hz, 4H), 3.61 (s, 4H), 4.89 (s, 1H), 6.91 (s, 1H), 7.02 (d, J=8.2 Hz, 2H), 7.19 (d, J=8.0 Hz, 1H), 7.33 (t, J=7.7 Hz, 1H), 7.43 (dd, J=14.5, 8.0 Hz, 2H), 7.48-7.57 (m, 3H), 7.59 (s, 1H), 7.72 (q, J=8.1 Hz, 2H), 7.89 (d, J=7.9 Hz, 1H), 8.04 (s, 1H), 10.39 (s, 1H).

Example 40

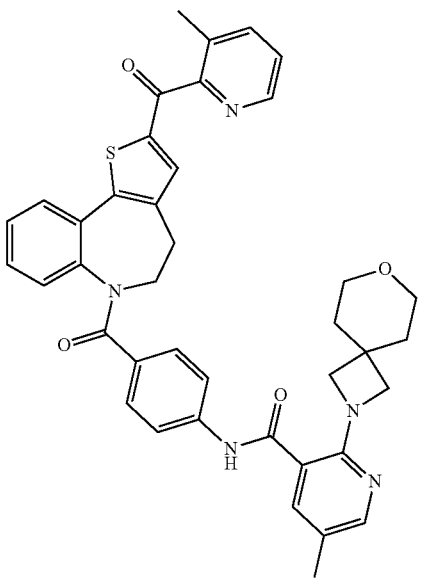 [SMILES: Cc1cnc(N2CC3(CCOCC3)C2)c(C(=O)Nc2ccc(C(=O)N3CCc4cc(C(=O)c5ncccc5C)sc4-c4ccccc43)cc2)c1]

The compound was prepared by the method similar to example 38. ESI-MS m/z: 684.25 [M+H]$^+$. $^1$H NMR (DMSO-d$_6$) δ 1.62 (s, 4H), 2.17 (s, 3H), 3.19 (d, J=66.9 Hz, 3H), 3.46 (s, 4H), 3.60 (s, 4H), 4.90 (s, 1H), 6.90 (s, 1H), 7.01 (s, 2H), 7.17 (s, 1H), 7.31 (d, J=8.1 Hz, 1H), 7.42-7.56 (m, 3H), 7.59 (d, J=7.0 Hz, 1H), 7.79 (s, 1H), 7.89 (d, J=7.8 Hz, 2H), 8.04 (s, 1H), 8.61 (d, J=4.7 Hz, 1H), 10.38 (s, 1H).

Assays

Introduction

RSV is a single stranded negative sense RNA virus that causes respiratory tract infections which can be dangerous to infants, the elderly, and immunosuppressed individuals. Currently there is no vaccine, and therapeutic options are both costly and of limited effectiveness. These approved treatments are Ribavirin, and Palivizumab/Synagis (a monoclonal antibody). RSV has two genotypes, A and B, which differ primarily in the structure of the virus' surface "G" attachment protein. Our current primary screen focuses on RSV-A and uses an in vitro cytoprotection assay where compounds are added in 2-fold dilutions to cells which are then subjected to fully replicative viral particles. Cell viability is measured several days later along with separate measurements of compound cytotoxicity. This report focuses on the results of our most recent screening of compounds.

Methods

HEp-2 cells, (originally derived from tumors grown in irradiated-cortisonised weanling rats that had been injected with epidermoid carcinoma tissue from a 56 year old male's larynx, but later found to be indistinguishable from HeLa cells by PCR DNA analysis), were used for the culturing of genotype A, "Long" strain RSV. Flasks were inoculated with RSV and viral stocks were collected once cytopathic effect (CPE) was greater than 90%. Viral stocks in 25% sucrose media were snap frozen using liquid nitrogen to increase viral stability. Viral stock titers were quantified by tissue culture infectious dose 50% ($TCID_{50}$) using 8,000 cells per well and 3-fold viral dilutions across a 96-well plate, cultured for 4 days.

The control compound currently used in the RSV assay is RSV-604, a ~2.4 μM $EC_{50}$ nucleocapsid inhibitor previously developed by Novartis. Following extensive parameter testing, the final assay is run as follows: HEp-2 cells are seeded into the inner 60 wells of a 96-well plate at 8,000 cells per well in a volume of 50 μL using Growth Media (DMEM without phenol red, 1% L-Glut, 1% Penn/Strep, 1% nonessential amino acids, 10% FBS). 2-Fold serial dilutions of control and test compounds are added to the wells in duplicate in a total volume of 25 μL. Viral stock is then added to the wells in a volume of 25 μL, bringing the total volume of each well to 100 μL. Each 96-well plate has a control column of 6 wells with cells and virus but no compound (negative control, max CPE), a column with cells but no compound or virus (positive control, minimum CPE), and a column with no cells or virus or compound (background plate/reagent control). The control wells with cells but no virus are given an additional 25 μL of growth media containing an equal quantity of sucrose as those wells receiving the viral stock in order to keep consistent in media and volume conditions. The outer wells of the plate are filled with 125 μL of growth media to act as a thermal and evaporative moat around the test wells. Following a 4-day incubation period, the plates are read using ATPlite (50 μL added per well), which quantifies the amount of ATP (a measure of cell health) present in each well. Assay plates are read using the Envision luminometer. In parallel, cytotoxicity is examined on an additional 96-well plate treated in an identical manner, but substituting the 25 μL of viral stock for 25 μL of growth media. These data are used to calculate the $EC_{50}$ of each compound. $EC_{50}$ ranges are as follows: A<0.1 μM; B 0.1-0.5 μM; C>0.5 μM

TABLE 14

Summary of Activities

| Example | Human RSV-A ("Long" strain) $EC_{50}$ | Example | Human RSV-A ("Long" strain) $EC_{50}$ |
|---|---|---|---|
| 1 | A | 2 | B |
| 3 | A | 4 | A |
| 5 | B | 6 | A |
| 7 | A | 8 | A |
| 9 | A | 10 | B |
| 11 | A | 12 | A |
| 13 | A | 14 | A |
| 15 | A | 16 | A |
| 17 | A | 18 | A |
| 19 | A | 20 | C |
| 21 | A | 22 | A |
| 23 | A | 24 | A |
| 25 | B | 26 | A |
| 27 | C | 28 | A |
| 29 | A | 30 | A |
| 31 | B | 32 | A |
| 33 | A | 34 | B |
| 35 | A | 36 | A |
| 37 | B | 38 | C |
| 39 | B | 40 | B |

While this invention has been particularly shown and described with references to preferred embodiments thereof, it will be understood by those skilled in the art that various changes in form and details may be made therein without departing from the scope of the invention encompassed by the appended claims.

What is claimed:

1. A compound represented by Formula (I):

(I)

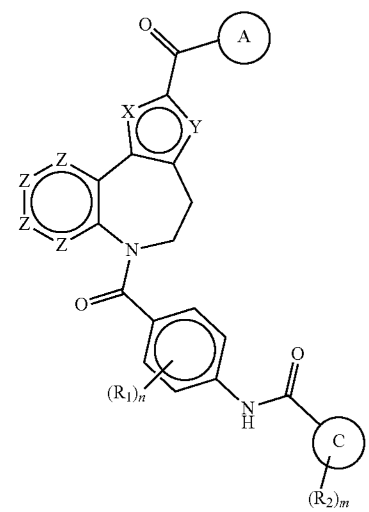

or a pharmaceutically acceptable salt thereof, wherein:

Ⓐ is optionally substituted aryl or optionally substituted heteroaryl;

Ⓒ is aryl or heteroaryl, which, when possible, is optionally substituted with one or more substituents which are not $R_2$;

X is O, S or $NR_4$, and Y is N or $CR_5$; or X is N or $CR_5$, and Y is O, S or $NR_4$;

One Z is $CR_3$, the other Zs are each independently selected from N and $CR_3$;

Each $R_1$ selected from the group consisting of: halogen, hydroxyl, protected hydroxyl, amino, protected amino, optionally substituted —$C_1$-$C_8$ alkyl, and optionally substituted —$C_1$-$C_8$ alkoxy;

Each $R_2$ is selected from the group consisting of:
1) halogen;
2) optionally substituted —$C_1$-$C_8$ alkoxy;
3) optionally substituted —$C_1$-$C_8$ alkyl;
4) optionally substituted —$C_2$-$C_8$ alkenyl;
5) optionally substituted —$C_2$-$C_8$ alkynyl;
6) optionally substituted —$C_3$-$C_{12}$ cycloalkyl;
7) optionally substituted —$C_3$-$C_{12}$ cycloalkenyl;
8) optionally substituted 3- to 12-membered heterocycloalkyl;
9) optionally substituted aryl;
10) optionally substituted heteroaryl;
11) optionally substituted arylalkyl;
12) optionally substituted aryloxy;
13) —$C(O)R_{12}$;
14) —$C(O)NR_{13}R_{14}$;
15) —$C(O)NR_{11}S(O)_2R_{12}$;
16) —$S(O)_2NR_{13}R_{14}$;
17) —$NR_{13}R_{14}$;
18) —$NR_{11}S(O)_2R_{12}$;
19) —$NR_{11}C(O)R_{12}$;
20) —$NR_{11}C(O)NR_{13}R_{14}$; and
21) —$NR_{11}C(O)NHS(O)_2R_{12}$;

n is 0, 1, 2, 3 or 4;
m is 0, 1, 2, or 3;

$R_3$ is selected from the group consisting of: hydrogen, halogen, cyano, nitro, hydroxyl, protected hydroxyl, amino, protected amino, optionally substituted —$C_1$-$C_8$ alkyl, and optionally substituted —$C_1$-$C_8$ alkoxy;

$R_4$ is hydrogen or optionally substituted —$C_1$-$C_8$ alkyl;
$R_5$ is hydrogen, halogen, optionally substituted —$C_1$-$C_8$ alkyl, or optionally substituted —$C_1$-$C_8$ alkoxy;

$R_{12}$ at each occurrence is independently selected from the group consisting of:
1) Hydrogen;
2) Halogen;
3) Hydroxyl;
4) optionally substituted —$C_1$-$C_8$ alkoxy;
5) optionally substituted —$C_1$-$C_8$ alkyl;
6) optionally substituted —$C_2$-$C_8$ alkenyl;
7) optionally substituted —$C_2$-$C_8$ alkynyl;
8) optionally substituted —$C_3$-$C_8$ cycloalkyl;
9) optionally substituted —$C_3$-$C_8$ cycloalkenyl;
10) optionally substituted 3- to 8-membered heterocycloalkyl;
11) optionally substituted aryl;
12) optionally substituted arylalkyl;
13) optionally substituted heteroaryl; and
14) optionally substituted heteroarylalkyl;

$R_{11}$, $R_{13}$ and $R_{14}$ are each independently selected from hydrogen, optionally substituted —$C_1$-$C_8$-alkyl, optionally substituted —$C_2$-$C_8$-alkenyl, optionally substituted —$C_2$-$C_8$-alkynyl; optionally substituted —$C_3$-$C_8$-cycloalkyl, optionally substituted 3- to 8-membered heterocyclic, optionally substituted aryl, optionally substituted arylalkyl, optionally substituted heteroaryl, and optionally substituted heteroarylalkyl; alternatively, $R_{13}$ and $R_{14}$ are taken together with the nitrogen atom they attached to form a heterocyclic ring.

2. The compound of claim 1, wherein Ⓐ is one of the following by removal of a hydrogen atom:

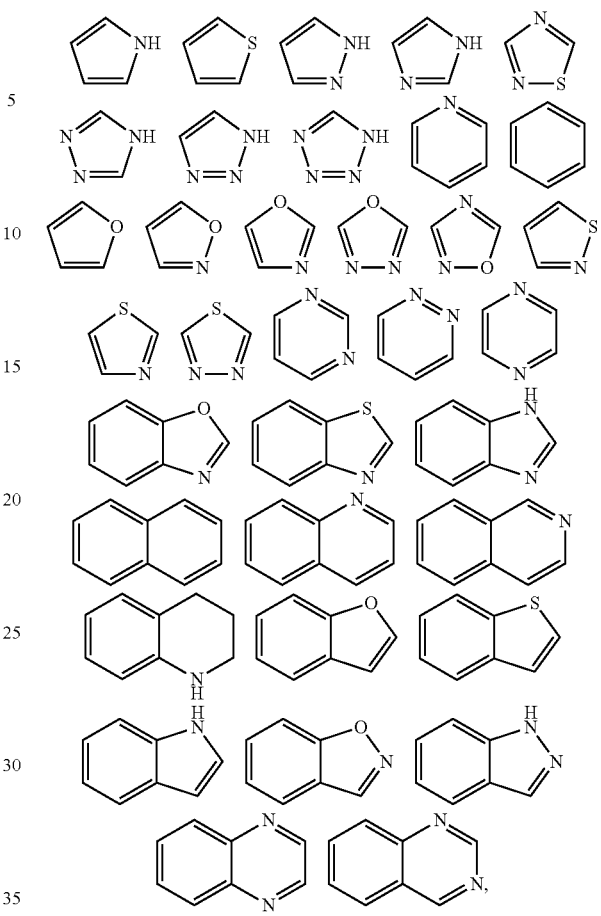

wherein each of the above is optionally substituted when possible.

3. The compound of claim 1, wherein Ⓒ is selected from one of the following groups by removal of one hydrogen atom, wherein each of the groups is optionally substituted:

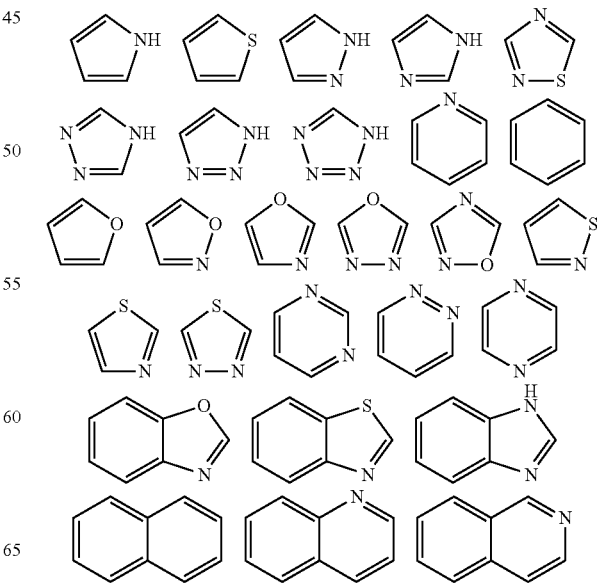

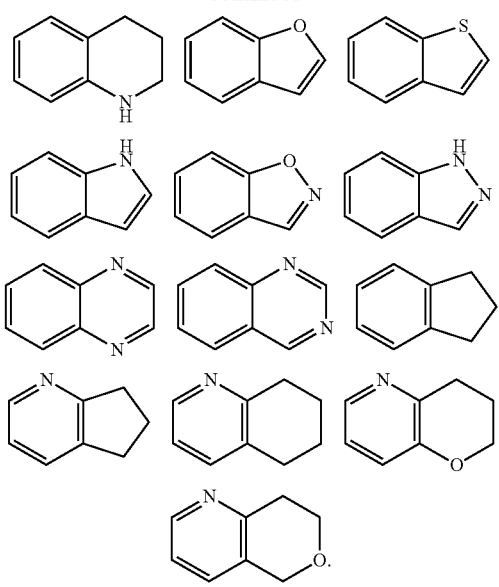
4. The compound of claim 1, wherein $R_2$ is selected from one of the following groups, wherein each of the groups is optionally substituted:
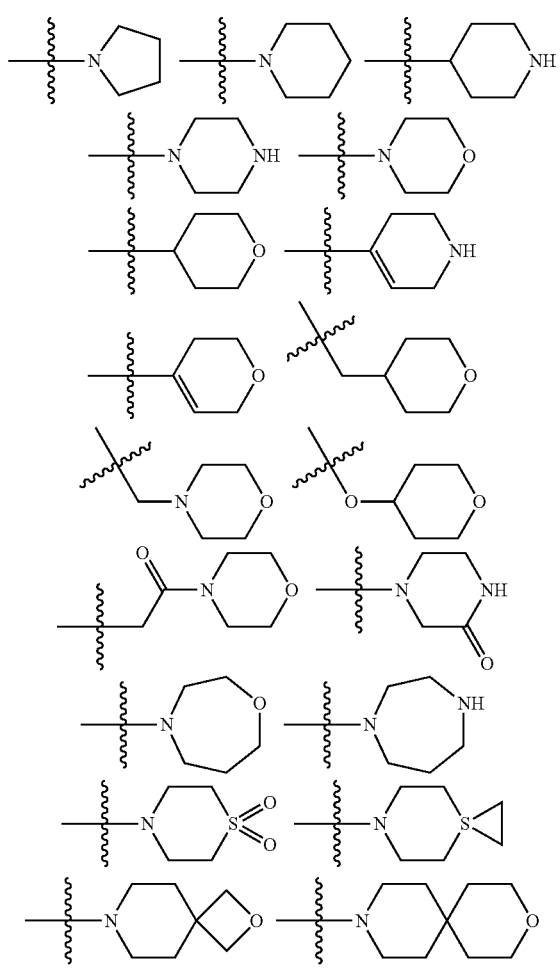
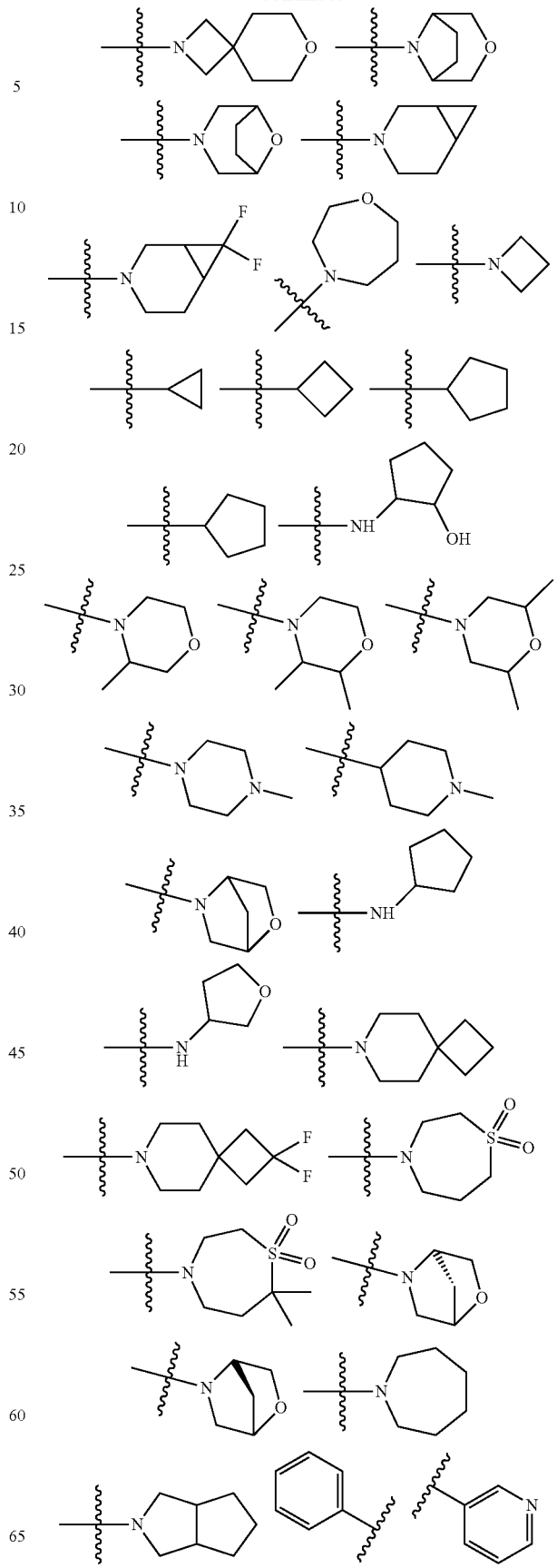

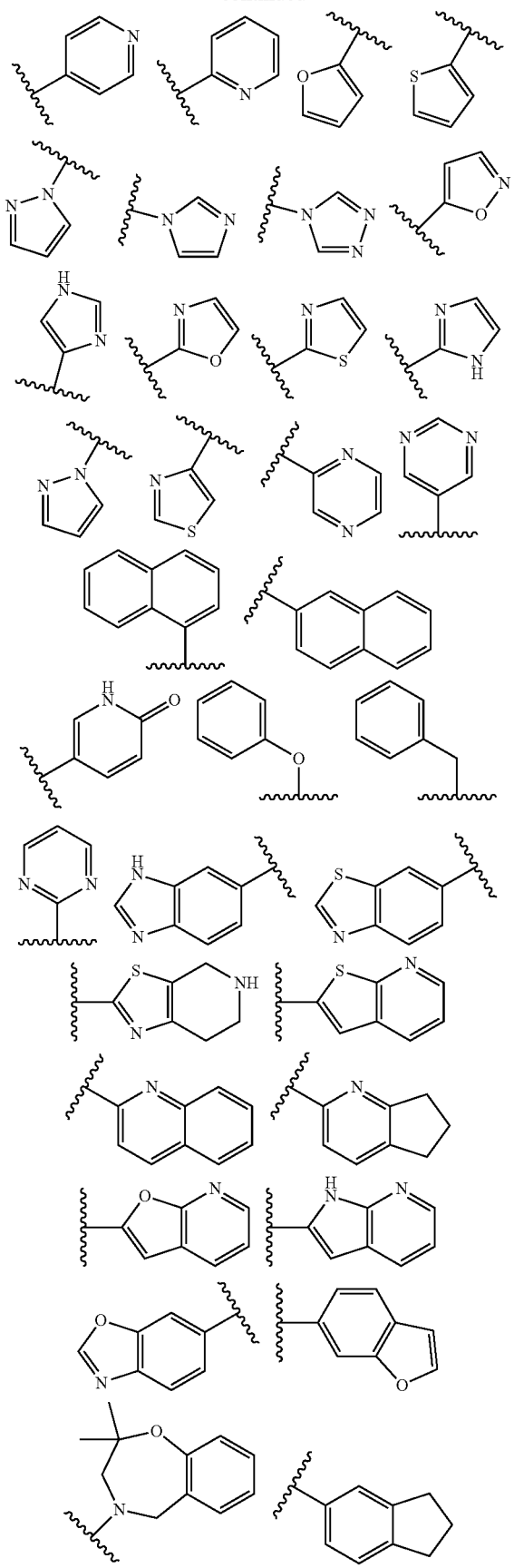
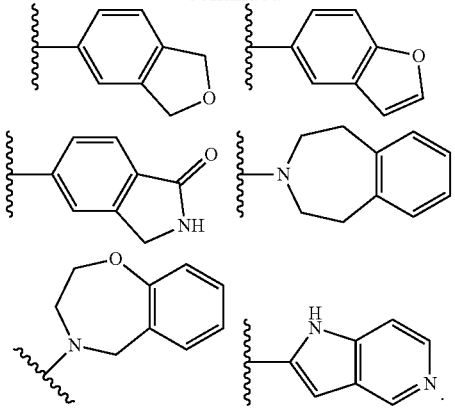
5. The compound of claim 1, represented by one of Formulas (IIa)~(IIe), or a pharmaceutically acceptable salt thereof:
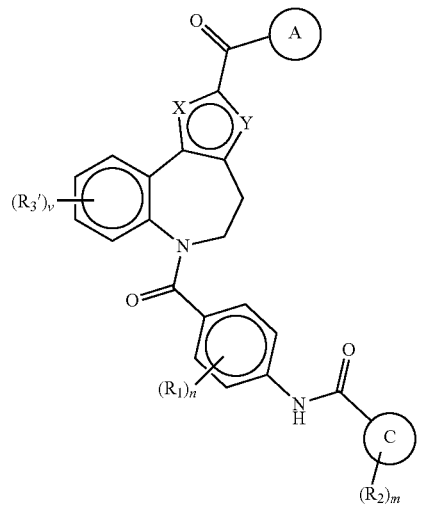
(IIa)
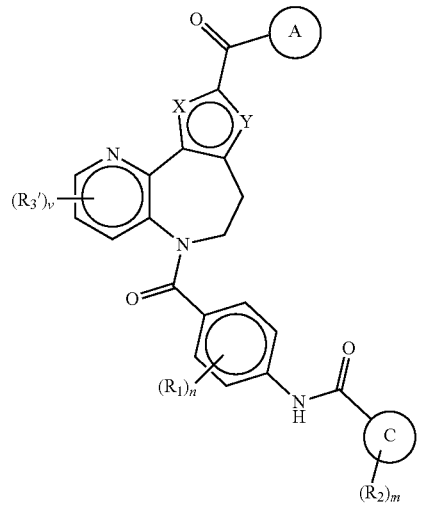
(IIb)

-continued

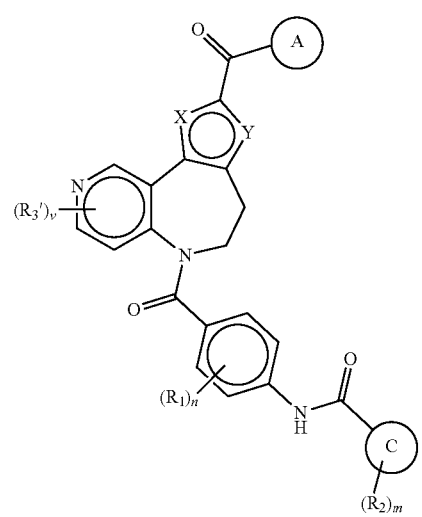

(IIc)

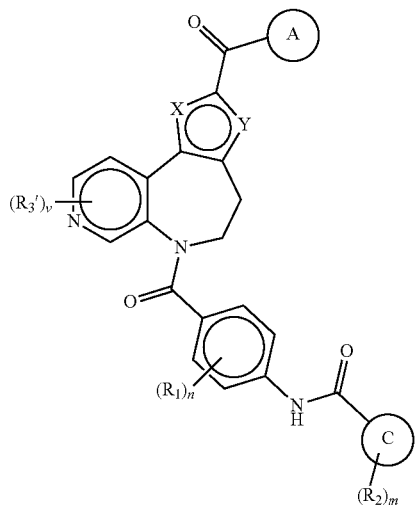

(IId)

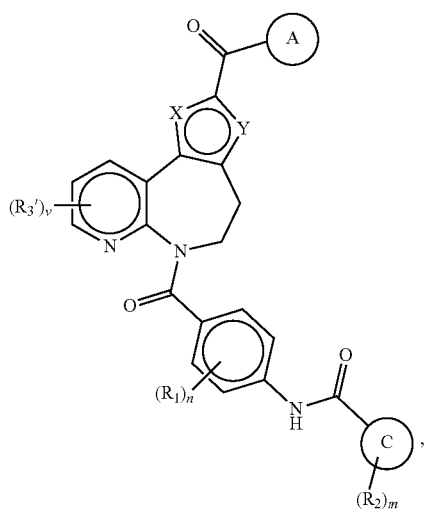

(IIe)

wherein R₃' is selected from the group consisting of: halogen, cyano, nitro, hydroxyl, protected hydroxyl, amino, protected amino, optionally substituted —$C_1$-$C_8$ alkyl, and optionally substituted —$C_1$-$C_8$ alkoxy; v is 0, 1, 2 or 3; Ⓐ, Ⓒ, X, Y, $R_1$, $R_2$, m, and n are as defined in claim 1.

6. The compound of claim 1, represented by one of Formulas (IIIa)~(IIId), or a pharmaceutically acceptable salt thereof:

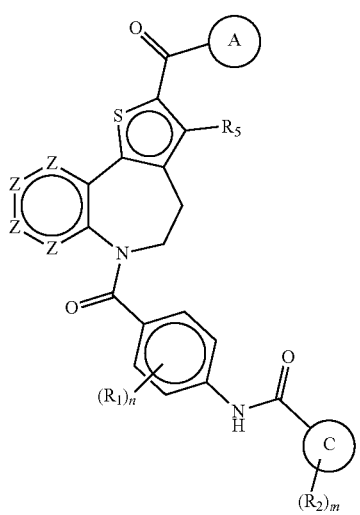

(IIIa)

and

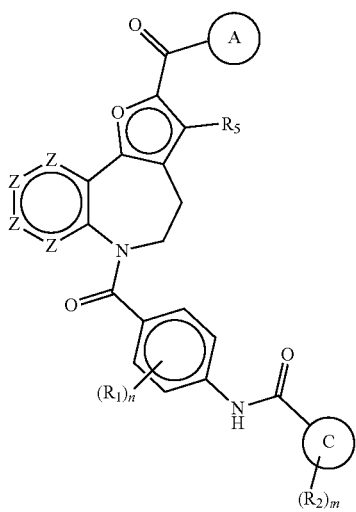

(IIIb)

141
-continued
(IIIc)
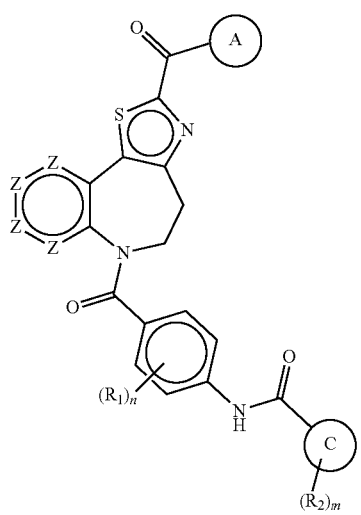
and
(IIId)
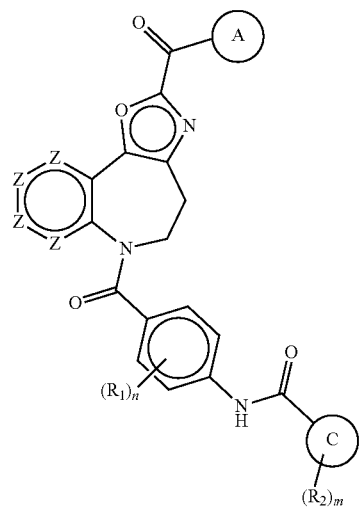
wherein Ⓐ, Ⓒ, $R_1$, $R_2$, $R_5$, n, m, and Z are as defined in claim 1.
7. The compound of claim 1, represented by one of Formulas (IVa)~(IVh), or a pharmaceutically acceptable salt thereof:
142
(IVa)
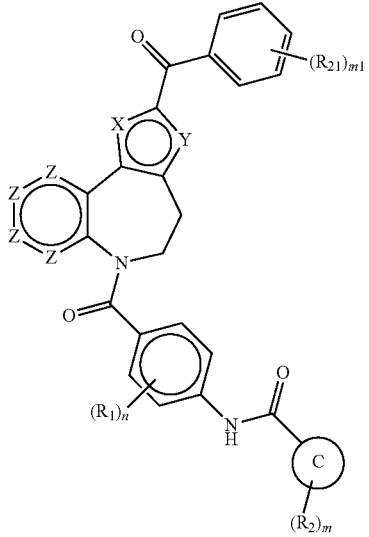
(IVb)
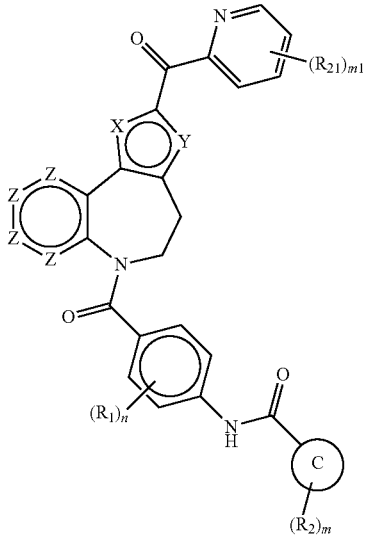
(IVc)
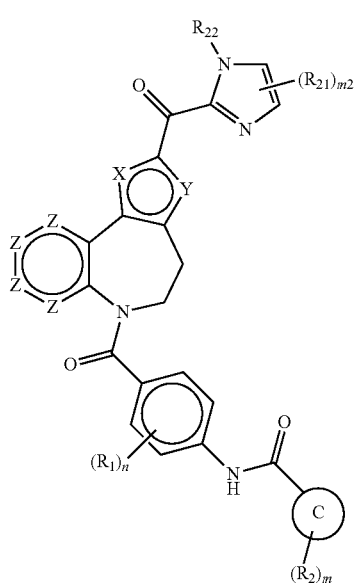

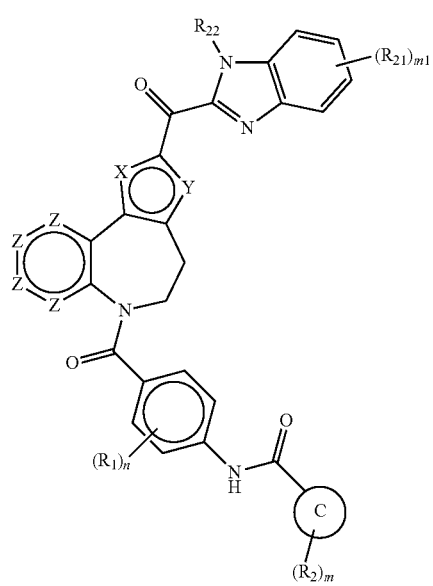 (IVd)
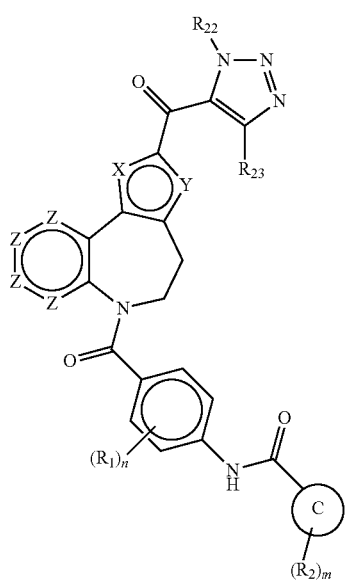 (IVf)
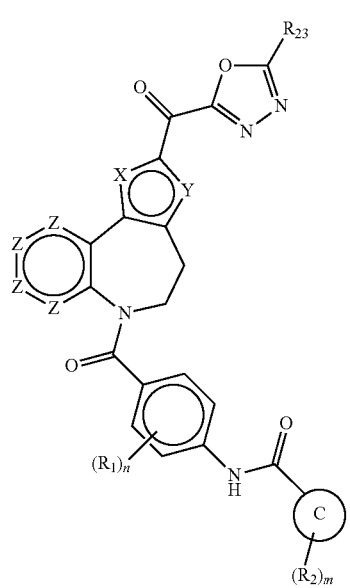 (IVe)
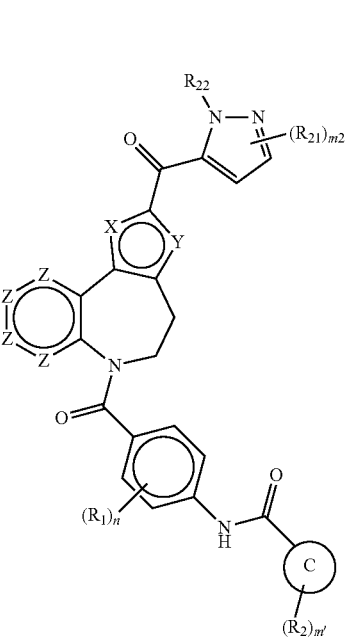 (IVg)
and

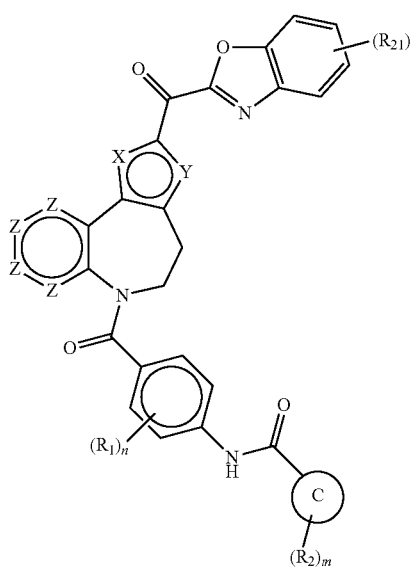

(IVh)

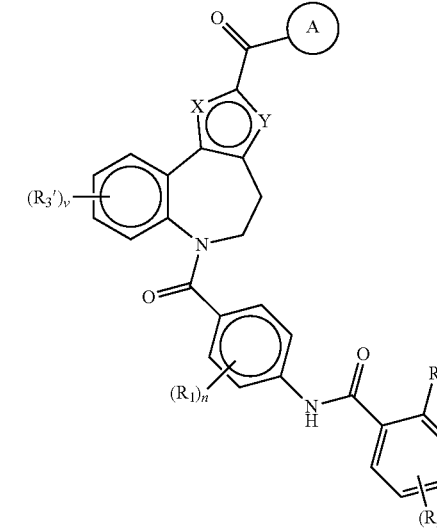

(Va-2)

wherein m1 is 0, 1, 2, 3 or 4; m2 is 0, 1 or 2; each $R_{21}$ is independently selected from halogen, —$NH_2$, optionally substituted —$C_1$-$C_3$ alkyl, and optionally substituted —$C_1$-$C_3$ alkoxy; each $R_{22}$ is independently selected from hydrogen and —$CH_3$; each $R_{23}$ is independently selected from hydrogen, halogen, —$NH_2$, optionally substituted —$C_1$-$C_3$ alkyl, and optionally substituted —$C_1$-$C_3$ alkoxy; Ⓒ, X, Y, Z, $R_1$, $R_2$, m, and n are as defined in claim 1.

8. The compound of claim 1, represented by one of Formulas (Va-1)~(Va-5), or Formulas (Vb-1)~(Vb-5), or a pharmaceutically acceptable salt thereof:

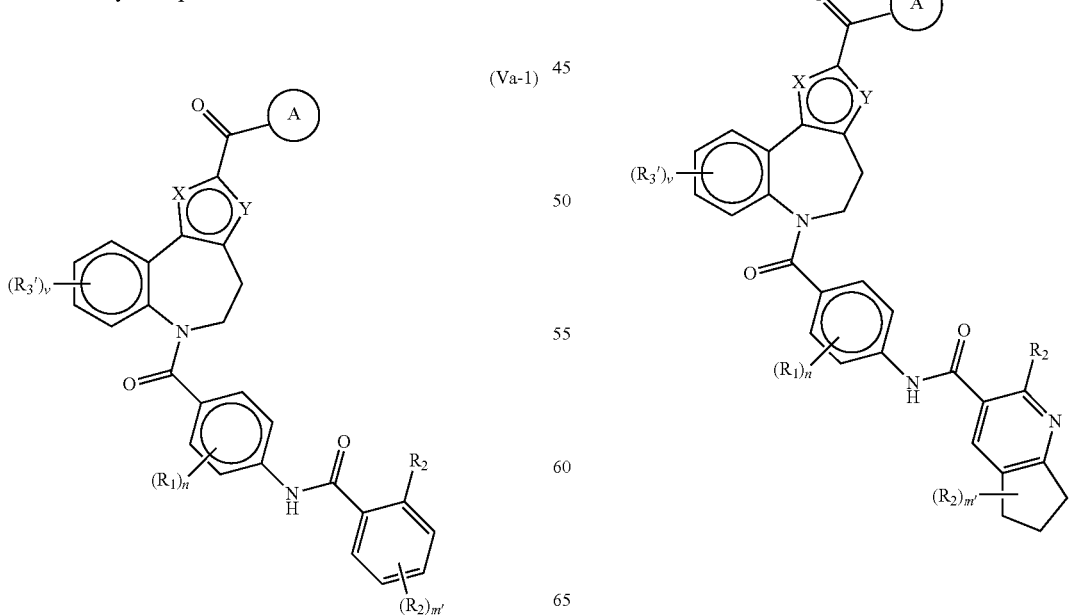

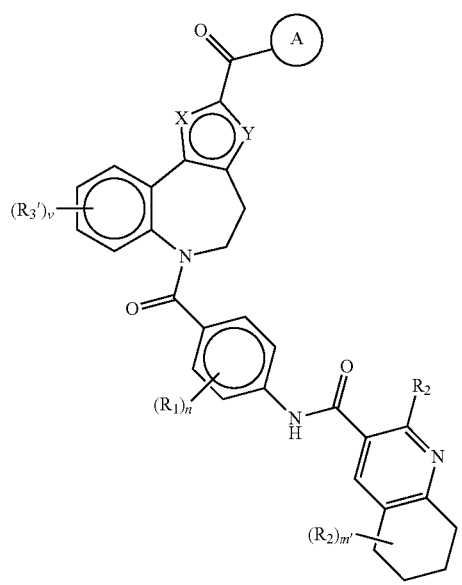
(Va-4)
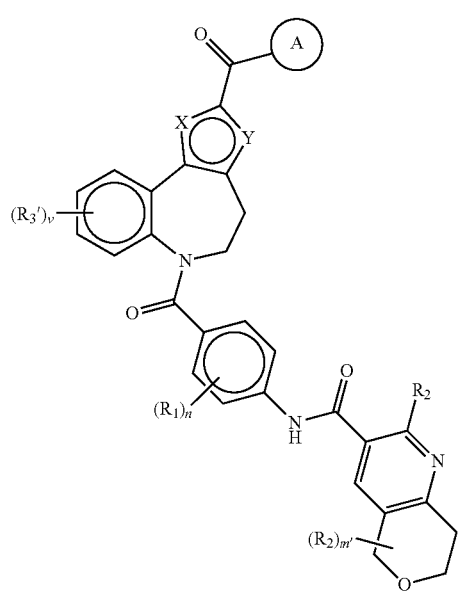
(Va-5)
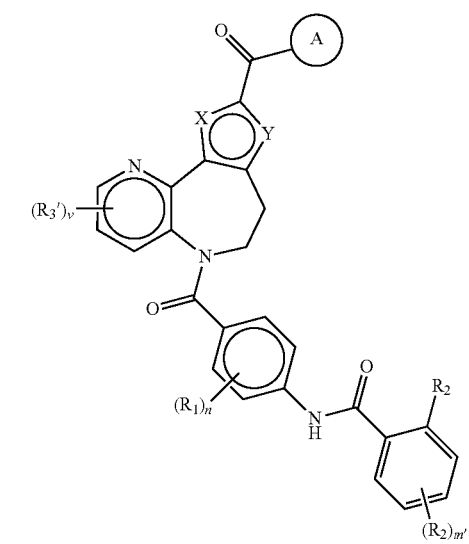
(Vb-1)
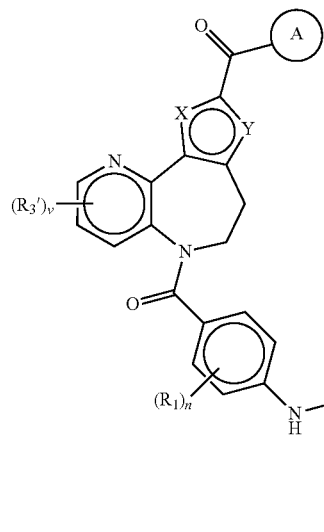
(Vb-2)
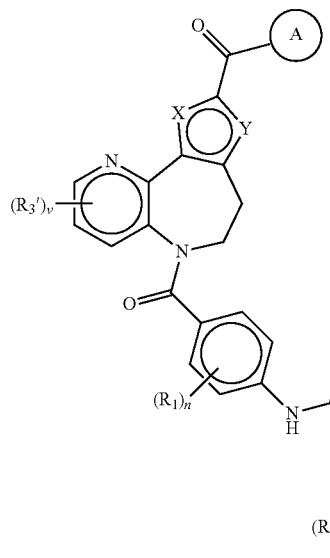
(Vb-3)

(Vb-4)

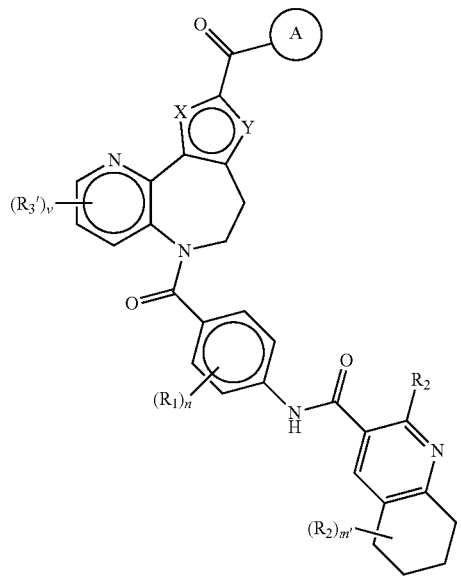

(VI-1)

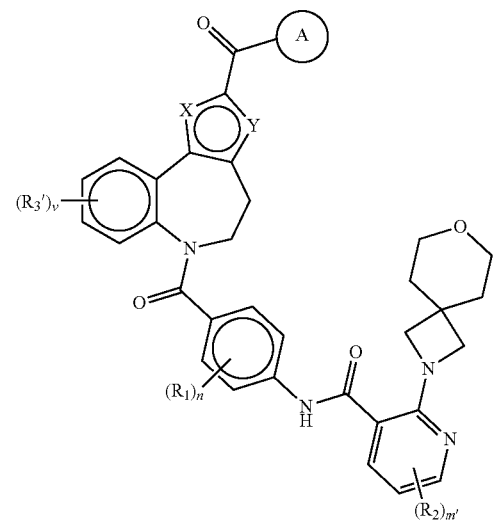

and (Vb-5)

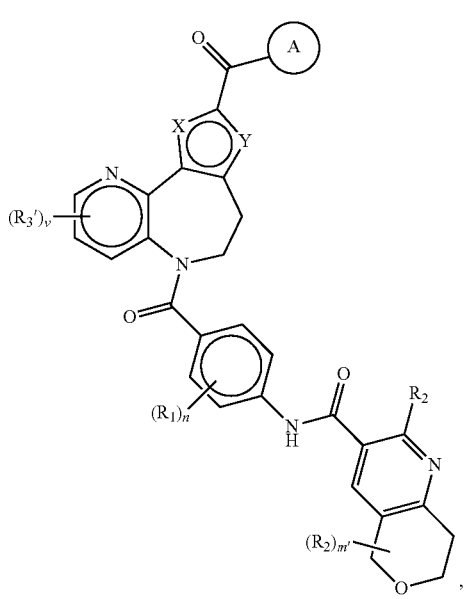

, (VI-2)

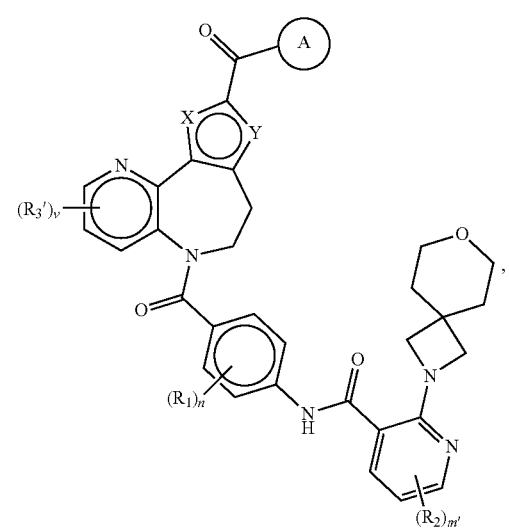

, wherein m' is 0, 1, or 2; $R_3'$ is selected from the group consisting of: halogen, cyano, nitro, hydroxyl, protected hydroxyl, amino, protected amino, optionally substituted —$C_1$-$C_8$ alkyl, and optionally substituted —$C_1$-$C_8$ alkoxy; v is 0, 1, 2 or 3; (A), X, Y, $R_1$, $R_2$, and n are as defined in claim 1.

9. The compound of claim 1, represented by one of Formulas (VI-1)~(VI-2), or a pharmaceutically acceptable salt thereof:

wherein m' is 0, 1, or 2; $R_3'$ is selected from the group consisting of: halogen, cyano, nitro, hydroxyl, protected hydroxyl, amino, protected amino, optionally substituted —$C_1$-$C_8$ alkyl, and optionally substituted —$C_1$-$C_8$ alkoxy; v is 0, 1, 2 or 3; and (A), X, Y, $R_1$, $R_2$, and n are as defined in claim 1.

10. The compound of claim 1, selected from the compounds set forth below or a pharmaceutically acceptable salt thereof:

| Compound | Structure |
|---|---|
| 1 | 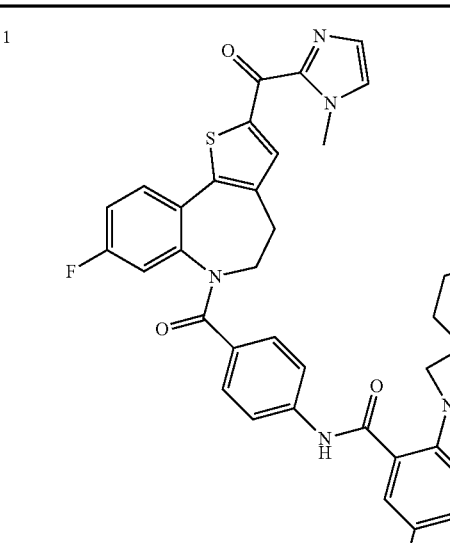 |
| 2 | 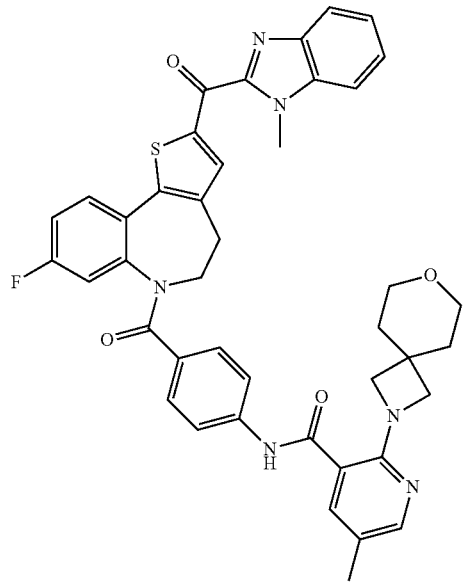 [SMILES: Cc1cnc(N2CC3(CCOCC3)C2)c(C(=O)Nc2ccc(C(=O)N3CCc4cc(C(=O)c5nc6ccccc6n5C)sc4-c4ccc(F)cc43)cc2)c1] |
-continued
| Compound | Structure |
|---|---|
| 3 | 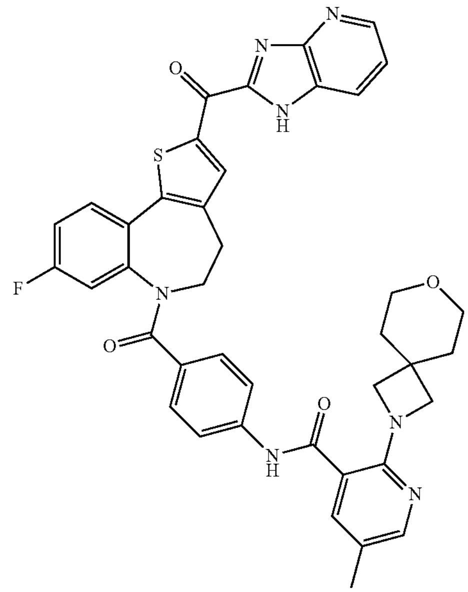 [SMILES: Cc1cnc(N2CC3(CCOCC3)C2)c(C(=O)Nc2ccc(C(=O)N3CCc4cc(C(=O)c5nc6ncccc6[nH]5)sc4-c4ccc(F)cc43)cc2)c1] |
| 4 | 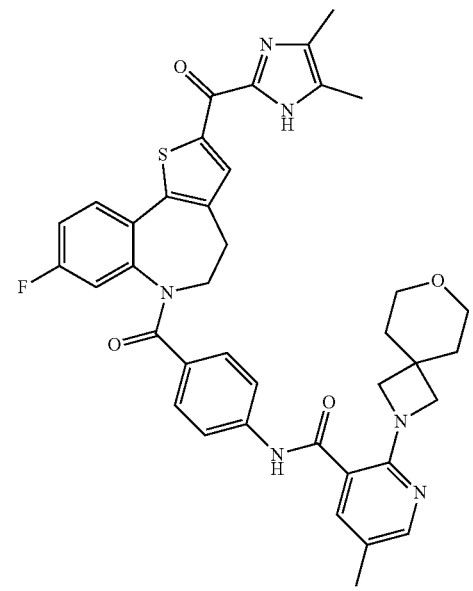 [SMILES: Cc1cnc(N2CC3(CCOCC3)C2)c(C(=O)Nc2ccc(C(=O)N3CCc4cc(C(=O)c5nc(C)c(C)[nH]5)sc4-c4ccc(F)cc43)cc2)c1] |

| Compound | Structure |
|---|---|
| 5 | 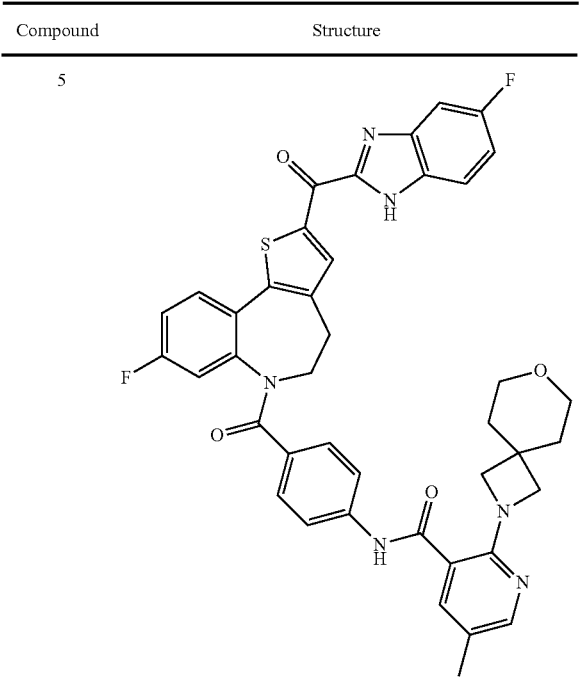 |
| 6 | 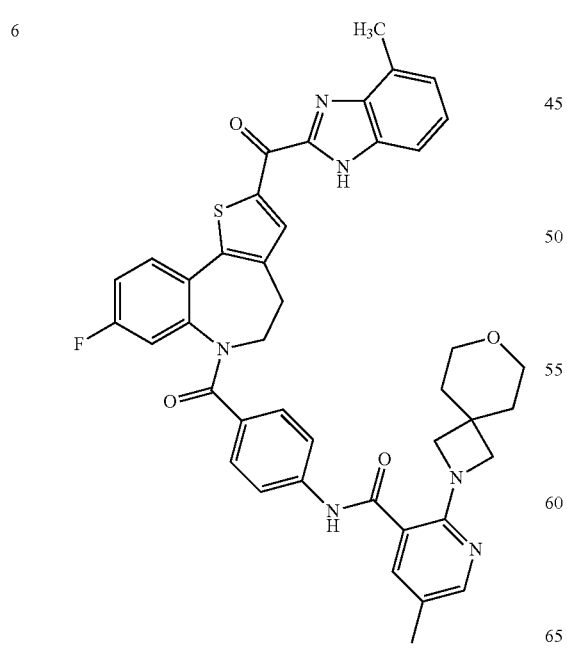 |
| 7 | 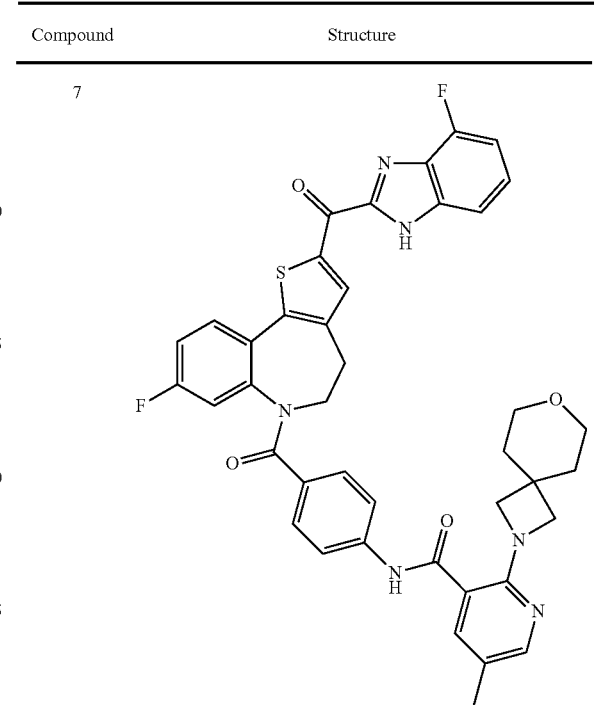 |
| 8 | 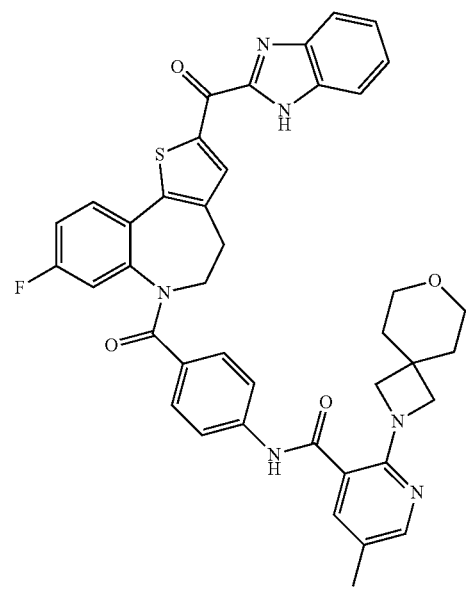 [SMILES: Cc1cnc(N2CC3(CCOCC3)C2)c(C(=O)Nc2ccc(C(=O)N3CCc4cc(C(=O)c5nc6ccccc6[nH]5)sc4-c4ccc(F)cc43)cc2)c1] |

TABLE-continued
| Compound | Structure |
|---|---|
| 9 | 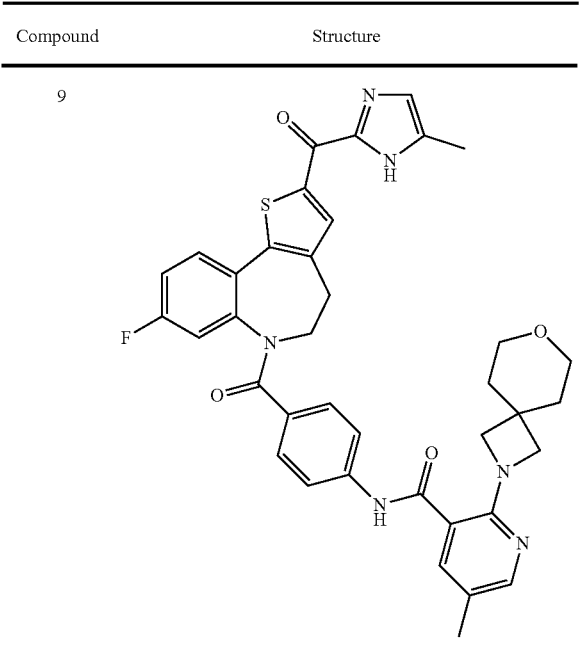 |
| 10 | 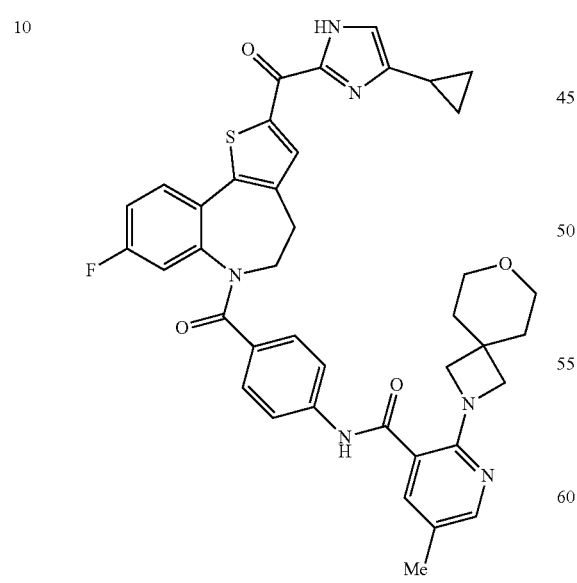 |
| 11 | 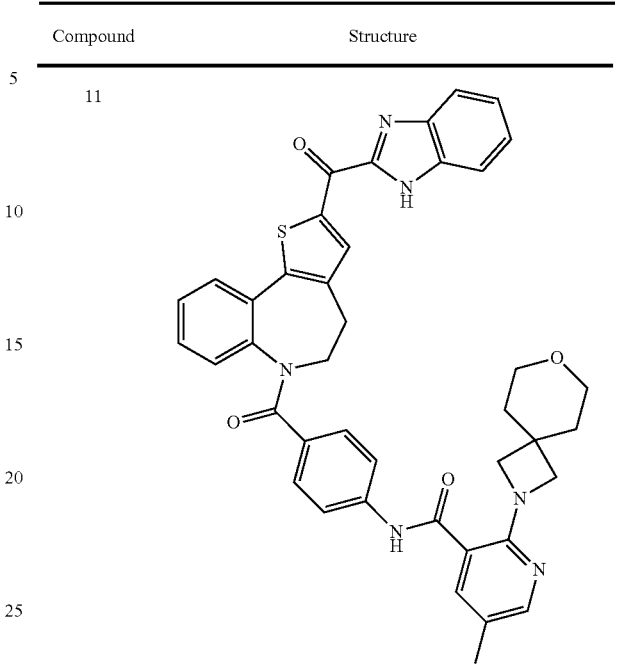 |
| 12 | 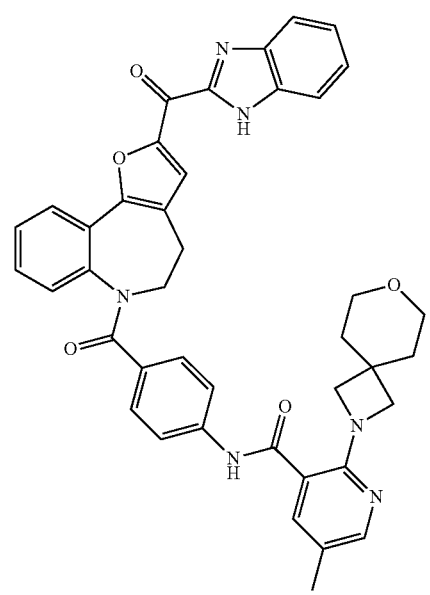 [SMILES: Cc1cnc(N2CC3(CCOCC3)C2)c(C(=O)Nc2ccc(C(=O)N3CCc4cc(C(=O)c5nc6ccccc6[nH]5)sc4-c4ccccc43)cc2)c1] |

| Compound | Structure |
|---|---|
| 13 | 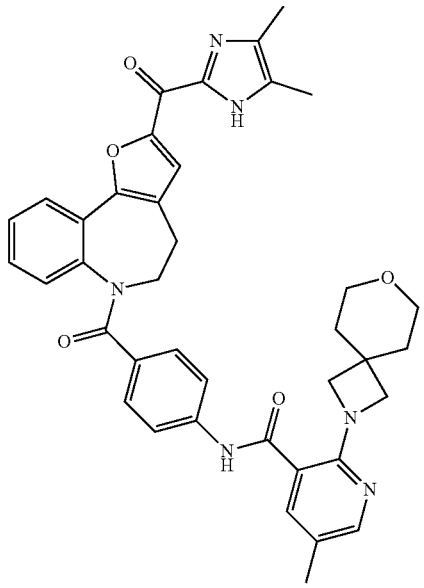 [SMILES: Cc1cnc(N2CC3(CCOCC3)C2)c(C(=O)Nc2ccc(C(=O)N3CCc4cc(C(=O)c5nc(C)c(C)[nH]5)oc4-c4ccccc43)cc2)c1] |
| 14 | 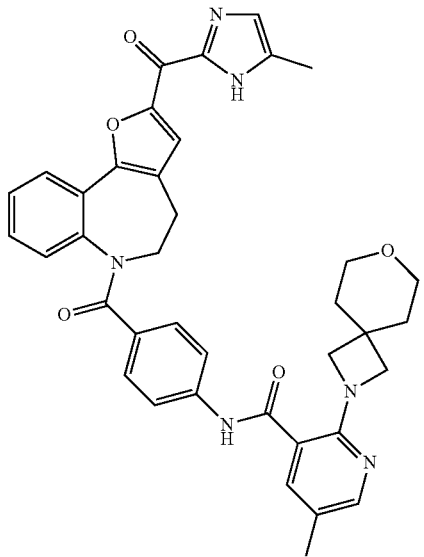 [SMILES: Cc1cnc(N2CC3(CCOCC3)C2)c(C(=O)Nc2ccc(C(=O)N3CCc4cc(C(=O)c5ncc(C)[nH]5)oc4-c4ccccc43)cc2)c1] |
| 15 | 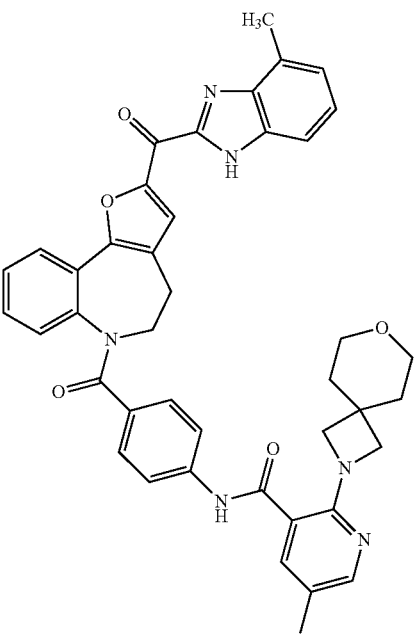 [SMILES: Cc1cnc(N2CC3(CCOCC3)C2)c(C(=O)Nc2ccc(C(=O)N3CCc4cc(C(=O)c5nc6c(C)cccc6[nH]5)oc4-c4ccccc43)cc2)c1] |
| 16 | 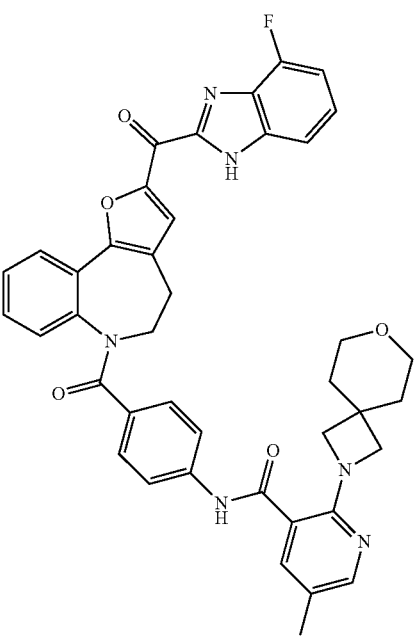 [SMILES: Cc1cnc(N2CC3(CCOCC3)C2)c(C(=O)Nc2ccc(C(=O)N3CCc4cc(C(=O)c5nc6c(F)cccc6[nH]5)oc4-c4ccccc43)cc2)c1] |

-continued
| Compound | Structure |
|---|---|
| 17 | 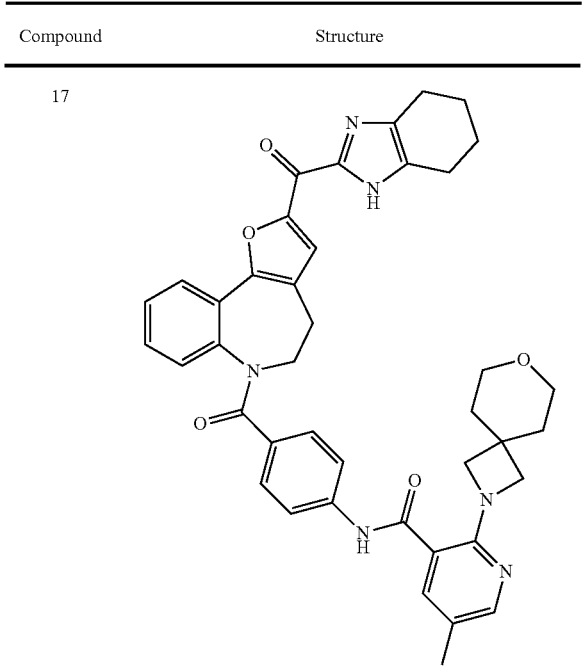 |
| 18 | 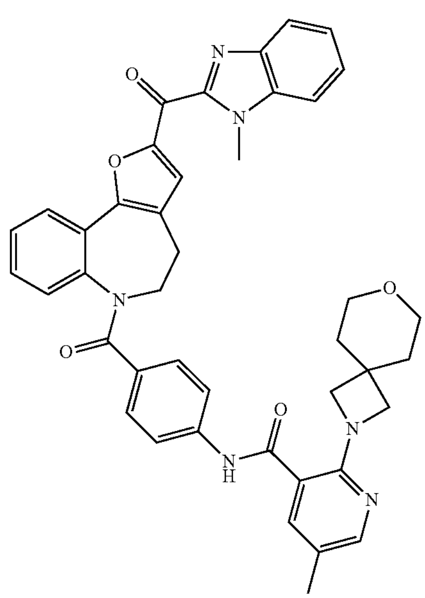 [SMILES: Cc1cnc(N2CC3(CCOCC3)C2)c(C(=O)Nc2ccc(C(=O)N3CCc4cc(C(=O)c5nc6ccccc6n5C)oc4-c4ccccc43)cc2)c1] |
-continued
| Compound | Structure |
|---|---|
| 19 | 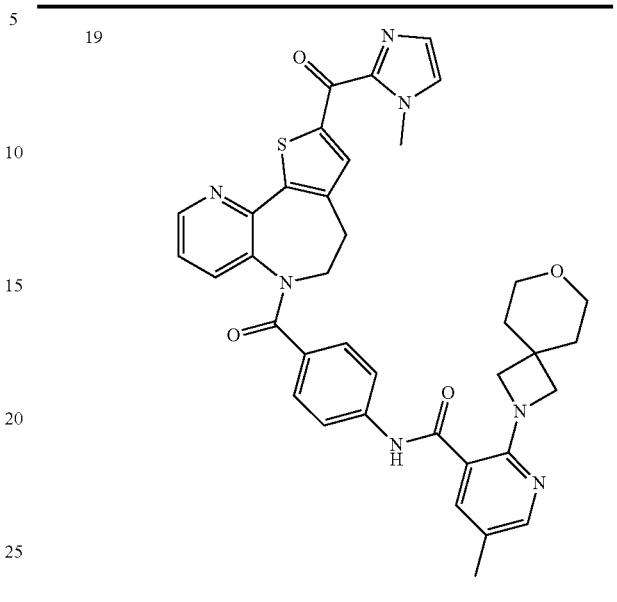 |
| 20 | 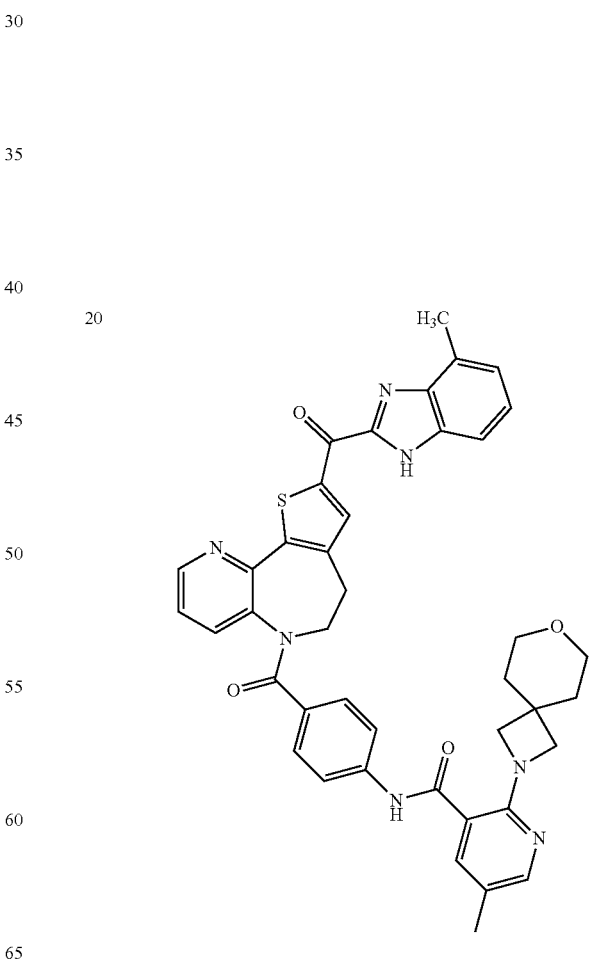 |

-continued
| Compound | Structure |
|---|---|
| 21 | 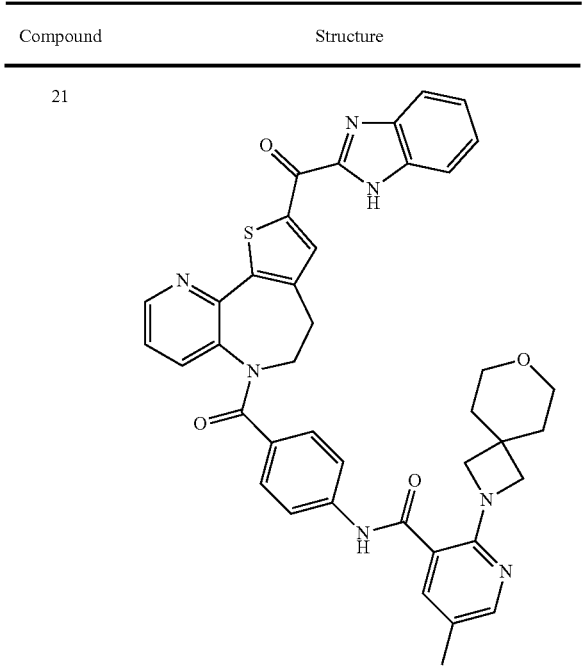 |
| 22 | 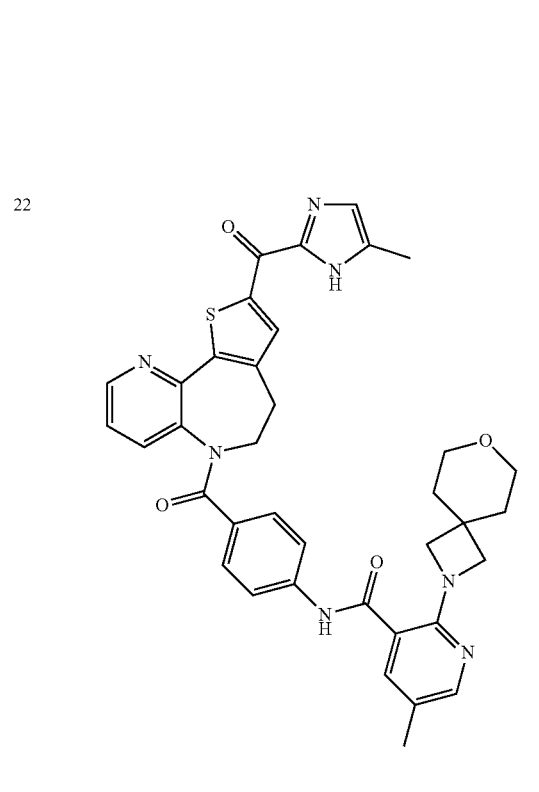 |
-continued
| Compound | Structure |
|---|---|
| 23 | 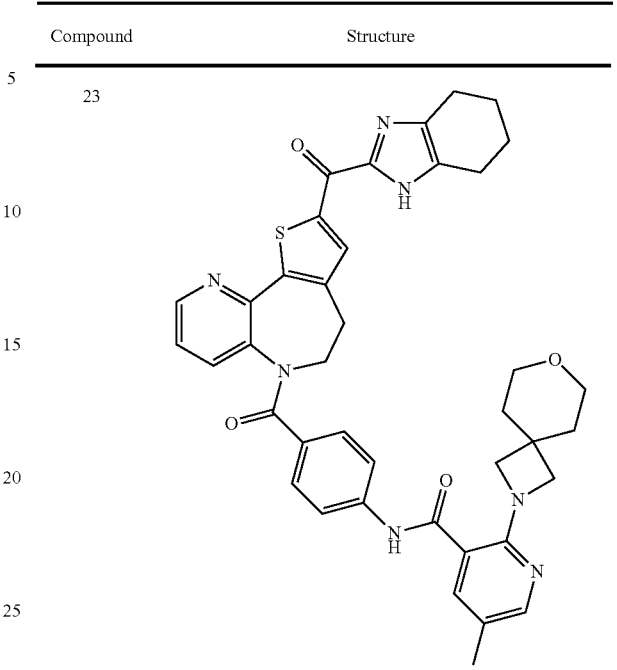 |
| 24 | 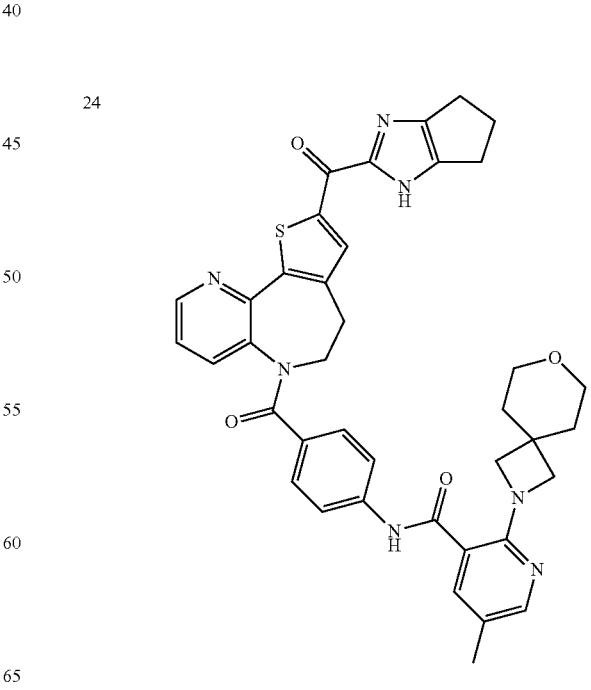 |

| Compound | Structure |
|---|---|
| 25 | 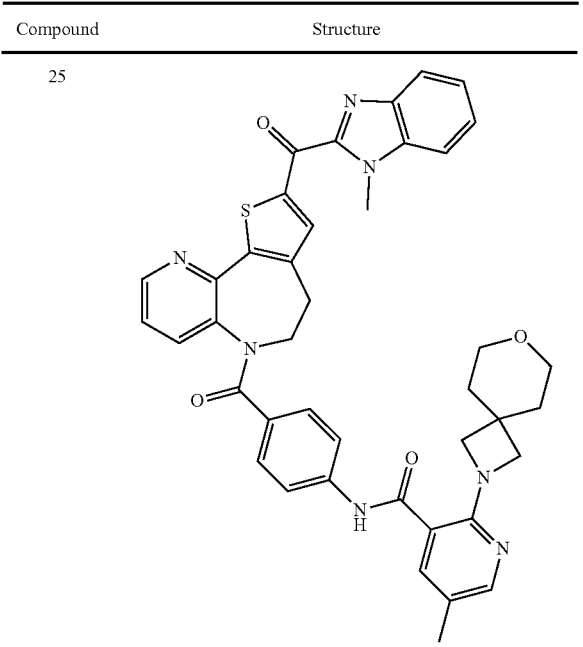 |
| 26 | 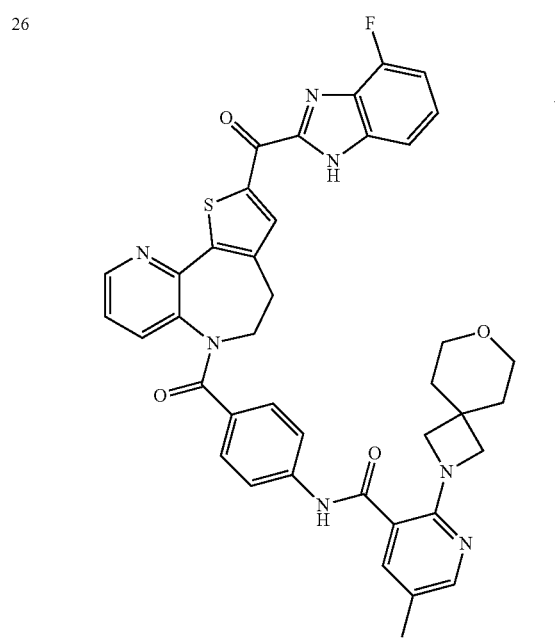 |
| Compound | Structure |
|---|---|
| 27 | 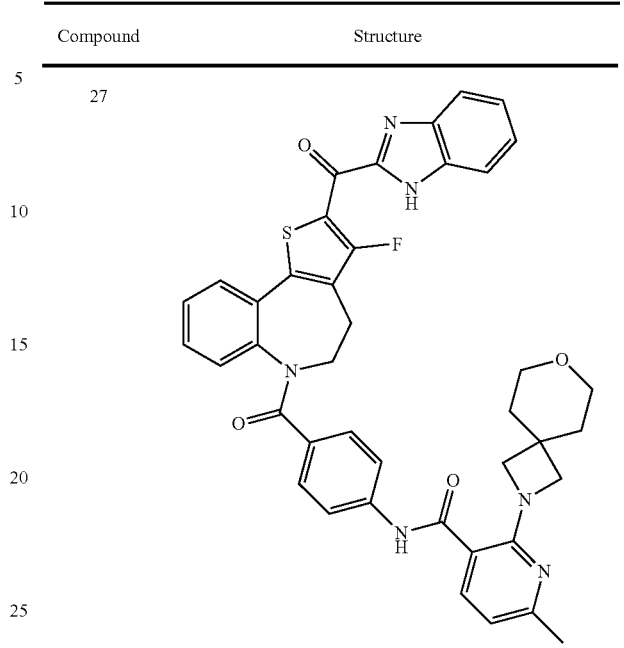 |
| 28 | 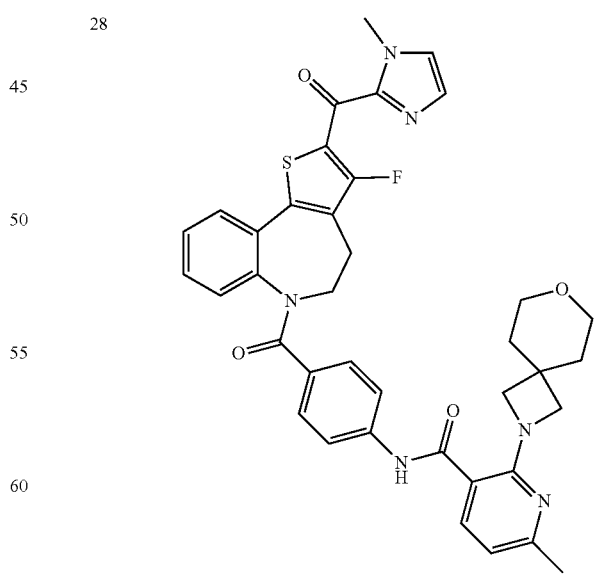 |

| Compound | Structure |
|---|---|
| 29 | 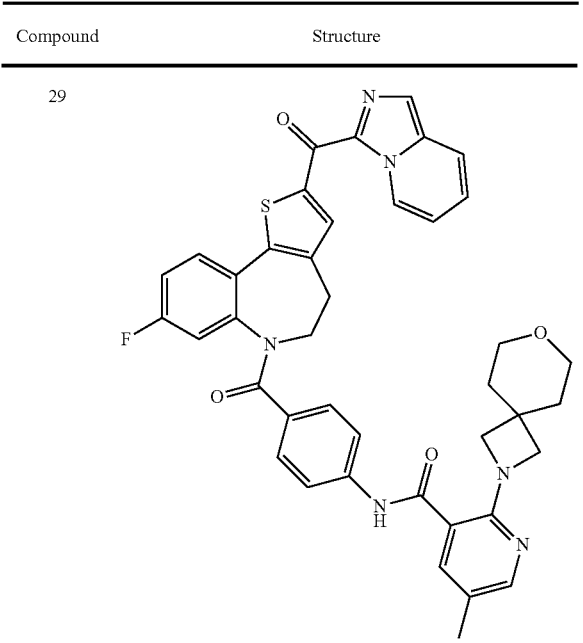 |
| 30 | 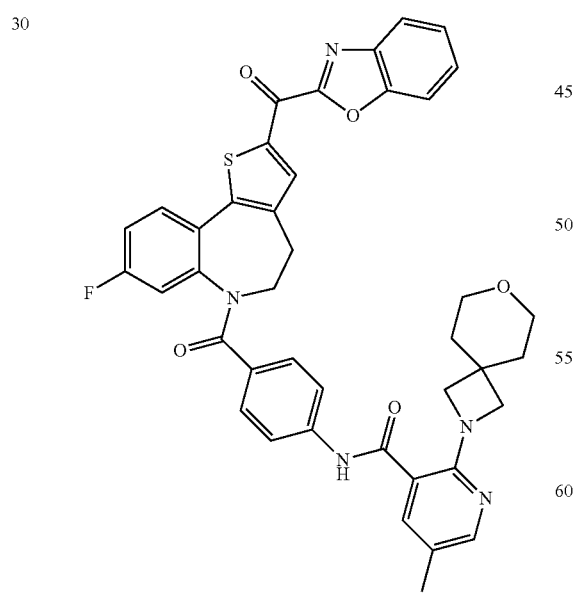 |
| Compound | Structure |
|---|---|
| 31 | 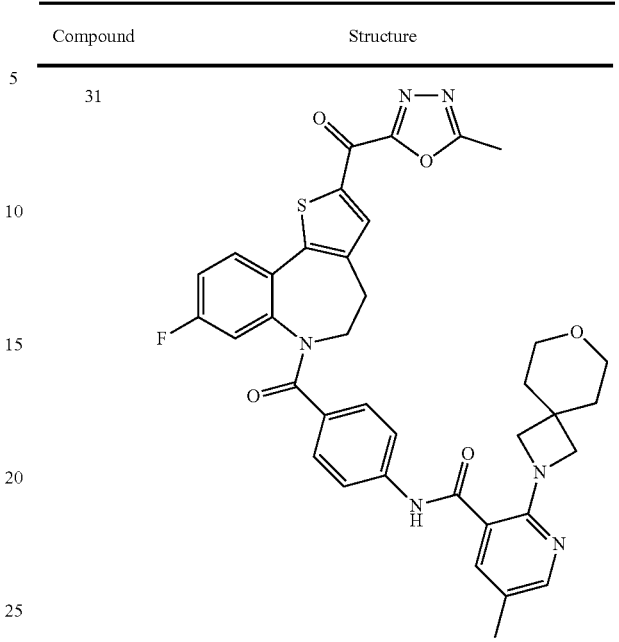 |
| 32 | 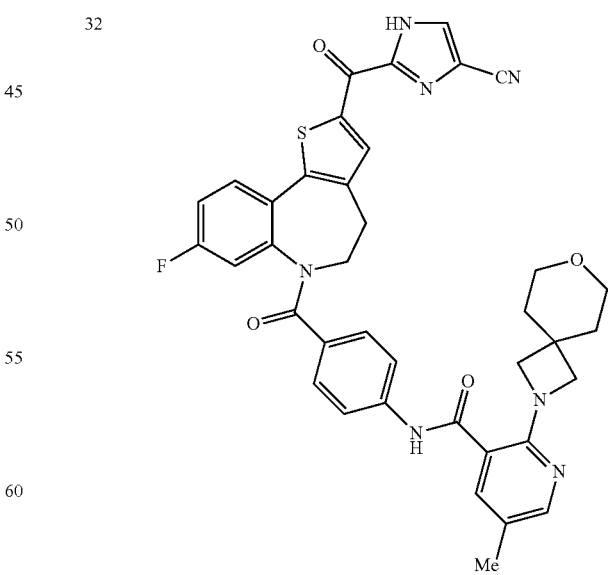 |

-continued
| Compound | Structure |
|---|---|
| 33 | 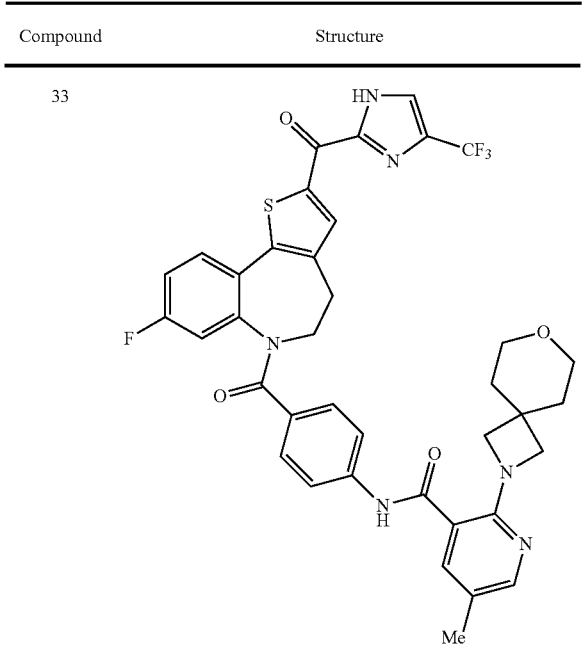 |
| 34 | 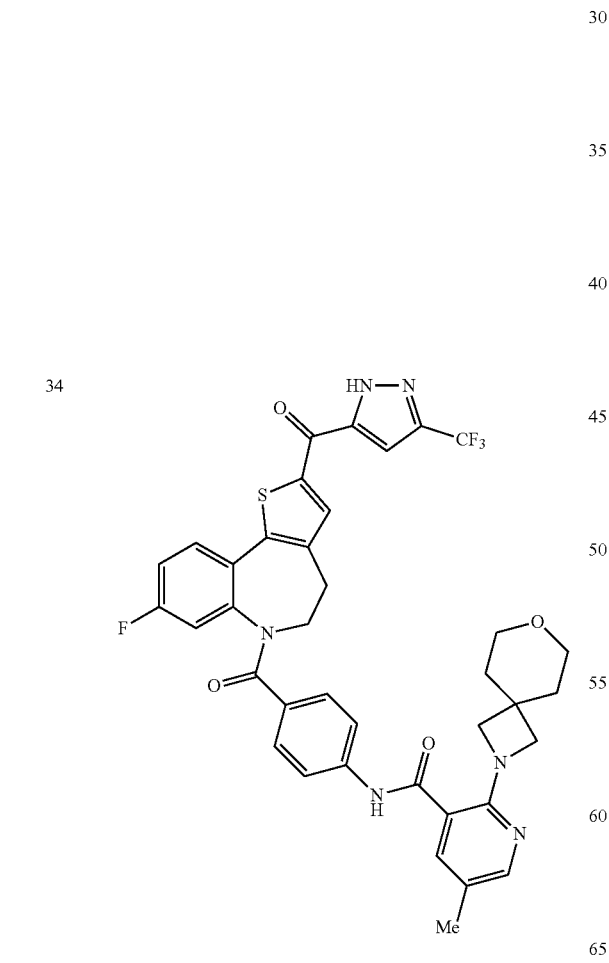 |
-continued
| Compound | Structure |
|---|---|
| 35 | 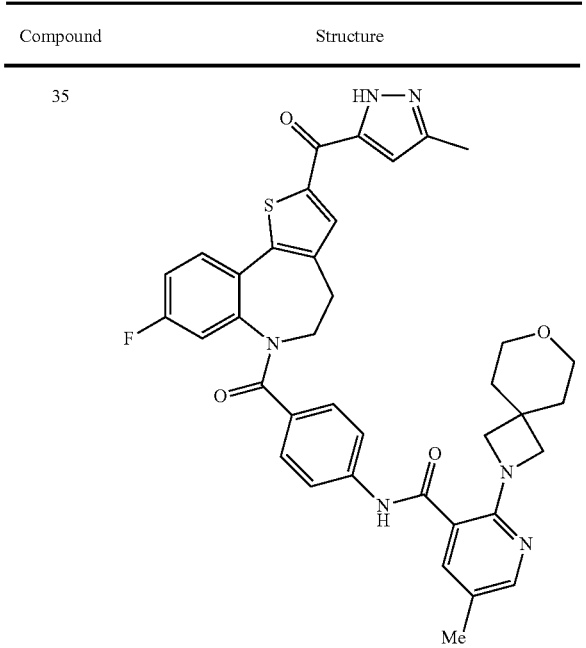 |
| 36 | 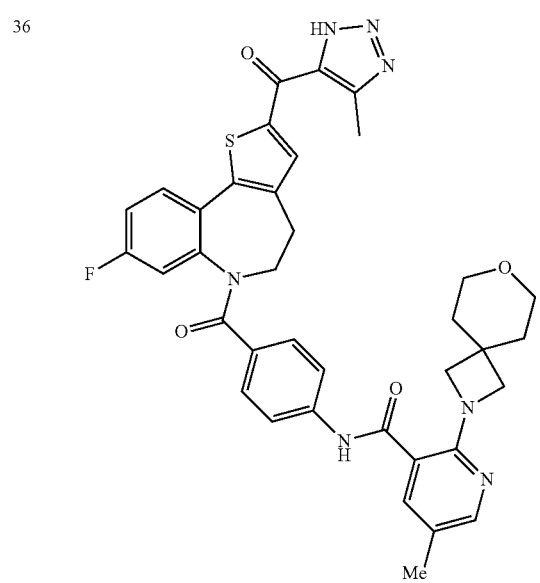 |

-continued

| Compound | Structure |
|---|---|
| 37 | 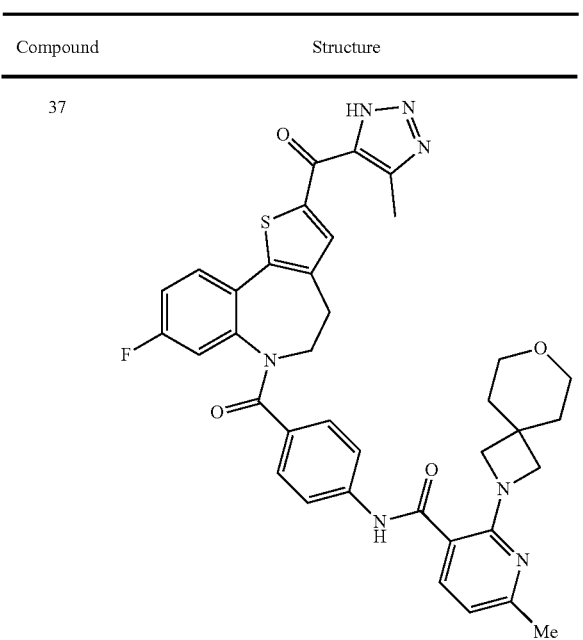 |
| 38 | |
| 39 | 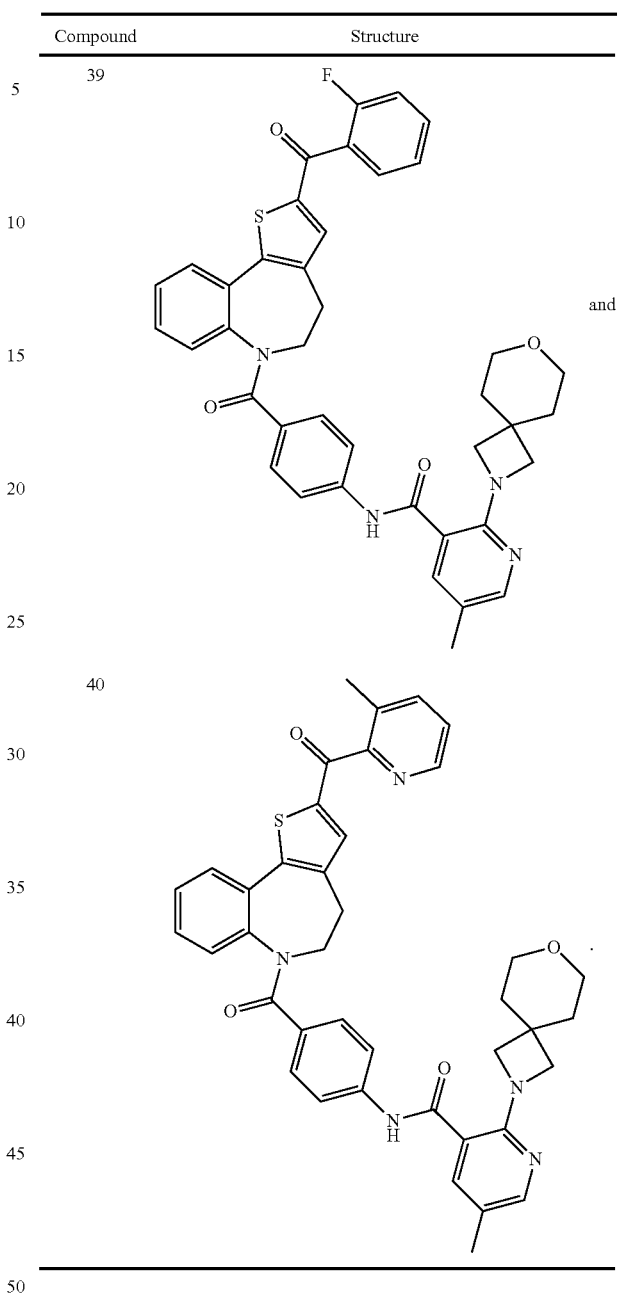 |
| 40 | | and

11. A pharmaceutical composition comprising a compound according to claim 1, and a pharmaceutically acceptable carrier, diluent or excipient.

12. A method of treating or preventing an RSV infection in a subject in need thereof, comprising administering to the subject a therapeutically effective amount of a compound or a combination of compounds of claim 1.

13. The method of claim 12, further comprising the step of administering to the subject an additional anti-RSV agent.

14. The method of claim 12, further comprising administering to the subject a steroid anti-inflammatory compound.

15. A method of treating RSV and influenza in a subject in need thereof, comprising administering to the subject a therapeutically effective amount of a compound of claim 1, and a therapeutically effective amount of an anti-influenza agent.

16. The method of claim 13, wherein the compound and the additional anti-RSV agent are co-formulated.

17. The method of claim 13, wherein the compound and the additional anti-RSV agent are co-administered.

* * * * *